(12) United States Patent
Fujii et al.

(10) Patent No.: US 9,822,387 B2
(45) Date of Patent: Nov. 21, 2017

(54) MICROORGANISM HAVING CARBON DIOXIDE FIXATION PATHWAY INTRODUCED THEREINTO

(75) Inventors: Ryota Fujii, Singapore (SG); Tomokazu Shirai, Yokohama (JP); Tadashi Araki, Chiba (JP); Koh Amano, Mobara (JP); Yoshiko Matsumoto, Mobara (JP); Toshihiro Tateno, Mobara (JP); Nozomi Takebayashi, Mobara (JP); Takashi Morishige, Chiba (JP); Hitoshi Takahashi, Chiba (JP); Mitsufumi Wada, Chiba (JP); Hiroshi Shimizu, Ibaraki (JP); Chikara Furusawa, Ibaraki (JP); Takashi Hirasawa, Machida (JP); Tomonori Hidesaki, Singapore (SG); Ayako Endo, Singapore (SG); Dominik Lukas Jürgen-Lohmann, Singapore (SG); Anjali Madhavan, Singapore (SG); Su Sun Chong, Singapore (SG)

(73) Assignee: MITSUI CHEMICALS, INC., Tokyo (JP)

( * ) Notice: Subject to any disclaimer, the term of this patent is extended or adjusted under 35 U.S.C. 154(b) by 383 days.

(21) Appl. No.: 14/235,756

(22) PCT Filed: Jul. 27, 2012

(86) PCT No.: PCT/JP2012/069247
§ 371 (c)(1),
(2), (4) Date: Jan. 28, 2014

(87) PCT Pub. No.: WO2013/018734
PCT Pub. Date: Feb. 7, 2013

(65) Prior Publication Data
US 2014/0363847 A1 Dec. 11, 2014

(30) Foreign Application Priority Data

Jul. 29, 2011 (JP) ................. 2011-167808

(51) Int. Cl.
| | |
|---|---|
| C12N 1/20 | (2006.01) |
| C12N 15/00 | (2006.01) |
| C12N 9/00 | (2006.01) |
| C12N 9/88 | (2006.01) |
| C12N 9/02 | (2006.01) |
| C07H 21/04 | (2006.01) |
| C12P 19/40 | (2006.01) |
| C12P 13/14 | (2006.01) |
| C12N 9/04 | (2006.01) |
| C12P 7/04 | (2006.01) |
| C12P 7/28 | (2006.01) |
| C12P 19/32 | (2006.01) |

(52) U.S. Cl.
CPC ............... *C12P 19/40* (2013.01); *C12N 1/20* (2013.01); *C12N 9/0006* (2013.01); *C12N 9/88* (2013.01); *C12N 9/93* (2013.01); *C12P 7/04* (2013.01); *C12P 7/28* (2013.01); *C12P 13/14* (2013.01); *C12P 19/32* (2013.01); *C12Y 101/0106* (2013.01); *C12Y 101/01081* (2013.01); *C12Y 401/01047* (2013.01); *C12Y 401/03024* (2013.01); *C12Y 602/01009* (2013.01)

(58) Field of Classification Search
CPC ................ C12P 7/40; C12P 7/28; C12N 9/93
See application file for complete search history.

(56) References Cited

FOREIGN PATENT DOCUMENTS

| | | |
|---|---|---|
| DE | 102007047206 A1 | 4/2009 |
| DE | 1020070 59 248 A1 | 6/2009 |
| WO | WO-2009/046929 A2 | 4/2009 |
| WO | WO-2009/094485 A1 | 7/2009 |
| WO | WO-2010/071697 A1 | 6/2010 |
| WO | WO-2011/099006 A2 | 8/2011 |

OTHER PUBLICATIONS

Erb et al. The Apparent Malate Synthase Activity of Rhodobacter sphaeroides Is Due to Two Paralogous Enzymes, (3S)-Malyl-Coenzyme A (CoA)/β-Methylmalyl-CoA Lyase and (3S)-Malyl-CoA Thioesterase. J. Bacteriol. Mar. 2010 vol. 192 No. 5 1249-1258.*
Chistoserdova et al. Genetics of the Serine Cycle in Methylobacterium extorquens AM1: Identification, Sequence, and Mutation of Three New Genes Involved in C1 Assimilation, orf4, mtkA, and mtkB. Journal of Bacteriology, Dec. 1994, p. 7398-7404.*
Friedmann et al. Properties of Succinyl-Coenzyme A:L-Malate Coenzyme A Transferase and Its Role in the Autotrophic 3-Hydroxypropionate Cycle of Chloroflexus aurantiacus. Journal of Bacteriology, Apr. 2006, p. 2646-2655.*
Extended European Search Report issued in Application No. 12819719.1 dated Jan. 29, 2015.
Berg, I. A., Ecological aspects of the distribution of different autotrophic CO2 fixation pathways, Applied and Environmental Microbiology, Mar. 2011, vol. 77 No. 6, pp. 1925-1936.
International Search Report dated Oct. 9, 2012 received in International Application No. PCT/JP2012/069247.

(Continued)

*Primary Examiner* — Yong Pak
(74) *Attorney, Agent, or Firm* — Foley and Lardner LLP

(57) ABSTRACT

An acetyl-CoA-producing microorganism, which is capable of efficiently synthesizing acetyl-CoA using carbon dioxide, and a substance production method using the same are provided. An acetyl-CoA-producing microorganism including an acetyl-CoA production cycle obtained by imparting at least one type of enzymatic activity selected from the group consisting of malate thiokinase, malyl-CoA lyase, glyoxylate carboligase, 2-hydroxy-3-oxopropionate reductase, and hydroxypyruvate reductase, to a microorganism.

23 Claims, 7 Drawing Sheets

(56) References Cited

OTHER PUBLICATIONS

Chinese Office Action issued in Chinese Patent Application No. 201280036982.9 dated Apr. 19, 2016.
Tobias J. Erb et al., "The Apparent Malate Synthase Activity of *Rhodobacter sphaeroides* Is Due to Two Paralogous Enzymes, (3S)-Malyl-Coenzyme A (CoA)/β-Methylmalyl-CoA Lyase and (3S)-Malyl-CoA Thioesterase", Journal of Bacterilogy, Mar. 2010, vol. 192, No. 5, pp. 1249-1258.

\* cited by examiner

```
                                   270                         300
Me  MtkB  238  G PREAQ A HN S TG EG I C VNGAGLAMA MDMIKHAGG PANFLD GGGAS DR
Rh  MtkB  238  E QRETYASD  LS VG  GN GC INGAGLAMA MDMIKI GG PANFLD GGGAS ER
Hd  MtkB  237  E PRETYASD  LS VG  GD GC VNGAGLAMA LDMIK AGG PANFLD GGGAS EK
HmeMtkB   237  E PRETYASD  LS VG  GD GC VNGAGLAMA LDMIK AGG PANFLD GGGAS EK
Ne  MtkB  238  I SR IAAA A  LS VG  GD GC MINGAGLAMA MDMIK GG PANFLD GGGAS AER
Mc  MtkB  240  E PK VEASGH LN AL  GN GC VNGAGLAMAS D T HGGRPANFLD GGGAS EK
gamMtkB   240  E PR VEA GH LN AL  GD GC VNGAGLAMA MDA VFHGGWPANFLD GGGAS EK
                 *    **  *  + * #* +                *    *              **

330                         360
Me  MtkB  298  V TAFR  GSD  V AI LVN  AG NRCDW A G V KAARE KIDV L IV L G NVD G
Rh  MtkB  298  VAKSFRA ET RQ ET  LVN  AG NRCDW A G VIK LR V GVPV L VV L S NM EG
Hd  MtkB  297  VTKS KA  R KN KA  LVN  AG NRCDW AKG V DA KE LD KL IV L AG NV EG
HmeMtkB   297  VTKS KA  R KN KA  LVN V AG NRCDW AKG V DA KE L KM IV L AG NV EG
Ne  MtkB  298  TEKA R  A NN KAM LVN  AG NRCD  A G V Q A N IGMTV L VR S NV ER
Mc  MtkB  300  V N CR V L PN RC LVN  AG NRCDW AK LIQ CDSLQ K V L V L AS NVD G
gamMtkB   300  VQN CR V Q QN RTLLVN  AG NRCDW A TGLVQ YTSLR DK CV L AG NV EG
                 # * *                        *     *    **    #         #
                *

390
Me  MtkB  358  RK LA S  DLITA DT L T AAR KA E CHGAKH---------
Rh  MtkB  358  RR LA S  EN IVAE   LA A DK VA WRSFTANKAA-----
Hd  MtkB  357  RK IDNS  TV SAE T LA A KQ VE AAKKA-----------
HmeMtkB   357  RK IDNS  T V SA T LA A KQ VD AAKKA-----------
Ne  MtkA  358  RR IADS  PI TA ET LA A EK V HARNQAAV---------
Mc  MtkB  360  RK LA S  SF T AEN DDA AKA A IVKG-----------
gamMtkB   360  LR T D   AFVK SN DDA AKA A IAHGRNV---------
                 #        *    * #* *    *
                                *
```

| Amino acids conserved in all species | ■ |
|---|---|
| Amino acids conserved in some species | Sequences common in Rh, Hd, Hme, Ne |
| | Sequences common in Mc, gam |

FIG.3A

```
              30                                                    60
Me  MtkA   1  MSILIDEKTPIIVQGITGDKGSFHAKDMLAYGSNVVGGVTPGKGKTHCG-----VPVEN
Rh  MtkA   1  MSILLDKNTRVIVQGTGKIGSFHAEDMKRYGTNVVGGVTPGKGGQAHLG-----MPVEN
Hd  MtkA   1  MAIFINEKTPILIQGTGRIGSFHAQEMIDYGSNVVGGVTPGKGGTSHLG-----RPVEN
HmeMtkA    1  MAIFINEKTPILIQGTGRIGSFHAQEMIDYGSNVVGGVTPGKGGTSHLG-----RPVEN
Ne  MtkA   1  MAILINEQTRIIVQGTGRIGSFHAQEMIDYGSNVVGGVTPGKGGQKHLG-----LPVEN
Mc  MtkA   1  MSVFVNKHSKVIFQGTGEHGTFHAKDAMRMGTRVVGGVTPGKGGTRGPDPELAHLPVED
gamMtkA    1  MSIFVNRHSRVIIQGTGQHGTFHASEAIRYGTQVVGGVTPGKGGSKHLG-----LPVED
              ***  ** **        +        #         *   *                *    *
                                         *

90                                                   120
Me  MtkA  56  TVKEAVEATGATTSITFVAEDLAFAMEAADAGLKLVCSIPDGIPAQDMMRVKRYLRRY
Rh  MtkA  56  TVKGAVQETGADASILFVPEIAFSEMEAVADAGRLCECIPDGIPESQDMIRVKRYLRRY
Hd  MtkA  56  TVKGAVDETGAEAIIVEVPEHIAFMEAIADAGKYCFCIPDGIPAQDMIRVKRYLRRY
HmeMtkA   56  TVKGAADETGAEASIVFVPEEAFAMEAADAGKYCFCIPDGIPAQDMIRVKRYLRRY
Ne  MtkA  56  TVREAVEQAGAEASIVFVPAIAFSTMEAADAGKYCESIPDGIPTQDMMTVKNFLRLF
Mc  MtkA  61  TVAEAVAAIGADVEAVFVPENIAFALMEAIDAGRVAETIADGIPVHDMIKLQRYRVGK
gamMtkA   56  TVSEAVSETGADVEGIFVPAIAFAIMEAIDAGRVIEVIADGIPVQDMIRVQRYRLGR
                  *#         +                *        +**#+       *       *        *    *    *    *  *
                *

150                                                 180
Me  MtkA 116  PKEKKTMVVGPNCAGLISPGESMLGIMPSHLYPGKVGVISRSGTIGYEAAAQMRELGIG
Rh  MtkA 116  REEDRMTLIGPNCAGMITPGEAAMGIMPGSIYLPGRIGIIGRSGTLGYEARSMKALGVG
Hd  MtkA 116  KKEARMILTGPNCASTISPGKAALGIMPGHIYLPGRMGIIGRSGTLGYEAAAQLKALGLG
HmeMtkA  116  KKESRMVLTGPNCASTISPCKAMLGIMPGHIFLPGRVGIIGRSGTLGYEAAAQLKALGLG
Ne  MtkA 116  PEEDRMMLTGPNCSGTISEGRAMLGIMPGHIYSRVVGVIGRSGTLGYEAADQMRRLNLG
Mc  MtkA 121  ----DSIVIGPNTPGILTTPGECKVGIMPSMIYKKGNVGIISRSGTLNYEATEQMAALGLS
gamMtkA  116  ----DCLVIGPNTPGILTTPGECKVGIMPAGIYREGRIGVSRSGTLNYEAVEQLGKLGLS
                  *# #       **  *   *#**                +       *        *       *
                                                *

210                                                 240
Me  MtkA 176  ISISVGIGGDPINSSTLDHLALEEQDPETEAVIMIGEIGGPQEADASAWIKENFSKEVI
Rh  MtkA 176  VSGSIGIGGDPVNGSSEKDMLELEEKDPGIDAVLMIGEIGGPQEAEAAALWRDHKKELI
Hd  MtkA 176  VSIEVGIGGDPTINGSSHRDVLEHENDPETDAIIMIGEIGGPQEAEAGLFKEHKKEVI
HmeMtkA  176  VSIEVGIGGDPTINGSSHRDILEARESDPETDAVLMIGEIGGPQEAEAGLFKEHKKEVI
Ne  MtkA 176  ISIEVGIGGDPTIESSHRNVLQKLEEDPETKVTLMIGEIGGPMEVEAGLFKENSKELV
Mc  MtkA 177  LTIEVGIGGDPLNGTDEVTVLRAEEADPETEIVVMIGEIGGPQEVAAARWKENTKEVI
gamMtkA  172  QSIAVGIGGDPVNETDEVTVLKAEEQDEDIDAIVMIGEIGGPQEVAAARWKENQKELI
                        *   ***   *               *              ** *#  +   +
                                                                         *
```

FIG.3B

```
Me  MtkA  236 GFV  LT  KGRRMCHAGAI SATGDSAA  A IMRSYGLTVA D GS  S VADV ARA
Rh  MtkA  236 AYI  ES  KGRRMGHAGAI SAFGESAQ  VE LKSA VTIV TSS  E VADV SAM
Hd  MtkA  236 AYI  ES  KGRRMGHAGAI V AFGESAA  VE ILKGC VAI  T SEM  S V Q  GKQ
HmeMtkA  236 AYI  ES  KGRRMGHAGAI V AFGESAA  VE ILKGCNV IA T SEM S V Q NQR
Ne  MtkA  236 AYI  LT  PGRRMGHAGAI SSAGE AA   VE RLKEL V IC T SLM E V K  AGL
Mc  MtkA  237 GFV  LA  TGRRMGHAGAI SSEA TAGA MDA EALG YV RN AQI Q VLRAAQEH
gamMtkA  232 GFV  AS  PGRRMGHAGAI EGEE TA A MDA EELG VYVRN ARI  E VLRA KER
                                  .   .        . .                 ..  .
              ###              *  # *   *  #**## * #*#  *# #  *   ***  *
                                                 *  *        * *
```

```
Me  MtkA  296 A------
Rh  MtkA  296 SKAA---
Hd  MtkA  296 KKVA---
HmeMtkA  296 KKVA---
Ne  MtkA  296 -------
Mc  MtkA  297 GIRF---
gamMtkA  292 LGSAVSG
```

| Amino acids conserved in all species | ■ |
| Amino acids conserved in some species | Sequences common in Rh, Hd, Hme, Ne |
| | Sequences common in Mc, gam |

MICROORGANISM HAVING CARBON DIOXIDE FIXATION PATHWAY INTRODUCED THEREINTO

This application is the National Phase of PCT/JP2012/069247, filed Jul. 27, 2012, which claims priority to Japanese Application No. 2011-167808, filed Jul. 29, 2011, the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jul. 30, 2014, is named 096949-0115_SL.txt and is 135,247 bytes in size.

TECHNICAL FIELD

The present invention relates to an acetyl-CoA producing microorganism and a method of producing a substance using the acetyl-CoA producing microorganism.

BACKGROUND ART

Acetyl-CoA is one of significantly important intermediates in metabolic pathways of microorganisms. Various metabolites are produced via acetyl-CoA. Well-known examples of such substances produced via acetyl-CoA include amino acids such as L-glutamic acid, L-glutamine, L-proline, L-arginine, L-leucine, and L-isoleucine; organic acids such as acetic acid, propionic acid, butyric acid, caproic acid, citric acid, 3-hydroxybutyric acid, 3-hydroxyisobutyric acid, 3-aminoisobutyric acid, 2-hydroxyisobutyric acid, methacrylic acid, and poly-3-hydroxybutyric acid; alcohols such as isopropyl alcohol, ethanol, and butanol; acetone; and polyglutamic acids.

In most microorganisms, acetyl-CoA is produced using a sugar such as glucose as a carbon source. The sugar is first converted into pyruvate via a metabolic pathway called the glycolytic pathway, such as the Embden-Meyerhof pathway, Entner-Doudoroff pathway, or the pentose phosphate pathway. Subsequently, the pyruvate is converted into acetyl-CoA by actions of decarboxylase, pyruvate formate-lyase, and the like. In this process, carbon dioxide and formate are generated as byproducts, and some of the carbons derived from the sugar will lost. Therefore, several studies have been carried out with the aim of achieving re-fixation of carbon dioxide in order to increase the yield of acetyl-CoA.

In microorganisms, there are several known pathways for fixing carbon dioxide as a carbon source (Appl. Environ. Microbiol. 77(6), 1925-1936, 2011). Specific examples of the pathways include the Calvin-Benson cycle, the reductive TCA cycle, the Wood-Ljungdahl pathway, the 3-hydroxypropionate cycle, and the 4-hydroxybutyrate cycle. The Calvin-Benson cycle is a $CO_2$ fixation pathway existing in plants and photosynthetic bacteria, and containing about 12 kinds of enzymes. In the Calvin-Benson cycle, $CO_2$ is fixed by ribulose-1,5-bisphosphate carboxylase (RubisCO) and, ultimately, glyceraldehyde 3-phosphate is produced. The reductive TCA cycle is found in microaerophilic bacteria and anaerobic bacteria including green sulfur bacteria, and contains 11 kinds of enzymes. This cycle is characterized by $CO_2$ fixation enzymes (i.e., acetyl-CoA carboxylase, 2-oxoglutarate synthase) that requires ferredoxin as a coenzyme. In the reductive TCA cycle, pyruvate is produced from $CO_2$ by the reverse reaction of the usual TCA cycle. The Wood-Ljungdahl pathway is found in anaerobic microorganisms such as acetic acid-producing bacteria, and contains 9 kinds of enzymes. In the Wood-Ljungdahl pathway, $CO_2$ and formate on a coenzyme are reduced by formate dehydrogenase, CO dehydrogenase, etc., and, ultimately converted into acetyl-CoA. The 3-hydroxypropionate cycle is found in *Chloroflexus* bacteria and the like, and contains 13 kinds of enzymes. In the 3-hydroxypropionate cycle, $CO_2$ is fixed by the action of acetyl-CoA (propionyl-CoA) carboxylase and acetyl-CoA is produced via malonyl-CoA and the like. The 4-hydroxybutyrate cycle exists in archaeabacteria and the like. In the 4-hydroxybutyrate cycle, $CO_2$ is fixed by the actions of pyruvate synthase, acetyl-CoA (propionyl-CoA) carboxylase, and phosphoenolpyruvate carboxylase, whereby acetyl-CoA is produced via 4-hydroxybutyryl CoA and the like.

In order to produce a useful substance, several approaches have been reported as ideas to introduce a carbon dioxide fixation pathway to a useful-compound-producing microorganism. For example, International Publication (WO) 2009/094485 and WO 2010/071697 disclose approaches to producing acetyl-CoA from carbon dioxide, by using a microorganism to which a pathway similar to the Wood-Ljungdahl pathway of acetic acid bacteria was introduced. As an example of $CO_2$ fixation for producing a useful compound, WO 2009/046929 discloses an approach to producing lactic acid from carbon dioxide by using a microorganism to which hydrogenase and tetrahydrofolate lyase were introduced. WO 2011/099006 proposes a cycle in which $CO_2$ is fixed via a carbon dioxide fixation reaction onto acetyl-CoA or a malonyl-CoA reduction reaction. German Patent No. 102007059248 proposes production of acetyl-CoA by a pathway similar to the 4-hydroxybutyrate cycle.

SUMMARY OF INVENTION

Technical Problem

However, known carbon dioxide fixation cycles are not necessarily efficient from the viewpoints of $CO_2$ fixation and production of useful chemical products derived from acetyl-CoA. For example, the Calvin-Benson cycle is most famous as a carbon dioxide fixation cycle found in nature, but RubisCO involved in carbon dioxide fixation has a low reaction rate and causes side reactions such as oxidative degradation. Therefore, RubisCO is inefficient as an enzyme (Journal of Bioscience and Bioengineering 94(6) 497-505, 2002). In the Wood-Ljungdahl pathway and the pathways described in WO 2009/094485, WO 2010/071697, WO 2009/046929 and the like, a pathway for reducing $CO_2$ into CO or formate is included. However, the reduction reaction hardly occurs under ordinal conditions, and the enzyme catalyzing this kind of strong reduction reaction often only acts under a reductive environment. Therefore, it is difficult to introduce this kind of pathway into microorganisms other than strictly anaerobic microorganisms. In the reductive TCA cycle, a reduction reaction by pyruvate synthase or 2-oxoglutarate synthase requires a strong reduction power from ferredoxin as an electron acceptor, and it is difficult to carry out the reaction. The 4-hydroxybutyrate cycle, 3-hydroxypropionate cycle, and the pathways described in WO 2011/099006, WO 2009/046929, and the like utilize the reduction reaction for carboxylic acid or a (thio)ester thereof, such as reduction of succinyl-CoA or reduction of malonyl-CoA. However, it is generally difficult to carry out this kind of reaction as an enzymatic reaction, and it is desirable to avoid them as fermentation pathways where possible (Atsumi et al., Nature, 451, (3), 86-89, 2008; Yim et al., Nat. Chem. Biol., 7, 445-452, 2011). The 4-hydroxybutyrate cycle proceeds via a dehydration reaction such as dehydration of 4-hydroxybutyryl CoA or dehydration of 3-hydroxypropionate, but this cycle has a disadvantage in that this kind of dehydration reaction often competes with the reverse reaction (hydration) in water. In the 4-hydroxybutyrate cycle, the 3-hydroxypropionate cycle, and the reductive TCA cycle, the acetyl-CoA produced is converted into other substances within the cycle by the action of malonyl-CoA synthase or pyruvate synthase. Therefore, these cycles are not necessarily efficient from the viewpoint of acetyl-CoA production.

When attempting to produce a certain substance by introducing this kind of cycle to a microorganism, it is necessary to consider the number of enzymes involved in the cycle and the number of enzymatic activities to be additionally imparted. That is, when the number of enzymes involved in the cycle or the number of enzymatic activities to be additionally imparted increases, regulation becomes more difficult and the burden on the microorganism increases. For example, in order to introduce the Wood-Ljungdahl pathway to *Escherichia coli*, it is required to introduce at least 9 kinds of genes. It would practically be a very difficult task to construct a substance-producing pathway and also introduce and regulate so many genes. It would clearly be advantageous to construct a cycle including a small number of enzymes by imparting a smaller number of enzymes, in terms of constructing the cycle and in terms of combination with another substance production pathway.

Accordingly, in order to fix $CO_2$ and convert it into acetyl-CoA, it would be ideal for (A) each enzyme involved in the pathway to have a sufficiently high activity; (B) the cycle to not include an enzyme that consumes acetyl-CoA; and (C) the cycle to have a simple configuration and a small number of newly imparted enzymes. However, none of the cycles for producing acetyl-CoA from $CO_2$ reported so far satisfies all of the conditions (A) to (C), and, therefore, the possibility of realizing such cycles is low. In fact, as regards the proposals concerning the existing carbon dioxide fixation cycles, there have been almost no actual examples of converting $CO_2$ into acetyl-CoA or a substance derived from acetyl-CoA for use in fermentation by imparting an enzymatic activity to an industrially-usable microorganism.

The present invention provides a microorganism useful for efficient production of acetyl-CoA using carbon dioxide, and a method of producing acetyl-CoA or a useful metabolite derived from acetyl-CoA using the microorganism.

Solution to Problem

The aspect of the invention is as follows.
[1] An acetyl-CoA producing microorganism including an acetyl-CoA production cycle obtained by imparting at least one type of enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of:
(a) a carbon dioxide fixation cycle having an enzymatic reaction from malonyl-CoA to malonate semialdehyde or 3-hydroxypropionate;
(b) a carbon dioxide fixation cycle having an enzymatic reaction from acetyl-CoA and $CO_2$ to pyruvate;
(c) a carbon dioxide fixation cycle having an enzymatic reaction from crotonyl-CoA and $CO_2$ to ethylmalonyl-CoA or glutaconyl-CoA;
(d) a carbon dioxide fixation cycle having an enzymatic reaction from $CO_2$ to formate; or
(e) at least one selected from the group consisting of malate thiokinase and malyl-CoA lyase,
wherein none of (a), (b), (c), or (d) is imparted to the microorganism, or the microorganism exhibits none of the functions of (a), (b), (c), and (d) even though at least one of (a), (b), (c), or (d) is imparted.
[2] The acetyl-CoA producing microorganism according to [1], including an acetyl-CoA production cycle wherein phosphoenolpyruvate or pyruvate is converted to oxaloacetate, and then to 2-hydroxy-3-oxopropionate due to actions of malate thiokinase, malyl-CoA lyase, glyoxylate carboligase, and then to phosphoenol pyruvate again via 2-phosphoglycerate.
[3] The acetyl-CoA producing microorganism according to [1] or [2], comprising an acetyl-CoA production cycle comprising:
(f) at least one selected from the group consisting of:
pyruvate kinase and pyruvate carboxylase;
phosphoenolpyruvate carboxylase; and
phosphoenolpyruvate carboxykinase;
(g) malate dehydrogenase;
(h) malate thiokinase;
(i) malyl-CoA lyase;
(j) glyoxylate carboligase;
(k) at least one selected from the group consisting of:
2-hydroxy-3-oxopropionate reductase; and
hydroxypyruvate isomerase and hydroxypyruvate reductase;
(l) at least one selected from the group consisting of:
glycerate 2-kinase; and
phosphoglycerate mutase and glycerate 3-kinase; and
(m) enolase.
[4] The acetyl-CoA producing microorganism according to any one of [1] to [3], wherein the microorganism is a microorganism belonging to Enterobacteriaceae or a microorganism belonging to coryneform bacteria.
[5] The acetyl-CoA producing microorganism according to any one of [1] to [4], wherein the microorganism is *Escherichia* bacteria or *Pantoea* bacteria belonging to Enterobacteriaceae, or the microorganism is *Corynebacterium* bacteria belonging to coryneform bacteria.
[6] The acetyl-CoA producing microorganism according to any one of [1] to [5], wherein the microorganism is an *Escherichia* bacterium in which an activity of lactate dehydrogenase possessed by the *Escherichia* bacterium is inactivated or reduced.
[7] The acetyl-CoA producing microorganism according to any one of [1] to [6], wherein the microorganism is an *Escherichia* bacterium in which an activity of at least one enzyme selected from the group consisting of isocitrate lyase and malate synthase possessed by the *Escherichia* bacterium is inactivated or reduced.
[8] The acetyl-CoA producing microorganism according to any one of [1] to [7], wherein the microorganism is an *Escherichia* bacterium in which a thiolase activity, a CoA transferase activity, and an acetoacetate decarboxylase activity are imparted or enhanced.
[9] The acetyl-CoA producing microorganism according to any one of [1] to [8], wherein the microorganism is an *Escherichia* bacterium in which a thiolase activity, a CoA transferase activity, an acetoacetate decarboxylase activity, and an isopropyl alcohol dehydrogenase activity are imparted or enhanced.

[10] The acetyl-CoA producing microorganism according to any one of [1] to [5], wherein the microorganism is a *Pantoea* bacterium in which activities of fumarate hydratase A and fumarate hydratase C possessed by the *Pantoea* bacterium are inactivated or reduced.

[11] The acetyl-CoA producing microorganism according to any one of [1] to [5] or [10], wherein the microorganism is a *Pantoea* bacterium in which an activity of malate synthase possessed by the *Pantoea* bacterium is inactivated or reduced.

[12] The acetyl-CoA producing microorganism according to any one of [1] to [11], wherein the malate thiokinase used is a malate thiokinase obtained by modifying mtkB derived from *Methylobacterium extorquens* so as to alter an amino acid corresponding to the 144th amino acid to isoleucine, asparagine, aspartic acid, lysine, arginine, histidine, glutamine, or proline, and/or so as to alter the 244th amino acid to glutamic acid, alanine, leucine, isoleucine, methionine, asparagine, tyrosine, lysine, or arginine.

[13] A method of producing acetyl-CoA, comprising producing acetyl-CoA from a carbon source material using the acetyl-CoA producing microorganism according to any one of [1] to [12].

[14] A method of producing acetone, comprising producing acetone from a carbon source material using the acetyl-CoA producing microorganism according to [9] or [12].

[15] A method of producing isopropyl alcohol, comprising producing isopropyl alcohol from a carbon source material using the acetyl-CoA producing microorganism according to [9] or [12].

[16] A method of producing glutamate, comprising producing glutamate from a carbon source material using the acetyl-CoA producing microorganism according to [5], [10], [11], or [12].

Advantageous Effects of Invention

The invention provides a microorganism useful for efficient conversion of carbon dioxide into acetyl-CoA, and a method of producing acetyl-CoA or a useful metabolite using the microorganism.

BRIEF DESCRIPTION OF THE DRAWINGS

FIG. 2A and FIG. 2B show the homology among various mtkB sequences (SEQ ID NOS 71, 76, 111, 73, 114, 117 and 119, respectively, in order of appearance).

FIG. 3A and FIG. 3B show the homology among various mtkA sequences (SEQ ID NOS 70, 75, 110, 74, 113, 116 and 118, respectively, in order of appearance).

DESCRIPTION OF EMBODIMENTS

Figure 1:
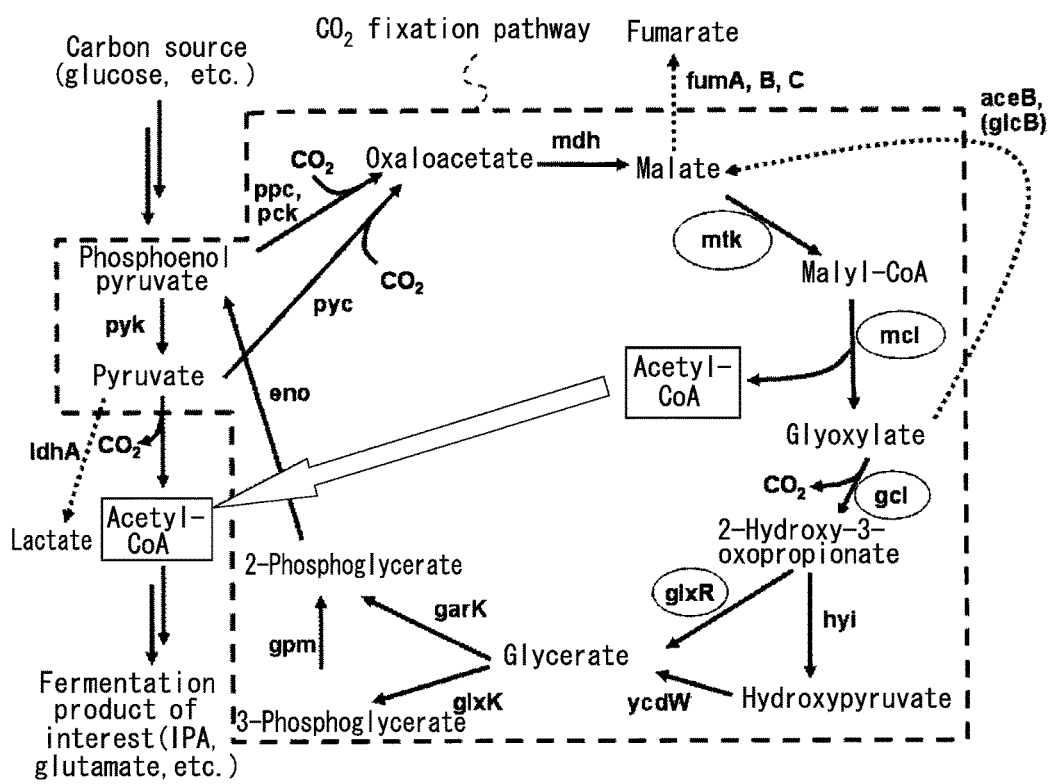
FIG. 1 is a pathway diagram for illustrating the outline of the carbon dioxide fixation pathway according to an embodiment of the invention.

The acetyl-CoA producing microorganism of the invention is an acetyl-CoA producing microorganism including an acetyl-CoA production cycle obtained by imparting at least one type of enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of the following (a), (b), (c), (d), or (e), in which none of (a), (b), (c), or (d) is imparted to the microorganism, or the microorganism exhibits none of the functions of (a), (b), (c), and (d) even though at least one of (a), (b), (c), or (d) is imparted.

(a) a carbon dioxide fixation cycle having an enzymatic reaction from malonyl-CoA to malonate semialdehyde or 3-hydroxypropionate;

(b) a carbon dioxide fixation cycle having an enzymatic reaction from acetyl-CoA and $CO_2$ to pyruvate;

(c) a carbon dioxide fixation cycle having an enzymatic reaction from crotonyl-CoA and $CO_2$ to ethylmalonyl-CoA or glutaconyl-CoA;

(d) a carbon dioxide fixation cycle having an enzymatic reaction from $CO_2$ to formate; or (e) at least one selected from the group consisting of malate thiokinase and malyl-CoA lyase.

According to the invention, by imparting a predetermined enzymatic activity, there can be constructed a carbon dioxide fixation cycle that fixes $CO_2$ generated during carbohydrate metabolism or $CO_2$ supplied from outside, and provided an acetyl-CoA producing microorganism having an acetyl-CoA production cycle in which $CO_2$ is efficiently converted to acetyl-CoA.

That is, as a result of various studies on conversion of $CO_2$ to acetyl-CoA, it was found that $CO_2$ was converted to acetyl-CoA by imparting at least one type of enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of:

(a) a carbon dioxide fixation cycle having an enzymatic reaction from malonyl-CoA to malonate semialdehyde or 3-hydroxypropionate;

(b) a carbon dioxide fixation cycle having an enzymatic reaction from acetyl-CoA and $CO_2$ to pyruvate;

(c) a carbon dioxide fixation cycle having an enzymatic reaction from crotonyl-CoA and $CO_2$ to ethylmalonyl-CoA or glutaconyl-CoA;

(d) a carbon dioxide fixation cycle having an enzymatic reaction from $CO_2$ to formate; or (e) at least one selected from the group consisting of malate thiokinase and malyl-CoA lyase, in which none of (a), (b), (c), or (d) is imparted to the microorganism, or the microorganism exhibits none of the functions of (a), (b), (c), and (d) even though at least one of (a), (b), (c), or (d) is imparted.

Furthermore, by using the acetyl-CoA producing microorganism that converts $CO_2$ into acetyl-CoA, or by additionally imparting a predetermined enzymatic activity to the microorganism, substances including acetyl-CoA and useful metabolites derived from acetyl-CoA such as isopropyl alcohol, ethanol, acetone, citric acid, itaconic acid, acetic acid, butyric acid, (poly-)3-hydroxybutyric acid, 3-hydroxyisobutyric acid, 3-aminoisobutyric acid, 2-hydroxyisobutyric acid, methacrylic acid, (poly)glutamic acid, glutamic acid, arginine, ornithine, citrulline, leucine, isoleucine, or proline, are efficiently produced.

The invention proposes the simplest and practical acetyl-CoA production cycle which fixes $CO_2$ and converts it into acetyl-CoA (FIG. 1).

Preferable embodiments of the acetyl-CoA production cycle according to the invention include the acetyl-CoA production cycle shown in FIG. 1 (hereinbelow may be referred to as "cycle of FIG. 1").

The cycle involves 8 to 10 types of enzymes, that is,
at least one selected from the group consisting of:
phosphoenolpyruvate carboxylase;
phosphoenolpyruvate carboxykinase, and
pyruvate carboxylase and pyruvate kinase;
malate dehydrogenase;
malate thiokinase;
malyl-CoA lyase;
glyoxylate carboligase;
at least one selected from the group consisting of:
hydroxypyruvate isomerase and hydroxypyruvate reductase; and
2-hydroxy-3-oxopropionate reductase;
at least one selected from the group consisting of:
glycerate 2-kinase; and
phosphoglycerate mutase and glycerate 3-kinase; and
enolase.

(Phosphoenol)pyruvate carboxylase or phosphoenolpyruvate carboxykinase is involved in carbon dioxide fixation. (Phosphoenol)pyruvate carboxylase is a carbon dioxide-fixing enzyme having a high activity. For example, RubisCO used in photosynthesis in plants or the like is known to have a specific activity of about 3 U/mg to 20 U/mg (J. Biol. Chem. 274(8) 5078-82 (1999), Anal. Biochem. 153(1) 97-101, 1986). On the other hand, (phosphoenol)pyruvate carboxylase is reported to have a specific activity of 30 U/mg in *Escherichia coli*, or as high as 100 U/mg to 150 U/mg (J. Biol. Chem. 247, 5785-5792 (1972); Biosci. Biotechnol. Biochem. 59, 140-142 (1995); Biochim Biophys Acta. 1475(3):191-206, 2000). In terms of malate thiokinase (mtk) that synthesizes malyl-CoA, the present study revealed that malate thiokinase according to the invention has a higher activity compared to that of the conventionally known enzymes (J. Biol. Chem. 248(21) 7295-303, 1973). The cycle of FIG. 1 is composed of 8 to 10 kinds of enzymes, and, therefore, the simplest cycle among the known acetyl-CoA production cycles. Only a small number of enzymes are required to be imparted to the microorganism. Furthermore, the cycle of FIG. 1 does not include an enzyme that consumes acetyl-CoA. Therefore, it can be said that the cycle of FIG. 1 is an ideal cycle for fixing $CO_2$ and convert it into acetyl-CoA.

Another advantage of the cycle of FIG. 1 is that, since the cycle is independent from glycolytic pathways, the cycle can be freely combined with various glycolytic pathways. For example, the cycle of FIG. 1 can be easily combined with, which produces NADPH with a high production rate and is often used in production of substances (Japanese National-phase publication (JP-A) No. 2007-510411), since the cycle of FIG. 1 is independent from the pentose phosphate pathway.

In the cycle of FIG. 1, each of malate dehydrogenase (mdh), 2-hydroxy-3-oxopropionate reductase (glxR), and hydroxypyruvate reductase (ycdW) consumes NADH (or NADPH) as the reduction power; each of malate thiokinase (mtk), glycerate 3-kinase (glxK), glycerate 2-kinase (garK), and pyruvate carboxylase (pyc) consumes ATP; and pyruvate kinase (pyk) produces pyruvate.

In a case in which phosphoenolpyruvate is used as the starting substance, the balanced equation for the cycle of FIG. 1 is: "phosphoenolpyruvate+2CoA+$CO_2$+3NAD(P)H+3ATP→2acetyl-CoA+3NAD(P)$^+$+3ADP".

In a case in which pyruvate is used as the starting substance, the balanced equation is: "pyruvate+2CoA+$CO_2$+3NAD(P)H+4ATP→2acetyl-CoA+3NAD(P)$^+$+4ADP".

That is, the cycle of FIG. 1 requires supplementation of phosphoenolpyruvate (or pyruvate), NAD(P)H, and ATP for fixing $CO_2$ and converting it into acetyl-CoA.

Among fermentation pathways that produce acetyl-CoA as an intermediate, balanced equations of pathways that consume oxygen during fermentation are listed in Table 1. It is assumed that, in these fermentation pathways, a reduced coenzyme such as NADH is produced during the pathway and the reduced coenzyme is reconverted into the oxidized form by the action of oxygen. Therefore, if it is possible to consume the produced reduced coenzyme by the cycle of FIG. 1 instead of consuming oxygen, it can be expected that the reduction power generated in fermentation could be efficiently used in the acetyl-CoA production cycles for fixing $CO_2$ and converting it into products.

Here, the reduced coenzyme refers to a coenzyme in the reduced state and involved in an oxidation-reduction reaction, and examples thereof include NADH, NADPH, $FADH_2$, $FMNH_2$, and a reduced quinone coenzyme. The reduced coenzyme is preferably NADH or NADPH, more preferably NADH. The oxidized coenzyme refers to the oxidized form of a reduced coenzyme, and examples thereof include $NAD^+$, $NADP^+$, FAD, FMN, and an oxidized quinone coenzyme. The oxidized coenzyme is preferably $NAD^+$ or $NADP^+$, more preferably $NAD^+$.

TABLE 1

| Compound Name | Fermentation equation |
|---|---|
| Isopropyl alcohol | $C_6H_{12}O_6 + H_2O + 3/2O_2 \rightarrow C_3H_8O + 3CO_2 + 3H_2O$ |
| Acetone | $C_6H_{12}O_6 + 2O_2 \rightarrow C_3H_6O + 3H_2O + 3CO_2$ |
| Glutamic acid | $C_6H_{12}O_6 + 3/2O_2 + NH_3 \rightarrow C_5H_9NO_4 + CO_2 + 3H_2O$ |
| Glutamine | $C_6H_{12}O_6 + 3/2O_2 + 2NH_3 \rightarrow C_5H_{10}N_2O_3 + CO_2 + 4H_2O$ |
| Arginine | $C_6H_{12}O_6 + 1/2O_2 + 4NH_3 \rightarrow C_6H_{14}N_2O_2 + 5H_2O$ |
| Ornithine | $C_6H_{12}O_6 + 1/2O_2 + NH_3 \rightarrow C_5H_{12}N_2O_2 + 2H_2O + CO_2$ |
| Citrulline | $C_6H_{12}O_6 + 1/2O_2 + 3NH_3 \rightarrow C_6H_{13}N_3O_3 + 4H_2O$ |
| Proline | $C_6H_{12}O_6 + 1/2O_2 + NH_3 \rightarrow C_5H_9NO_2 + 3H_2O + CO_2$ |
| Acetic acid | $C_6H_{12}O_6 + 2O_2 \rightarrow 2C_2H_4O_2 + 2CO_2 + 2H_2O$ |
| (poly-)3-hydroxybutyric acid | $C_6H_{12}O_6 + 3/2O_2 \rightarrow C_4H_8O_3 + 2CO_2 + 2H_2O$ |
| Itaconic acid | $C_6H_{12}O_6 + 1.5O_2 \rightarrow C_5H_6O_4 + CO_2 + 3H_2O$ |
| Critic acid | $C_6H_{12}O_6 + 3/2O_2 \rightarrow C_6H_8O_7 + 2H_2O$ |
| Butyric acid | $C_6H_{12}O_6 + 2O_2 \rightarrow C_3H_8O_2 + 2H_2O + 3CO_2$ |
| Leucine (Isoleucine) | $3/2C_6H_{12}O_6 + 3/2O_2 + NH_3 \rightarrow C_6H_{13}NO_2 + 4H_2O + 3CO_2$ |
| 4-Aminobutyric acid | $C_6H_{12}O_6 + 3/2O_2 + NH_3 \rightarrow C_4H_9NO_2 + 3H_2O + 2CO_2$ |
| 4-hydroxybutyric acid | $C_6H_{12}O_6 + 3/2O_2 \rightarrow C_4H_8O_3 + 2H_2O + 2CO_2$ |

As shown in Table 1, fermentation in which oxygen is present on the left side of the fermentation equation often requires a large amount oxygen. In such cases, extensive aeration and/or vigorous stirring may be required, which results in increases in equipment costs and electric power costs. Therefore, by introducing the cycle of FIG. 1, surplus reduction power can be consumed and excessive aeration/stirring can be moderated, and the cost of fermentative production can be expected to be reduced.

In order to supply the reduction power to the cycle according to the invention, the reduction power may be provided by adding a substance that can generate a reduction power, or imparting energies from outside. Specific examples thereof include using a substance that has a higher reduction degree (e.g., hydrogen, sulfite, alcohols, or paraffin) as a substrate; supplying reduction energies directly by electric culture; and supplying a reduction power by a photochemical reaction in an organism. Other than the fermentation shown in Table 1, as long as the reduction power can be supplied from outside, it is possible to drive the intended carbon dioxide fixation pathway even in fermentation in which a reduced coenzyme is not produced.

The aspects of the present invention are described below.

The "$CO_2$ fixation" in the invention refers to conversion of $CO_2$ generated in carbohydrate metabolism or $CO_2$ supplied from outside into an organic compound. The $CO_2$ may be $HCO_3^-$. Here, "$CO_2$ fixation" may also be referred to as "carbon dioxide fixation".

The term "process" in the present specification encompasses an independent process, as well as a process that attains an intended effect of the process although it cannot be clearly distinguished from another process. In the present specification, a numerical range indicated using "to" means a range including numerical values given before and after "to" as a minimum value and a maximum value, respectively.

In the invention, in the reference to the amount of each ingredient in the composition, when the composition includes plural substances corresponding to each ingredient, the amount of the each ingredient means the total amount of the plural substances unless otherwise specified.

As used herein, the term "inactivation" refers to a condition in which the activity of the enzyme (here, a factor that exhibit no enzymatic activity by themselves are also included in the scope of "enzyme", unless specifically indicated to be excluded) as measured by any existing measurement system is not higher than $1/10$ of the activity in the microorganism before inactivation, assuming that the activity in the microorganism before inactivation is 100.

The "reduction" of an enzymatic activity in the invention means a condition in which the activity of the enzyme is significantly reduced by a genetic recombination technique for a gene encoding the enzyme compared to those before such treatment.

The "enhancement" of an "activity" in the invention broadly means that the an enzymatic activity in microorganisms becomes higher after enhancement compared to the enzymatic activity before enhancement.

Methods for the enhancement are not particularly restricted as long as the activity of an enzyme possessed by microorganisms is enhanced. Examples thereof include enhancement by an enzyme gene introduced from outside the cell, enhancement by augmented expression of an enzyme gene inside the cell, and any combination thereof.

Specific examples of enhancement by an enzyme gene introduced from outside the cell include: introducing a gene encoding an active enzyme having a higher activity than the enzyme of host from outside the cell of the host microorganism by the genetic recombination technique, thereby adding the enzymatic activity of the introduced enzyme gene; substituting the introduced enzymatic activity for an intrinsic enzymatic activity that the host originally possesses; increasing the copy number of an enzyme gene of the host or an enzyme gene introduced from outside the cell to two or more; and any combination thereof.

Specific examples of enhancement by augmented expression of an enzyme gene in the microorganism include: introducing a base sequence that enhances the expression of an enzyme gene from the outside of the host microorganism into inside the microorganism; substitute another promoter for the promoter of an enzyme gene that the host microorganism possesses on its genome, thereby enhancing the expression of the enzyme gene; and any combination thereof.

The "imparting" of an "activity" in the invention broadly means the provision of the activity of an intended enzyme by introducing, from the outside, a gene encoding the enzyme into an organism that does not possess a gene encoding the intended enzyme. The method of imparting an activity is not particularly limited as long as the activity of an intended enzyme can be imparted to a microorganism, and examples thereof include transformation with a plasmid harboring an enzyme gene, introduction of an enzyme gene into the genome, and any combination thereof.

The promoter to be used for "enhancing" or "imparting" of an "activity" is not particularly limited as long as the promoter allows the gene expression, and examples thereof include constitutive promoters and inducible promoters.

Whether or not the microorganism has the intended enzyme gene can be determined, with reference to, for example, the gene information of respective strains registered in KEGG (Kyoto Encyclopedia of Genes and Genomes; http://www.genome.jp/kegg/) or NCBI (National Center for Biotechnology Information; http://www.ncbi.nlm.nih.gov/gene/). In the invention, only the gene information of respective strains registered in KEGG or NCBI is used.

In the invention, the enzymatic activity may be imparted by introducing, from the outside, a gene encoding the enzyme into the cell using the genetic recombination technique. In this case, the enzyme gene to be introduced may be either homologous or heterologous to the host cell.

Methods for preparation of a genomic DNA necessary to introduce a gene from outside the cell into the cell, cleavage and ligation of DNA, transformation, PCR (Polymerase Chain Reaction), the design and synthesis of oligonucleotides to be used as primers, etc. may be carried out by usual methods well known to those skilled in the art. These methods are described in Sambrook, J., et al., "Molecular Cloning A Laboratory Manual, Second Edition", Cold Spring Harbor Laboratory Press (1989), etc.

The expression "by the genetic recombination technique" in the invention encompasses any alternation to the base sequence caused by the insertion of another DNA into the base sequence of a native gene, substitution or deletion of a certain site of a gene, or any combinations thereof. For example, the alternation may result from a mutation.

In the invention, the microorganism in which the activity of a factor or enzyme is inactivated refers to a microorganism in which the native activity is impaired by a certain method applied from outside the cell to inside the cell. Such microorganism can be generated by, for example, disrupting a gene encoding the protein or enzyme (gene disruption).

Examples of the gene disruption in the invention include introduction of a mutation to the base sequence of a gene, insertion of another DNA into the base sequence, or deletion of a certain part of a gene, which are carried out with a view to preventing the function of the gene from being performed. As a result of the gene disruption, for example, the gene becomes unable to be transcribed into mRNA, and the structural gene ceases to be translated. Alternatively, due to incompleteness of transcribed mRNA, the amino acid sequence of the translated structural protein is mutated or deleted, and, therefore, the intrinsic functions of the structural protein becomes unable to be realized.

The gene disruption variant may be prepared using any method as long as a disruption variant in which the target enzyme or protein is not expressed can be obtained. Various methods for gene disruption have been reported (natural breeding, addition of a mutagen, UV irradiation, radiation irradiation, random mutagenesis, transposons, site-directed gene disruption). In view of disrupting only a specific gene, gene disruption by homologous recombination is preferable. Methods of gene disruption by homologous recombination are described in J. Bacteriol., 161, 1219-1221 (1985), J. Bacteriol., 177, 1511-1519 (1995), Proc. Natl. Acad. Sci. U.S.A, 97, 6640-6645 (2000), and the like, and those skilled in the art may easily perform homologous recombination using these methods or applying these methods.

The "host" in the invention means a microorganism in a state that the effect of the invention can be exerted as a result of the introduction of one or more genes from outside the microorganism.

More specifically, the "host" in the invention means a microorganism that can be made to possess the ability to produce acetyl-CoA from a carbon source material by using a certain means, regardless of whether or not the microorganism intrinsically has the innate ability to produce acetyl-CoA from a carbon source material.

The "host" in the invention may have a pathway for producing a useful metabolite. The "useful metabolite" in the invention is used as a generic name for major metabolites in the metabolic pathways of microorganisms, such as alcohols, amino acids, organic acids, and terpenes. The microorganism may be any microorganism as long as it can be made to possess the ability to produce a useful metabolite by using any means, regardless of whether or not the microorganism intrinsically has the innate ability to produce the useful metabolite.

The "useful metabolite derived from acetyl-CoA" in the invention refers to any of various metabolites produced via acetyl-CoA in metabolic pathways. Examples thereof include alcohols such as isopropyl alcohol, ethanol, or butanol; amino acids such as L-glutamic acid, L-glutamine, L-arginine, L-ornithine, L-citrulline, L-isoleucine, or L-proline; organic acids such as 3-hydroxybutyric acid, poly-3-hydroxybutyric acid, polyglutamic acid, 3-hydroxyisobutyric acid, 3-aminoisobutyric acid, 2-hydroxyisobutyric acid, methacrylic acid, citric acid, acetic acid, propionic acid, butyric acid, caproic acid, or mevalonic acid; and terpenes such as isoprene, squalene, steroid, or carotenoid. Other examples thereof include acetone. The microorganism may be any microorganism as long as it can be made to possess the ability to produce a useful metabolite derived from acetyl-CoA by using a certain means, regardless of whether or not the microorganism intrinsically has the innate ability to produce the useful metabolite derived from acetyl-CoA.

The "production of acetyl-CoA" in the invention refers to conversion of any substance into acetyl-CoA in a metabolic pathway. Since acetyl-CoA is a metabolic intermediate and quickly converted into various substances in metabolic pathways, the apparent amount of acetyl-CoA does not necessarily increase. However, the effect can be confirmed indirectly by detection of a $CO_2$-derived label in a substance derived from acetyl-CoA, by an increase in the yield of a substance derived from acetyl-CoA relative to sugar consumption, or the like. Since various factors (e.g., the quantity of a coenzyme, the quantity of a substrate, or a change in metabolism caused by a feedback inhibition) are involved in conversion, the production amount of acetyl-CoA is not always proportional to the amount of each of the substances derived from acetyl-CoA. However, in a case in which a pathway to produce a specific substance from acetyl-CoA is enhanced or a case in which such pathway is intrinsically enhanced (for example, in the case of an isopropyl alcohol-producing microorganism or a glutamate-producing microorganism described below), the efficiency of conversion from acetyl-CoA is hardly affected by external factors, and, therefore, the production efficiency of the specific substance can be regarded as an index of the production efficiency of acetyl-CoA.

The acetyl-CoA producing microorganism according to the invention includes an acetyl-CoA production cycle obtained by imparting at least one type of enzymatic activity selected from the group consisting of malate thiokinase, malyl-CoA lyase, glyoxylate carboligase, 2-hydroxy-3-oxopropionate reductase, and hydroxypyruvate reductase, to a microorganism that does not have any of:

(a) a carbon dioxide fixation cycle having an enzymatic reaction from malonyl-CoA to malonate semialdehyde or 3-hydroxypropionate;

(b) a carbon dioxide fixation cycle having an enzymatic reaction from acetyl-CoA and $CO_2$ to pyruvate;

(c) a carbon dioxide fixation cycle having an enzymatic reaction from crotonyl-CoA and $CO_2$ to ethylmalonyl-CoA or glutaconyl-CoA;

(d) a carbon dioxide fixation cycle having an enzymatic reaction from $CO_2$ to formate; or (e) at least one selected from the group consisting of malate thiokinase and malyl-CoA lyase, in which none of (a), (b), (c), or (d) is imparted to the microorganism, or the microorganism exhibits none of the functions of (a), (b), (c), and (d) even though at least one of (a), (b), (c), or (d) is imparted.

In view of the production efficiency of acetyl-CoA, the acetyl-CoA producing microorganism is preferably imparted with the enzymatic activities of malate thiokinase and malyl-CoA lyase, more preferably imparted with the enzymatic activities of malate thiokinase, malyl-CoA lyase, and glyoxylate carboligase, still more preferably imparted with the enzymatic activities of malate thiokinase, malyl-CoA lyase, glyoxylate carboligase, and 2-hydroxy-3-oxopropionate reductase, and/or hydroxypyruvate reductase.

The expression "does not (naturally) have" herein means that the host microorganism does not intrinsically possess an attribute in nature.

Here, the "carbon dioxide fixation cycle having an enzymatic reaction from malonyl-CoA to malonate semialdehyde or 3-hydroxypropionate" refers to the following cycles (1) to (7):

(1) the cycle shown in FIG. 1 of WO 2011/099006, in which acetyl-CoA is converted into malonyl-CoA, 3-hydroxypropionate, propionyl-CoA, malate, and malyl-CoA, which are again converted into acetyl-CoA;

(2) the cycle shown in FIG. 4A of WO 2011/099006, in which acetyl-CoA is converted into malonyl-CoA, malonate semialdehyde, β-alanine, malate, and malyl-CoA, which are again converted into acetyl-CoA;

(3) the cycle shown in FIG. 4B, 16, or 18 of WO 2011/099006, in which acetyl-CoA is converted into malonyl-CoA, hydroxypropionate, (R)-lactate or (S)-lactate, malate, and malyl-CoA, which are again converted into acetyl-CoA;

(4) the cycle shown in FIG. 8 of WO 2011/099006, in which acetyl-CoA is converted into malonyl-CoA, malonate semialdehyde or hydroxypropionate, pyruvate, malate, and malyl-CoA, which are again converted into acetyl-CoA;

(5) the cycle shown in FIG. 9A, 9B, or 9C of WO 2011/099006, in which acetyl-CoA is converted into malonyl-CoA, hydroxypropionate, 2-ketoglutarate, malate, and malyl-CoA, which are again converted into acetyl-CoA;

(6) the cycle shown in FIG. 9D or 9F of WO 2011/099006, in which acetyl-CoA is converted into malonyl-CoA, hydroxypropionate, methylmalonyl-CoA, malate, and malyl-CoA, which are again converted into acetyl-CoA; and (7) the cycle shown in FIG. 17 of WO 2011/099006, in which acetyl-CoA is converted into malonyl-CoA, malonate semialdehyde or hydroxypropionate, methylmalonyl-CoA, pyruvate, oxaloacetate, malate, and malyl-CoA, which are again converted into acetyl-CoA.

All of carbon dioxide fixation cycles (1) to (7) described above have an enzymatic reaction from malonyl-CoA to malonate semialdehyde or from malonyl-CoA to 3-hydroxypropionate. This kind of reaction is catalyzed by malonate semialdehyde dehydrogenase or malonyl-CoA reductase (WO 2011/099006). It is thought that the reduction reaction of carboxylic acid or a (thio)ester thereof, such as reduction of succinyl-CoA or reduction of malonyl-CoA, is generally difficult to carry out as enzymatic reactions and should be avoided them as fermentation pathways where possible (Atsumi et al., Nature, 451, (3), 86-89, 2008; Yim et al., Nat. Chem. Biol., 7, 445-452, 2011).

The "carbon dioxide fixation cycle having an enzymatic reaction from acetyl-CoA and $CO_2$ to pyruvate" in the present specification refers to the following cycles (8) to (10):

(8) the cycle shown in FIG. 1 of WO 2011/099006, in which acetyl-CoA is converted into pyruvate, phosphoenolpyruvate, oxaloacetate, malate, and malyl-CoA, which are again converted into acetyl-CoA;

(9) the cycle shown in FIG. 7C, 7D or 7E of WO 2011/099006, in which acetyl-CoA is converted into pyruvate, malate, and malyl-CoA, which are again converted into acetyl-CoA; and

(10) the cycle shown in FIG. 9M of WO 2011/099006, in which acetyl-CoA is converted into pyruvate, 2-ketoglutarate, malate, and malyl-CoA, which are again converted into acetyl-CoA.

All of carbon dioxide fixation cycles (8) to (10) have an enzyme reaction converting acetyl-CoA and $CO_2$ into pyruvate. This reaction is catalyzed by pyruvate synthase (WO 2011/099006). The synthetic reaction of pyruvate by pyruvate synthase requires a strong reduction power from ferredoxin and proceeds slowly, and proceeds only under strictly anaerobic conditions because the reaction is sensitive to oxygen.

The "carbon dioxide fixation cycle having an enzymatic reaction from crotonyl-CoA and $CO_2$ to ethylmalonyl-CoA or glutaconyl-CoA" in the present specification refers to the cycle shown in FIG. 9H or 9J of WO 2011/099006, in which acetyl-CoA is converted into crotonyl-CoA, ethylmalonyl-CoA or glutaconyl-CoA, oxaloacetate, malate, and malyl-CoA, which are again converted into acetyl-CoA.

The conversion of crotonyl-CoA and $CO_2$ to ethylmalonyl-CoA or glutaconyl-CoA is catalyzed by crotonyl-CoA carboxylase-reductase or methylcrotonyl-CoA carboxylase. Since the Km value of crotonyl-CoA carboxylase-reductase for carbonates is high (14 mM; PNAS 104(25) 10631-10636, 2007), sufficient activity at low substrate concentration cannot be expected. Crotonyl-CoA, which is a substrate of crotonyl-CoA carboxylase-reductase, is produced from 3-hydroxybutyryl-CoA by a dehydration reaction. In general, an enzyme involved in a dehydration reaction predominantly catalyzes the reverse reaction (i.e., hydration reaction) in an aqueous environment. Therefore, a sufficiently high production rate of crotonyl-CoA cannot be expected. Further, the reported specific activity of methylcrotonyl-CoA carboxylase is not so high (0.2 U/mg to 0.6 U/mg; Arch Biochem Biophys. 310(1) 64-75, 1994), and a sufficiently high production rate of crotonyl-CoA as a substrate cannot be expected for the same reason.

The "carbon dioxide fixation cycle having an enzymatic reaction from $CO_2$ to formate" in the present specification refers to the cycle shown in FIG. 5, 6, 13 or 14 of WO 2009/046929, that is, a cycle having a pathway in which the reaction proceeds from $CO_2$ via formate and serine, and oxaloacetate is converted into malate, malyl-CoA, and glycerate, which are again converted into oxaloacetate.

The enzymatic reaction from $CO_2$ to formate requires a strong reduction power, proceeds slowly, and proceeds only under strictly anaerobic conditions because the reaction is sensitive to oxygen.

In the present specification, "exhibits none of the functions" of the carbon dioxide fixation cycle "even though imparted" means that the carbon dioxide fixation cycle does not exhibit function even when the activity of the intended enzyme is imparted by introducing a gene encoding the enzyme having the activity is introduced to a microorganism that does not possess the gene encoding the intended enzyme. The fact that "the carbon dioxide fixation cycle does not function" can be confirmed indirectly, for example, by no detection of a label derived from $CO_2$ in a metabolite in the cycle or a substance derived from the metabolite in a test using a labeled $CO_2$, or by no increase in the yield of a substance derived from a metabolite in the cycle relative to sugar consumption.

The acetyl-CoA production cycle to be constructed in the acetyl-CoA producing microorganism includes malate thiokinase, malyl-CoA lyase, hydroxypyruvate reductase, glyoxylate carboligase, or 2-hydroxy-3-oxopropionate reductase. An example of the acetyl-CoA production cycle is shown in FIG. 1. The acetyl-CoA production cycle does not include an enzyme that consumes acetyl-CoA, such as acetyl-CoA carboxylase or pyruvate synthase.

In the acetyl-CoA production cycle of FIG. 1, carbon dioxide is first bound to phosphoenolpyruvate or pyruvate by the action of phosphoenolpyruvate carboxylase (ppc), pyruvate carboxylase (pyc), or phosphoenolpyruvate carboxykinase (pck), and converted into oxaloacetate. The oxaloacetate is converted into malate by the action of malate dehydrogenase (mdh). The malate is converted into malyl-CoA (malate CoA) by the action of malate thiokinase (mtk). The malyl-CoA (malate CoA) is converted into acetyl-CoA and glyoxylate by the action of malyl-CoA lyase (Mcl). The glyoxylate is converted into 2-hydroxy-3-oxopropionate by the action of glyoxylate carboligase (gcl). The 3-hydroxy-2-oxopropionate is converted into glycerate by the action of 2-hydroxy-3-oxopropionate reductase (glxR), or alternatively, converted into hydroxypyruvate by the action of hydroxypyruvate isomerase (hyi) and then into glycerate by the action of hydroxypyruvate reductase (ycdW). The glycerate is converted into 3-phosphoglycerate by the action of glycerate 3-kinase (glxK), or converted into 2-phosphoglycerate by the action of glycerate 2-kinase (garK). The 3-phosphoglycerate is converted into 2-phosphoglycerate by the action of phosphoglycerate mutase (gpm). The 2-phosphoglycerate is converted into phosphoenolpyruvate by the action of enolase (eno). In a case in which pyruvate carboxylase is included in the cycle, the phosphoenolpyruvate is converted into pyruvate by the action of pyruvate kinase (pyk).

The enzymatic activity to be imparted to the acetyl-CoA producing microorganism is not particularly limited as long as the acetyl-CoA production cycle can be functionally constructed thereby, and may be appropriately selected within the scope described in the present specification depending on the host microorganism.

In a microorganism in which a closed cycle cannot be formed with any of the pathways in FIG. 1 because of partial absence of the enzymes in the cycle of FIG. 1, the missing enzyme(s) need(s) to be supplied. For example, among *Escherichia* bacteria, *Escherichia coli* does not possess malate thiokinase and malyl-CoA lyase, so that at least these two enzymes need to be imparted.

*Pantoea* bacteria such as *Pantoea ananatis* does not possess malate thiokinase, malyl-CoA lyase, and glyoxylate carboligase, so that at least malate thiokinase, malyl-CoA lyase, and glyoxylate carboligase need to be imparted.

Among coryneform bacteria, for example, *Corynebacterium glutamicum* does not possess malate thiokinase, malyl-CoA lyase, glyoxylate carboligase, 2-hydroxy-3-oxopropionate reductase, and hydroxypyruvate reductase, so that at least malate thiokinase, malyl-CoA lyase, glyoxylate carboligase, and 2-hydroxy-3-oxopropionate reductase, and/or hydroxypyruvate reductase need to be imparted.

The enzyme that consumes acetyl-CoA as described above refers to an enzyme that uses acetyl-CoA as a substrate and catalyzes the conversion of acetyl-CoA into another substance. Examples thereof include acetyl-CoA carboxylase, which is classified as enzyme code number: 6.4.1.2 based on the report of the Enzyme Commission of International Union of Biochemistry (I.U.B.) and catalyzes a reaction of converting acetyl-CoA into malonyl-CoA; and pyruvate synthase, which is classified as enzyme code number: 1.2.7.1 and catalyzes a reaction of converting acetyl-CoA into pyruvate.

The cycle including an enzyme that consumes acetyl-CoA as described above refers to a closed cycle in which acetyl-CoA is converted, via the cycle, into acetyl-CoA again by the action of an enzyme that consumes acetyl-CoA. In a case in which a substance produced by the conversion reaction of an enzyme that consumes acetyl-CoA is further converted into another product without being converted into acetyl-CoA again (for example, in a case in which the substance is converted via an isopropyl alcohol-producing pathway into the end-product, isopropyl alcohol), the cycle is not closed, and, therefore, the cycle is excluded from the "cycle including an enzyme that consumes acetyl-CoA".

The closed cycle refers to a pathway starting from an arbitrary substance in the cycle, in which the substance is converted via the cycle into another substance and, ultimately, converted into the same substance as the initial substance.

Malate thiokinase is a generic name for enzymes which are classified as enzyme code number: 6.2.1.9 based on the report of the Enzyme Commission of International Union of Biochemistry (I.U.B.), and which catalyze a reaction of binding of malate to CoA and converting malate into malyl-CoA. In this reaction, one molecule of ATP is consumed, and one molecule of ADP and one molecule of phosphate are produced. Malate thiokinase has a large subunit of approximately 400 amino acids and a small subunit of 300 amino acids. In the gene, the large subunit is usually followed by the small subunit. Here, for convenience, the large subunit is referred to as mtkB, and the small subunit is referred to as mtkA. It is reported that the specific activity of the purified malate thiokinase is, for example, 2.5 U/mg (Anal Biochem. 227(2), 363-367, 1995).

Malate thiokinase is mainly found in an assimilation pathway for C1 carbon sources such as methane (J. Bacteriol. 176(23), 7398-7404, 1994) and a 3-hydroxypropionate pathway (Arch. Microbiol., 151, 252-256, 1989), and is characterized in that malyl-CoA lyase is present in its vicinity in the genome. Such enzyme may be suitably used. An example of evaluation of the activity of a purified malate thiokinase is known in malate thiokinase derived from *Methylobacterium extorquens*, but there are only a few examples of comparing an activity with an actual sequence. The only example of evaluating an activity together with a sequence is known in an enzyme derived from *Methylobacterium extorquens* AM1 (GenBank Accession Numbers AAA62654 and AAA62655) (J. Bacteriol. 176(23), 7398-7404, 1994). In this literature, the gene for malate thiokinase was cloned, and the cloned gene was introduced into the same *Methylobacterium extorquens* strain for evaluating the activity. However, when the present inventors actually synthesized the sequence and evaluated, no activity could be detected. In view of this, the sequence of AAA62655 was compared with the sequence of malate thiokinase derived from *Methylobacterium extorquens* newly acquired in the invention (SEQ ID NO: 70). As a result, it was found that AAA62655 has a large deletion (36 amino acids) at the carboxy terminus, and is abnormally short compared to sequences of other malate thiokinases (e.g., in FIG. 3). Therefore, it is thought that a wrong inactive-type sequence is described in the above literature.

This invention is, in actual fact, a first reported example in which malate thiokinase is actually cloned and expressed by a microorganism of another species, and the activity is correlated with the sequence.

Examples of malate thiokinase include those derived from *Methylobacterium* such as *Methylobacterium extorquens* (SEQ ID NOs:70 and 71), those derived from *Hyphomicrobium* such as *Hyphomicrobium methylovorum* or *Hyphomicrobium denitrificans*, those derived from *Rhizobium* such as *Rhizobium* sp. NGR234, those derived from *Granulibacter* such as *Granulibacter bethesdensis* (SEQ ID NOs:107 and 108), those derived from *Nitrosomonas* such as *Nitrosomonas europaea*, those derived from *Methylococcus* such as *Methylococcus capsulatus*, and those derived from Gammaproteobacteria.

In view of the production efficiency of useful substances produced via acetyl-CoA, specific examples of the preferable amino acid sequence include the amino acid sequences derived from *Hyphomicrobium* (SEQ ID NOs:73, 74, 110, and 111), amino acid sequences derived from *Rhizobium* (SEQ ID NOs:75 and 76), amino acid sequences derived from *Nitrosomonas* (SEQ ID NOs:113 and 114), amino acid sequences derived from *Methylococcus* (SEQ ID NOs:116 and 117), and amino acid sequences derived from Gammaproteobacteria (e.g., SEQ ID NOs:118 and 119).

The malate thiokinase derived from *Hyphomicrobium* (SEQ ID NOs:73, 74, 110, and 111), malate thiokinase derived from *Rhizobium* (SEQ ID NOs:75 and 76) and malate thiokinase derived from *Nitrosomonas* (SEQ ID NOs:113 and 114) share 65% to 80% sequence homology with one another. The malate thiokinase derived from *Methylococcus* (SEQ ID NOs:116 and 117) has 70% to 80% sequence homology with the malate thiokinase derived from Gammaproteobacteria (e.g., SEQ ID NOs:118 and 119).

Malate thiokinases having at least 70% amino acid sequence homology with each of the amino acid sequences of malate thiokinase derived from *Hyphomicrobium*, malate thiokinase derived from *Rhizobium*, malate thiokinase derived from *Nitrosomonas*, malate thiokinase derived from

*Methylococcus*, and malate thiokinase derived from Gammaproteobacteria disclosed here, and having the malate thiokinase activity may be suitably used for the production of acetyl-CoA or the production of a useful product derived from acetyl-CoA according to the invention.

Figure 2A:
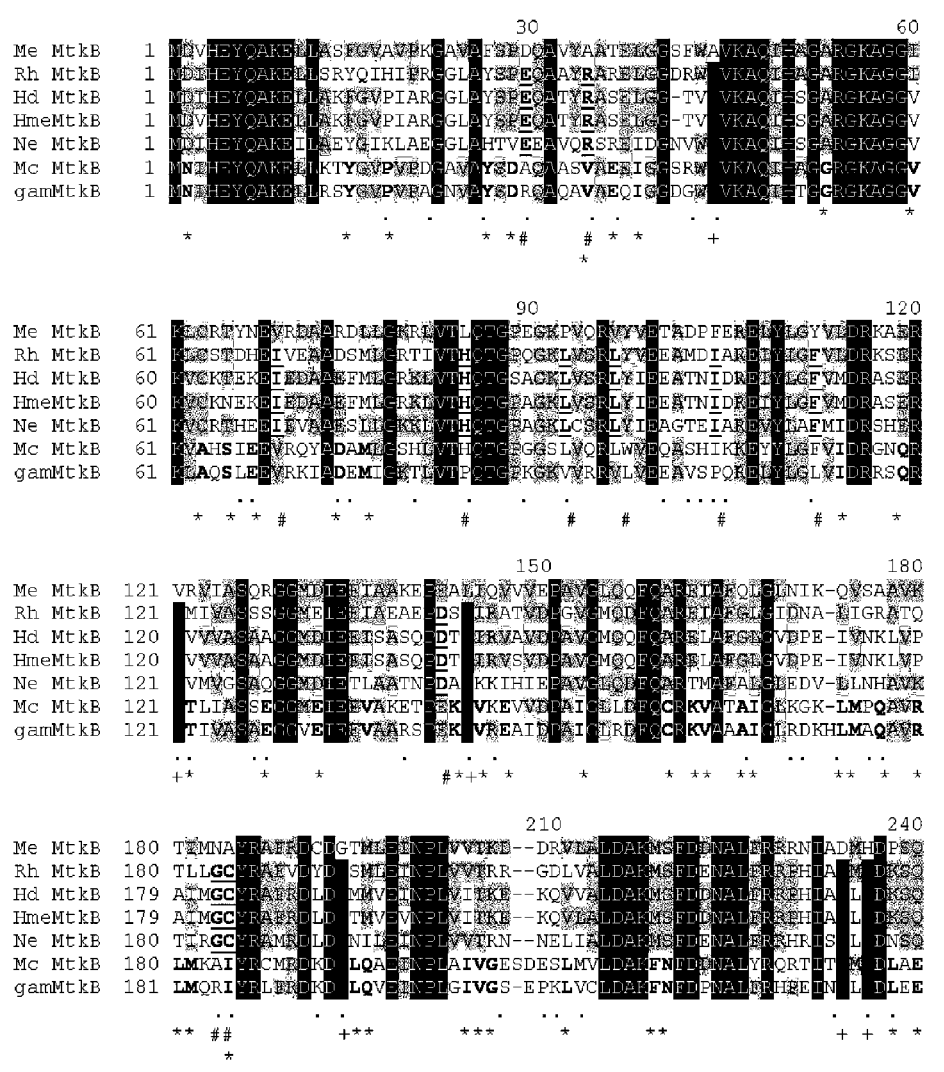

The alignment result of malate thiokinases shown in Examples is shown in FIG. 2A and FIG. 2B (MtkB: large subunit of mtk; FIG. 2A and FIG. 2B are hereinbelow collectively referred to as "FIG. 2") and FIG. 3A and FIG. 3B (MtkA: small subunit of mtk; FIG. 3A and FIG. 3B are hereinbelow collectively referred to as "FIG. 3"). As shown in FIG. 2 and FIG. 3, it was found that malate thiokinases share highly homologous common sequences over the entire length, in which identical or homologous amino acids are conserved.

Regarding amino acids, malate thiokinase derived from *Methylobacterium extorquens* (indicated by Me in FIG. 2 and FIG. 3), and malate thiokinases having high enzymatic activity derived from *Rhizobium* sp. (indicated by Rh in FIG. 2 and FIG. 3), *Hyphomicrobium methylovorum* (indicated by Hme in FIG. 2 and FIG. 3), *Hyphomicrobium denitrificans* (indicated by Hd in FIG. 2 and FIG. 3), *Nitrosomonas europaea* (indicated by Ne in FIG. 2 and FIG. 3), *Methylococcus capsulatus* (indicated by Mc in FIG. 2 and FIG. 3), and Gammaproteobacteria (indicated by gam in FIG. 2 and FIG. 3) were classified into 4 groups composed of the first to fourth group described below. In FIG. 2 and FIG. 3, these groups were indicated by 4 kinds of symbols, ".+#*", respectively.

The first group includes the sites at which *Rhizobium* sp., *Hyphomicrobium methylovorum*, *Hyphomicrobium denitrificans*, *Nitrosomonas europaea*, *Methylococcus capsulatus*, and Gammaproteobacteria, which have high enzymatic activities, have different sequences from that of *Methylobacterium extorquens*, and is indicated by the symbol "." in FIG. 2 and FIG. 3. The sequence position is described in accordance with the position in the amino acid sequence of *Methylobacterium extorquens*.

The first group in MtkBs (FIG. 2) include histidine, proline or lysine at position 18; arginine, glutamic acid, aspartic acid, or alanine at position 21; tyrosine or histidine at position 26; glutamic acid, alanine, or arginine at position 29; arginine or valine at position 34; arginine, serine or glutamic acid at position 36; arginine, threonine, valine, or glycine at position 42; valine at position 44; aspartic acid, glutamic acid, histidine, isoleucine, or leucine at position 66; histidine, lysine, or glutamic acid at position 67; aspartic acid or glutamic acid at position 74; serine, phenylalanine, alanine, or glutamic acid at position 75; threonine, lysine, or histidine at position 80; histidine or proline at position 84; glutamine, alanine, glycine, or lysine at position 89; leucine or valine at position 92; glutamic acid, alanine, or glutamine at position 100; methionine, threonine, serine, or valine at position 102; aspartic acid, asparagine, glutamic acid, histidine, or serine at position 103; isoleucine or proline at position 104; alanine, aspartic acid, lysine, or glutamine at position 105; phenylalanine or leucine at position 112; isoleucine at position 121; methionine, valine, or threonine at position 122; serine or alanine at position 127; serine, alanine, glutamine, or glutamic acid at position 128; alanine, serine, threonine, glutamic acid, or arginine at position 139; isoleucine at position 144; arginine or lysine at position 146; glycine or alanine at position 166; aspartic acid, glutamic acid, lysine, or arginine at position 170; asparagine, proline, aspartic acid, or glycine at position 171; isoleucine or leucine at position 173; glycine, asparagine, proline, or alanine at position 175; arginine, lysine, histidine, or glutamine at position 176; glycine, alanine or arginine at position 183; cysteine or isoleucine at position 184; tyrosine, leucine, or lysine at position 191; alanine at position 193; arginine, glutamic acid, asparagine, or serine at position 206; glycine, lysine, asparagine, glutamic acid, or proline at position 207; aspartic acid, glutamine, glutamic acid, serine, or lysine at position 208; glutamic acid at position 231; arginine at position 233; lysine, asparagine, or leucine at position 235; glutamic acid or isoleucine at position 238; threonine, isoleucine, or valine at position 243; tyrosine, alanine, or glutamic acid at position 244; glycine at position 249; aspartic acid at position 256; asparagine or aspartic acid at position 258; isoleucine, leucine, or phenylalanine at position 278; lysine or asparagine at position 300; threonine, arginine, alanine, glutamic acid, or glutamine at position 307; leucine, valine, cysteine, or tyrosine at position 336; glycine, aspartic acid, glutamic acid, glutamine, or arginine at position 340; arginine or leucine at position 358; alanine or aspartic acid at position 375; aspartic acid, lysine, glutamic acid, or alanine at position 379; and tryptophan, alanine, arginine, or valine at position 385.

The first group in MtkAs (FIG. 3) include phenylalanine at position 16; lysine, arginine, glutamic acid, or glutamine at position 19; isoleucine or histidine at position 20; arginine or aspartic acid at position 30; glutamine, threonine, or serine at position 46; alanine, serine, lysine, or arginine at position 47; leucine or proline at position 49; methionine, arginine, or leucine at position 51; aspartic acid or glutamic acid at position 67; alanine or valine at position 68; valine or isoleucine at position 71; proline at position 74; isoleucine at position 90; cysteine, alanine, or isoleucine at position 93; valine at position 94; aspartic acid, alanine, or serine at position 119; methionine, serine, or cysteine at position 121; isoleucine, threonine, or leucine at position 124; alanine or cysteine at position 137; arginine, valine, or asparagine at position 151; valine at position 155; alanine, arginine or lysine at position 171; lysine, arginine, or valine at position 193; methionine, valine, or isoleucine at position 195; glutamic acid, glutamine, arginine, or lysine at position 197; alanine or glycine at position 223; leucine or arginine at position 224; alanine at position 226; methionine at position 230; phenylalanine, alanine or glutamic acid at position 259; valine or methionine at position 267; glutamic acid or lysine at position 271; alanine, cysteine, or leucine at position 273; threonine or asparagine at position 280; serine or alanine at position 282; alanine, lysine, glutamine, glycine, or glutamic acid at position 294; and methionine, glutamine, arginine, leucine, or histidine at position 295.

Malate thiokinases having one or more of these amino acid sequences are more preferable in view of the enzymatic activity.

The second group includes common sequences characteristic to all of *Rhizobium* sp., *Hyphomicrobium methylovorum*, *Hyphomicrobium denitrificans*, *Nitrosomonas europaea*, *Methylococcus capsulatus*, and Gammaproteobacteria, and is indicated by the symbol "+" in FIG. 2 and FIG. 3. The positions of the characteristic sequences are described in accordance with the positions in the amino acid sequence of *Hyphomicrobium methylovorum*.

The second group in MtkBs (FIG. 2) includes valine at position 43; isoleucine at position 120; isoleucine at position 143; alanine at position 192; glutamic acid at position 230; arginine at position 232; glycine at position 248; and aspartic acid at position 255.

The second group in MtkAs (FIG. 3) includes phenylalanine at position 16; proline at position 74; isoleucine at position 90; valine at position 94; valine at position 155; alanine at position 226; and methionine at position 230.

The region having no homology, that is, the region other than these characteristic common sequences and the common sequences conserved among all sequences, may have a mutation. Malate thiokinases having any of these amino acid sequences are more preferable, in view of the enzymatic activity.

The third group includes common sequences characteristic to *Rhizobium* sp., *Hyphomicrobium methylovorum*, *Hyphomicrobium denitrificans*, and *Nitrosomonas europaea*, and is indicated by the symbol "#" in FIG. 2 and FIG. 3. The positions of the characteristic common sequences are described in accordance with the positions in the amino acid sequence of *Hyphomicrobium methylovorum*.

The third group in MtkBs (FIG. 2) includes glutamic acid at position 29; arginine at position 34; isoleucine at position 68; histidine at position 83; leucine at position 91; leucine at position 95; isoleucine at position 103; phenylalanine at position 111; aspartic acid at position 141; glycine at position 182; cysteine at position 183; valine at position 252; lysine at position 299; valine at position 345; glutamic acid at position 354; arginine at position 357; and alanine at position 374.

The third group in MtkAs (FIG. 3) includes isoleucine at position 20; alanine at position 68; cysteine at position 93; methionine at position 121; leucine at position 123; alanine at position 137; leucine at position 224; alanine at position 236; tyrosine at position 237; isoleucine at position 238; glutamic acid at position 261; valine at position 267; leucine at position 270; lysine at position 271; valine at position 275; isoleucine at position 277; threonine at position 280; and serine at position 282.

The region having no homology, that is, the region other than these characteristic common sequences and the common sequences conserved among all sequences, may have a mutation. Malate thiokinases having any of these amino acid sequences are more preferable in view of the enzymatic activity.

The fourth group includes common sequences characteristic to *Methylococcus capsulatus* and Gammaproteobacteria, and is indicated by the symbol "*" in FIG. 2 and FIG. 3. The positions of the characteristic common sequences are described in accordance with the positions in the amino acid sequence of *Methylococcus capsulatus*.

The fourth group in MtkBs (FIG. 2) includes asparagine at position 2; tyrosine at position 15; proline at position 18; tyrosine at position 26; aspartic acid at position 28; valine at position 34; glutamic acid at position 36; isoleucine at position 38; glycine at position 53; valine at position 60; alanine at position 63; serine at position 65; glutamic acid at position 67; aspartic acid at position 74; methionine at position 76; isoleucine at position 114; glutamine at position 119; threonine at position 122; glutamic acid at position 128; glutamic acid at position 132; valine at position 136; lysine at position 143; valine at position 145; glutamic acid at position 147; isoleucine at position 153; cysteine at position 160; lysine at position 162; valine at position 163; alanine at position 166; isoleucine at position 167; leucine at position 173; methionine at position 174; glutamine at position 176; arginine at position 179; leucine at position 180; methionine at position 181; isoleucine at position 184; leucine at position 194; glutamine at position 195; isoleucine at position 203; valine at position 204; glycine at position 205; leucine at position 211; phenylalanine at position 218; asparagine at position 219; leucine at position 237; glutamic acid at position 239; glutamic acid at position 240; valine at position 245; glutamic acid at position 246; glycine at position 249; asparagine at position 253; alanine at position 256; alanine at position 277; histidine at position 281; glutamic acid at position 298; lysine at position 299; asparagine at position 302; cysteine at position 304; isoleucine at position 306; isoleucine at position 330; leucine at position 334; glutamine at position 336; serine at position 340; leucine at position 341; phenylalanine at position 370; asparagine at position 375; aspartic acid at position 377; aspartic acid at position 378; alanine at position 381; and isoleucine at position 386.

The fourth group in MtkAs (FIG. 3) includes phenylalanine at position 4; valine at position 5; asparagine at position 6; histidine at position 8; serine at position 9; valine at position 11; isoleucine at position 12; histidine at position 20; alanine at position 28; arginine at position 30; threonine at position 33; leucine at position 56; aspartic acid at position 60; aspartic acid at position 72; valine at position 73; isoleucine at position 91; arginine at position 96; valine at position 97; alanine at position 102; valine at position 107; isoleucine at position 111; glutamine at position 114; arginine at position 117; glycine at position 119; aspartic acid at position 121; threonine at position 129; proline at position 130; threonine at position 134; glutamic acid at position 137; cysteine at position 138; lysine at position 139; valine at position 140; asparagine at position 163; glutamic acid at position 168; leucine at position 175; threonine at position 191; aspartic acid at position 192; valine at position 194; threonine at position 195; valine at position 196; alanine at position 199; valine at position 210; valine at position 221; alanine at position 222; alanine at position 224; arginine at position 225; alanine at position 227; glutamic acid at position 260; threonine at position 263; alanine at position 266; methionine at position 268; aspartic acid at position 269; alanine at position 270; glutamic acid at position 272; leucine at position 274; tyrosine at position 277; arginine at position 280; asparagine at position 281; alanine at position 283; isoleucine at position 285; leucine at position 290; arginine at position 291; alanine at position 292; and glutamic acid at position 295.

The region having no homology, that is, the region other than these characteristic common sequences and the common sequences conserved among all sequences, may have a mutation.

Malate thiokinases having any of these amino acid sequences are most preferable in view of the enzymatic activity.

As a gene of malate thiokinase (mtk), a DNA having the base sequence of a gene encoding malate thiokinase obtained from each of the above-mentioned enzyme origin organisms, or a synthetic DNA sequence that is synthesized based on a known base sequence of the gene, may be used.

Preferable examples thereof include a DNA having the base sequence of a gene derived from *Methylobacterium* such as *Methylobacterium extorquens* (SEQ ID NOs: 67 and 68), *Hyphomicrobium* such as *Hyphomicrobium methylovorum* or *Hyphomicrobium denitrificans*, *Rhizobium* such as *Rhizobium* sp. NGR234, *Granulibacter* such as *Granulibacter bethesdensis*, *Nitrosomonas* such as *Nitrosomonas europaea*, *Methylococcus* such as *Methylococcus capsulatus*, or Gammaproteobacteria.

In view of the production efficiency of acetyl-CoA, a DNA having the base sequence of a gene derived from *Hyphomicrobium* (SEQ ID NOs: 61, 62, 86, and 87), *Rhizobium* (e.g., SEQ ID NO: 63), *Granulibacter* (SEQ ID NOs: 81 and 82), *Nitrosomonas* (SEQ ID NOs: 91 and 92),

*Methylococcus* (SEQ ID NOs: 96 and 97), or Gammaproteobacteria (SEQ ID NOs: 102 and 103) is preferable.

In particular, the base sequence of a gene derived from *Hyphomicrobium* (SEQ ID NOs: 61, 62, 86, and 87), *Rhizobium* of which codon usage is optimized (e.g., SEQ ID NO: 63), *Nitrosomonas* (SEQ ID NOs: 91 and 92), *Methylococcus* (SEQ ID NOs: 96 and 97), or Gammaproteobacteria (SEQ ID NOs: 102 and 103) is preferable.

Malyl-CoA lyase is an enzyme which is classified as enzyme code number: 4.1.3.24 based on the report of the Enzyme Commission of International Union of Biochemistry (I.U.B.), and which catalyzes a reaction of producing glyoxylate and acetyl-CoA from malyl-CoA. Examples of malyl-CoA lyase include those derived from *Methylobacterium* such as *Methylobacterium extorquens*, *Hyphomicrobium* such as *Hyphomicrobium methylovorum* or *Hyphomicrobium denitrificans*, *Chloroflexus* such as *Chloroflexus aurantiacus*, *Nitrosomonas* such as *Nitrosomonas europaea*, or *Methylococcus* such as *Methylococcus capsulatus*.

In view of the production efficiency of acetyl-CoA, specific examples of the preferable amino acid sequences include an amino acid sequence derived from *Methylobacterium* (SEQ ID NO: 69), *Hyphomicrobium* (SEQ ID NO: 72 and 109), *Nitrosomonas* (SEQ ID NO: 112), or *Methylococcus* (SEQ ID NO: 115).

It is reported that the specific activity of purified malyl-CoA lyase in *Methylobacterium extorquens* is, for example, 28.1 U/mg (Biochem. J. 139, 399-405, 1974).

As a gene of malyl-CoA lyase (mcl), a DNA having the base sequence of a gene encoding malyl-CoA lyase obtained from any of the above-listed enzyme origin organisms, or a synthesized DNA sequence that is synthesized based on a known base sequence of the gene, may be used. Preferable examples thereof include a DNA having the base sequence of a gene derived from *Methylobacterium* such as *Methylobacterium extorquens*, *Hyphomicrobium* such as *Hyphomicrobium methylovorum* or *Hyphomicrobium denitrificans*, or *Chloroflexus* such as *Chloroflexus aurantiacus*. In view of the production efficiency of acetyl-CoA, more preferable examples thereof include a DNA having the base sequence of a gene derived from *Methylobacterium* and a gene having the base sequence of a gene derived from *Hyphomicrobium*.

Specific examples of the preferable base sequence of the gene derived from *Methylobacterium* include the base sequence of a gene derived from *Methylobacterium extorquens* (SEQ ID NO: 66). Specific examples of the preferable base sequence of a gene derived from *Hyphomicrobium* include the base sequence of a gene derived from *Hyphomicrobium methylovorum* (SEQ ID NO: 60) or *Hyphomicrobium denitrificans* (SEQ ID NO: 85). Specific examples of the preferable base sequence of a gene derived from *Nitrosomonas* include the base sequence of a gene derived from *Nitrosomonas europaea* (SEQ ID NO: 90). Specific examples of the preferable base sequence of the gene derived from *Methylococcus* include the base sequence of a gene derived from *Methylococcus capsulatus* (SEQ ID NO: 95).

Acetyl-CoA carboxylase is a general name for enzymes which are classified as enzyme code number: 6.4.1.2 based on the report of the Enzyme Commission of International Union of Biochemistry (I.U.B.), and which catalyze a reaction of converting acetyl-CoA and $CO_2$ into malonyl-CoA.

Malonate semialdehyde dehydrogenase is classified as enzyme code number: 1.2.1.18 based on the report of the Enzyme Commission of International Union of Biochemistry (I.U.B.), and which catalyze a reaction of converting malonyl-CoA into malonate semialdehyde.

Malonyl-CoA reductase is a generic name for enzymes that catalyze a reaction of converting malonyl-CoA into malonate semialdehyde or 3-hydroxypropionate.

Crotonyl-CoA carboxylase-reductase is a generic name for enzymes which are classified as enzyme code number: 1.3.1.85 based on the report of the Enzyme Commission of International Union of Biochemistry (I.U.B.), and which catalyze the conversion of crotonyl-CoA into ethylmalonyl-CoA.

Methylcrotonyl-CoA carboxylase is a generic name for enzymes which are classified as enzyme code number: 6.4.1.4 based on the report of the Enzyme Commission of International Union of Biochemistry (I.U.B.), and which catalyze a reaction of converting crotonyl-CoA into glutaconyl-CoA.

Pyruvate synthase is a generic name for enzymes which are classified as enzyme code number: 1.2.7.1 based on the report of the enzyme commission of International Union of Biochemistry (I.U.B.), and which catalyze a reaction of converting acetyl-CoA into pyruvate.

It is preferable that, in the acetyl-CoA producing microorganism, the activity of at least one enzyme selected from the group consisting of lactate dehydrogenase, malate synthase, and fumarate hydratase is inactivated or reduced. As a result, acetyl-CoA can be produced more efficiently.

Among the above-mentioned lactate dehydrogenase, malate synthase, and fumarate hydratase, each of which is the target enzyme whose activity may be inactivated or reduced, malate synthase catalyzes a reaction of converting acetyl-CoA and glyoxylate into malate. This reaction is the reverse reaction of a reaction catalyzed by malate thiokinase and malyl-CoA lyase. Therefore, it is preferable to inactivate or reduce the activity of malate synthase, since the reaction of converting acetyl-CoA and glyoxylate into malate again can be blocked or reduced and the yield of acetyl-CoA is improved.

Among lactate dehydrogenase, malate synthase, and fumarate hydratase, the activity of which may be inactivated or reduced, it is preferable to inactivate fumarate hydratase in view of the production efficiency of acetyl-CoA. Inactivating fumarate hydratase prevents a conversion of malate into other substances including fumarate and a reduction in the amount of malate, and hence improves the yield of acetyl-CoA.

Lactate dehydrogenase (ldhA) is a generic name for enzymes which are classified as enzyme code number: 1.1.1.28 based on the report of the Enzyme Commission of International Union of Biochemistry (I.U.B.), and which catalyze a reaction of converting pyruvate into lactate, or converting lactate into pyruvate.

Isocitrate lyase (aceA) is classified under enzyme code number: 4.1.3.1 based on the Report of the Commission on Enzymes, International Union of Biochemistry (I.U.B.), and is a generic name for enzymes that catalyze a reaction of converting isocitrate into succinate and glyoxylate.

Malate synthase (aceB and glcB) is a generic name for enzymes which are classified as enzyme code number: 2.3.3.9 based on the report of the Enzyme Commission of International Union of Biochemistry (I.U.B.), and which catalyze a reaction of converting acetyl-CoA and glyoxylate into malate and CoA. Depending on the microorganisms, plural isomers of malate synthase is encoded in the genome. Most *Escherichia coli* strains possess two genes named aceB and glcB, respectively, and both are described in the present specification. Each of *Pantoea ananatis* and *Corynebacterium glutamicum* possesses a single type of gene corresponding to aceB or glcB, and the gene is collectively described as aceB in the present specification, for convenience.

Fumarate hydratase (fum) is a generic name for enzymes which are classified as enzyme code number: 4.2.1.2 based on the report of the Enzyme Commission of International Union of Biochemistry (I.U.B.), and which catalyze a reaction of converting malate into fumarate. Depending on the microorganisms, plural isomers of fumarate hydratase in encoded in the genome. For example, *Escherichia coli* has three types of fumarate hydratase, fumA, fumB, and fumC. *Pantoea ananatis* has fumA and fumC, and *Corynebacterium glutamicum* has fumC.

Phosphoenolpyruvate carboxylase is a generic name for enzymes which are classified as enzyme code number: 4.1.1.31 based on the report of the enzyme commission of International Union of Biochemistry (I.U.B.), and which catalyze a reaction of converting phosphoenolpyruvate and carbon dioxide into oxaloacetate and phosphate. Examples of phosphoenolpyruvate carboxylase include those derived from *Corynebacterium* bacteria such as *Corynebacterium glutamicum*, *Escherichia* bacteria such as *Escherichia coli*, *Pantoea* bacteria such as *Pantoea ananatis*, *Hyphomicrobium* bacteria such as *Hyphomicrobium methylovorum*, *Starkeya* bacteria such as *Starkeya novella*, *Rhodopseudomonas* bacteria such as *Rhodopseudomonas* sp., or *Streptomyces* bacteria such as *Streptomyces coelicolor*.

As a gene of phosphoenolpyruvate carboxylase (ppc), a DNA having the base sequence of a gene encoding phosphoenolpyruvate carboxylase obtained from any of the above-listed enzyme origin organisms, or a synthesized DNA sequence that is synthesized based on a known base sequence of the gene, may be used. Preferable examples thereof include a DNA having the base sequence of a gene derived from *Corynebacterium* bacteria such as *Corynebacterium glutamicum*, *Escherichia* bacteria such as *Escherichia coli*, *Pantoea* bacteria such as *Pantoea ananatis*, *Hyphomicrobium* bacteria such as *Hyphomicrobium methylovorum*, *Starkeya* bacteria such as *Starkeya novella*, *Rhodopseudomonas* bacteria such as *Rhodopseudomonas* sp., or *Streptomyces* bacteria such as *Streptomyces coelicolor*.

Phosphoenolpyruvate carboxykinase is a generic name for enzymes which are classified as enzyme code number: 4.1.1.32, enzyme code number: 4.1.1.38, or enzyme code number: 4.1.1.49 based on the report of the Enzyme Commission of International Union of Biochemistry (I.U.B.), and which catalyze a reaction of converting phosphoenolpyruvate and carbon dioxide into oxaloacetate. Among the enzyme code numbers, the enzymes classified as enzyme code number: 4.1.1.32 are involved in a reaction of converting GDP into GTP; the enzymes classified as enzyme code number: 4.1.1.38 are involved in a reaction of converting phosphate into pyrophosphate; and the enzymes classified as enzyme code number: 4.1.1.49 are involved in a reaction of converting ADP into ATP. Examples of phosphoenolpyruvate carboxykinase include those derived from *Actinobacillus* bacteria such as *Actinobacillus succinogenes*, *Mycobacterium* bacteria such as *Mycobacterium smegmatis*, or *Trypanosoma* bacteria such as *Trypanosoma brucei*.

As a gene of phosphoenolpyruvate carboxykinase (pck), a DNA having the base sequence of a gene encoding phosphoenolpyruvate carboxykinase obtained from any of the above-listed enzyme origin organisms, or a synthesized DNA sequence that is synthesized based on a known base sequence of the gene, may be used. Preferable examples thereof include a DNA having the base sequence of a gene derived from *Actinobacillus* such as *Actinobacillus succinogenes*, *Mycobacterium* bacteria such as *Mycobacterium smegmatis*, or *Trypanosoma* bacteria such as *Trypanosoma brucei*.

Pyruvate carboxylase is a generic name for enzymes which are classified as enzyme code number: 6.4.1.1 based on the report of the Enzyme Commission of International Union of Biochemistry (I.U.B.), and which catalyze a reaction of converting pyruvate and carbon dioxide into oxaloacetate. The reaction consumes ATP, and produces ADP and phosphate. Examples of pyruvate carboxylase include those derived from *Corynebacterium* bacteria such as *Corynebacterium glutamicum* or *Mycobacterium* bacteria such as *Mycobacterium smegmatis*.

As a gene of pyruvate carboxylase (pyc), a DNA having the base sequence of a gene encoding phosphoenolpyruvate carboxylase obtained from any of the above-listed enzyme origin organisms, or a synthesized DNA sequence that is synthesized based on a known base sequence of the gene, may be used. Preferable examples thereof include a DNA having the base sequence of a gene derived from *Corynebacterium* bacteria such as *Corynebacterium glutamicum*, or *Mycobacterium* bacteria such as *Mycobacterium smegmatis*.

Malate dehydrogenase is a generic name for enzymes which are classified as enzyme code number: 1.1.1.37 based on the report of the Enzyme Commission of International Union of Biochemistry (I.U.B.), and which use NADH as a coenzyme and catalyze a reaction of producing malate from oxaloacetate. Examples of malate dehydrogenase include those derived from *Corynebacterium* bacteria such as *Corynebacterium glutamicum*, or *Escherichia* bacteria such as *Escherichia coli*.

As a gene of malate dehydrogenase (mdh), a DNA having the base sequence of a gene encoding malate dehydrogenase obtained from any of the above-listed enzyme origin organisms, or a synthesized DNA sequence that is synthesized based on a known base sequence of the gene, may be used. Preferable examples thereof include a DNA having the base sequence of a gene derived from *Corynebacterium* bacteria such as *Corynebacterium glutamicum*, *Escherichia* bacteria such as *Escherichia coli*, or *Pantoea* bacteria such as *Pantoea ananatis*.

Glyoxylate carboligase is a generic name for enzymes which are classified as enzyme code number: 4.1.1.47 based on the report of the Enzyme Commission of International Union of Biochemistry (I.U.B.), and which catalyze a reaction of converting two molecules of glyoxylate into one molecule of 2-hydroxy-3-oxopropionate. This reaction is accompanied by decarboxylation of one molecule of carbon dioxide. Examples of glyoxylate carboligase include those derived from *Escherichia* bacteria such as *Escherichia coli*, or *Rhodococcus* bacteria such as *Rhodococcus jostii*.

As a gene of glyoxylate carboligase (gcl), a DNA having the base sequence of a gene encoding glyoxylate carboligase obtained from any of the above-listed enzyme origin organisms, or a synthesized DNA sequence that is synthesized based on a known base sequence of the gene, may be used. Preferable examples thereof include a DNA having the base sequence of a gene derived from *Rhodococcus* bacteria such as *Rhodococcus jostii*, or *Escherichia* bacteria such as *Escherichia coli*.

2-hydroxy-3-oxopropionate reductase is a generic name for enzymes which are classified as enzyme code number: 1.1.1.60 based on the report of the Enzyme Commission of International Union of Biochemistry (I.U.B.), and which use NADH as a coenzyme and catalyze a reaction of converting 2-hydroxy-3-oxopropionate into glycerate. Examples of 2-hydroxy-3-oxopropionate reductase include those derived from *Escherichia* bacteria such as *Escherichia coli*.

As a gene of 2-hydroxy-3-oxopropionate reductase (glxR), a DNA having the base sequence of a gene encoding 2-hydroxy-3-oxopropionate reductase obtained from any of the above-listed enzyme origin organisms, or a synthesized DNA sequence that is synthesized based on a known base sequence of the gene, may be used. Preferable examples thereof include a DNA having the base sequence of a gene derived from *Escherichia* bacteria such as *Escherichia coli*.

Hydroxypyruvate isomerase is a generic name for enzymes which are classified as enzyme code number: 5.3.1.22 based on the report of the Enzyme Commission of International Union of Biochemistry (I.U.B.), and which catalyze a reaction of isomerizing 2-hydroxy-3-oxopropionate to hydroxypyruvate. Examples of hydroxypyruvate isomerase include those derived from *Corynebacterium* bacteria such as *Corynebacterium glutamicum*, *Escherichia* bacteria such as *Escherichia coli*, or *Pantoea* bacteria such as *Pantoea ananatis*.

As a gene of hydroxypyruvate isomerase (hyi), a DNA having the base sequence of a gene encoding hydroxypyruvate isomerase obtained from any of the above-listed enzyme origin organisms, or a synthesized DNA sequence that is synthesized based on a known base sequence of the gene, may be used. Preferable examples thereof include a DNA having the base sequence of a gene derived from *Corynebacterium* bacteria such as *Corynebacterium glutamicum*, *Escherichia* bacteria such as *Escherichia coli*, or *Pantoea* bacteria such as *Pantoea ananatis*.

Hydroxypyruvate reductase is a generic name for enzymes which are classified as enzyme code number: 1.1.1.81 based on the report of the Enzyme Commission of International Union of Biochemistry (I.U.B.), and which use NADH or NADPH as a coenzyme and catalyze a reaction of converting hydroxypyruvate into glycerate.

Examples of hydroxypyruvate reductase include those derived from *Escherichia* bacteria such as *Escherichia coli*, or *Pantoea* bacteria such as *Pantoea ananatis*.

As a gene for hydroxypyruvate reductase (ycdW), a DNA having the base sequence of a gene encoding hydroxypyruvate reductase obtained from any of the above-listed enzyme origin organisms, or a synthetic DNA sequence synthesized based on a known base sequence of the gene, may be used. Preferable examples thereof include a DNA having the base sequence of a gene derived from *Escherichia* bacteria such as *Escherichia coli*, or *Pantoea* bacteria such as *Pantoea ananatis*.

Glycerate 3-kinase is a generic name for enzymes which are classified as enzyme code number: 2.7.1.31 based on the report of the Enzyme Commission of International Union of Biochemistry (I.U.B.), and which catalyze a reaction of converting glycerate into 3-phosphoglycerate. In this reaction, one molecule of ATP is consumed, and one molecule of ADP and one molecule of phosphate are produced. Examples of the glycerate 3-kinase include those derived from *Corynebacterium* bacteria such as *Corynebacterium glutamicum*, or *Escherichia* bacteria such as *Escherichia coli*.

As a gene of glycerate 3-kinase (glxK) according to the invention, a DNA having the base sequence of a gene encoding glycerate 3-kinase obtained from any of the above-listed enzyme origin organisms, or a synthesized DNA sequence that is synthesized based on a known base sequence of the gene, may be used. Preferable examples thereof include a DNA having the base sequence of a gene derived from *Corynebacterium* bacteria such as *Corynebacterium glutamicum*, *Escherichia* bacteria such as *Escherichia coli*, or *Pantoea* bacteria such as *Pantoea ananatis*.

Glycerate 2-kinase is a generic name for enzymes which are classified as enzyme code number: 2.7.1.165 based on the report of the Enzyme Commission of International Union of Biochemistry (I.U.B.), and which catalyze a reaction of converting glycerate into 2-phosphoglycerate. In this reaction, one molecule of ATP is consumed, and one molecule of ADP and one molecule of phosphate are produced. Examples of glycerate 2-kinase include those derived from *Corynebacterium* bacteria such as *Corynebacterium glutamicum*, or *Escherichia* bacteria such as *Escherichia coli*.

As a gene of glycerate 2-kinase (garK) according to the invention, a DNA having the base sequence of a gene encoding glycerate 2-kinase obtained from any of the above-listed enzyme origin organisms, or a synthesized DNA sequence that is synthesized based on a known base sequence of the gene, may be used. Preferable examples thereof include a DNA having the base sequence of a gene derived from *Corynebacterium* bacteria such as *Corynebacterium glutamicum*, *Escherichia* bacteria such as *Escherichia coli*, or *Pantoea* bacteria such as *Pantoea ananatis*.

Phosphoglycerate mutase is a generic name for enzymes which are classified as enzyme code number: 5.4.2.1 based on the report of the Enzyme Commission of International Union of Biochemistry (I.U.B.), and which catalyze a reaction of converting 3-phosphoglycerate into 2-phosphoglycerate. Examples of the phosphoglycerate mutase include those derived from *Corynebacterium* bacteria such as *Corynebacterium glutamicum*, *Escherichia* bacteria such as *Escherichia coli*, or *Pantoea* bacteria such as *Pantoea ananatis*.

As a gene of phosphoglycerate mutase (gpm), a DNA having the base sequence of a gene encoding phosphoglycerate mutase obtained from any of the above-listed enzyme origin organisms, or a synthesized DNA sequence that is synthesized based on a known base sequence of the gene, may be used. Preferable examples thereof include a DNA having the base sequence of a gene derived from *Corynebacterium* bacteria such as *Corynebacterium glutamicum*, *Escherichia* bacteria such as *Escherichia coli*, or *Pantoea* bacteria such as *Pantoea ananatis*.

Enolase is a generic name for enzymes which are classified as enzyme code number: 4.2.1.11 based on the report of the Enzyme Commission of International Union of Biochemistry (I.U.B.), and which catalyze a reaction of converting 2-phosphoglycerate into phosphoenolpyruvate. Examples of enolase include those derived from *Corynebacterium* bacteria such as *Corynebacterium glutamicum*, *Escherichia* bacteria such as *Escherichia coli*, or *Pantoea* bacteria such as *Pantoea ananatis*.

As a gene of enolase (eno), a DNA having the base sequence of a gene encoding enolase obtained from any of the above-listed enzyme origin organisms, or a synthesized DNA sequence that is synthesized based on a known base sequence of the gene, may be used. Preferable examples thereof include a DNA having the base sequence of a gene derived from *Corynebacterium* bacteria such as *Corynebacterium glutamicum*, *Escherichia* bacteria such as *Escherichia coli*, or *Pantoea* bacteria such as *Pantoea ananatis*.

Pyruvate kinase is a generic name for enzymes which are classified as enzyme code number: 2.7.1.40 based on the report of the Enzyme Commission of International Union of Biochemistry (I.U.B.), and which catalyze a reaction of converting phosphoenolpyruvate and ADP into pyruvate and ATP. Examples of pyruvate kinase include those derived from *Corynebacterium* bacteria such as *Corynebacterium* glutamicum, Escherichia bacteria such as Escherichia coli, or Pantoea bacteria such as Pantoea ananatis.

As a gene of pyruvate kinase (pyk), a DNA having the base sequence of a gene encoding pyruvate kinase obtained from any of the above-listed enzyme origin organisms, or a synthesized DNA sequence that is synthesized based on a known base sequence of the gene, may be used. Preferable examples thereof include a DNA having the base sequence of a gene derived from Corynebacterium bacteria such as Corynebacterium glutamicum, Escherichia bacteria such as Escherichia coli, or Pantoea bacteria such as Pantoea ananatis.

Acetyl-CoA producing microorganism may be a microorganism having, in addition to the pathway for converting acetyl-CoA into a useful metabolite, a pathway that produces another metabolite by using acetyl-CoA as a raw material, or may be a microorganism whose enzymatic activity involved in a pathway that produces another metabolite is enhanced. As a result, the useful metabolites derived from acetyl-CoA can be produced from a carbon source material and carbon dioxide, and the productivity of the useful metabolite derived from acetyl-CoA can be increased.

The microorganism used in the invention is not particularly limited as long as the microorganism does not have any of:

(a) a carbon dioxide fixation cycle having an enzymatic reaction from malonyl-CoA to malonate semialdehyde or 3-hydroxypropionate;

(b) a carbon dioxide fixation cycle having an enzymatic reaction from acetyl-CoA and $CO_2$ to pyruvate;

(c) a carbon dioxide fixation cycle having an enzymatic reaction from crotonyl-CoA and $CO_2$ to ethylmalonyl-CoA or glutaconyl-CoA;

(d) a carbon dioxide fixation cycle having an enzymatic reaction from $CO_2$ to formate; or (e) at least one selected from the group consisting of malate thiokinase and malyl-CoA lyase.

Examples of the microorganism include microorganisms belonging to Enterobacteriaceae and microorganisms belonging to coryneform bacteria. Specific examples of the microorganism include microorganisms belonging to Enterobacteriaceae such as Escherichia bacteria and Pantoea bacteria; microorganisms belonging to coryneform bacteria such as Corynebacterium bacteria and Brevibacterium bacteria; filamentous fungi; and actinomycetes.

Specific examples of the microorganisms belonging to Enterobacteriaceae include bacteria belonging to Enterobacter, Erwinia, Escherichia, Klebsiella, Pantoea, Providencia, Salmonella, Serratia, Shigella, Morganella, or Erwinia. Among these, microorganisms belonging to Escherichia and microorganisms belonging to Pantoea are preferable from the viewpoint of efficient production of useful metabolites.

Examples of the Corynebacterium bacteria include Corynebacterium glutamicum.

The Escherichia bacteria are not particularly limited, and examples thereof include Escherichia coli. Specific examples of the Escherichia coli include Escherichia coli W3110 (ATCC 27325) and Escherichia coli MG1655 (ATCC 47076), derived from the prototype wild-type strain K12, and Escherichia coli B (ATCC 11303) derived from the prototype wild-type strain B.

Both Escherichia bacteria and Pantoea bacteria belong to Enterobacteriaceae, and are closely related to each other (J. Gen. Appl. Microbiol. 43(6) 355-361 (1997); International Journal of Systematic Bacteriology, p 1061-1067, 1997).

In recent years, some bacteria belonging to Enterobacter have been reclassified into Pantoea agglomerans, Pantoea dispersa, or the like (International Journal of Systematic Bacteriology, July 39(3) 337-345, 1989).

Further, some bacteria belonging to Erwinia have been reclassified into Pantoea ananas or Pantoea stewartii (International Journal of Systematic Bacteriology, 43(1), 162-173, 1993).

Examples of the Enterobacter bacteria include Enterobacter agglomerans and Enterobacter aerogenes. More specifically, strains exemplified in European Patent Laid-open No. 952221 may be used. Examples of representative strains of Enterobacter include the Enterobacter agglomerans ATCC 12287.

Examples of representative strains of the Pantoea bacteria include Pantoea ananatis, Pantoea stewartii, Pantoea agglomerans, and Pantoea citrea. Specific examples of the strains include the following.

Pantoea ananatis AJ13355 (FERM BP-6614) (European Patent Laid-open No. 0952221)

Pantoea ananatis AJ13356 (FERM BP-6615) (European Patent Laid-open No. 0952221)

Although these strains are described as Enterobacter agglomerans in European Patent Laid-open No. 0952221, the strains were reclassified into Pantoea ananatis as described above based on base sequence analysis of 16S rRNA and the like.

The "coryneform bacteria" in the invention refers to the microorganisms belonging to Corynebacterium, Brevibacterium, or Microbacterium, as defined in Bergey's Manual of Determinative Bacteriology, 8, 599 (1974).

Examples of the coryneform bacteria further include microorganisms which had been classified into Brevibacterium but was reclassified later into Corynebacterium (Int. J. Syst. Bacteriol., 41, 255, 1991), and related bacteria such as microorganisms belonging to Brevibacterium. Examples of the coryneform bacteria are listed below.

That is, examples thereof include Corynebacterium acetoacidophilum, Corynebacterium acetoglutamicum, Corynebacterium alkanolyticum, Corynebacterium callunae, Corynebacterium glutamicum, Corynebacterium lilium, Corynebacterium melassecola, Corynebacterium thermoaminogenes, Corynebacterium herculis, Brevibacterium divaricatum, Brevibacterium flavum, Brevibacterium immariophilum, Brevibacterium lactofermentum, Brevibacterium roseum, Brevibacterium saccharolyticum, Brevibacterium thiogenitalis, Corynebacterium ammoniagenes, Brevibacterium album, Brevibacterium cerinum, and Microbacterium ammoniaphilum.

Specific examples thereof include the following strains.

Corynebacterium acetoacidophilum ATCC 13870, Corynebacterium acetoglutamicum ATCC 15806, Corynebacterium alkanolyticum ATCC 21511, Corynebacterium callunae ATCC 15991, Corynebacterium glutamicum ATCC 13020, ATCC 13032 and ATCC 13060, Corynebacterium lilium ATCC 15990, Corynebacterium melassecola ATCC 17965, Corynebacterium thermoaminogenes AJ 12340 (FERM BP-1539), Corynebacterium herculis ATCC13868, Brevibacterium divaricatum ATCC 14020, Brevibacterium flavum ATCC 13826, ATCC 14067, and AJ 12418 (FERM BP-2205), Brevibacterium immariophilum ATCC 14068, Brevibacterium lactofermentum (Corynebacterium glutamicum) ATCC 13869, Brevibacterium roseum ATCC 13825, Brevibacterium saccharolyticum ATCC 14066, Brevibacterium thiogenitalis ATCC 19240, Corynebacterium ammoniagenes ATCC 6871 and ATCC 6872,

*Brevibacterium album* ATCC 15111, *Brevibacterium cerinum* ATCC 15112, and *Microbacterium ammoniaphilum* ATCC 15354.

In a case in which the *Escherichia* bacterium is used as the microorganism, preferable examples of the acetyl-CoA producing microorganism in the invention include an acetyl-CoA producing *Escherichia* bacterium in which the thiolase activity, the CoA transferase activity, and the acetoacetate decarboxylase activity are imparted or enhanced.

In a case in which the *Escherichia* bacterium is used as the microorganism, preferable examples of the acetyl-CoA producing microorganism in the invention further include an acetyl-CoA producing *Escherichia* bacterium in which the thiolase activity, the CoA transferase activity, the acetoacetate decarboxylase activity, and the isopropyl alcohol dehydrogenase activity are imparted or enhanced.

Thiolase is a generic name for enzymes which are classified as enzyme code number: 2.3.1.9 based on the report of the Enzyme Commission of International Union of Biochemistry (I.U.B.), and which catalyze a reaction of producing acetoacetyl-CoA from acetyl-CoA.

Examples of thiolase include those derived from *Clostridium* bacteria such as *Clostridium acetobutylicum* or *Clostridium beijerinckii*, *Escherichia* bacteria such as *Escherichia coli*, *Halobacterium* sp., *Zoogloea* bacteria such as *Zoogloea ramigera*, *Rhizobium* sp., *Bradyrhizobium* bacteria such as *Bradyrhizobium japonicum*, *Candida* such as *Candida tropicalis*, *Caulobacter* bacteria such as *Caulobacter crescentus*, *Streptomyces* bacteria such as *Streptomyces collinus*, or *Enterococcus* bacteria such as *Enterococcus faecalis*.

As a gene of thiolase, a DNA having the base sequence of a gene encoding thiolase obtained from any of the above-listed enzyme origin organisms, or a synthesized DNA sequence that is synthesized based on a known base sequence of the gene, may be used. Preferable examples thereof include a DNA having the base sequence of a gene derived from *Clostridium* bacteria such as *Clostridium acetobutylicum* or *Clostridium beijerinckii*; *Escherichia* bacteria such as *Escherichia coli*, *Halobacterium* sp., *Zoogloea* bacteria such as *Zoogloea ramigera*, *Rhizobium* sp., *Bradyrhizobium* bacteria such as *Bradyrhizobium japonicum*, *Candida* such as *Candida tropicalis*, *Caulobacter* bacteria such as *Caulobacter crescentus*, *Streptomyces* bacteria such as *Streptomyces collinus*, or *Enterococcus* bacteria such as *Enterococcus faecalis*. More preferable examples thereof include a DNA having the base sequence of a gene derived from a prokaryote such as *Clostridium* bacteria or *Escherichia* bacteria, and a DNA having the base sequence of a gene derived from *Clostridium acetobutylicum* or *Escherichia coli* is particularly preferable.

Acetoacetate decarboxylase is a generic name for enzymes which are classified as enzyme code number: 4.1.1.4 based on the report of the Enzyme Commission of International Union of Biochemistry (I.U.B.), and which catalyze a reaction of producing acetone from acetoacetate.

Examples of acetoacetate decarboxylase include those derived from *Clostridium* bacteria such as *Clostridium acetobutylicum* or *Clostridium beijerinckii*; or *Bacillus* bacteria such as *Bacillus polymyxa*.

As a gene of acetoacetate decarboxylase, a DNA having the base sequence of a gene encoding acetoacetate decarboxylase obtained from any of the above-listed enzyme origin organisms, or a synthesized DNA sequence that is synthesized based on a known base sequence of the gene, may be used. Preferable examples thereof include a DNA having the base sequence of a gene derived from *Clostridium* bacteria or *Bacillus* bacteria. Specific examples thereof include a DNA having the base sequence of a gene derived from *Clostridium acetobutylicum* or *Bacillus polymyxa*. The DNA is more preferably a DNA having the base sequence of a gene derived from *Clostridium acetobutylicum*.

As a gene of acetoacetate decarboxylase, a DNA having the base sequence of a gene encoding acetoacetate decarboxylase obtained from any of the above-listed enzyme origin organisms may be used. Preferable examples thereof include a DNA having the base sequence of a gene derived from *Clostridium* bacteria or *Bacillus* bacteria. Specific examples thereof include a DNA having the base sequence of a gene derived from *Clostridium acetobutylicum* or *Bacillus polymyxa*. The DNA is more preferably a DNA having the base sequence of a gene derived from *Clostridium acetobutylicum*.

Isopropyl alcohol dehydrogenase is a generic name for enzymes which are classified as enzyme code number: 1.1.1.80 based on the report of the Enzyme Commission of International Union of Biochemistry (I.U.B.), and which catalyze a reaction of producing isopropyl alcohol from acetone.

Examples of isopropyl alcohol dehydrogenase include those derived from *Clostridium* bacteria such as *Clostridium beijerinckii*.

As a gene of isopropyl alcohol dehydrogenase, a DNA having the base sequence of a gene encoding isopropyl alcohol dehydrogenase obtained from any of the above-listed enzyme origin organisms may be used. Preferable examples thereof include a DNA having the base sequence of a gene derived from *Clostridium* bacteria, such as *Clostridium beijerinckii*.

CoA transferase is a generic name for enzymes which are classified as enzyme code number: 2.8.3.8 based on the report of the Enzyme Commission of International Union of Biochemistry (I.U.B.), and which catalyze a reaction of producing acetoacetate from acetoacetyl-CoA.

Examples of CoA transferase include those derived from *Clostridium* bacteria such as *Clostridium acetobutylicum* or *Clostridium beijerinckii*; *Roseburia* bacteria such as *Roseburia intestinalis*; *Faecalibacterium* bacteria such as *Faecalibacterium prausnitzii*; *Coprococcus* bacteria; trypanosomes such as *Trypanosoma brucei*; or *Escherichia* bacteria such as *Escherichia coli*.

As a gene of CoA transferase, a DNA having the base sequence of a gene encoding CoA transferase obtained from any of the above-listed enzyme origin organisms, or a synthesized DNA sequence synthesized based on a known base sequence of the gene, may be used. Preferable examples thereof include a DNA having the base sequence of a gene derived from *Clostridium* bacteria such as *Clostridium acetobutylicum*, *Roseburia* bacteria such as *Roseburia intestinalis*, *Faecalibacterium* bacteria such as *Faecalibacterium prausnitzii*, *Coprococcus* bacteria, trypanosomes such as *Trypanosoma brucei*, or *Escherichia* bacteria such as *Escherichia coli*. More preferred examples thereof include a DNA having the base sequence of a gene derived from *Clostridium* bacteria or *Escherichia* bacteria, and a DNA having the base sequence of a gene derived from *Clostridium acetobutylicum* or *Escherichia coli* is still more preferable.

From the viewpoint of the enzymatic activity, it is preferable that each of the four kinds of enzymes is an enzyme derived from at least one selected from the group consisting of *Clostridium* bacteria, *Bacillus* bacteria, and *Escherichia* bacteria. In particular, a case in which that acetoacetate decarboxylase and isopropyl alcohol dehydrogenase are derived from *Clostridium* bacteria, and in which the CoA transferase activity and the thiolase activity are derived from *Escherichia* bacteria, is more preferable.

In particular, from the viewpoint of the enzymatic activity, it is preferable that each of the four kinds of enzymes are derived from any of *Clostridium acetobutylicum*, *Clostridium beijerinckii*, or *Escherichia coli*. It is more preferable that acetoacetate decarboxylase is an enzyme derived from *Clostridium acetobutylicum*, and that each of CoA transferase and thiolase is derived from *Clostridium acetobutylicum* or *Escherichia coli*, and that isopropyl alcohol dehydrogenase is derived from *Clostridium beijerinckii*. Regarding the four kinds of enzymes, it is preferable that the acetoacetate decarboxylase activity is derived from *Clostridium acetobutylicum*, and that the isopropyl alcohol dehydrogenase activity is derived from *Clostridium beijerinckii*, and that the CoA transferase activity and the thiolase activity are derived from *Escherichia coli*, from the viewpoint of the enzymatic activity.

The CoA transferase genes (atoD and atoA) and the thiolase gene (atoB) derived from *Escherichia coli* form an operon on the genome of *Escherichia coli* in the order of atoD, atoA, and atoB (Journal of Bacteriology Vol. 169 pp 42-52 Lauren Sallus Jenkins et al.). Therefore, the expression of the CoA transferase genes and the thiolase gene can be simultaneously controlled by modifying the atoD promoter.

In view of above, when the CoA transferase activity and the thiolase activity are those obtained from the genomic genes of the host *Escherichia coli*, it is preferable to enhance the expression of both enzyme genes by, for example, replacing the promoter responsible for the expression of both enzyme genes by another promoter, from the viewpoint of obtaining sufficient isopropyl alcohol production ability. Examples of the promoter to be used in order to enhance the expression of the CoA transferase activity and the thiolase activity include the above-described *Escherichia coli*-derived GAPDH promoter.

Examples of the acetyl-CoA producing microorganism that produces another metabolite by using acetyl-CoA as a raw material include a microorganism obtained by imparting or enhancing, or inactivating or reducing, any of the above-described enzymatic activities, using *Escherichia coli* having an isopropyl alcohol production system (hereinafter referred to as "isopropyl alcohol-producing *Escherichia coli*") as a host.

The isopropyl alcohol-producing *Escherichia coli* may be any *Escherichia coli* as long as the respective genes for imparting the isopropyl alcohol-producing ability can be introduced or modified.

The *Escherichia coli* is more preferably *Escherichia coli* to which the isopropyl alcohol production ability has been imparted in advance. By using such *Escherichia coli*, isopropyl alcohol can be efficiently produced.

An example of the isopropyl alcohol-producing *Escherichia coli* is an isopropyl alcohol-producing *Escherichia coli* to which the acetoacetate decarboxylase activity, the isopropyl alcohol dehydrogenase activity, the CoA transferase activity, and the thiolase activity have been imparted so as to be capable of producing isopropyl alcohol from a plant-derived raw material, and which is described in, for example, WO 2009/008377. Other examples of the isopropyl alcohol-producing *Escherichia coli* include microorganisms described in WO 2009/094485, WO 2009/094485, WO 2009/046929, or WO 2009/046929.

The isopropyl alcohol-producing *Escherichia coli* is *Escherichia coli* having an isopropyl alcohol production system, and has an isopropyl alcohol production ability that is introduced by a genetic recombination technique. The isopropyl alcohol production system may be any system that causes *Escherichia coli* of interest to produce isopropyl alcohol.

In the isopropyl alcohol-producing *Escherichia coli* according to the invention, preferably, four enzymatic activities—an acetoacetate decarboxylase activity, an isopropyl alcohol dehydrogenase activity, a CoA transferase activity, and the above-mentioned thiolase activity—are imparted from outside the cell.

In the invention, examples of the isopropyl alcohol-producing *Escherichia coli* having an isopropyl alcohol production system include a pIPA/B variant and a pIaaa/B variant described in WO 2009/008377. Examples of the isopropyl alcohol-producing *Escherichia coli* further include a variant in which, from among the enzymes involved in the production of isopropyl alcohol, the CoA transferase activity and the thiolase activity are enhanced by enhancing the expression of the respective genes on the genome of the *Escherichia coli*, and in which the isopropyl alcohol dehydrogenase activity and the acetoacetate decarboxylase activity are enhanced by enhancing the expression of the respective genes using a plasmid or plasmids (sometimes referred to as "pIa/B::atoDAB variant").

In the invention, the isopropyl alcohol-producing *Escherichia coli* may be an isopropyl alcohol-producing *Escherichia coli* including an isopropyl alcohol production system, in which the activity of transcriptional repressor GntR is inactivated, and the isopropyl alcohol-producing *Escherichia coli* includes a group of auxiliary enzymes having an enzymatic activity pattern with which isopropyl alcohol production ability achieved by the inactivation of the GntR activity is maintained or enhanced. Consequently, production of isopropyl alcohol can be further increased.

The term "a group of auxiliary enzymes" in the invention refers to one enzyme or two or more enzymes, which affect(s) isopropyl alcohol production ability. Further, the activity of enzymes included in the group of auxiliary enzymes is inactivated, activated, or enhanced. The phrase the "enzymatic activity pattern of the group of auxiliary enzymes" as used herein refers to the enzymatic activity pattern of the enzymes that is capable of maintaining or increasing the improved isopropyl alcohol production amount achieved by inactivation of the GntR activity alone, and encompasses one enzyme of a combination of two or more of enzymes.

Examples of preferable enzymatic activity patterns of the group of auxiliary enzymes include the following patterns:

(1) maintenance of the wild-type activities of glucose-6-phosphate isomerase (Pgi), glucose-6-phosphate-1-dehydrogenase (Zwf), and the phosphogluconate dehydrogenase (Gnd);

(2) inactivation of glucose-6-phosphate isomerase (Pgi) activity, and enhancement of glucose-6-phosphate-1-dehydrogenase (Zwf) activity; and (3) inactivation of glucose-6-phosphate isomerase (Pgi) activity, enhancement of glucose-6-phosphate-1-dehydrogenase (Zwf) activity, and inactivation of phosphogluconate dehydrogenase (Gnd) activity.

Among these, the enzymatic activity pattern of the group of auxiliary enzymes described in item (3) above is more preferable from the viewpoint of the isopropyl alcohol production ability.

The group of auxiliary enzymes and the enzymatic activity pattern thereof are not limited to those described above. Any group of auxiliary enzymes and enzymatic activity pattern thereof which include inactivation of the GntR activity, and with which the amount of isopropyl alcohol production in an isopropyl alcohol-producing *Escherichia coli* can be increased, are within the scope of the invention. The group of auxiliary enzymes is not necessarily constituted by plural enzymes, and may be constituted by one enzyme.

GntR refers to a transcription factor that negatively regulates an operon involved in gluconate metabolism via the Entner-Doudoroff pathway. GntR is a generic name for GntR transcriptional repressors that suppress the functions of two group of genes (GntI and GntII), which are responsible for the uptake and metabolism of gluconic acid.

Glucose-6-phosphate isomerase (Pgi) is a generic name for enzymes which are classified as enzyme code number: 5.3.1.9 based on the report of the Enzyme Commission of International Union of Biochemistry (I.U.B.), and which catalyze a reaction of producing D-fructose-6-phosphate from D-glucose-6-phosphate.

Glucose-6-phosphate-1-dehydrogenase (Zwf) is classified as enzyme code number: 1.1.1.49 based on the report of the Enzyme Commission of International Union of Biochemistry (I.U.B.) and which catalyzes a reaction to producing D-glucono-1,5-lactone-6-phosphate from D-glucose-6-phosphate.

Examples of glucose-6-phosphate-1-dehydrogenase include those derived from *Deinococcus* bacteria such as *Deinococcus radiophilus*; *Aspergillus* fungi such as *Aspergillus niger* or *Aspergillus aculeatus*; *Acetobacter* bacteria such as *Acetobacter hansenii*; *Thermotoga* bacteria such as *Thermotoga maritima*; *Cryptococcus* fungi such as *Cryptococcus neoformans*; *Dictyostelium* fungi such as *Dictyostelium discoideum*; *Pseudomonas* such as *Pseudomonas fluorescens* or *Pseudomonas aeruginosa*; *Saccharomyces* such as *Saccharomyces cerevisiae*; *Bacillus* bacteria such as *Bacillus megaterium*; or *Escherichia* bacteria such as *Escherichia coli*.

As a gene of glucose-6-phosphate-1-dehydrogenase (Zwf), a DNA having the base sequence of gene encoding thiolase obtained from any of the above-listed enzyme origin organisms, or a synthesized DNA sequence that is synthesized based on a known base sequence of the gene, may be used. Preferable examples thereof include a DNA having the base sequence of a gene derived from *Deinococcus* bacteria such as *Deinococcus radiophilus*, *Aspergillus* fungi such as *Aspergillus niger* or *Aspergillus aculeatus*; *Acetobacter* bacteria such as *Acetobacter hansenii*, *Thermotoga* bacteria such as *Thermotoga maritima*, *Cryptococcus* fungi such as *Cryptococcus neoformans*, *Dictyostelium* fungi such as *Dictyostelium discoideum*, *Pseudomonas* such as *Pseudomonas fluorescens* or *Pseudomonas aeruginosa*, *Saccharomyces* such as *Saccharomyces cerevisiae*, *Bacillus* bacteria such as *Bacillus megaterium*, or *Escherichia* bacteria such as *Escherichia coli*. More preferable examples thereof include a DNA having the base sequence of a gene derived from a prokaryote such as *Deinococcus* bacteria, *Aspergillus* fungi, *Acetobacter* bacteria, *Thermotoga* bacteria, *Pseudomonas*, *Bacillus* bacteria, or *Escherichia* bacteria. The DNA is more preferably a DNA having the base sequence of a gene derived from *Escherichia coli*.

Phosphogluconate dehydrogenase (Gnd) is a generic name for enzymes which are classified as enzyme code number: 1.1.1.44 based on the report of the Enzyme Commission of International Union of Biochemistry (I.U.B.), and which catalyze a reaction of producing D-ribulose-5-phosphate and $CO_2$ from 6-phospho-D-gluconate.

Each of the activities of these enzymes in the invention may be an activity introduced from outside the cell into the cell, or an activity obtained by of overexpression of the enzyme gene that the host bacterium possesses on its genome via enhancement of the promoter activity for the enzyme gene or replacement of the promoter with another promoter.

The *Escherichia coli* having enhanced enzymatic activity in the invention refers to *Escherichia coli* in which the enzymatic activity is enhanced by a certain method. This kind of *Escherichia coli* can be constructed by introducing a gene encoding the enzyme or protein from outside the cell into the cell using a plasmid by the gene recombination technology as described above; or by overexpressing the enzyme gene that the host bacterium possesses on its genome via enhancement of the promoter activity for the enzyme gene or replacing the promoter with another promoter; or the combination of these methods.

The gene promoter applicable to the isopropyl alcohol-producing *Escherichia coli* may be any promoter capable of controlling the expression of any of the genes described above. The gene promoter is preferably a potent promoter that constitutively works in the microorganism, and which is not susceptible to repression of expression even in the presence of glucose. Specific examples thereof include the promoter of glyceraldehyde-3-phosphate dehydrogenase (hereinafter sometimes referred to as "GAPDH") or the promoter of serine hydroxymethyltransferase.

The promoter in the isopropyl alcohol-producing *Escherichia coli* means a regain to which an RNA polymerase having a sigma factor binds to start transcription. For example, a GAPDH promoter derived from *Escherichia coli* is described at Base Nos. 397 to 440 in the base sequence information of GenBank accession number X02662.

In the isopropyl alcohol-producing *Escherichia coli*, lactate dehydrogenase (LdhA) may be disrupted. The disruption of lactate dehydrogenase suppresses lactate production even under culture conditions in which oxygen supply is restricted, as a result of which isopropyl alcohol can be efficiently produced. The "conditions in which oxygen supply is restricted" generally means conditions: 0.02 vvm to 2.0 vvm (vvm: aeration volume [mL]/liquid volume [mL]/time [min]) at an agitation speed of 200 to 600 rpm, when air alone is used as the gas.

The lactate dehydrogenase (LdhA) refers to an enzyme that produces D-lactate and NAD from pyruvate and NADH.

The acetyl-CoA producing microorganism for producing acetone may be one having only thiolase activity, CoA transferase activity, and acetoacetate decarboxylase activity among activity in the isopropyl alcohol production system. That is, when producing acetone by using the acetyl-CoA producing microorganism, the microorganism having no isopropyl alcohol dehydrogenase activity may be used.

Other examples of the pathway for producing another metabolite by using acetyl-CoA as a raw material include a pathway that produces glutamate from acetyl-CoA. Preferable example of the microorganism having a pathway that produces another metabolite or the microorganism whose enzymatic activity involved in a pathway that produces another metabolite is enhanced include a microorganism obtained by imparting or enhancing or inactivating the enzymatic activities in the above-described pathway that produces glutamate from acetyl-CoA or reducing an enzymatic activity that inhibits the production of glutamate from acetyl-CoA by using a microorganism having a pathway that efficiently produces a glutamate (hereinafter sometimes referred to as "glutamate-producing microorganism") or by using a glutamate-producing microorganism as a host.

Examples of the glutamate-producing microorganism include the above-mentioned microorganisms having an ability to produce L-amino acids.

Specific examples of the glutamate-producing microorganism include, but not limited thereto, Enterobacteriaceae bacteria such as *Escherichia* bacteria or *Pantoea* bacteria, and coryneform bacteria such as *Corynebacterium glutamicum*.

The glutamate-producing microorganism may be any microorganism that allows the introduction or modification of a gene for imparting the glutamate production ability. It is more preferable that the glutamate-producing microorganism is a *Pantoea* bacterium or coryneform bacterium to which glutamate production ability has been imparted in advance. By using this kind of microorganism, glutamate can be more efficiently produced.

Examples of a method of imparting the glutamate production ability to a microorganism include modifying the microorganism such that expression of a gene encoding an enzyme involved in L-glutamate biosynthesis is increased and/or is overexpressed. Examples of the enzyme involved in L-glutamate biosynthetic include glutamate dehydrogenase, glutamine synthetase, glutamate synthase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phosphate dehydrogenase, triose-phosphate isomerase, fructose-bisphosphate aldolase, phosphofructokinase, and glucose-phosphate isomerase. Among these enzymes, it is preferable that one or more of citrate synthase, phosphoenolpyruvate carboxylase, and glutamate dehydrogenase has an increased activity, and it is more preferable that 4 all of the three enzymes have enhanced activities.

Examples of the glutamate-producing microorganism include a glutamate-producing microorganism described in Japanese Patent Application Laid-Open (JP-A) No. 2005-278643.

The L-glutamate-producing microorganism to be used may be a microorganism having an ability to accumulate L-glutamate in an amount exceeding the saturation concentration of L-glutamate in a liquid medium when the microorganism was cultured under acidic conditions (hereinafter referred to as "L-glutamate-accumulating ability under acidic conditions"). For example, a variant having increased resistance to L-glutamate in a low-pH environment may be obtained by a method described in European Patent Laid-open No. 1078989, whereby the ability to accumulate L-glutamate in an amount exceeding the saturation concentration is imparted.

Specific examples of the microorganism having an intrinsic L-glutamate-accumulating ability under acidic conditions include *Pantoea ananatis* AJ13356 (FERM BP-6615) and AJ13601 (FERM BP-7207) (see European Patent Laid-open No. 0952221). *Pantoea ananatis* AJ13356 was deposited with National Institute of Bioscience and Human-Technology, Agency of Industrial Science and Technology, Ministry of International Trade and Industry (present name: International Patent Organism Depositary, National Institute of Technology and Evaluation (IPOD, NITE); address: Tsukuba Central 6, 1-1-1 Higashi, Tsukuba, Ibaraki 305-8566, Japan) under accession No. FERM P-16645 on Feb. 19, 1998, and then transferred to an international depository authority under the Budapest Treaty under accession No. FERM BP-6615 on Jan. 11, 1999. This strain was identified as *Enterobacter agglomerans* and deposited as *Enterobacter agglomerans* AJ13355 when first isolated, but, according to recent base sequence analysis of 16S rRNA and the like, the strain was reclassified as *Pantoea ananatis* (see Examples below). Similarly, AJ13356 and AJ13601 mentioned below induced from AJ13355 were deposited to the above depositary as *Enterobacter agglomerans*, but these strains are described as *Pantoea ananatis* in the present specification. AJ13601 was deposited with National Institute of Bioscience and Human-Technology, Agency of Industrial Science and Technology, Ministry of International Trade and Industry (present name: International Patent Organism Depositary, National Institute of Technology and Evaluation (IPOD, NITE) under accession No. FERM P-17156 on Aug. 18, 1999, and then transferred to an international depository authority under the Budapest Treaty under accession No. FERM BP-7207 on Jul. 6, 2000.

Other examples of the method of imparting or enhancing the L-glutamate production ability include a method of imparting resistance to an organic acid analogue or a respiratory inhibitor, and a method of imparting sensitivity to a cell wall synthesis inhibitor. Specific examples of the method include imparting resistance to monofluoroacetic acid (JP-A No. S50-113209), imparting resistance to adenine or resistance to thymine (JP-A No. S57-065198), weakening urease (JP-A No. S52-038088), imparting resistance to malonic acid (JP-A No. S52-038088), imparting resistance to benzopyrone or naphthoquinones (JP-A No. S56-001889), imparting resistance to HOQNO (JP-A No. S56-140895 A), imparting resistance to α-ketomalonic acid (JP-A No. S57-002689 A), imparting resistance to guanidine (JP-A No. S56-035981), and method of imparting resistance to penicillin (JP-A No. H04-088994).

Specific examples of the resistant microorganisms include the following strains.

*Brevibacterium flavum* AJ3949 (FERM BP-2632; see JP-A No. S50-113209)

*Corynebacterium glutamicum* AJ11628 (FERM P-5736; see JP-A No. S57-065198)

*Brevibacterium flavum* AJ11355 (FERM P-5007; see JP-A No. S56-001889)

*Corynebacterium glutamicum* AJ11368 (FERM P-5020; see JP-A S56-001889)

*Brevibacterium flavum* AJ11217 (FERM P-4318; see JP-A No. S57-002689)

*Corynebacterium glutamicum* AJ11218 (FERM P-4319; see JP-A No. S57-002689)

*Brevibacterium flavum* AJ11564 (FERM P-5472; see JP-A No. S56-140895)

*Brevibacterium flavum* AJ11439 (FERM P-5136; see JP-A No. S56-035981)

*Corynebacterium glutamicum* H7684 (FERM BP-3004; see JP-A No. H04-088994)

*Brevibacterium lactofermentum* AJ11426 (FERM P-5123; see JP-A No. S56-048890)

*Corynebacterium glutamicum* AJ11440 (FERM P-5137; see JP-A No. S56-048890)

*Brevibacterium lactofermentum* AJ11796 (FERM P-6402; see JP-A No. S58-158192)

Preferable examples of the microorganism having an L-glutamine production ability include a microorganism in which the glutamate dehydrogenase activity is enhanced, a microorganism in which the glutamine synthetase (glnA) activity is enhanced, and a microorganism in which the glutaminase gene is disrupted (European Patent Laid-open Nos. 1229121 and 1424398). Enhancement of the glutamine synthetase activity can also be achieved by disrupting glutamine adenylyl transferase (glnF) or disrupting the PII regulation protein (glnB). Other preferable examples of the L-glutamine-producing microorganism include a variant belonging to genus *Escherichia*, and the variant harbors a mutant glutamine synthetase in which the tyrosine residue at position 397 in glutamine synthetase is replaced by another amino acid residue (U.S. Patent Published Application No. 2003-0148474).

Another method of imparting or enhancing the L-glutamine production ability include imparting resistance to 6-diazo-5-oxo-norleucine (JP-A No. H03-232497), imparting resistance to a purine analogue and resistance to methionine sulfoxide (JP-A No. S61-202694), and imparting resistance to α-ketomaleic acid (JP-A No. S56-151495). Specific examples of coryneform bacteria having the L-glutamine production ability include the following microorganisms.

*Brevibacterium flavum* AJ11573 (FERM P-5492; JP-A No. S56-161495)

*Brevibacterium flavum* AJ11576 (FERM BP-10381; JP-A No. S56-161495)

*Brevibacterium flavum* AJ12212 (FERM P-8123; JP-A No. S61-202694)

Preferable examples of microorganisms that produce proline, leucine, isoleucine, valine, arginine, citrulline, ornithine, and/or polyglutamic acid include a microorganism described in JP-A No. 2010-41920. Microorganisms that produce acetic acid, (poly)3-hydroxybutyric acid, itaconic acid, citric acid, and/or butyric acid are described in Fermentation Handbook (Kyoritsu Shuppan Co., Ltd.).

Examples of microorganisms that produce 4-aminobutyric acid include a microorganism in which glutamate decarboxylase is introduced to a glutamate-producing microorganism, such as those described in JP-A No. 2011-167097.

Examples of microorganisms that produce 4-hydroxybutyric acid include a microorganism in which glutamate decarboxylase, transaminase, and/or aldehyde dehydrogenase are introduced to a glutamate-producing microorganism, such as those described in JP-A No. 2009-171960.

Examples of microorganisms that produce 3-hydroxyisobutyric acid include a microorganism to which a pathway described in WO 2009/135074 or WO 2008/145737 was introduced.

Examples of microorganisms that produce 2-hydroxyisobutyric acid include a microorganism to which a pathway described in WO 2009/135074 or WO 2009/156214 was introduced.

Examples of microorganisms that produce 3-aminoisobutyric acid or methacrylic acid include a microorganism to which a pathway described in WO 2009/135074 was introduced.

The microorganism in the invention is a microorganism that is constructed to have the acetyl-CoA production cycle of FIG. 1. by imparting at least both malate thiokinase and malyl-CoA lyase. Therefore, microorganisms intrinsically having malate thiokinase and malyl-CoA lyase are not included in the acetyl-CoA producing microorganism of the invention.

Examples of the microorganisms intrinsically having Mtk and mcl include methanotrophic microorganisms such as *Methylobacterium extorquens*. Since vector systems suitable for methanotrophic microorganisms or techniques for modification of genomic genes of methanotrophic microorganisms have not been developed, genetic manipulation of microorganisms is more difficult than industrial microorganisms such as *Escherichia coli* and *Corynebacterium*. Further, these microorganisms grow slowly in many cases and therefore are not suitable for producing useful metabolites.

The method of producing acetyl-CoA, acetone, isopropyl alcohol, or glutamate according to the invention includes producing acetyl-CoA, acetone, isopropyl alcohol, or glutamate as the product of interest from a carbon source material using the above-described acetyl-CoA producing microorganism. That is, the method of producing acetyl-CoA includes: culturing the acetyl-CoA producing microorganism in a state in which the acetyl-CoA producing microorganism contacts with a carbon source material (hereinafter, culture process), and collecting the product of interest (acetyl-CoA, acetone, isopropyl alcohol, or glutamate) obtained by the contact (hereinafter, collection process).

According to the method of producing acetyl-CoA, since the acetyl-CoA producing microorganism is cultured in a state in which the acetyl-CoA producing microorganism contacts with a carbon source material, the carbon source material is assimilated by the acetyl-CoA producing microorganism, and the product of interest can be efficiently produced while carbon dioxide is fixed.

The carbon source material is not restricted as long as the material contains a carbon source that can be assimilated by the microorganism, and the material is preferably a plant-derived raw material.

In the invention, the plant-derived raw material refers to organs such as roots, stems, trunks, branches, leaves, flowers, and seeds; plant bodies containing the organs; and decomposition products of the plant organs, and further encompasses carbon sources that can be used as carbon sources by microorganisms during cultivation for among carbon sources obtained from the plant bodies, the plant organs and the decomposition products thereof.

General examples of the carbon sources in the plant-derived raw material include sugars such as starch, sucrose, glucose, fructose, xylose, and arabinose; herbaceous and ligneous plant decomposition products or cellulose hydrolysates, each of which contains the above ingredients in large amounts; and combinations thereof. The carbon source in the invention may further include vegetable oil-derived glycerin and fatty acids.

Preferable examples of the plant-derived raw material include agricultural crops such as grain, corn, rice, wheat, soybean, sugarcane, beet, cotton, and the like, and combinations thereof. The form thereof as the raw materials is not specifically limited, and may be a crude products, squeezed juice, a crushed products, or the like. Alternatively, the plant-derived raw material may be in a form that consists only of carbon source described above.

In the culture process, the contact between the acetyl-CoA producing microorganism and plant-derived raw material is generally made by culturing the acetyl-CoA producing microorganism in a culture medium containing the plant-derived raw material.

The density of contact between the plant-derived raw material and the acetyl-CoA producing microorganism may be varied depending on the activity of the acetyl-CoA producing microorganism. In general, the concentration of the plant-derived raw material in the culture medium may be such that the initial sugar concentration in terms of glucose may be set to be 20% by mass or lower relative to the total mass of the mixture. From the viewpoint of sugar tolerance of the acetyl-CoA producing microorganism, the initial sugar concentration is preferably set to be 15% by mass or lower. Other components may be added in usual addition amounts for microorganisms culture media, without particular limitation.

The content of the acetyl-CoA producing microorganism in the culture medium may be varied with the kind and the activity of the microorganism, and the amount of a preculture bacterial liquid (OD 660 nm=4 to 8) to be added when starting initially cultivation may generally set to be 0.1% by mass to 30% by mass relative to the culture liquid, and is preferably set to be 1% by mass to 10% by mass relative to the culture liquid from the viewpoint of controlling culture conditions.

The medium to be used for culture of the acetyl-CoA producing microorganism may be any usually-employed culture medium that includes a carbon source, a nitrogen source, and an inorganic ion, and further an inorganic trace element, a nucleic acid, and a vitamin, etc., required by microorganisms to produce the product of interest, without particular limitation.

Culture conditions for the culture process are not particularly restricted, and culturing may be carried out, for example, under aerobic conditions at an appropriately controlled pH and temperature within a range of pH 4 to 9, preferably pH 6 to 8, and within a range of 20° C. to 50° C., preferably 25° C. to 42° C.

The aeration volume of gas into the mixture described above is not particularly restricted. When air alone is used as the gas, the aeration volume is generally 0.02 vvm to 2.0 vvm (vvm: aeration volume [mL]/liquid volume [mL]/time [min]) at 50 to 600 rpm. From the viewpoint of suppressing physical damage to *Escherichia coli*, the aeration is carried out preferably at 0.1 vvm to 2.0 vvm, more preferably at 0.1 win to 1.0 vvm.

The culture process may be continued from the beginning of the culturing until the carbon source material in the mixture is exhausted, or until the activity of the acetyl-CoA producing microorganism disappears. The duration of the culture process may be varied with the number and the activity of the acetyl-CoA producing microorganism in the mixture and the amount of the carbon source material. In general, the duration may be at least one hour, and preferably at least four hours. The duration of the culture process may be unlimitedly continued by anew addition of the carbon source material or the acetyl-CoA producing microorganism, However, from the viewpoint of process efficiency, the duration may generally be set 5 days or less, preferably 72 hours or less. With regard to other conditions, conditions employed for usual cultivation may be applied as they are.

Methods of collecting the product of interest accumulated in the culture medium are not particularly restricted. For example, a method may be employed which includes removing microorganism cells from the culture medium by, for example, centrifugal separation, and thereafter separating the product of interest using a usual separation method such as distillation or membrane separation under conditions suitable for the kind of the product of interest.

The method of producing acetyl-CoA according to the invention may further include, before the culture process, a preculture process for achieving an appropriate cells number and/or appropriate activated state of the acetyl-CoA producing microorganism to be used. The preculture process may be any cultivation conducted under usually-employed conditions suitable for the type of the acetyl-CoA producing microorganism.

The acetyl-CoA producing microorganism used in the method of producing acetone is preferably the acetyl-CoA producing microorganism having the thiolase activity, the CoA transferase activity, and the acetoacetate decarboxylase activity, described above as a preferable aspect of the acetyl-CoA producing microorganism, from the viewpoint of the efficiency acetone production.

The acetyl-CoA producing microorganism used in the method of producing isopropyl alcohol is preferably the acetyl-CoA producing microorganism having the thiolase activity, the CoA transferase activity, the acetoacetate decarboxylase activity, and the isopropyl alcohol dehydrogenase activity, described above as a preferable aspect of the acetyl-CoA producing microorganism, from the viewpoint of the efficiency of isopropyl alcohol production.

The method of producing isopropyl alcohol or the method of producing acetone preferably includes a culture process in which the acetyl-CoA producing microorganism is cultured while gas is supplied into the mixture containing the acetyl-CoA producing microorganism and the carbon source material; and a collection process for collecting the product of interest, in which isopropyl alcohol or acetone produced by the culturing is separated and collected from the mixture.

According to the method of producing isopropyl alcohol or the method of producing acetone, the acetyl-CoA producing microorganism is cultured while gas is supplied into the mixture (aeration culture). In this aeration culture, isopropyl alcohol produced or acetone produced is released into the mixture, and evaporated from the mixture. As a result, the isopropyl alcohol produced or the acetone produced can be easily separated from the mixture. Further, since the isopropyl alcohol produced or the acetone produced is continuously separated from the mixture, an increase in the concentration of the isopropyl alcohol or acetone in the mixture can be suppressed. Therefore, it is not necessary to pay particular attention to the tolerance of the acetyl-CoA producing microorganism against isopropyl alcohol or acetone.

The mixture in this method may be mainly composed of a basic medium generally used fin culture of the host microorganism. With regard to culture conditions, those described above shall apply as they are.

In the collection process, isopropyl alcohol or acetone produced in the culture process and separated from the mixture is collected. The collection method may be any method capable of collecting isopropyl alcohol or acetone in the gaseous or droplet state evaporated from the mixture by usual cultivation. Examples thereof include a method of collecting into a collecting member such as a commonly-employed airtight container. In particular, the method preferably includes contacting a trap solution for trapping isopropyl alcohol or acetone with the isopropyl alcohol or acetone separated from the mixture, from the viewpoint of collecting only isopropyl alcohol or acetone with high purity.

In the method of producing isopropyl alcohol or the method of producing acetone, the isopropyl alcohol or acetone can be collected in a state in which isopropyl alcohol or acetone is dissolved in a trap solution or the mixture. Examples of the collection method include a method described in WO 2009/008377. The isopropyl alcohol or acetone collected can be confirmed using a usual detection means such as HPLC. The isopropyl alcohol collected may be further purified, if necessary. Examples of the purification method include distillation, etc.

In a case in which the isopropyl alcohol or acetone collected is in the state of aqueous solution, the method of producing isopropyl alcohol or the method of producing acetone may further include a dehydration process in addition to the collection process. The dehydration of isopropyl alcohol or acetone can be carried out by an ordinary method.

Examples of apparatuses applicable to the method of producing isopropyl alcohol or acetone in which isopropyl alcohol or acetone can be collected in the state being dissolved in the trap solution or the mixture include the production apparatus shown in FIG. 1 of WO 2009/008377.

In this production apparatus, an injection pipe for injecting a gas from outside the apparatus is connected to the culture tank that contains a culture medium including a microorganism to be used and a plant-derived raw material, thereby enabling aeration to the culture medium.

A trap tank that contains a trap solution as the trap liquid is connected to the culture tank via a connecting pipe. A gas or liquid that has moved to the trap tank contacts the trap solution, and bubbling occurs.

As a result, isopropyl alcohol or acetone, which has been produced in the culture tank by cultivation under aeration, is evaporated due to aeration, and, therefore, easily separated from the culture medium, and is trapped in the trap solution in the trap tank. As a result, isopropyl alcohol or acetone can be produced in a more purified state in a simple and continuous manner.

A method of producing glutamate according to the invention includes producing glutamate as the product of interest from a carbon source material using the above-described acetyl-CoA producing microorganism. Specifically, the method of producing glutamate includes culturing the acetyl-CoA producing microorganism in a state in which the acetyl-CoA producing microorganism contacts with a carbon source material (hereinafter, culture process), and collecting the product of interest (glutamate) obtained by the contact (hereinafter, collection process).

According to the method of producing glutamate, since the acetyl-CoA producing microorganism is cultured in a state in which the acetyl-CoA producing microorganism contacts with a carbon source material, the carbon source material is assimilated by the acetyl-CoA producing microorganism, and the product of interest can be efficiently produced while carbon dioxide is fixed.

The culture medium to be used for culture may be any usually-employed culture medium that includes a carbon source, a nitrogen source, and an inorganic salt; and an organic trace nutrient such as an amino acid or a vitamins as necessary. Either a synthetic culture medium or natural culture medium may be used. The carbon source and nitrogen source used in the culture medium may be of any types that can be utilized by the microorganisms to be cultured.

Examples of the carbon source material which may be used include sugars such as glucose, glycerol, fructose, sucrose, maltose, mannose, galactose, starch hydrolysates, and molasses; and organic acids such as acetic acid or citric acid, and alcohols such as ethanol may be used singly or in combination with other carbon sources.

Examples of the nitrogen source which may be used include ammonia, ammonium salts such as ammonium sulfate, ammonium carbonate, ammonium chloride, ammonium phosphate, or ammonium acetate, and nitric acid salts.

Examples of the organic micronutrient which may be used include amino acids, vitamins, fatty acids, and nucleic acids; and peptones, casamino acids, yeast extracts, and soybean protein hydrolysates, each of which contains the above ingredients. In a case in which an auxotrophic mutant that requires an amino acid and the like for growth is used, it is preferable to supply a nutrient to be required.

Examples of the inorganic salt which may be used include phosphoric acid salts, magnesium salts, calcium salts, iron salts, and manganese salts.

The culture is preferably carried out at a fermentation temperature of 20° C. to 45° C. at a pH of 3 to 9 under aeration. For adjusting the pH, an inorganic or organic, acidic or alkaline substance, ammonia gas, etc. may be used. L-amino acid is accumulated in the culture medium or in the cells by culturing the microorganism preferably for 10 hours to 120 hours under these conditions.

In a case in which the L-amino acid of interest is L-glutamate, the culture may be carried out such that L-glutamate produced is precipitated and accumulated in the culture medium, by using a liquid medium whose conditions are adjusted to precipitate L-glutamate. For example, the conditions to precipitate L-glutamate may be a pH of 5.0 to 4.0, preferably a pH of 4.5 to 4.0, more preferably a pH of 4.3 to 4.0, still more preferably a pH of 4.0. For achieving both increased growth under acidic conditions and efficient precipitation of L-glutamate, the pH is preferably from 5.0 to 4.0, more preferably from 4.5 to 4.0, still more preferably from 4.3 to 4.0. The culture at the above-described pH may be carried out either through the whole culture period or during a part of the culture period.

The L-amino acid may be collected from the culture liquid after completion of the culture according to a known collection method. For example, the collection may be carried out by a method in which concentration crystallization is carried out after removal of bacterial cells from a culture medium, or by ion-exchange chromatography. In a case in which the culture was carried out under conditions that allow precipitation of L-glutamate in a culture medium, the L-glutamate precipitated into the culture medium can be collected by centrifugal separation, filtration, or the like. In such cases, L-glutamate remaining dissolved in the culture medium may be crystallized, and the crystallized L-glutamate may be isolated together.

Examples of methods for producing proline, leucine, isoleucine, valine, arginine, citrulline, ornithine, acetic acid, (poly)3-hydroxybutyric acid, itaconic acid, citric acid, butyric acid, or polyglutamic acid include methods described in Fermentation Handbook (Kyoritsu Shuppan Co., Ltd.).

Examples of methods for producing 4-aminobutyric acid include a production method using a microorganism obtained by introducing glutamate decarboxylase to a glutamate-producing microorganism, and which is described, in for example, JP-A No. 2011-167097.

Examples of methods for producing 4-hydroxybutyric acid include a production method using a microorganism obtained by introducing glutamate decarboxylase, aminotransferase, and aldehyde dehydrogenase to a glutamate-producing microorganism, and which is described in, for example, JP-A No. 2009-171960.

Examples of methods for producing 3-hydroxyisobutyric acid include a production method using a microorganism to which the pathway described in, for example, WO 2009/135074 or WO 2008/145737 was introduced.

Examples of methods for producing 2-hydroxyisobutyric acid include a production method using a microorganism to which the pathway described in, for example, WO 2009/135074 or WO 2009/156214 was introduced.

Examples of methods for producing 3-aminoisobutyric acid or methacrylic acid include a production method using a microorganism to which the pathway described in, for example, WO 2009/135074 was introduced.

EXAMPLES

Hereinbelow, examples of the present invention is described in detail. However, the invention is by no means limited to these examples.

Example 1

<Preparation of *Escherichia coli* B, atoD Genome-Enhanced Variant>

The whole sequence of the genomic DNA of *Escherichia coli* MG1655 is known (GenBank accession number U00096), and the base sequence of a gene encoding CoA transferase a subunit (hereinafter sometimes abbreviated to "atoD") of *Escherichia coli* MG1655 has also been reported. That is, atoD is described in 2321469 to 2322131 of the *Escherichia coli* MG1655 genome sequence, which is described in GenBank accession number U00096.

As the base sequence of a promoter necessary for express the above-mentioned gene, the promoter sequence of glyceraldehyde-3-phosphate dehydrogenase (hereinafter sometimes referred to as "GAPDH") derived from *Escherichia coli*, which is described in 397 to 440 in the base sequence information with a GenBank accession number X02662, can be used. In order to obtain the GAPDH promoter, amplification by a PCR method was carried out using the genomic DNA of *Escherichia coli* MG1655 as a template and using CGCTCAATTGCAATGATTGACACGATTCCG (SEQ ID NO: 1) and ACAGAATTCGCTATTTGTTAGT-GAATAAAAGG (SEQ ID NO: 2) as primers and the DNA fragment obtained was digested with restriction enzymes MfeI and EcoRI, thereby obtaining a DNA fragment of about 100 bp encoding the GAPDH promoter. The obtained DNA fragment and a fragment obtained by digesting plasmid pUC19 (GenBank accession number X02514) with restriction enzyme EcoRI followed by alkaline phosphatase treatment were mixed, and the mixed fragments were ligated using a ligase. Thereafter, *Escherichia coli* DH5α competent cells (DNA-903, manufactured by Toyobo Co., Ltd.) were transformed with the ligation product, and transformants that grew on an LB agar plate containing 50 μg/mL ampicillin were obtained. Ten of the colonies obtained were individually cultured at 37° C. overnight in an LB liquid medium containing 50 μg/mL ampicillin, and the plasmids were recovered, and plasmids from which the GAPDH promoter was not cut out when digested with restriction enzymes EcoRI and KpnI were selected. Further, the DNA sequence thereof was checked, and a plasmid in which the GAPDH promoter was properly inserted was named pGAP. The pGAP obtained was digested with restriction enzymes EcoRI and KpnI.

Furthermore, in order to obtain atoD, amplification by a PCR method was carried out using the genomic DNA of *Escherichia coli* MG1655 as a template and using CGAAT-TCGCTGGTGGAACATATGAAAACAAAATTGAT-GACATTACAAGAC (SEQ ID NO: 3) and GCGGTACCT-TATTTGCTCTCCTGTGAAACG (SEQ ID NO: 4) as primers, and the DNA fragment obtained was digested with restriction enzymes EcoRI and KpnI, thereby obtaining an atoD fragment of about 690 bp. This DNA fragment was mixed with pGAP that had previously been digested with restriction enzymes EcoRI and KpnI. The mixed fragments were ligated using a ligase. Thereafter, *Escherichia coli* DH5α competent cells (DNA-903, manufactured by Toyobo Co., Ltd.) were transformed with the ligation product, and transformants that grew on an LB agar plate containing 50 μg/mL ampicillin were obtained. A plasmid was recovered from the bacterial cells obtained, and it was confirmed that atoD was properly inserted. The plasmid obtained was named pGAPatoD.

Here, *Escherichia coli* MG1655 is available from American Type Culture Collection.

As described above, the base sequence of atoD in the genomic DNA of *Escherichia coli* MG1655 has also been reported. PCR was carried out using genomic DNA of *Escherichia coli* MG1655 as a template and using GCTCTAGATGCTGAAATCCACTAGTCTTGTC (SEQ ID NO: 5) and TACTGCAGCGTTCCAGCACCTTAT-CAACC (SEQ ID NO: 6) as primers, which were prepared based on the gene information of the 5'-flanking region of atoD of *Escherichia coli* MG1655, as a result of which a DNA fragment of about 1.1 kbp was amplified.

In addition, PCR was carried out using the expression vector pGAPatoD prepared above as a template, and using GGTCTAGAGCAATGATTGACACGATTCCG (SEQ ID NO: 7) prepared based on the sequence information of the GAPDH promoter of *Escherichia coli* MG1655 and a primer of SEQ ID NO:4 prepared based on the sequence information of atoD of *Escherichia coli* MG1655, as a result of which a DNA fragment of about 790 bp having the GAPDH promoter and atoD was obtained.

The fragments obtained from the above were digested with restriction enzymes PstI and XbaI, and XbaI and KpnI, respectively, and the resulting fragments were mixed with a fragment obtained by digesting a temperature-sensitive plasmid pTH18cs1 (GenBank accession number AB019610) [Hashimoto-Gotoh, T., Gene, 241, 185-191 (2000)] with PstI and KpnI, and the mixed fragments were ligating using a ligase. Thereafter, DH5α cells were transformed with the ligation product, and transformants that grew on an LB agar plate containing 10 μg/ml chloramphenicol at 30° C. were obtained. The colonies obtained were cultured at 30° C. overnight in an LB liquid medium containing 10 μg/ml chloramphenicol, and plasmids were recovered from the bacterial cells obtained. *Escherichia coli* B (ATCC 11303) was transformed with the plasmid, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. The obtained cultured bacterial cells were applied to an LB agar plate containing 10 μg/ml chloramphenicol and cultured at 42° C., as a result of which colonies were obtained. The obtained colonies were cultured in an LB liquid medium containing no antibiotic at 30° C. for 2 hours, and the resulting culture was then applied to an LB agar plate containing no antibiotic, as a result of which colonies that grew at 42° C. were obtained.

From the colonies that appeared, 100 colonies were randomly picked up, and each individually grown on an antibiotic-free both an LB agar plate and an LB agar plate containing 10 μg/ml chloramphenicol, and chloramphenicol-sensitive clones were selected. Furthermore, a fragment of about 790 bp that contained the GAPDH promoter and atoD was amplified by PCR, from the chromosomal DNA of these clones, and a variant in which an atoD promoter region was replaced by the GAPDH promoter was selected. Then, a clone satisfying the above conditions was named *Escherichia coli* B, atoD genome-enhanced variant (hereinafter sometimes abbreviated to "B::atoDAB variant").

Here, *Escherichia coli* B (ATCC 11303) is available from American Type Culture Collection, which is a bank of cells, microorganisms, and genes.

Example 2

<Preparation of *Escherichia coli* B, atoD Genome-Enhanced, Pgi Gene-Deleted Variant>

The whole sequence of the genomic DNA of *Escherichia coli* MG1655 is known (GenBank accession number U00096), and the base sequence of a gene encoding phosphoglucose isomerase (hereinafter sometimes referred to as "pgi") of *Escherichia coli* has also been reported (GenBank accession number X15196). In order to clone a region flanking the base sequence of the gene encoding pgi (1,650 bp), four types of oligonucleotide primers represented by CAGGAATTCGCTATATCTGGCTCTGCACG (SEQ ID NO: 8), CAGTCTAGAGCAATACTCTTCTGATTTTGAG (SEQ ID NO: 9), CAGTCTAGATCATCGTCGATATGTAGGCC (SEQ ID NO: 10), and GACCTGCAGATCATCCGTCAGCTGTACGC (SEQ ID NO: 11) were synthesized. The primer of SEQ ID NO: 8 has an EcoRI recognition site in the 5'-end side thereof, each of the primers of SEQ ID NOs: 9 and 10 has an XbaI recognition site in the 5'-end side thereof, and the primer of SEQ ID NO: 11 has a PstI recognition site in the 5'-end side thereof.

The genomic DNA of the *Escherichia coli* MG1655 (ATCC 700926) was prepared, and PCR was carried out using the obtained genomic DNA as a template and using a primer pair of SEQ ID NO: 8 and SEQ ID NO: 9, as a result of which a DNA fragment of about 1.0 kb (hereinafter sometimes referred to as "pgi-L fragment") was amplified. In addition, PCR was carried out using a primer pair of SEQ ID NO: 10 and SEQ ID NO: 11, as a result of which a DNA fragment of about 1.0 kb (hereinafter sometimes referred to as "pgi-R fragment") was amplified. These DNA fragments were separated by agarose electrophoresis, and recovered. The pgi-L fragment was digested with EcoRI and XbaI, and the pgi-R fragment was digested with XbaI and PstI. The two types of digested fragments and a fragment obtained by digesting a temperature-sensitive plasmid pTH18cs1 (GenBank accession number AB019610) with EcoRI and PstI were mixed, and allowed to react using T4 DNA ligase. Thereafter, *Escherichia coli* DH5α competent cells (manufactured by Toyobo Co., Ltd.) were transformed with the ligation product, and transformants that grew on an LB agar plate containing 10 µg/ml chloramphenicol at 30° C. were obtained. Plasmid were recovered from the transformants obtained, and it was confirmed that the two fragments—the 5'-upstream flanking region fragment and 3'-downstream flanking region fragment of the gene encoding pgi—were properly inserted in pTH18cs1. The plasmid obtained was digested with XbaI, and then subjected to blunt-end treatment with T4 DNA polymerase. The resultant DNA fragment was mixed with a kanamycin-resistance gene obtained by digesting pUC4K plasmid (GenBank accession number X06404) (Pharmacia) with EcoRI and subjecting the resulting product to blunt-end treatment with T4 DNA polymerase, and the mixed fragments were ligated using T4 DNA ligase. Subsequently, *Escherichia coli* DH5α competent cells were transformed with the ligation product, and transformants that grew on an LB agar plate containing 10 µg/ml chloramphenicol and 50 µg/ml kanamycin at 30° C. were obtained. A plasmid was recovered from the transformants obtained, and it was confirmed that the kanamycin-resistance gene was properly inserted between the 5'-upstream flanking region fragment and 3'-downstream flanking region fragment of the gene encoding pgi. The plasmid obtained was named pTH18cs1-pgi.

Here, *Escherichia coli* MG1655 can be obtained from American Type Culture Collection.

The B::atoDAB variants prepared in Example 1 were transformed with the thus-obtained plasmid pTH18cs1-pgi, and was cultured at 30° C. overnight on an LB agar plate containing 10 µg/ml chloramphenicol and 50 µg/ml kanamycin, as a result of which transformants were obtained. The transformants obtained were inoculated into an LB liquid medium containing 50 µg/ml kanamycin, and cultured at 30° C. overnight. Subsequently, part of the resulting culture liquid was applied to an LB agar plate containing 50 µg/ml kanamycin, as a result of which colonies that grew at 42° C. were obtained. The colonies obtained were cultured at 30° C. for 24 hours in an LB liquid medium containing 50 µg/ml kanamycin, and was applied to an LB agar plate containing 50 µg/ml kanamycin, as a result of which colonies that grew at 42° C. were obtained.

From the colonies that appeared, 100 colonies were randomly picked up, and each individually grown on an LB agar plate containing 50 µg/ml kanamycin and an LB agar plate containing 10 µg/ml chloramphenicol, and chloramphenicol-sensitive clones that grew only on the LB agar plate containing kanamycin were selected. Furthermore, the chromosomal DNAs of these target clones were amplified by PCR, and a variant from which a fragment of about 3.3 kbp, which indicates replacement of the pgi gene by the kanamycin-resistance gene, could be amplified was selected. The variant obtained was named *Escherichia coli* B, atoD genome-enhanced, pgi gene-deleted variant (hereinafter sometimes abbreviated to "B::atoDABΔpgi variant").

Here, *Escherichia coli* MG1655 and *Escherichia coli* B are available from American Type Culture Collection.

Example 3

<Preparation of *Escherichia coli* B atoD Genome-Enhanced, Pgi Gene-Deleted, gntR Gene-Deleted Variant>

The whole sequence of the genomic DNA of *Escherichia coli* B is known (GenBank accession No. CP000819), and the base sequence encoding GntR is described in 3509184 to 3510179 of the genomic sequence of *Escherichia coli* B, which is described in GenBank accession No. CP000819. In order to clone a region flanking the base sequence of the gene encoding GntR (gntR), four types of oligonucleotide primers represented by GGAATTCGGGTCAATTTTCACCCTCTATC (SEQ ID NO: 12), GTGGGCCGTCCTGAAGGTACAAAAGAGATAGATTCTC (SEQ ID NO: 13), CTCTTTTGTACCTTCAGGACGGCCCACAAATTTGAAG (SEQ ID NO: 14), and GGAATTCCCAGCCCCGCAAGGCCGATGGC (SEQ ID NO: 15) were synthesized. Each of the primers of SEQ ID NOs: 12 and 13 has an EcoRI recognition site in the 5'-end side thereof.

The genomic DNA of *Escherichia coli* B (GenBank accession No. CP000819) was prepared, and PCR was carried out using the obtained genomic DNA as a template and a primer pair of SEQ ID NO: 12 and SEQ ID NO: 13, as a result of which a DNA fragment of about 1.0 kb (hereinafter sometimes referred to as "gntR-L fragment") was amplified. In addition, PCR was carried out using a primer pair of SEQ ID NO: 14 and SEQ ID NO: 15, as a result of which a DNA fragment of about 1.0 kb (hereinafter sometimes referred to as "gntR-R fragment") was amplified. These DNA fragments were separated by agarose electrophoresis, and recovered. PCR was carried out using the gntR-L and gntR-R fragments as templates and using a primer pair of SEQ ID NO: 12 and SEQ ID NO: 15, as a result of which a DNA fragment of about 2.0 kbp (hereinafter sometimes referred to as "gntR-LR fragment") was amplified. This gntR-LR fragment was separated by agarose electrophoresis, recovered, digested with EcoRI, and mixed with a fragment obtained by digesting a temperature-sensitive plasmid pTH18cs1 (GenBank accession number AB019610) with EcoRI. The mixed fragments were allowed to react using T4 DNA ligase. Thereafter, *Escherichia coli* DH5α competent cells (manufactured by Toyobo Co., Ltd.) were transformed with the ligation product, and transformants that grew on an LB agar plate containing 10 µg/ml chloramphenicol at 30° C. were obtained. A plasmid was recovered from the transformants obtained, and it was confirmed that the gntLR fragment was properly inserted in pTH18cs1. The plasmid obtained was named pTH18cs1-gntR.

The *Escherichia coli* B::atoDABΔpgi variant prepared in Example 2 was transformed with the thus-obtained plasmid pTH18cs1-gntR, and was cultured at 30° C. overnight on an LB agar plate containing 10 µg/ml chloramphenicol, as a result of which transformants were obtained. The transformants obtained were inoculated into an LB liquid medium containing 10 µg/ml chloramphenicol, and cultured at 30° C. overnight. Subsequently, part of the culture liquid was applied to an LB agar plate containing 10 µg/ml chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 µg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the gntR gene, could be amplified was selected. The variant obtained was named *Escherichia coli* B, atoD genome-enhanced, pgi gene-deleted, gntR gene-deleted variant (hereinafter sometimes abbreviated to "B::atoDABΔpgiΔgntR variant").

Example 4

<Preparation of *Escherichia coli* B, atoD Genome-Enhanced, Pgi Gene-Deleted, gntR Gene-Deleted, Gnd Gene-Deleted Variant>

In order to clone a region flanking the base sequence of the gene encoding phosphogluconate dehydrogenase (gnd), four types of oligonucleotide primers represented by CGCCATATGAATGGCGCGGCGGGGCCGGTGG (SEQ ID NO: 16), TGGAGCTCTGTTTACTCCTGTCAGGGGG (SEQ ID NO: 17), TGGAGCTCTCTGATTTAATCAACAATAAAATTG (SEQ ID NO: 18), and CGGGATCCACCACCATAACCAAACGACGG (SEQ ID NO: 19) were synthesized. The primer of SEQ ID NO: 16 has an NdeI recognition site in the 5'-end side thereof, and each of the primers of SEQ ID NOs: 17 and 18 has a SacI recognition site in the 5'-end side thereof. Further, the primer of SEQ ID NO: 19 has a BamHI recognition site in the 5'-end side thereof.

The genomic DNA of *Escherichia coli* B (GenBank accession No. CP000819) was prepared, and PCR was carried out using a primer pair of SEQ ID NO: 16 and SEQ ID NO: 17, as a result of which a DNA fragment of about 1.0 kb (hereinafter sometimes referred to as "gnd-L fragment") was amplified. In addition, PCR was carried out using a primer pair of SEQ ID NO: 18 and SEQ ID NO: 19, as a result of which a DNA fragment of about 1.0 kb (hereinafter sometimes referred to as "gnd-R fragment") was amplified. These DNA fragments were separated by agarose electrophoresis, and recovered. The gnd-L fragment was digested with NdeI and SacI, and the gnd-R fragment was digested with SacI and BamHI. These two types of digested fragments were mixed with a fragment obtained by digesting a temperature-sensitive plasmid pTH18cs1 (GenBank accession number AB019610) with NdeI and BamHI, and the mixed fragments were allowed to react using T4 DNA ligase. Thereafter, s competent cells (manufactured by Toyobo Co., Ltd.) were transformed with the ligation product, and transformants that grew on an LB agar plate containing 10 µg/ml chloramphenicol at 30° C. were obtained. Plasmids were recovered from the transformants obtained, and it was confirmed that the two fragments—the 5'-upstream flanking region fragment and 3'-downstream flanking region fragment of the gene encoding gnd—were properly inserted in pTH18cs1. The plasmid obtained was named pTH18cs1-gnd.

The *Escherichia coli* B::atoDABΔpgiΔgntR variant prepared in Example 3 was transformed with the thus-obtained plasmid pTH18cs1-gnd, and was cultured at 30° C. overnight on an LB agar plate containing 10 µg/ml chloramphenicol, as a result of which transformants were obtained. The transformants obtained were inoculated into an LB liquid medium containing 10 µg/ml chloramphenicol, and cultured at 30° C. overnight. Next, part of this culture liquid was applied to an LB agar plate containing 10 µg/ml kanamycin, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 µg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the gnd gene, could be amplified was selected. The variant obtained was named *Escherichia coli* B, atoD genome-enhanced, pgi gene-deleted, gntR gene-deleted, gnd gene-deleted variant (B::atoDABΔpgiΔgntRΔgnd variant).

Example 5

<Preparation of *Escherichia coli* B, atoD Genome-Enhanced, Pgi Gene-Deleted, gntR Gene-Deleted, Gnd Gene-Deleted, ldhA Gene-Deleted Variant>

In order to clone a region flanking the base sequence of the gene encoding D-lactate dehydrogenase (hereinafter sometimes abbreviated to "ldhA") (990 bp), four types of oligonucleotide primers represented by GGAATTCGACCATCGCTTACGGTCAATTG (SEQ ID NO: 20), GAGCGGCAAGAAAGACTTTCTCCAGTGATMTG (SEQ ID NO: 21), GGAGAAAGTCTTTCTTGCCGCTCCCCTGCAAC (SEQ ID NO: 22), and GGAATTCTTTAGCAAATGGCTTTCTTC (SEQ ID NO: 23) were synthesized. Each of the primers of SEQ ID NOs: 20 and 23 has an EcoRI recognition site in the 5'-end side thereof.

The genomic DNA of *Escherichia coli* B (GenBank accession No. CP000819) was prepared, and PCR was carried out using the obtained genomic DNA as a template and a primer pair of SEQ ID NO: 20 and SEQ ID NO: 21, as a result of which a DNA fragment of about 1.0 kb (hereinafter sometimes referred to as "ldhA-L fragment") was amplified. In addition, PCR was carried out using a primer pair of SEQ ID NO: 22 and SEQ ID NO: 23, as a result of which a DNA fragment of about 1.0 kb (hereinafter sometimes referred to as "ldhA-R fragment") was amplified. These DNA fragments were separated by agarose electrophoresis, and recovered. PCR was carried out using the ldhA-L and ldhA-R fragments as templates and using a primer pair of SEQ ID NO: 20 and SEQ ID NO: 23, as a result of which a DNA fragment of about 2.0 kbp (hereinafter sometimes referred to as "ldhA-LR fragment") was amplified. This ldhA-LR fragment was separated by agarose electrophoresis, recovered, digested with EcoRI, and mixed with a fragment obtained by digesting a temperature-sensitive plasmid pTH18cs1 (GenBank accession number AB019610) with EcoRI. The mixed fragments were allowed to react using T4 DNA ligase. Thereafter, *Escherichia coli* DH5α competent cells (manufactured by Toyobo Co., Ltd.) were transformed with the ligation product, and transformants that grew on an LB agar plate containing 10 μg/ml chloramphenicol at 30° C. were obtained. A plasmid was recovered from the transformants obtained, and it was confirmed that the ldhA-LR fragment was properly inserted in pTH18cs1. The plasmid obtained was named pTH18cs1-ldhA.

The *Escherichia coli* B::atoDABΔpgiΔgntRΔgnd variant prepared in Example 4 was transformed with the thus-obtained plasmid pTH18cs1-ldhA, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Subsequently, part of the culture liquid was applied to an LB agar plate containing 10 μg/ml chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the ldhA gene, could be amplified was selected. The variant obtained was named *Escherichia coli* B, atoD genome-enhanced, pgi gene-deleted, gntR gene-deleted, gnd gene-deleted, ldhA gene-deleted variant (hereinafter sometimes abbreviated to "B::atoDABΔpgiΔgntRΔgndΔldhA variant").

Example 6

<Preparation of *Escherichia coli* B, atoD Genome-Enhanced, Pgi Gene-Deleted, gntR Gene-Deleted, Gnd Gene-Deleted, ldhA Gene-Deleted, aceBA Gene-Deleted Variant>

In order to clone a region flanking the base sequence of the gene encoding isocitrate lyase and the gene encoding malate synthase (hereinafter sometimes abbreviated to "aceBA") (2936 bp), four types of oligonucleotide primers represented by GGAATTCATTCAGCTGTTGCGCATC-GATTC (SEQ ID NO: 24), CGGTTGTTGTTGCCGTGCA-GCTCCTCGTCATGGATC (SEQ ID NO: 25), GGAGCT-GCACGGCAACAACAACCGTTGCTGACTG (SEQ ID NO: 26), and GGAATTCCAGGCAGGTAT-CAATAAATAAC (SEQ ID NO: 27) were synthesized. Each of the primers of SEQ ID NOs: 24 and 27 has an EcoRI recognition site in the 5'-end side thereof.

The genomic DNA of *Escherichia coli* B (GenBank accession No. CP000819) was prepared, and PCR was carried out using the obtained genomic DNA as a template and a primer pair of SEQ ID NO: 24 and SEQ ID NO: 25, as a result of which a DNA fragment of about 1.0 kb (hereinafter sometimes referred to as "aceBA-L fragment") was amplified. In addition, PCR was carried out using a primer pair of SEQ ID NO: 26 and SEQ ID NO: 27, as a result of which a DNA fragment of about 1.0 kb (hereinafter sometimes referred to as "aceBA-R fragment") was amplified. These DNA fragments were separated by agarose electrophoresis, and recovered. PCR was carried out using the aceBA-L and aceBA-R fragments as templates and using a primer pair of SEQ ID NO: 24 and SEQ ID NO: 27, as a result of which a DNA fragment of about 2.0 kbp (hereinafter sometimes referred to as "aceBA-LR fragment") was amplified. This aceBA-LR fragment was separated by agarose electrophoresis, recovered, digested with EcoRI, and mixed with a fragment obtained by digesting a temperature-sensitive plasmid pTH18cs1 (GenBank accession number AB019610) with EcoRI. The mixed fragments were allowed to react using T4 DNA ligase. Thereafter, *Escherichia coli* DH5α competent cells (manufactured by Toyobo Co., Ltd.) were transformed with the ligation product, and transformants that grew on an LB agar plate containing 10 μg/ml chloramphenicol at 30° C. were obtained. A plasmid was recovered from the transformants obtained, and it was confirmed that the aceBA-LR fragment was properly inserted in pTH18cs1. The plasmid obtained was named pTH18cs1-aceBA.

The *Escherichia coli* B::atoDABΔpgiΔgntRΔgndΔldhA variant prepared in Example 5 was transformed with the thus-obtained plasmid pTH18cs1-aceBA, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Subsequently, part of the culture liquid was applied to an LB agar plate containing 10 μg/ml chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the aceBA gene, could be amplified was selected. The variant obtained was named *Escherichia coli* B, atoD genome-enhanced, pgi gene-deleted, gntR gene-deleted, gnd gene-deleted, ldhA gene-deleted, aceBA gene-deleted variant (hereinafter sometimes abbreviated to "B::atoDABΔpgiΔgntRΔgndΔldhAΔaceBA variant").

Example 7

<Preparation of *Escherichia coli* B, atoD Genome-Enhanced, Pgi Gene-Deleted, gntR Gene-Deleted, Gnd Gene-Deleted, ldhA Gene-Deleted, aceBA Gene-Deleted, glcB Gene-Deleted Variant>

In order to clone a region flanking the base sequence of the gene encoding malate synthase G (hereinafter sometimes abbreviated to "glcB") (723 bp), four types of oligonucleotide primers represented by GGAATTCCAGGA-GAAAGGGCTGGCACGGG (SEQ ID NO: 28), CTTTTTTGACGCTATGTTTATCTCCTCGTTTTCGC (SEQ ID NO: 29), GAGATAAACATAGCGT-CAAAAAAGCCCCGGC (SEQ ID NO: 30), and GGAAT-TCCGTCCATCATTGCTACCAGCC (SEQ ID NO: 31) were synthesized. Each of the primers of SEQ ID NOs: 28 and 31 has an EcoRI recognition site in the 5'-end side thereof.

The genomic DNA of *Escherichia coli* B (GenBank accession No. CP000819) was prepared, and PCR was carried out using the obtained genomic DNA as a template and a primer pair of SEQ ID NO: 28 and SEQ ID NO: 29, as a result of which a DNA fragment of about 1.0 kb (hereinafter sometimes referred to as "glcB-L fragment") was amplified. In addition, PCR was carried out using a primer pair of SEQ ID NO: 30 and SEQ ID NO: 31, as a result of which a DNA fragment of about 1.0 kb (hereinafter sometimes referred to as "glcB-R fragment") was amplified. These DNA fragments were separated by agarose electrophoresis, and recovered. PCR was carried out using the glcB-L and glcB-R fragments as templates and using a primer pair of SEQ ID NO: 28 and SEQ ID NO: 31, as a result of which a DNA fragment of about 2.0 kbp (hereinafter sometimes referred to as "glcB-LR fragment") was amplified. This glcB-LR fragment was separated by agarose electrophoresis, recovered, digested with EcoRI, and mixed with a fragment obtained by digesting a temperature-sensitive plasmid pTH18cs1 (GenBank accession number AB019610) with EcoRI. The mixed fragments were allowed to react using T4 DNA ligase. Thereafter, *Escherichia coli* DH5α competent cells (manufactured by Toyobo Co., Ltd.) were transformed with the ligation product, and transformants that grew on an LB agar plate containing 10 μg/ml chloramphenicol at 30° C. were obtained. A plasmid was recovered from the transformants obtained, and it was confirmed that the glcB-LR fragment was properly inserted in pTH18cs1. The plasmid obtained was named pTH18cs1-glcB.

The *Escherichia coli* B::atoDABΔpgiΔgntRΔgndΔldhAΔaceBA variant prepared in Example 6 was transformed with the thus-obtained plasmid pTH18cs1-glcB, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Subsequently, part of the culture liquid was applied to an LB agar plate containing 10 μg/ml chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the glcB gene, could be amplified was selected. The variant obtained was named *Escherichia coli* B, atoD genome-enhanced, pgi gene-deleted, gntR gene-deleted, gnd gene-deleted, ldhA gene-deleted, aceBA gene-deleted, glcB gene-deleted variant (hereinafter sometimes abbreviated to "B::atoDABΔpgiΔgntRΔgndΔldhAΔaceBAΔglcB variant").

Example 8

<Preparation of *Escherichia coli* B, atoD Genome-Enhanced, Pgi Gene-Deleted, gntR Gene-Deleted, Gnd Gene-Deleted, ldhA Gene-Deleted, aceBA Gene-Deleted, glcB Gene-Deleted, fumAC Gene-Deleted Variant>

In order to clone a region flanking the base sequence of the gene encoding fumarate hydratase A and the gene encoding fumarate hydratase C (hereinafter sometimes abbreviated to "fumAC") (3193 bp), four types of oligonucleotide primers represented by CGCCATATGATCGC-CAGCGCGCGGGATTTTTC (SEQ ID NO: 32), CGAGCTCTGTTCTCTCACTTACTGCCTGG (SEQ ID NO: 33), ATGAGCTCTCTGCAACATACAGGTGCAG (SEQ ID NO: 34), and CGGGATCCACTACGCGCAC-GATGGTCAAG (SEQ ID NO: 35) were synthesized. The primer of SEQ ID NO: 32 has a NdeI recognition site in the 5'-end side thereof. Each of the primers of SEQ ID NOs: 33 and 34 has a SacI recognition site in the 5'-end side thereof. The primer of SEQ ID NO: 35 has a BamHI recognition site in the 5'-end side thereof.

The genomic DNA of *Escherichia coli* B (GenBank accession No. CP000819) was prepared, and PCR was carried out using the obtained genomic DNA as a template and a primer pair of SEQ ID NO: 32 and SEQ ID NO: 33, as a result of which a DNA fragment of about 1.0 kb (hereinafter sometimes referred to as "fumA-L fragment") was amplified. In addition, PCR was carried out using a primer pair of SEQ ID NO: 34 and SEQ ID NO: 35, as a result of which a DNA fragment of about 1.0 kb (hereinafter sometimes referred to as "fumC-R fragment") was amplified. These DNA fragments were separated by agarose electrophoresis, and recovered. The fumA-L fragment was digested with NdeI and SacI, and the fumC-R fragment was digested with SacI and BamHI. These digested fragments were mixed with a fragment obtained by digesting a temperature-sensitive plasmid pTH18cs1 (GenBank accession number AB019610) with NdeI and BamHI. The mixed fragments were allowed to react using T4 DNA ligase. Thereafter, *Escherichia coli* DH5α competent cells (manufactured by Toyobo Co., Ltd.) were transformed with the ligation product, and transformants that grew on an LB agar plate containing 10 μg/ml chloramphenicol at 30° C. were obtained. A plasmid was recovered from the transformants obtained, and it was confirmed that the fumA-L fragment and the fumC-R fragment were properly inserted in pTH18cs1. The plasmid obtained was named pTH18cs1-fumAC.

The *Escherichia coli* B::atoDABΔpgiΔgntRΔgndΔldhAΔaceBAΔglcB variant prepared in Example 7 was transformed with the thus-obtained plasmid pTH18cs1-fumAC, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Subsequently, part of the culture liquid was applied to an LB agar plate containing 10 μg/ml chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the fumAC gene, could be amplified was selected. The variant obtained was named *Escherichia coli* B, atoD genome-enhanced, pgi gene-deleted, gntR gene-deleted, gnd gene-deleted, ldhA gene-deleted, aceBA gene-deleted, glcB gene-deleted, fumAC gene-deleted variant (hereinafter sometimes abbreviated to "B:: atoDABΔpgiΔgntRΔgndΔldhAΔaceBAΔglcBΔfumAC variant").

Example 9

<Preparation of Plasmid pIaz>

Acetoacetate decarboxylase of *Clostridium* bacteria is described in GenBank accession number M55392, and isopropyl alcohol dehydrogenase of *Clostridium* bacteria is described in GenBank accession number AF157307.

As the base sequence of a promoter necessary to express the above-mentioned gene group, the promoter sequence of glyceraldehyde-3-phosphate dehydrogenase (hereinafter sometimes referred to as "GAPDH") from *Escherichia coli*, which is described at 397 to 440 in the base sequence information with a GenBank accession number X02662, can be used.

In order to obtain the GAPDH promoter, amplification by a PCR method was carried out using the genomic DNA of *Escherichia coli* MG1655 as a template and using CGAGC-TACATATGCAATGATTGACACGATTCCG (SEQ ID NO: 36) and CGCGCGCATGCTATTTGTTAGT-GAATAAAAGG (SEQ ID NO: 37), and the DNA fragment obtained was digested with restriction enzymes NdeI and SphI, as a result of which a DNA fragment of about 110 bp corresponding to the GAPDH promoter was obtained. The DNA fragment obtained was mixed with a fragment obtained by digesting plasmid pBR322 (GenBank accession number J01749) with restriction enzymes NdeI and SphI, and the mixed fragments were ligated using a ligase. Thereafter, *Escherichia coli* DH5α competent cells (Toyobo Co., Ltd., DNA-903) were transformed with the ligation product, and transformants that grew on an LB agar plate containing 50 μg/mL ampicillin were obtained. The colonies obtained were cultured at 37° C. overnight in an LB liquid medium containing 50 μg/mL ampicillin, and plasmid pBRgapP was recovered from the bacterial cells obtained.

In order to obtain the isopropyl alcohol dehydrogenase gene, amplification by a PCR method was carried out using the genomic DNA of *Clostridium beijerinckii* NRRL B-593 as a template and using AATATGCATGCTGGTG-GAACATATGAAAGGTTTTGCAATGCTAGG (SEQ ID NO: 38) and ACGCGTCGACTTATAATATAACTACT-GCTTTAATTAAGTC (SEQ ID NO: 39), and the DNA fragment obtained was digested with restriction enzymes SphI and SalI, as a result of which an isopropyl alcohol dehydrogenase fragment of about 1.1 kbp was obtained. The DNA fragment obtained was mixed with a fragment obtained by digesting plasmid pUC119 with restriction enzymes SphI and SalI, and these fragments were ligated together using ligase. Thereafter, *Escherichia coli* DH5α competent cells were transformed with the ligation product, and transformants that grew on an LB agar plate containing 50 μg/mL ampicillin were obtained. The obtained colonies were cultured at 37° C. overnight in an LB liquid medium containing 50 μg/mL ampicillin, and plasmids were recovered from the obtained bacterial cells. Correct insertion of the IPAdh was confirmed, and the plasmid obtained was named pUC-I.

The fragment having IPAdh obtained by digesting plasmid pUC-I with restriction enzymes SphI and EcoRI was mixed with a fragment obtained by digesting plasmid pBR-gapP with restriction enzymes SphI and EcoRI, and the mixed fragments were ligated using a ligase. Thereafter, *Escherichia coli* DH5α competent cells were transformed with the ligation product, and transformants that grew on an LB agar plate containing 50 μg/mL ampicillin were obtained. The colonies obtained were cultured at 37° C. overnight in an LB liquid medium containing 50 μg/mL ampicillin, and plasmids were recovered from the bacterial cells obtained, and it was confirmed that IPAdh was properly inserted. The plasmid obtained was named pGAP-I.

In order to obtain the acetoacetate decarboxylase gene, amplification by a PCR method was carried out using the genomic DNA of *Clostridium acetobutylicum* ATCC 824 as a template and using ACGCGTCGACGCTGGTG-GAACATATGTTAAAGGATGAAGTAAT-TAAACAAATTAGC (SEQ ID NO: 40) and GCTCTA-GAGGTACCTTACTTAAGATAATCATATATAACTTCAGC (SEQ ID NO: 41), and the DNA fragment obtained was digested with restriction enzymes SalI and XbaI, as a result of which an acetoacetate decarboxylase fragment of about 700 bp was obtained. The DNA fragment obtained was mixed with a fragment obtained by digesting the plasmid pGAP-I prepared above with restriction enzymes SalI and XbaI, and the mixed fragments were ligated using a ligase. Thereafter, *Escherichia coli* DH5α competent cells were transformed with the ligation product, and transformants that grew on an LB agar plate containing 50 μg/mL ampicillin were obtained. The colonies obtained were cultured at 37° C. overnight in an LB liquid medium containing 50 μg/mL ampicillin, and plasmids were recovered from the bacterial cells obtained, and it is confirmed that adc was correctly inserted. The plasmid obtained was named pIa.

In order to obtain the glucose-6-phosphate-1-dehydrogenase gene (zwf), amplification by a PCR method was carried out using the genomic DNA of *Escherichia coli* B (GenBank accession No. CP000819) as a template and using GCTCTAGACGGAGAAAGTCTTATGGCGGTAACG-CAAACAGCCCAGG (SEQ ID NO: 42) and CGGGATC-CCGGAGAAAGTCTTATGAAGCAAACAGTT-TATATCGCC (SEQ ID NO: 43), and the DNA fragment obtained was digested with restriction enzymes BamHI and XbaI, as a result of which a glucose-6-phosphate-1-dehydrogenase fragment of about 1,500 bp was obtained. The DNA fragment obtained was mixed with a fragment obtained by digesting the plasmid pIa prepared above with restriction enzymes BamHI and XbaI, and the mixed fragments were ligated using a ligase. Thereafter, *Escherichia coli* DH5α competent cells were transformed with the ligation product, and transformants that grew on an LB agar plate containing 50 μg/mL ampicillin were obtained. The colonies obtained was cultured at 37° C. overnight in an LB liquid medium containing 50 μg/mL ampicillin, and this plasmid was named pIaz.

Example 10

<Preparation of Plasmid pMWGKC>

Amplification by a PCR method was carried out using pBRgapP as a template and using CCGCTCGAGCATAT-GCTGTCGCAATGATTGACACG (SEQ ID NO: 44) and GCTATTCCATATGCAGGGTTATTGTCTCATGAGC (SEQ ID NO: 45), and the DNA fragment obtained was phosphorylated using T4 Polynucleotide kinase (Takara), as a result of which a DNA fragment harboring the GAPDH promoter was obtained. Further, plasmid pMW119 (GenBank accession number AB005476) was treated with restriction enzymes NdeI, and the DNA fragment obtained was subjected to blunt-end treatment with KOD plus DNA polymerase (Takara), as a result of which a DNA fragment harboring the replication origin of pMW119 was obtained. The DNA fragment harboring the GAPDH promoter and the DNA fragment harboring the replication origin of pMW119 were mixed, and the mixed fragments were ligated using a ligase. Thereafter, *Escherichia coli* DH5α competent cells were transformed with the ligation product, and transformants that grew on an LB agar plate containing 50 μg/mL ampicillin were obtained. The colonies obtained were cultured at 37° C. overnight in an LB liquid medium containing 50 μg/mL ampicillin, and plasmid pMWG was recovered from the bacterial cells obtained.

In order to obtain a chloramphenicol-resistance gene, amplification by a PCR method was carried out using pTH18cs1 (GenBank accession No. AB019610) as a template and using TCGGCACGTAAGAGGTTCC (SEQ ID NO: 46) and CGGGTCGAATTTGCTTTCG (SEQ ID NO: 47), and the DNA fragment obtained was phosphorylated using T4 Polynucleotide kinase (Takara), as a result of which a DNA fragment containing a chloramphenicol-resistance gene was obtained. In addition, amplification by a PCR method was carried out using pMWG as a template and using CTAGATCTGACAGTAAGACGGGTAAGCC (SEQ ID NO: 48) and CTAGATCTCAGGGTTATTGTCTCATGAGC (SEQ ID NO: 49). The DNA fragment obtained was mixed with the DNA fragment containing the chloramphenicol-resistance gene, and the mixed fragments were ligated using a ligase. Thereafter, *Escherichia coli* DH5α competent cells were transformed with the ligation product, and transformants that grew on an LB agar plate containing 25 μg/mL chloramphenicol were obtained. The colonies obtained were cultured at 37° C. overnight in an LB liquid medium containing 25 μg/mL chloramphenicol, and the plasmid obtained was named pMWGC.

Amplification by a PCR method was carried out using the pMWGC gene as a template and using CCTTTGGT-TAAAGGCTTTAAGATCTTCCAGTGGACAAACTAT-GCC (SEQ ID NO: 50) and GGCATAGTTTGTCCACTG-GAAGATCTTAAAGCCTTTAACCAAAGG (SEQ ID NO: 51). Thereafter, *Escherichia coli* DH5α competent cells were transformed with the DNA fragment obtained, and transformants that grew on an LB agar plate containing 25 μg/mL chloramphenicol were obtained. The colonies obtained were cultured at 37° C. overnight in an LB liquid medium containing 25 μg/mL chloramphenicol, and plasmid pMWGKC was recovered from the bacterial cells obtained.

Example 11

<Construction of Expression Plasmid for Malate Thiokinase Derived from *Methylobacterium extorquens* IAM12632>

*Methylobacterium extorquens* IAM 12632 was purchased from IAM Culture Collection, Institute of Molecular and Cellular Biosciences, the University of Tokyo. IAM 12632 was cultured in a medium (medium number: 352, NBRC), and chromosomal DNA was obtained therefrom using DNeasy Blood &Tissue Kit (QIAGEN).

PCR was carried out using the chromosomal DNA of *Methylobacterium extorquens* IAM 12632 as a template and using AAAAGGCGGAATTCACAAAAAGGA-TAAAACAATGGACGTTCACGAGTACCAAGC C (SEQ ID NO: 52) and CATGCCTGCAGGTCGACTCTAGAG-GCGAGGTTCTTTTTCCGGACTC (SEQ ID NO: 53) as primers, as a result of which a malate thiokinase fragment was obtained. In addition, PCR was carried out using the chromosomal DNA of *Methylobacterium extorquens* as a template and using GGATCCTCTAGACTGGTG-GAATATATGAGCTTCACCCTGATCCAGCAG (SEQ ID NO: 54) and GGCATGCAAGCTTTTACTTTCCGC-CCATCGCGTC (SEQ ID NO: 55) as primers, as a result of which a malyl-CoA lyase fragment was obtained. The malate thiokinase fragment and the malyl-CoA lyase fragment of *Methylobacterium extorquens* were ligated to pMWGKC, and the plasmid obtained was named pMWG-KC_mtk(Mex)_mcl.

pMWGKC_mtk(Mex)_mcl harbors the base sequence of the mcl gene (SEQ ID NO: 66), the base sequence of the mtkA gene (SEQ ID NO: 67), and the base sequence of the mtkB gene (SEQ ID NO: 68) derived from *Methylobacterium extorquens*. The amino acid sequences of mcl, mtkA, and mtkB derived from *Methylobacterium extorquens* are shown in SEQ ID NO: 69, SEQ ID NO: 70, and SEQ ID NO: 71, respectively.

Example 12

<Construction of Expression Plasmid for Malate Thiokinase Derived from *Hyphomicrobium methylovorum* NBRC 14180>

*Hyphomicrobium methylovorum* NBRC 14180 was purchased from NBRC (Biological Resource Center, Biotechnology Field, National Institute of Technology and Evaluation). NBRC 14180 was cultured in a medium (medium number: 233, NBRC), and chromosomal DNA was obtained therefrom using DNeasy Blood &Tissue Kit (QIAGEN).

A primer (SEQ ID NO: 56) was prepared based on the DNA sequence of the N-terminal region of serine-glyoxylate aminotransferase of NBRC 14180 (GenBank Accession No. D13739).

Based on the amino acid sequence of phosphoenolpyruvate carboxylase of *Hyphomicrobium denitrificans* (http://www.ncbi.nlm.nih.gov/nuccore/300021538?from=3218417&to=3221272&report=gbw ithparts), sequence homology was compared using a homology search tool by NCBI (National Center for Biotechnology Information) (http://blast.ncbinlm.nih.gov/Blast.cgi?PROGRAM=blastp&BLAST_PROGRAMS=blastp&PAGE_TYPE=BlastSearch&SHOW_DEFAULTS=on&LINK_LOC=blasthome).

A primer (SEQ ID NO: 57) was prepared based on an amino acid sequence having high homology.

PCR was carried out using primers of SEQ ID NO:56 and SEQ ID NO:57 obtained as described above and the chromosomal DNA obtained above as a template. The fragment obtained was ligated to a DNA prepared by digesting pUC19 with SmaI, whereby part of the phosphoenolpyruvate carboxylase gene was cloned from the serine-glyoxylate aminotransferase gene derived from *Hyphomicrobium methylovorum* NBRC 14180. After confirming the sequence of the clone, primers (SEQ ID NOs: 58 and 59) were prepared.

PCR was carried out using the chromosomal DNA of *Hyphomicrobium methylovorum* NBRC 14180 as a template and primers of SEQ ID NOs: 58 and 59 obtained as described above, and the DNA obtained was digested with EcoRI and XbaI, as a result of which a DNA fragment containing the mcl and mtk genes of *Hyphomicrobium* was obtained. In addition, the above-described plasmid pMWG-KC_mtk(Mex)_mcl was digested, and a fragment of about 4.3 kb containing mcl was recovered. This fragment obtained was ligated to the DNA fragment containing the mcl and mtk genes of *Hyphomicrobium*. The obtained plasmid was named pMWGKC_mcl(Hme)_mtk(Hme)_mcl.

pMWGKC_mcl(Hme)_mtk(Hme)_mcl contains the base sequence of the mcl gene (SEQ ID NO: 60), the base sequence of the mtkA gene (SEQ ID NO: 61), and the base sequence of the mtkB gene (SEQ ID NO: 62) derived from *Hyphomicrobium methylovorum*. The amino acid sequences of mcl, mtkA, and mtkB derived from *Hyphomicrobium methylovorum* are as shown in SEQ ID NO: 72, SEQ ID NO: 73 and SEQ ID NO: 74, respectively.

Example 13

<Construction of Expression Plasmid for Malate Thiokinase Derived from *Rhizobium* sp. NGR234>

Based on the amino acid sequence information of the malate thiokinase beta subunit (GenBank Accession No. ACP26381) and the succinyl-CoA synthetase alpha subunit (GenBank Accession No. ACP26382) of *Rhizobium* sp. NGR234, full length of the malate thiokinase gene was synthesized (SEQ ID NO: 63). The gene obtained was digested with NdeI and XbaI, and ligated to pMWGKC digested with NdeI and XbaI. The plasmid obtained was named pMWGKC_mtk(Rhi). Further, PCR was carried out using the chromosomal DNA of *Methylobacterium extorquens* as a template and primers of SEQ ID NOs: 64 and 65, and the DNA obtained was digested with XbaI and HindIII. The fragment obtained was subjected to blunt-end treatment, and ligated to a gene obtained by digesting MWGKC_mtk(Rhi) with XbaI and subjecting the resultant fragment to blunt-end treatment and phosphorylation treatment. A resulting plasmid in which the mtk gene and mcl gene were introduced in the same direction was named pMWGKC_mtk(Rhi)_mcl. The amino acid sequences of mtkA and mtkB derived from *Rhizobium* sp. are as shown in SEQ ID NO: 75 and SEQ ID NO: 76, respectively.

Example 14

<Preparation of Malate Thiokinase and Malyl-CoA Lyase-Introduced Isopropyl Alcohol-Producing Variant>

Competent cells of the *Escherichia coli* B variant (atoDAB, Δpgi_gntR_gnd_ldhA_aceBA_glcB_fumAC) prepared in Example 8 were transformed with the plasmid pIaz prepared in Example 9 and each of the plasmids expressing mtk and mcl. Transformants that grew on an LB agar plate containing 25 mg/L chloramphenicol and 100 mg/L ampicillin were named as follows (see Table 2).

The variant numbers in Table 2 represent the variants prepared by introducing pIaz and each of the plasmids described in Table 2 into the *Escherichia coli* B variant (atoDAB, Δpgi_gntR_gnd_ldhA_aceBA_glcB_fumAC).

TABLE 2

| Variant Number | Plasmid | mtk Origin | mcl Origin |
|---|---|---|---|
| MT-1 | pMWGKC_mtk(Mex)_mcl | Methylobacterium extorquens | Methylobacterium extorquens |
| MT-2 | pMWGKC_mcl(Hme)_mtk(Hme)_mcl | Hyphomicrobium methylovorum | Methylobacterium extorquens, Hyphomicrobium methylovorum |
| MT-3 | pMWGKC_mtk(Rhi)_mcl | *Rhizobium* sp. NGR234 | Methylobacterium extorquens |
| Control | pMWGKC | None | None |

Example 15

<Confirmation of Incorporation of $^{13}$C-Labeled $CO_2$ into Isopropyl Alcohol>

100 ml of LB liquid medium was added into 500-ml Erlenmeyer flask equipped with a baffle, and was sterilized by autoclaving at 121° C. for 20 minutes. To the sterilized medium, ampicillin was added to have a final concentration of 50 μg/ml, and chloramphenicol was added to have a final concentration of 34 μg/ml. Subsequently, one platinum loop of each of the variants shown in Table 2 having a carbon dioxide fixation pathway introduced thereto were inoculated into the medium, and cultured at 30° C. and 130 rpm for about 20 hours. Only the bacterial cells were separated from the culture liquid by centrifugation (5,000 G for 15 minutes), and then the separated bacterial cells were resuspended in 10 mL of physiologic saline, thereby obtaining the respective bacterial suspensions.

In a 100-mL Erlenmeyer flask, 30 mL of M9 minimal medium containing 100 mM $^{13}$C-labeled sodium hydrogen carbonate, 50 g/L glucose, 34 μg/ml chloramphenicol, and 50 μg/ml ampicillin was prepared. 3 mL of the bacterial suspension obtained above was inoculated into this medium, and cultured at 30° C., 100 rpm for 24 hours, while the flask was tightly sealed with a silicone plug. The culture liquid obtained was filtered under reduced pressure using a hydrophilic PTFE membrane filter (H050A047A, pore size: 0.5 μm; diameter: 47 mm; manufactured by ADVANTEC) placed in a filter holder for filtration under reduced pressure (KGS-47; manufactured by ADVANTEC), thereby separating the bacterial cells from the culture supernatant.

The membrane filter to which the bacterial cells were attached was immediately immersed in 1.6 mL methanol (LC/MS grade) cooled to −20° C. and stirred, and the membrane was left to stand at −20° C. for 1 hour. Thereafter, 1.6 mL of chloroform (HPLC grade) cooled to −20° C. and 0.64 mL of pure water cooled to 4° C. were added thereto, followed by vortex-mixing for 30 seconds. Subsequently, the supernatant was collected by centrifugal separation at 4° C., thereby obtaining a methanol extract of the bacterial cells. The obtained extract was analyzed by LC-MS/MS and the molecular weight distribution of acetyl-CoA in the bacterial cells was determined. The results are shown in Table 3. The molecular weight distribution of acetyl-CoA was calculated by defining the ratios of mass spectrometry peaks at molecular weights of 808, 809, and 810 as M+0, M+1, and M+2, respectively.

Separately, from the culture supernatant obtain above, alcohols and acetone were recovered at high concentrations by distillation, and used as raw materials for measurement of the molecular weight distribution. The molecular weight distributions of isopropyl alcohol and ethanol in the culture supernatant were analyzed by GC-MS. The results are shown in Tables 4 and 5. The molecular weight distribution of isopropyl alcohol (IPA) (Table 4) was calculated by defining the ratios of mass spectrometry peaks at molecular weights of 117, 118, and 119 from the as M+0, M+1, and M+2, respectively. The molecular weight distribution of ethanol (EtOH) (Table 5) was calculated by defining the ratios of mass spectrometry peaks at molecular weights of 103, 104, and 105 as M+0, M+1, and M+2, respectively.

TABLE 3

| Sample Name | M + 0 | M + 1 | M + 2 |
|---|---|---|---|
| MT-1 | 0.80 | 0.14 | 0.06 |
| MT-2 | 0.76 | 0.18 | 0.06 |
| Control | 0.81 | 0.13 | 0.06 |

TABLE 4

| Sample Name | M + 0 | M + 1 | M + 2 |
|---|---|---|---|
| MT-1 | 0.87 ± 0.01 | 0.10 ± 0.01 | 0.03 ± 0.00 |
| MT-2 | 0.84 ± 0.00 | 0.12 ± 0.00 | 0.04 ± 0.00 |
| Commercially available IPA | 0.87 ± 0.00 | 0.10 ± 0.00 | 0.04 ± 0.00 |

TABLE 5

| Sample Name | M + 0 | M + 1 | M + 2 |
|---|---|---|---|
| MT-1 | 0.87 ± 0.00 | 0.09 ± 0.00 | 0.04 ± 0.00 |
| MT-2 | 0.85 ± 0.01 | 0.11 ± 0.01 | 0.04 ± 0.00 |
| Commercially available EtOH | 0.88 ± 0.00 | 0.09 ± 0.00 | 0.03 ± 0.00 |

As shown in Table 3, the MT-1 variant and the MT-2 variant had a high ratio of acetyl-CoA into which $^{13}C$ was not incorporated (M+0) and a high ratio of acetyl-CoA into which one atom of $^{13}C$ was incorporated (M+1), as compared to the control strain. In particular, the ration of M+1 was high in the MT-2 variant. From this result, it was found that carbon derived from the $^{13}C$-labeled carbonate was incorporated into acetyl-CoA in the MT-1 variant and the MT-2 variant, and that the effect was especially pronounced for the MT-2 variant.

Furthermore, the MT-2 variant had a low ratio of isopropyl alcohol or ethanol into which $^{13}C$ was not incorporated (M+0) and a high ratio of isopropyl alcohol or ethanol into which one atom of $^{13}C$ was incorporated (M+1), as compared to the commercially available isopropyl alcohol or ethanol (Table 4 and Table 5). From this result, it was found that carbon derived from the $^{13}C$-labeled carbonate was incorporated also into isopropyl alcohol or ethanol in the MT-2 variant.

Example 16

<Measurement of Glyoxylate Production Activity Using Malate as Substrate>

The variants expressing mtk and mcl described above were cultured in 2 mL of LB medium containing 25 μg/ml chloramphenicol and 100 μg/ml ampicillin. A crude enzyme solution was extracted according to the following method. That is, bacterial cells in logarithmic growth phase were collected by centrifugation, and washed with 200 mM MOPS-K buffer (pH 7.7) and then dissolved in MOPS-K buffer, followed by sonication. The supernatant obtained by centrifugal separation (12,000 rpm for 2 minutes) was used as the crude enzyme solution.

The protein concentration in the crude enzyme solution was determined based on a calibration curve generated with OD values at 595 nm measured with a UV plate reader (Molecular Devices, SpectraMax 190) using the crude enzyme solution and known concentrations of BSA for preparing the calibration curve, each of which had been reacted with Quick Start Bradford Dye Reagent (manufactured by Bio-Rad Laboratories, Inc.) and subject to color development.

The enzymatic activity in the solution was determined according to the following procedure. That is, MOPS-K buffer (pH 7.7), 3.5 mM phenylhydrazine, 10 mM $MgCl_2$, 3 mM ATP, 0.3 mM CoA, and 10% by mass of crude enzyme solution were mixed in a microwell and the mixture was incubated at room temperature for 30 minutes. As background values, changes in OD values at 324 nm with time were measured using a UV plate reader. To the mixture, sodium (S)-L-malate solution (pH 7.5) was added to have a final concentration of 5 nm, and changes in OD values at 324 nm with time was measured. In order to generate a calibration curve for glyoxylate, glyoxylate was added to the above buffer and the mixture was left to stand for 5 minutes at room temperature and then OD values at 324 nm was measured. Regarding the value of enzymatic activity, the slope of the background values was subtracted from the slope of OD values at 324 nm after the addition of sodium (S)-L-malate, and the obtained value was converted into a glyoxylate consumption rate based on the calibration curve for glyoxylate. The enzymatic activity per protein was determined by dividing the glyoxylate consumption rate by the protein concentration (Table 6).

As shown in Table 6, it was confirmed that all of the MT-1, MT-2, and MT-3 variants have enzymatic activity. It was found that the MT-2 variant and the MT-3 variant have a higher enzymatic activity compared to the MT-1 variant. In contrast, no enzymatic activity was shown in the control.

TABLE 6

| Sample Name | Activity (nmol/min/mg protein) |
|---|---|
| MT-1 | 2 ± 0 |
| MT-2 | 29 ± 0 |
| MT-3 | 23 ± 0 |
| Control | 0 ± 0 |

Example 17

<Number of Viable Cells and Plasmid Retention Rate in Malate Thiokinase and Malyl-CoA Lyase-Introduced Variant>

In a 100-mL Erlenmeyer flask, 30 mL of M9 minimal medium or LB medium each containing 50 g/L glucose, 30 µg/ml chloramphenicol, and 100 µg/ml ampicillin was prepared. Each of the above variants expressing mtk and mcl were inoculated into the M9 minimal medium or LB medium and cultured at 30° C., 100 rpm for 24 hours, while the flask tightly sealed with a silicone plug. The culture liquid was diluted with water, and 100 µL of the diluted culture liquid was applied to an antibiotic-free LB plate. The total number of viable cells was counted. Furthermore, the diluted culture liquid was applied to an LB plate containing 30 µg/ml chloramphenicol, and the number of bacterial cells retaining the plasmid harboring mtk (smt) and mcl was counted.

As shown in Table 7, it was found that each of the MT-2 variant and the MT-3 variant had a higher number of viable cells in the culture liquid and grew better, as compared with the MT-1 variant. The plasmids harboring mtk and mcl were stably maintained in all of the MT-1, MT-2, and MT-3 variants.

TABLE 7

| Sample Name | Medium | Total Number of Viable cells | Number of Cells Having mtk-mcl Plasmid |
| --- | --- | --- | --- |
| MT-1 | M9 | $1.3 \times 10^6$/mL | $0.8 \times 10^6$/mL |
| MT-2 | M9 | $6.8 \times 10^8$/mL | $9.1 \times 10^8$/mL |
| MT-3 | LB | $2.6 \times 10^9$/mL | $9.2 \times 10^9$/mL |

Example 18

<Construction of Expression Plasmid for Malate Thiokinase Derived from *Granulibacter bethesdensis* BAA-1260>

The genomic DNA of *Granulibacter bethesdensis* BAA-1260D-5 was purchased from ATCC.

PCR was carried out using the genomic DNA of *Granulibacter bethesdensis* as a template and using CCCTGAGGAGGGTCCAAGAGATGGACGTCCATGAGTACCA (SEQ ID NO: 77) and GCTCTAGATCAGGCTGCCTGACGCCCA (SEQ ID NO: 78) as primers, as a result of which an mtk fragment of *Granulibacter* was obtained. In addition, PCR was carried out using pMWGKC_mcl(Hme)_mtk(Hme)_mcl prepared in Example 12 as a template and using GGAATTCACAAAAAGGATAAAA (SEQ ID NO: 79) and TGGTACTCATGGACGTCCATCTCTTGGACCCTCCTCAGGG (SEQ ID NO: 80) as primers, as a result of which an mcl fragment of *Hyphomicrobium* was obtained. PCR was carried out using the obtained mtk fragment of *Granulibacter* and mcl fragment of *Hyphomicrobium* as templates and primers of SEQ ID NO: 79 and SEQ ID NO: 78, thereby obtaining a DNA fragment containing mcl from *Hyphomicrobium* and the mtk fragment gene from *Granulibacter*. The DNA fragment obtained was digested with restriction enzymes EcoRI and XbaI, and ligated to the plasmid pMWGKC prepared in Example 10. The plasmid obtained was named pMWGKC_mcl(Hme)_mtk(Gb).

pMWGKC_mcl(Hme)_mtk(Gb) harbors the mtkA gene (SEQ ID NO: 81) and the mtkB gene (SEQ ID NO:82) derived from *Granulibacter bethesdensis*. The amino acid sequences of mtkA and mtkB derived from *Granulibacter bethesdensis* are shown in SEQ ID NO: 107 and SEQ ID NO: 108, respectively.

Example 19

<Construction of Expression Plasmid for Malate Thiokinase Derived from *Hyphomicrobium denitrificans* DSMZ 1869>

*Hyphomicrobium denitrificans* DSMZ 1869 was purchased from DSMZ (Deutsche Sammlung von Mikroorganismen and Zellkulturen GmbH, Germany). DSMZ 1869 was cultured in a medium (medium number: 803, DSMZ), and chromosomal DNA was obtained therefrom using DNeasy Blood &Tissue Kit (QIAGEN).

PCR was carried out using the chromosomal DNA of *Hyphomicrobium denitrificans* as a template and using ACCAGGGAATTCACAAAAAGGATAAAACAATGAGCTATACCCTCTACCCAACCGTA AGC (SEQ ID NO: 83) and GCCCACTCTAGATCAGGCAACTTTTTTCTGCTTGCCGAGAACC (SEQ ID NO: 84) as primers, as a result of which an mcl-mtk fragment of *Hyphomicrobium* was obtained. The fragment obtained was ligated to the plasmid pMWGKC_mcl(Hme) mtk(Hme)_mcl prepared in Example 12. The plasmid obtained was named pMWGKC_mcl(Hde)_mtk(Hde)_mcl.

pMWGKC_mcl(Hde)_mtk(Hde)_mcl harbors the base sequence of the mcl gene (SEQ ID NO: 85), the base sequence of the mtkA gene (SEQ ID NO: 86), and the base sequence of the mtkB gene (SEQ ID NO: 87) derived from *Hyphomicrobium denitrificans*. The amino acid sequences of mcl, mtkA, and mtkB derived from *Hyphomicrobium denitrificans* are shown in SEQ ID NO: 109, SEQ ID NO: 110, and SEQ ID NO: 111, respectively.

Example 20

<Construction of Expression Plasmid for Malate Thiokinase Derived from *Nitrosomonas europaea* NBRC 14298>

*Nitrosomonas europaea* NBRC 14298 was purchased from NBRC (Biological Resource Center, NITE). NBRC 14298 was cultured in a medium (medium number: 829, NBRC), and chromosomal DNA was obtained therefrom using DNeasy Blood &Tissue Kit (QIAGEN).

PCR was carried out using the chromosomal DNA of *Nitrosomonas europaea* as a template and using GCGGGGGAATTCACAAAAAGGATAAAACAATGAGTCATACCCTGTATGAACCAAA ACACC (SEQ ID NO: 88) and CAGGCGTCTAGATTAGAGTCCGGCCAGAACTTTTGCGACG (SEQ ID NO: 89) as primers, as a result of which an mtk fragment of *Nitrosomonas europaea* was obtained. The fragment obtained was ligated to the plasmid pMWGKC_mcl(Hme)_mtk(Hme)_mcl prepared in Example 12. The plasmid obtained was named pMWGKC_mcl(Ne)_mtk(Ne)_mcl.

pMWGKC_mcl(Ne)_mtk(Ne)_mcl harbors the base sequence of the mcl gene (SEQ ID NO: 90), the base sequence of the mtkA gene (SEQ ID NO: 91), and the base sequence of the mtkB gene (SEQ ID NO: 92) derived from *Nitrosomonas europaea*. The amino acid sequences of mcl, mtkA, and mtkB derived from *Nitrosomonas europaea* are shown in SEQ ID NO: 112, SEQ ID NO: 113, and SEQ ID NO: 114, respectively.

Example 21

<Construction of Expression Plasmids for Malate Thiokinase Derived from *Methylococcus capsulatus* ATCC 33009>

Genomic DNA of *Methylococcus capsulatus* ATCC 33009D-5 was purchased from ATCC.

PCR was carried out using the chromosomal DNA of *Methylococcus capsulatus* as a template and using GGAATTCCATATGGCTGTTAAAAATCGTCTAC (SEQ ID NO: 93) and GCTCTAGATCAGAATCTGATTCCGTGTTC (SEQ ID NO: 94) as primers, as a result of which an mcl-mtk fragment of *Methylococcus* was obtained. The fragment obtained was ligated to the plasmid pMWGKC prepared in Example 10 or to the plasmid pMWGC prepared in Example 10. The plasmid obtained was named pMWGKC_mcl(Mc)_mtk(Mc) or pMWGC_mcl(Mc)_mtk(Mc).

Each of pMWGKC_mcl(Mc)_mtk(Mc) and pMWGC_mcl(Mc)_mtk(Mc) harbours the base sequence of the mcl gene (SEQ ID NO: 95), the base sequence of the mtkA gene (SEQ ID NO: 96), and the base sequence of the mtkB gene (SEQ ID NO: 97) derived from *Methylococcus capsulatus*. The amino acid sequences of mcl, mtkA, and mtkB derived from *Methylococcus capsulatus* are shown in SEQ ID NO: 115, SEQ ID NO: 116, and SEQ ID NO: 117, respectively.

Example 22

<Construction of Expression Plasmid for Malate Thiokinase Derived from Uncultured Gamma Proteobacterium (GenBank: AP011641.1)>

In order to obtain mtk derived from an uncultured gamma proteobacterium, a gamma proteobacterium-derived mtk was designed based on the amino acid sequence of GenBank: AP011641.1, and the following DNA fragment (SEQ ID NO: 98) was prepared by DNA synthesis.

PCR was carried out using the prepared DNA fragment as a template and using GTTGAACGAGGAGATCGTCCATGAACATTCACGAATATCA (SEQ ID NO: 99) and GCTCTAGATTAGCCAGAAACTGCAGATCC (SEQ ID NO: 100) as primers, as a result of which an mtk fragment of the gamma proteobacterium was obtained. In addition, PCR was carried out using pMWGKC_mcl(Mc)_mtk(Mc) or pMWGC_mcl(Mc)_mtk(Mc) prepared in Example 21 as a template and using primers of SEQ ID NO: 93 and TGATATTCGTGAATGTTCATGGACGATCTCCTCGTTCAAC (SEQ ID NO: 101), thereby obtaining an mcl fragment of *Methylococcus*. In addition, PCR was carried out using the gamma proteobacterium mtk fragment obtained and the *Methylococcus* mcl fragment obtained as templates and using primers of SEQ ID NO: 93 and SEQ ID NO: 100, thereby obtaining a DNA fragment containing the mcl gene of *Methylococcus* and the mtk fragment gene of the gamma proteobacterium. The DNA fragment obtained was ligated to the plasmid pMWGKC prepared in Example 10. The plasmid obtained was named pMWGKC_mcl(Mc)_mtk(gamma).

pMWGKC_mcl(Mc)_mtk(gamma) harbors the mtkA gene (SEQ ID NO: 102) and the mtkB gene (SEQ ID NO: 103) derived from the uncultured gamma proteobacterium. The amino acid sequences of mtkA and mtkB derived from the uncultured gamma proteobacterium are shown in SEQ ID NO: 118 and SEQ ID NO:119, respectively.

Example 23

<Preparation of Malate Thiokinase- and Malyl-CoA Lyase-Introduced, Isopropyl Alcohol-Producing, atoD Genome-Enhanced, Pgi Gene-Deleted, gntR Gene-Deleted, Gnd Gene-Deleted, ldhA Gene-Deleted, fumAC Gene-Deleted, aceBA Gene-Deleted, glcB Gene-Deleted Variant>

Competent cells of the *Escherichia coli* B variant (atoDAB, Δpgi_gntR_gnd_ldhA_aceBA_glcB_fumAC) prepared in Example 8 were transformed with plasmid pIaz and each of the plasmids expressing mtk and mcl prepared in Examples 18 to 22. Transformants that grew on an LB agar medium containing 25 mg/L chloramphenicol and 100 mg/L ampicillin were named as follows (see Table 8).

The variant numbers described in Table 8 represent the variants prepared by introducing pIaz and each of the plasmids described in Table 8 into the *Escherichia coli* B variant (atoDAB, Δpgi_gntR_gnd_ldhA_aceBA_glcB_fumAC).

TABLE 8

| Variant Number | Plasmid | mtk Origin | mcl Origin |
| --- | --- | --- | --- |
| MT-4 | pMWGKC_mcl(Hme)_mtk(Gb) | Granulibacter bethesdensis | Hyphomicrobium methylovorum |
| MT-5 | pMWGKC_mcl(Hde)_mtk(Hde)_mcl | Hyphomicrobium denitrificans | Hyphomicrobium denitrificans, Methylobacterium extorquens |
| MT-6 | pMWGKC_mcl(Ne)_mtk(Ne)_mcl | Nitrosomonas europaea | Nitrosomonas europaea, Methylobacterium extorquens |
| MT-7 | pMWGKC_mcl(Mc)_mtk(Mc) | Methylococcus capsulatus | Methylococcus capsulatus |
| MT-8 | pMWGKC_mcl(Mc)_mtk(gamma) | Uncultured gamma proteobacterium DNA | Methylococcus capsulatus |

Example 24

<Measurement of Glyoxylate Production Activity Using Malate as Substrate>

In the same manner as in Example 16, the enzymatic activity per protein was determined (Table 9).

As shown in Table 9, it was confirmed that each of the MT-4 to MT-8 variants has enzymatic activity, and that the enzymatic activity was higher compared to the MT-1 variant. In particular, it was found that the MT-5 variant, the MT-6 variant, the MT-7 variant, and the MT-8 variant have an equivalent or higher activity compared to the MT-2 variant and the MT-3 variant shown in Example 16. In contrast, no enzymatic activity was detected in the control.

TABLE 9

| Sample Name | Activity (nmol/min/mg protein) |
|---|---|
| MT-4 | 7.5 ± 0 |
| MT-5 | 34.0 ± 0 |
| MT-6 | 54.0 ± 0 |
| MT-7 | 68.3 ± 0 |
| MT-8 | 43.4 ± 0 |
| MT-1 | 2 ± 0 |
| MT-2 | 29 ± 0 |
| MT-3 | 23 ± 0 |
| Control | 0 ± 0 |

Example 25

<Preparation of atoD Genome-Enhanced, aceB Gene-Deleted Variant>

In order to clone a region flanking the base sequence of the gene encoding malate synthase (hereinafter sometimes abbreviated to "aceB") (1602 bp), four types of oligonucleotide primers represented by GGAATTCATTCAGCTGTTGCGCATCGATTC (SEQ ID NO: 24), GTTATGTGGTGGTCGTGCAGCTCCTCGTCATGG (SEQ ID NO: 104), GAGCTGCACGACCACCACATAACTATGGAG (SEQ ID NO: 105), and GGAATTCCAGTTGAACGACGGCGAGCAG (SEQ ID NO: 106) were synthesized. Each of these primers has an EcoRI recognition site in the 5'-end side thereof.

The genomic DNA of the *Escherichia coli* B (accession No. CP000819) was prepared, and PCR was carried out using the obtained genomic DNA as a template and using a primer pair of SEQ ID NO: 24 and SEQ ID NO: 106, as a result of which a DNA fragment of about 1.0 kb (hereinafter sometimes referred to as "aceB-L fragment") was amplified. In addition, PCR was carried out using a primer pair of SEQ ID NO: 105 and SEQ ID NO: 106, as a result of which a DNA fragment of about 1.0 kb (hereinafter sometimes referred to as "aceB-R fragment") was amplified. These DNA fragments were separated by agarose electrophoresis, and recovered. PCR was carried out using the aceB-L and aceB-R fragments as templates and using a primer pair of SEQ ID NO: 24 and SEQ ID NO: 108, as a result of which a DNA fragment of about 2.0 kbp (hereinafter sometimes referred to as "aceB-LR fragment") was amplified. The aceB-LR fragment was separated by agarose electrophoresis, and recovered, digested with EcoRI, and mixed with a fragment obtained by digesting a temperature-sensitive plasmid pTH18cs1 (GenBank accession number AB019610) with EcoRI and dephosphorylating the same. The mixed fragments were allowed to react using T4 DNA ligase. Thereafter, *Escherichia coli* DH5α competent cells (manufactured by Toyobo Co., Ltd.) were transformed with the ligation product, and transformants that grew on an LB agar plate containing 10 μg/ml chloramphenicol at 30° C. were obtained. A plasmid was recovered from the transformants obtained, and it was confirmed that the aceB-LR fragment was properly inserted in pTH18cs1. The plasmid obtained was named pTH18cs1-aceB.

The *Escherichia coli* B::atoDAB variant prepared in Example 1 was transformed with the thus-obtained plasmid pTH18cs1-aceB, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Subsequently, part of the culture liquid was applied to an LB agar plate containing 10 μg/ml chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the aceB gene, could be amplified was selected. The variant obtained was named atoD genome-enhanced, aceB gene-deleted variant (hereinafter sometimes abbreviated to "B::atoDABΔaceB variant").

Example 26

<Preparation of atoD Genome-Enhanced, aceB Gene-Deleted, glcB Gene-Deleted Variant>

The *Escherichia coli* B::atoDABΔaceB variant prepared in Example 25 was transformed with the plasmid pTH18cs1-gclB prepared in Example 7, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Subsequently, part of the culture liquid was applied to an LB agar plate containing 10 μg/ml chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the AglcB gene, could be amplified was selected. The variant obtained was named atoD genome-enhanced, aceB gene-deleted, glcB gene-deleted variant (hereinafter sometimes abbreviated to "B::atoDABΔaceBΔgclB variant").

Example 27

<Preparation of atoD Genome-Enhanced, ldhA Gene-Deleted Variant>

The *Escherichia coli* B::atoDAB variant prepared in Example 1 was transformed with the plasmid pTH18cs1-ldhA prepared in Example 5, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Subsequently, part of the culture liquid was applied to an LB agar plate containing 10 μg/ml chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp, which indicates deletion of the ldhA gene, could be amplified was selected. The variant obtained was named atoD genome-enhanced, ldhA gene-deleted variant (hereinafter sometimes abbreviated to "B::atoDABΔldhA variant").

Example 28

<Preparation of pBRgapP, pMWGC_mcl(Mc)_mtk(Mc)/B Variant and pBRgapP, pMWGC/B Variant>

Competent cells of *Escherichia coli* B was transformed with the plasmid pBRgapP prepared in Example 2, and the plasmid pMWGC_mcl(Mc)_mtk(Mc) prepared in Example 21 or the plasmid pMWGC prepared in Example 21, and applied to an LB agar plate containing 25 mg/L chloramphenicol and 100 mg/L ampicillin. As a result, transformants that grew on the medium were obtained.

Example 29

<Preparation of pIa, pMWGC_mcl(Mc)_mtk(Mc)/B::atoDAB Variant, and pIa, pMWGC/B::atoDAB Variant>

Competent cells of the *Escherichia coli* B variant (B::atoDAB) prepared in Example 1 were transformed with the plasmid pIa prepared in Example 9, and the plasmid pMWGC_mcl(Mc)_mtk(Mc) prepared in Example 21 or the plasmid pMWGC prepared in Example 21, and applied to an LB agar plate containing 25 mg/L chloramphenicol and 100 mg/L ampicillin. As a result, transformants grew on the medium were obtained.

Example 30

<Preparation of pIa, pMWGC_mcl(Mc)_mtk(Mc)/B::atoDABΔaceB Variant, and pIa, pMWGC/B::atoDABΔaceB Variant>

Competent cells of the *Escherichia coli* B variant (B::atoDABΔaceB) prepared in Example 25 were transformed with the plasmid pIa prepared in Example 9, and the plasmid pMWGC_mcl(Mc)_mtk(Mc) prepared in Example 21 or the plasmid pMWGC prepared in Example 21, and applied on an LB agar medium containing 25 mg/L chloramphenicol and 100 mg/L ampicillin, and transformants grown on the medium were obtained.

Example 31

<Preparation of pIa, pMWGC_mcl(Mc)_mtk(Mc)/B::atoDABΔaceBΔglcB Variant, and pIa, pMWGC/B::atoDABΔaceBΔglcB Variant>

Competent cells of the *Escherichia coli* B variant (B::atoDABΔaceBΔglcB) prepared in Example 26 were transformed with the plasmid pIa prepared in Example 9, and the plasmid pMWGC_mcl(Mc)_mtk(Mc) prepared in Example 21 or the plasmid pMWGC prepared in Example 21, and applied on an LB agar medium containing 25 mg/L chloramphenicol and 100 mg/L ampicillin. As a result, transformants grew on the medium were obtained.

Example 32

<Preparation of pIa, pMWGC_mcl(Mc)_mtk(Mc)/B::atoDABΔldhA Variant, and pIa, pMWGC/B::atoDABΔldhA Variant>

Competent cells of the *Escherichia coli* B variant (B::atoDABΔldhA) prepared in Example 27 were transformed with the plasmid pIa prepared in Example 9, and the plasmid pMWGC_mcl(Mc)_mtk(Mc) prepared in Example 21 or the plasmid pMWGC prepared in Example 21, and applied on an LB agar medium containing 25 mg/L chloramphenicol and 100 mg/L ampicillin. As a result, transformants grew on the medium were obtained.

Example 33

<Production of Isopropyl Alcohol>

In this example, isopropyl alcohol was produced using a production apparatus shown in FIG. 1 of WO 2009/008377. The culture tank used was a tank having a capacity of 3 L and made of glass. Into the trap tanks, water as a trap solution (trap water) in an amount of 9 L per tank was injected, and the two trap tanks were connected to for use.

A list of variants used in the evaluation of isopropyl alcohol production is shown in Table 10.

TABLE 10

| Variant Name | Plasmid/ Variant | Feature | Referenced Description |
|---|---|---|---|
| vec/B | pBRgapP, pMWGC/B | No IPA producing system, no expression of mtk and mcl | Example 28 |
| mtk_mcl/B | pBRgapP, pMWGC_mcl(Mc)_mtk(Mc)/B | No IPA producing system, expression of mtk and mcl | Example 28 |
| vec/atoDAB | pIa, pMWGC/B::atoDAB | Containing IPA producing system, no expression of mtk and mcl | Example 29 |
| mtk_mcl/atoDAB | pIa, pMWGC_mcl(Mc)_mtk(Mc)/B::atoDAB | Containing IPA producing system, expression of mtk and mcl | Example 29 |
| vec/atoDAB ΔaceB | pIa, pMWGC/B::atoDABΔaceB | Containing IPA producing system, no expression of mtk and mcl, disruption of aceB gene | Example 30 |
| mtk_mcl/atoDAB ΔaceB | pIa, pMWGC_mcl(Mc)_mtk(Mc)/B::atoDAB ΔaceB | Containing IPA producing system, expression of mtk and mcl, disruption of aceB gene | Example 30 |
| vec/atoDAB ΔaceBΔglcB | pIa, pMWGC/B::atoDABΔaceBΔglcB | Containing IPA producing system, no expression of mtk and mcl, disruption of aceB and glcB genes | Example 31 |
| mtk_mcl/atoDAB ΔaceBΔglcB | pIa, pMWGC_mcl(Mc)_mtk(Mc)/ B::atoDABΔaceBΔglcB | Containing IPA producing system, expression of mtk and mcl, disruption of aceB and glcB genes | Example 31 |
| vec/atoDABΔldhA | pIa, pMWGC/B::atoDABΔldhA | Containing IPA producing system, no expression of mtk and mcl, disruption of ldhA gene | Example 32 |
| mtk_mcl/atoDAB ΔldhA | pIa, pMWGC_mcl(Mc)_mtk(Mc)/ B::atoDABΔldhA | Containing IPA producing system, expression of mtk and mcl, disruption of ldhA gene | Example 32 |

As preculture, each of the variants to be evaluated was individually inoculated into an Erlenmeyer flask having a capacity of 500 mL and containing 50 mL of a Miller's LB broth (Difco 244620) that contains 25 mg/L chloramphenicol and 100 mg/L ampicillin, and cultured overnight at a culture temperature of 30° C. while stirring at 120 rpm. Thereafter, 45 mL of the preculture was transferred to a culture tank (culture device BMS-PI manufactured by ABLE corporation) having a capacity of 3 L and containing 900 g of the medium having the following composition, and was cultured. The culture was carried out at an aeration volume of 0.45 L/min, a stirring rate of 490 rpm, a culture temperature of 30° C., and a pH of 7.0 (adjusted with $NH_3$ aqueous solution) under atmospheric pressure. To the culture, a 50 wt/wt % glucose aqueous solution was added at a flow rate of 20 g/L/hour during the period from the initiation of the cultivation to 8 hours after the initiation of the cultivation. Thereafter, a 50 wt/wt % glucose aqueous solution was added at a flow rate of 20 g/L/hour, as appropriate, such that the amount of glucose left in the culture tank was minimized. The bacterial culture liquid was sampled several times during the period from the initiation of the cultivation to 30 hours after the initiation of the cultivation, and, after the bacterial cells were removed by centrifugal operation, the amounts of isopropyl alcohol, acetone, and major byproducts accumulated in the culture supernatants and trap waters obtained were measured by HPLC according to an ordinary method. Each of the measurement values is a sum of the amounts in the culture liquid and the two trap tanks after the cultivation. The results are shown in Table 11, and the byproducts are shown in Table 12.

TABLE 11

| Variant Name | Production Amount (g/30 h) | | Glucose Usage (g/30 h) | Yield Relative to Sugar Consumption (30 h) | |
|---|---|---|---|---|---|
| | IPA | Acetone | | IPA | IPA + Acetone |
| vec/B | — | — | 212.7 | — | — |
| mtk_mcl/B | — | — | 257.9 | — | — |
| vec/atoDAB | 33.2 | 6.0 | 210.0 | 15.8 | 18.6 |
| mtk_mcl/atoDAB | 34.6 | 8.8 | 209.5 | 16.5 | 20.7 |
| vec/atoDAB ΔaceB | 30.8 | 6.1 | 205.3 | 15.0 | 18.0 |
| mtk_mcl/atoDAB ΔaceB | 32.8 | 6.6 | 202.6 | 16.2 | 19.5 |
| vec/atoDAB ΔaceBΔglcB | 31.9 | 5.5 | 204.1 | 15.6 | 18.4 |
| mtk_mcl/atoDAB ΔaceBΔglcB | 31.9 | 5.6 | 195.3 | 16.3 | 19.1 |
| vec/atoDABΔldhA | 32.0 | 5.3 | 197.2 | 16.2 | 18.9 |
| mtk_mcl/atoDAB ΔldhA | 38.6 | 6.8 | 197.9 | 17.4 | 21.3 |

TABLE 12

| Variant Name | Byproducts (g/L/30 h) | | | | | | | |
|---|---|---|---|---|---|---|---|---|
| | Ethanol | Pyruvate | Succinate | Lactate | Formate | Acetate | Fumarate | Total Amount of Byproducts |
| vec/B | 0.3 | 0.5 | 1.8 | 0.3 | 0.6 | 28.1 | 0.0 | 31.6 |
| mtk_mcl/B | 0.4 | 0.1 | 0.5 | 0.4 | 0.3 | 28.2 | 0.0 | 29.8 |
| vec/atoDAB | 2.5 | 1.3 | 5.8 | 9.2 | 2.6 | 4.6 | 0.2 | 26.1 |
| mtk_mcl/atoDAB | 2.0 | 0.0 | 5.0 | 6.3 | 5.6 | 4.5 | 0.2 | 23.4 |
| vec/atoDABΔaceB | 2.8 | 0.1 | 2.4 | 1.1 | 4.0 | 3.8 | 0.0 | 14.3 |
| mtk_mcl/atoDABΔaceB | 1.7 | 0.1 | 1.9 | 1.3 | 3.3 | 3.5 | 0.1 | 11.8 |
| vec/atoDABΔaceBΔglcB | 2.6 | 0.1 | 1.7 | 0.7 | 4.0 | 3.7 | 0.1 | 12.8 |
| mtk_mcl/atoDABΔaceBΔglcB | 1.3 | 0.1 | 2.2 | 0.9 | 3.0 | 3.3 | 0.1 | 10.8 |
| vec/atoDABΔldhA | 3.3 | 4.5 | 4.0 | 0.0 | 3.9 | 3.8 | 0.3 | 19.6 |
| mtk_mcl/atoDABΔldhA | 1.9 | 0.7 | 2.2 | 0.0 | 5.7 | 4.6 | 0.0 | 15.2 |

<Composition of Culture Medium>

Corn steep liquor (manufactured by Nihon Shokuhin Kako Co., Ltd.), 50 g/L
$Fe_2SO_4 \cdot 7H_2O$: 0.1 g/L
$K_2HPO_4$: 2 g/L,
$KH_2PO_4$: 2 g/L
$MgSO_4 \cdot 7H_2O$: 2 g/L
$(NH_4)_2SO_4$: 2 g/L
ADEKANOL LG126 (ADEKA Corporation): 0.1 g/L
(Blance: water)

As a result of the evaluation, the amount of isopropyl alcohol produced by the control strain (vec/atoDAB) was 33.2 g/30 h, and the amount produced by the mtk-introduced variant (mtk_mcl/atoDAB) was 34.6 g/30 h. The amount of acetone produced was 6.0 g/30 h in the control strain (vec/atoDAB), and 8.8 g/30 h in the mtk-introduced variant (mtk_mcl/atoDAB). From these results, it was found that the production amounts of isopropyl alcohol and acetone are increased by the introduction of mtk and mcl. The yield of isopropyl alcohol relative to sugar consumption at 30 hours after the initiation of the cultivation was 15.8% in the control strain (vec/atoDAB), and 16.5% in the mtk+mcl-introduced variant (mtk_mcl/atoDAB). The yield of isopropyl alcohol and acetone relative to sugar consumption at 30 hours after the initiation of the cultivation was 18.6% in the control strain (vec/atoDAB), and 20.7% in the mtk+mcl-introduced variant (mtk_mcl/atoDAB). From these results, it was shown that the conversion efficiencies of sugar into isopropyl alcohol or acetone were increased by the introduction of the mtk+mcl pathway.

Regarding atoDABΔldhA, the production amounts of isopropyl alcohol and acetone and the yields of isopropyl alcohol and acetone relative to sugar consumption were improved in the mtk+mcl-introduced variant similarly to the case of atoDAB. Regarding atoDABΔldhA, atoDABΔaceB, and atoDABΔaceBΔglcB, the yields relative to sugar consumption were increased in the mtk+mcl-introduced variant, as compared with that of the control strain (vec) of each variant. Therefore, it is thought that the production of acetyl-CoA and the useful substances derived from acetyl-CoA were efficiently increased by mtk+mcl.

Table 12 shows the byproducts. Compared with the control strain (vec/B), it was found that the amounts of ethanol, pyruvate, and succinate were reduced in the mtk+mcl-introduced variant (mtk_mcl/B) at 30 hours after the initiation of the cultivation, and the total amount of byproducts was also unexpectedly reduced in the mtk+mcl-introduced variant. Similarly, regarding atoDAB, atoDABΔaceB, atoDABΔaceBΔglcB, and atoDABΔldhA, the amounts of ethanol, pyruvate, and succinate and the total amount of byproducts were reduced in the mtk+mcl-introduced variants as compared with the respective control strains. From these results, it was found that mtk+mcl produced similar effects with or without atoDAB.

Regarding atoDABΔaceB and atoDABΔaceBΔglcB, the yield of IPA and the yield of IPA and acetone relative to sugar consumption were almost the same as those in the atoDAB variant. However, the total amount of byproducts was reduced in both the vec-introduced variants and the mtk-introduced variants. Unexpectedly, the amounts of lactate and succinate accumulated were significantly decreased in the mtk+mcl-introduced variants. Therefore, atoDABΔaceB and atoDABΔaceBΔglcB are industrially preferable, since a smaller amount of byproducts allow a significant reduction in the purification load when isopropyl alcohol or acetone is collected from a culture liquid.

Regarding atoDABΔldhA, it was shown that the production amounts of alcohol and acetone and the yields of alcohol and acetone relative to sugar consumption were improved in the mtk+mcl introduced variant similarly to the case of atoDAB. Regarding all of the above variants, the yields relative to sugar consumption were improved in the mtk+mcl-introduced variants as compared with the control strain (vec). Therefore, it is thought that acetyl-CoA and the useful substances derived from acetyl-CoA were efficiently increased.

Regarding atoDABΔldhA, the total amount of byproducts was reduced, and the amount of pyruvate accumulated was significantly reduced in the mtk+mcl-introduced variant. Furthermore, the yields of isopropyl alcohol and acetone relative to sugar consumption were increased in the mtk+mcl-introduced atoDABΔldhA variant, indicating that isopropyl alcohol and acetone were efficiently produced by both the glucose and mtk+mcl pathways. The amount of byproducts in atoDABΔldhA was reduced similarly to the cases of atoDABΔaceB and atoDABΔaceBΔglcB. In addition, the yields of isopropyl alcohol and acetone relative to sugar consumption was improved in atoDABΔldhA when mtk+mcl was introduced. These results indicate that, in the industrial production of isopropyl alcohol and/or acetone, disruption of ldhA is preferable in view of reducing the purification load during collection of isopropyl alcohol and/or acetone and in view of increasing their yields.

The isopropyl alcohol production pathway and acetone production pathway have not been introduced into the B variants. Since the amount of acetate was significantly increased in the B variants, it is thought that acetyl-CoA was mainly converted into acetate. Further, it is assumed that the increased acetyl-CoA was converted into acetate and ethanol in the mtk+mcl-introduced variant (mtk_mcl/B). These results indicate that the amount of acetyl-CoA was increased by the effect of mtk+mcl even in the B variants.

Example 34

<Construction of Plasmid pGAPS>

In order to obtain a spectinomycin-resistance gene, amplification by a PCR method was carried out using plasmid pIC156 (Steinmetz et. Al., Gene, 1994, 142(1): 79-83) as a template and CCGCGGTACCGTATAATAAAGAATAATTATTAATCTGTAGACAAATTGTGAAAGG (SEQ ID NO: 120) and CTTTTGTTTATAAGTGGGTAAACCGTGAATATCGTGTTCTTTTCAC (SEQ ID NO: 121), and the DNA fragment obtained was phosphorylated using T4 Polynucleotide kinase (Toyobo), as a result of which a DNA fragment containing a spectinomycin-resistance gene was obtained. In addition, the plasmid pGAP was treated with PvuI, and the DNA fragment obtained was subjected to blunt-end treatment with Toyobo BLUNTING HIGH, and ligated to the above-described DNA fragment containing the spectinomycin-resistance gene. Thereafter, Escherichia coli DH5α competent cells were transformed with the ligation product, and transformants that grew on an LB agar plate containing 120 μg/mL spectinomycin were obtained. The colonies obtained were cultured overnight in an LB liquid medium containing 120 μg/mL spectinomycin, and the plasmid obtained was named pGAPS.

Example 35

<Preparation of Plasmid pGAPS_gcl>

Chromosomal DNA was obtained from Escherichia coli MG1655 using DNeasy Blood &Tissue Kit (QIAGEN). Based on the operon containing glyoxylate carboligase (gcl, NCBI-GI: 945394), two types of primers represented by AAGAACTCTAGAACAAAAAGGATAAAACAATGGCAAAAATGAGAGCCGTTGACG CGGCAATG (SEQ ID NO: 122) and GACCAGCTGCAGTCAGGCCAGTTTATGGTTAGCCATTAATTCCAGC (SEQ ID NO: 123) were prepared.

Further, two types of primers represented by ACACAACTGCAGACAAAAAGGATAAAACAATGAAGATTGTCATTGCGCCAGACTC TTTTAAAGAGAGCT (SEQ ID NO: 124) and GCCCCCAAGCTTTCAGTTTTTAATTCCCTGACCTATTTTAATGGCGCAGG (SEQ ID NO: 125) were prepared.

Amplification by PCR was carried out the chromosomal DNA of Escherichia coli MG1655 as a template and using primers of SEQ ID NOs: 122 and 123 obtained as described above, as a result of which a DNA fragment of about 3 kb was obtained. In addition, amplification by PCR was carried out using the chromosomal DNA of Escherichia coli MG1655 as a template and using primers of SEQ ID NOs:124 and 125 obtained as described above, as a result of which a DNA fragment of about 1.1 kb was obtained. These DNAs obtained were digested with PstI, and these fragments were ligated together. Amplification by PCR was carried out using the ligated DNA as a template and using AAGAACTCTAGAACAAAAAGGATAAAACAATG-GCAAAAATGAGAGCCGTTGACG CGGCAATG (SEQ ID NO: 126) and GCCCCCAAGCTTTCAGTTTTTAAT-TCCCTGACCTATTTTAATGGCGCAGG (SEQ ID NO: 127) as primers, as a result of which a DNA fragment was obtained. The DNA fragment obtained was digested with restriction enzymes XbaI and HindIII, and ligated to a plasmid pGAPS that had been digested with restriction enzymes XbaI and HindIII. Thereafter, *Escherichia coli* DH5α was transformed with the ligation product, and cultured on an LB agar plate containing spectinomycin, and a plasmid was recovered from transformants obtained.

The plasmid was digested with restriction enzymes ClaI and HindIII, and a DNA fragment of about 4 kb harboring pGAPS and the gcl gene was recovered. The DNA fragment was subjected to blunt-end treatment and self-ligation. *Escherichia coli* DH5α was transformed with the ligation product, and cultured on an LB agar plate containing 120 μg/mL spectinomycin. Bacterial cells that grew on the plate were cultured in an LB liquid medium containing 120 μg/mL spectinomycin, as a result of which transformants were obtained. A plasmid was recovered from the transformants obtained, as a result of which plasmid pGAPS_gcl was obtained.

Example 36

<Obtaining *Pantoea ananatis* PA Variant>

Plasmid RSFCPG was recovered from *Pantoea ananatis* AJ13601 (patent deposited strain BP-7207). The plasmid RSFCPG is a tetracycline resistance plasmid having the enzymes glutamate dehydrogenase, citrate synthase, and phosphoenolpyruvate carboxylase that catalyze the reaction of L-glutamate biosynthesis (JP-A No. 2001-333769). *Pantoea ananatis* AJ417 (patent deposited strain BP-8646) was transformed with RSFCPG using the CaCl$_2$ method (Molecular Cloning, 3rd edition, Cold Spring Harbor press, 2001), and cultured in an LB liquid medium containing 10 μg/mL tetracycline, as a result of which *Pantoea ananatis* AJ417/RSFCPG (hereinafter sometimes abbreviated to "PA variant") was obtained.

Example 37

<Preparation of *Pantoea ananatis* aceB Gene-Deleted Variant>

The whole sequence of the genomic DNA of *Pantoea ananatis* AJ13355 (patent deposited strain BP-6614) is known (GenBank accession number AP012032), and the base sequence of the gene encoding malate synthase of *Pantoea ananatis* (hereinafter sometimes referred to as "PAaceB") has also been reported (GenBank accession number NC_017531). In order to clone a region flanking the base sequence of the gene encoding aceB (1,599 bp), four types of oligonucleotide primers represented by GACTCTA-GAGGATCCCCGGGATGACAGACTCGGTTAT-CAACAGTGAATTACTTTTC AG (SEQ ID NO: 128), GACGGGACGGCGGCTTTGTTGGCTTCCGCGTTAT-GAAAAAAGTAGAGAGC (SEQ ID NO: 129), TTGAGA-CACAACGTGGCTTTCCCAGCAAGGACAGCGCGCG-CAATGAATG (SEQ ID NO: 130), and ATGACCATGATTACGAATTCTCAGGGAAGCAGGCG-GTAGCCTGGCAGAGTCAG (SEQ ID NO: 131) were synthesized.

Further, in order to clone a kanamycin-resistance gene, two types of oligonucleotide primers represented by TTTTTCATAACGCGGAAGCCAACAAAGCCGC-CGTCCCGTCAAGTCAGC (SEQ ID NO: 132) and CGCGCGCTGTCCTTGCTGGGAAAGCCACGTTGT-GTCTCAAAATCTCTGATGTTACA TTGC (SEQ ID NO: 133) were synthesized.

The genomic DNA of *Pantoea ananatis* AJ417 was prepared, and amplification by PCR was carried out using the obtained genomic DNA as a template and a primer pair of SEQ ID NO: 128 and SEQ ID NO: 129, as a result of which a DNA fragment containing a sequence flanking the aceB gene (hereinafter sometimes referred to as "PAaceB-L fragment") was obtained. In addition, amplification by PCR was carried out using a primer pair of SEQ ID NO:130 and SEQ ID NO: 131, as a result of which a DNA fragment containing a sequence flanking the aceB gene (hereinafter sometimes referred to as "PAaceB-R fragment") was obtained. Further, amplification by PCR was carried out using plasmid pUC4K having a kanamycin-resistance gene and using a primer pair of SEQ ID NO: 132 and SEQ ID NO: 133, as a result of which a DNA fragment containing the kanamycin resistance gene (hereinafter sometimes referred to as "KanR fragment") was amplified. Plasmid pUC18 was treated with EcoRI and XmaI, thereby preparing a pUC18 fragment. These PAaceB-L fragment, PAaceB-R fragment, KanR fragment, and pUC18 fragment were recovered, and the fragments were mixed together and treated using In-fusion HD cloning kit (Invitrogen). *Escherichia coli* DH5α competent cells (NEB5α; New England Biolabs) were transformed with the reaction product, and cultured on an LB plate containing 30 μg/mL kanamycin. A plasmid was recovered from a transformants obtained, and it was confirmed by DNA sequencing that the pUC 18 vector was constructed such that the sequence of "the 5'-flanking sequence of aceB_kanamycin-resistance gene_the 3'-flanking sequence of aceB" was included. PCR was carried out using this plasmid as a template and using GCCGCCGAATTC-CCGAAAAGTGCCACCTGACGTCTAAGAAACC (SEQ ID NO: 134) and ATGACCATGATTACGAATTCTCA-GGGAAGCAGGCGGTAGCCTGGCAGAGTCAG (SEQ ID NO: 135). The amplification product was purified and digested with EcoRI, followed by self-ligation of the resulting fragment using DNA ligase (Takara), as a result of which a plasmid having no replication origin was obtained. *Pantoea ananatis* AJ417 was transformed with the plasmid obtained, and cultured on an LB plate containing 30 μg/mL kanamycin. The colonies obtained were subjected to genomic PCR and DNA sequencing, and it was confirmed that the aceB gene was properly deleted. The bacteria obtained were transformed with RSFCPG using the CaCl$_2$ method, and cultured in LB medium containing 10 μg/mL tetracycline. The variant obtained was named the *Pantoea ananatis* AJ417 aceB gene-deleted variant (hereinafter sometimes abbreviated to "PAΔaceB variant").

Example 38

<Preparation of *Pantoea ananatis* fumA Gene-Deleted Variant>

The genomic DNA of *Bacillus subtilis* subsp. *subtilis* str. 168 (ATCC 23857) was prepared, and amplification by a PCR method was carried out using the obtained genomic DNA as a template and using AGTCTAGAGATCCTTTT-TAACCCATCAC (SEQ ID NO: 136) and AGTCTA-GAAGTCGATAAACAGCAATATT (SEQ ID NO: 137) as primers. The DNA fragment obtained was digested with restriction enzyme XbaI, thereby obtaining a DNA fragment of about 2.0 kbp containing the sacB gene. The DNA fragment obtained was mixed with a DNA fragment prepared by digesting plasmid pHSG298 (Takara) with restriction enzyme XbaI and subjecting the resulting product to alkaline phosphatase treatment, and the mixed fragments were ligated using a ligase. *Escherichia coli* DH5α competent cells (Toyobo Co., Ltd., DNA-903) were transformed with the resulting ligation product, and transformants that grew on an LB agar plate containing 25 μg/mL kanamycin were obtained. A plasmid was recovered from the bacterial cells obtained, as a result of which the plasmid pHSG-sacB, in which the DNA fragment containing the sacB gene was inserted in pHSG298, was obtained.

The whole sequence of the plasmid pEA320, originally found in *Pantoea ananatis* AJ13355, is known (NCBI Reference Sequence NC_017533.1), and the base sequence of the gene encoding fumarate hydratase class I (hereinafter sometimes referred to as "fumA") has also been reported. In order to clone a region flanking the base sequence of the gene encoding fumA (1,647 bp), four types of oligonucleotide primers represented by GCAACGTTGGCTCTCATCT (SEQ ID NO: 138), CGGGATCCAAACACGCGGCGGAAAACA (SEQ ID NO: 139), CGGGATCCGTTAACGCAGGCTGAC (SEQ ID NO: 140), and GCTGCTGGCGTACTGGTTC (SEQ ID NO: 141) were synthesized.

The genomic DNA of *Pantoea ananatis* AJ417 was prepared, and PCR was carried out using the obtained genomic DNA as a template and using a primer pair of SEQ ID NO:138 and SEQ ID NO:139, as a result of which a DNA fragment of about 0.7 kb (hereinafter sometimes referred to as "fumA-L fragment") was amplified. In addition, PCR was carried out using a primer pair of SEQ ID NO:140 and SEQ ID NO:141, as a result of which a DNA fragment of about 0.9 kb was amplified (hereinafter sometimes referred to as "fumA-R fragment") was amplified.

These DNA fragments were separated by agarose electrophoresis and recovered, and each of the fumA-L fragment and the fumA-R fragment was digested with BamHI. The resulting fragments were ligated using a ligase, and the 5'-ends of the ligated product was phosphorylated using T4 polynucleotide kinase. The DNA fragment obtained was mixed with a DNA fragment prepared by digesting the above-described pHSG-sacB with BamHI and further subjecting the resulting product to blunt-end treatment with T4 DNA polymerase and alkaline phosphatase treatment, and the mixed fragments were ligated using a ligase. Thereafter, *Escherichia coli* DH5α competent cells (manufactured by Toyobo Co., Ltd.) were transformed with the ligation product, and transformants that grew on an LB agar plate containing 25 μg/ml kanamycin at 30° C. were obtained. A plasmid was recovered from an obtained transformants, and it was confirmed that the two fragments—the 5'-upstream flanking region fragment and 3'-downstream flanking region fragment of the gene encoding fumA—were properly inserted in pHSG-sacB. The plasmid obtained was named psacB-PAfumA.

The plasmid psacB-PAfumA is replicable in *Pantoea ananatis*. Therefore, in order to obtain a plasmid for deleting fumA gene that lacks a replication origin and would not be replicated in *Pantoea ananatis*, amplification by PCR was carried out using psacB-PAfumA as a template and a primer pair of CITIACACTTTATGCTTCC (SEQ ID NO: 142) and TTGAGCTCGAGAGGTCTGCCTCGTGA (SEQ ID NO: 143) having a SacI recognition site in the 5'-end side thereof, as a result of which a DNA fragment of about 5 kb was obtained. The DNA fragment obtained was digested with SacI and allowed to ligate using a ligase, as a result of which plasmid pPAfumA was obtained. The obtained pPAfumA harbors the fumA-L fragment, the fumA-R fragment, the sacB gene, and the kanamycin-resistance gene, but no replication origin. *Pantoea ananatis* AJ417 was transformed with pPAfumA by electroporation, and applied to an LB agar plate containing 40 μg/ml kanamycin. The single-crossover clone that grew on the above medium were cultured overnight in an LB liquid medium, and part of the culture liquid was applied to an LB agar medium containing 10% (w/v) sucrose.

Subsequently, among the clones obtained with the above medium, kanamycin-sensitive clones that grew on the sucrose-containing medium were selected. Furthermore, the chromosomal DNAs of these clones were amplified by PCR using a primer pair of SEQ ID NO: 138 and SEQ ID NO: 141, and a variant from which a fragment of about 1.5 kbp, which indicates deletion of the fumA gene, could be amplified was selected. The variant obtained was named *Pantoea ananatis* AJ417 fumA gene-deleted variant (hereinafter sometimes abbreviated to "PAΔfumA variant").

Example 39

<Preparation of *Pantoea ananatis* fumA Gene-Deled, fumC Gene-Deleted Variant>

In order to clone a region flanking the base sequence of the gene encoding fumarate hydratase class II (hereinafter sometimes referred to as "fumC") (1,398 bp), four types of oligonucleotide primers represented by TCGCCATGATGCTGCTGTG (SEQ ID NO: 144), CGGGATCCGACTTAGCGTCATCGGTTG (SEQ ID NO: 145), CGGGATCCGATGAAGATTGCTAACGACG (SEQ ID NO: 146), and TGATGCCGACAATATTACGC (SEQ ID NO: 147) were synthesized.

The genomic DNA of the *Pantoea ananatis* AJ417 was prepared, and PCR was carried out using the obtained genomic DNA as a template and using a primer pair of SEQ ID NO: 144 and SEQ ID NO: 145, as a result of which a DNA fragment of about 0.8 kb (hereinafter sometimes referred to as "fumC-L fragment") was amplified. In addition, PCR was carrying out using a primer pair of SEQ ID NO: 146 and SEQ ID NO: 147, as a result of which a DNA fragment of about 0.7 kb (hereinafter sometimes referred to as "fumC-R fragment") was amplified.

These DNA fragments were separated by agarose electrophoresis, and recovered. Each of the fumC-L fragment and the fumC-R fragment was digested with BamHI, and these fragments were allowed to ligate using a ligase, followed by phosphorylation treatment of the 5'-ends using T4 polynucleotide kinase. The resulting DNA fragment was mixed with a DNA fragment prepared by digesting pHSG-sacB prepared in Example 38 with BamHI and further subjecting the resulting product to blunt-end treatment with T4 DNA polymerase and alkaline phosphatase treatment, and the mixed fragments were ligated using a ligase. Thereafter, *Escherichia coli* DH5α competent cells (manufactured by Toyobo Co., Ltd.) were transformed with the resulting ligation product, and transformants growing on an LB agar plate containing 25 μg/mL kanamycin at 30° C. were obtained. A plasmid was recovered from transformants obtained, and it was confirmed that the two fragments—the 5'-upstream flanking region fragment and 3'-downstream flanking region fragment of the gene encoding fumC—were properly inserted in pHSG-sacB. The plasmid obtained was named psacB-PAfumC.

Plasmid pPAfumC for deleting the fumC gene that lacks a replication origin and would not be replicated in *Pantoea ananatis* was obtained in the same manner as in Example 38, except that the plasmid psacB-PAfumC was used instead of psacB-PAfumA. Furthermore, kanamycin-sensitive clones that grew on a sucrose-containing medium were selected in the same manner as in Example 38, except that the plasmid pPAfumC was used instead of pPAfumA and that the PAΔfumA variant was used instead of the *Pantoea ananatis* AJ417. The chromosomal DNAs of these clones were amplified by PCR using a primer pair of SEQ ID NO: 138 and SEQ ID NO: 141, and a variant from which a fragment of about 1.5 kbp, which indicates deletion of the fumC gene, could be amplified was selected. The variant obtained was transformed with RSFCPG by the $CaCl_2$ method, and cultured in LB medium containing 10 µg/mL tetracycline. The variant obtained was named *Pantoea ananatis*, fumA gene-deleted, fumC gene-deleted variant (hereinafter sometimes abbreviated to "PAΔfumAC variant").

Example 40

<Construction of *Pantoea ananatis* Variants for Evaluation>

Each of the *Pantoea ananatis* PA variant prepared in Example 36, the PAΔaceB variant prepared in Example 37, and the PAΔfumAC variant prepared in Example 39, was transformed with pGAPS prepared in Example 34, pGAPS_gcl prepared in Example 35, pMWGKC prepared in Example 10, and/or pMWGKC_mcl(Mc)_mtk(Mc) in Example 21 by the $CaCl_2$ method or electroporation, and was applied to an LB agar plate containing 30 µg/mL chloramphenicol, 120 µg/mL spectinomycin, and 15 µg/mL tetracycline. The colony that grew on the plate was used as the variant for evaluation. The obtained variants are summarized in Table 13.

through a hydrophilic PTFE membrane filter (Millipore Corporation, MSGVN2B50), thereby obtaining a culture sample. The variants used as culture samples are summarized in Table 13.

For measuring the $^{13}C$ content of glutamate in each culture sample, 500 µL of MTBSTFA with 1% TBDMSCl (manufactured by Sigma-Aldrich Co., 375934) and 500 µL of dry DMF were added to an appropriate amount of the sample, which was dried by, for example, freeze-drying or vacuum drying. The mixture obtained was heated at 80° C. for 2 hours, and then separated by centrifugation (14,000 rpm for 5 minutes). The supernatant obtained was analyzed by GC-MS (Agilent 7890A and 5975c). Respective areas of the mass spectrum peaks at molecular weights of 432, 433, and 434, each of which was assumed to correspond to a structure in which one t-butyl group was removed from a glutamate derivative, were measured. Here, it is assumed that the molecular weight of 432 corresponds to a structure in which all atoms are formed from most abundant isotopes, that the molecular weight of 433 corresponds to a structure containing one neutron, and that the molecular weight of 434 corresponds to a structure containing two neutrons. The peaks at molecular weights of 432, 433, and 434 were defined as [M+0], [M+1], and [M+2], respectively. The value of [M+1]/[M+0] was plotted on the x-axis and the value of [M+2]/[M+0] was plotted on the y-axis. The analysis results are shown in Table 4.

In general glutamate fermentation, $^{13}C$ derived from $NaH^{13}CO_3$ is incorporated via oxaloacetate into glutamate only at the C1- or C5-position. Therefore, the above-mentioned values will be positioned on a reference line. The reference line was determined according to the following equations.

TABLE 13

| Variant Name | Plasmid/ Variant | Feature |
| --- | --- | --- |
| PA/vec | pMWGKC/pGAPS/RSFCPG/P. ananatis | No expression of mtk, mcl, and gcl |
| PA/mtk_mcl | pMWGKC_mcl(Mc)_mtk(Mc)/pGAPS/RSFCPG/P. ananatis | Expression of mtk and mcl, no expression of gcl |
| PA/mtk_mcl/gcl | pMWGKC_mcl(Mc)_mtk(Mc)/pGAPS_gcl(Ec)/RSFCPG/P. ananatis | Expression of mtk, mcl, and gcl |
| PAΔaceB/mtk_mcl/gcl | pMWGKC_mcl(Mc)_mtk(Mc)/pGAPS_gcl(Ec)/RSFCPG/P. ananatisΔaceB | Expression of mtk, mcl, and gcl, disruption of aceB gene |
| PAΔfumAC/mtk_mcl/gcl | pMWGKC_mcl(Mc)_mtk(Mc)/pGAPS_gcl(Ec)/RSFCPG/P. ananatisΔfumAC | Expression of mtk, mcl, and gcl, disruption of fumAC gene |

Example 41

<Confirmation of Incorporation of $^{13}C$-Labeled $CO_2$ into Glutamate in *Pantoea* Variants>

Each of the target *Pantoea* variants was pre-cultured in an LB medium containing 30 µg/mL chloramphenicol, 120 µg/mL spectinomycin, and 15 µg/mL tetracycline at 30° C., 220 rpm. The bacterial cells were collected from the pre-culture by centrifugal separation (5,000 rpm for 5 minutes). 2 mL of minimal medium for *Pantoea* (17 g/L $Na_2HPO_4 \cdot 12H_2O$, 3 g/L $KH_2PO_4$, 0.5 g/L NaCl, 1 g/L $NH_4Cl$, 10 mM $MgSO_4$, 10 µM $CaCl_2$, 50 mg/L L-lysine, 50 mg/L L-Methionine, pH 6.0) containing 100 mM sodium hydrogen carbonate ($^{13}C$-labeled), 20 g/L glucose, 30 µg/mL chloramphenicol, 120 µg/mL spectinomycin, and 15 µg/mL tetracycline was prepared, and the bacterial cells obtained were added thereto such that the OD was adjusted to within the range of 1 to 5. After tightly sealing the culture vessel, the bacterial cells were cultured at 30° C., 220 rpm for 1 day. The culture liquid was periodically sampled, and the bacterial cells were removed by centrifugal separation (12,000 rpm for 3 minutes). The supernatant obtained was filtered $x=(x_0-x_0 \times \alpha+\alpha)/(1-\alpha).$ $y=(y_0-y_0 \times \alpha+x_0 \times \alpha)/(1-\alpha).$ α represents the ratio of the $^{13}C$ isotope in the $CO_2$-derived carbon (at the C1-position or C5-position) in glutamate [≈$^{13}C/(^{13}C+^{12}C)$]. x and y represent the coordinates of an arbitrary point on the reference line. $x_0$ and $y_0$ represent the values of x and y, assuming that the isotope ratio of $^{12}C$ in the $CO_2$-derived carbon (at one of the 1-position and 5-position of glutamate) in glutamate is 100% and that the isotope ratios of other atoms are the same as their natural isotope ratios (that is, the values of x and y, if α=0). $x_0$ and $y_0$ were set to 0.358527 and 0.16822084314, respectively. By solving the above equations, the reference line is expressed in the following equation.

$y=x_0 \cdot x+y_0-x_0^2$

In the intrinsic glutamate production pathway, $^{13}C$ derived from $NaH^{13}CO_3$-derived is fixed by a carbon dioxide fixation enzyme such as phosphoenolpyruvate carboxylase (ppc), pyruvate carboxylase (pyc), or phosphoenolpyruvate carboxykinase (pck), and incorporated via oxaloacetate into glutamate either at the C1-position or C5-position. Although values of [M+1] and [M+2] vary depending on the ratios of $^{12}CO_2$ and $^{13}CO_2$ incorporated by ppc, the values are always plotted on the reference line in a case in which the incorporation occurs at a single position. On the other hand, in a case in which the intended carbon dioxide fixation pathway functions, $^{13}C$ is incorporated into glutamate via both oxaloacetate and acetyl-CoA. In this case, there is a possibility that $^{13}C$ is incorporated into glutamate both at the C1-position and the C5-position, as a result of which the [M+2] value should be increased to give a value plotted above the reference line.

Figure 4:
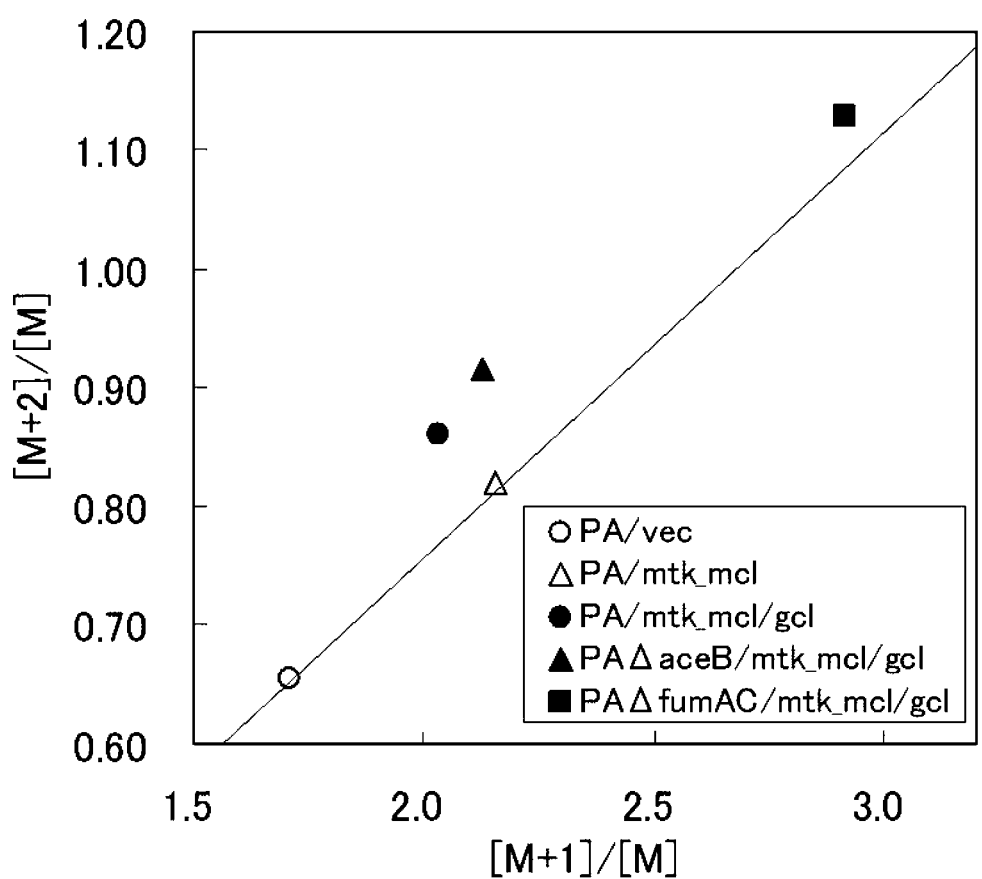
FIG. 4 is a graph showing $^{13}C$-incorporation pattern of glutamate produced by various *Pantoea* bacteria according to Example 41.

As shown in FIG. 4, each of the PA/mtk_mcl_gcl variant, the PAΔaceB/mtk_mcl_gcl variant, and the PAΔfumAC/mtk_mcl_gcl variant gave a value plotted significantly above the reference line. That is, it is thought that fixed $CO_2$ was incorporated into glutamate via acetyl-CoA. On the other hand, the control strain (PA/vec) gave a value plotted on the reference line, and incorporation of $^{13}C$ via acetyl-CoA was not observed. Similarly, incorporation of $^{13}C$ via acetyl-CoA was not observed in the variant into which only mtk+mcl was introduced (PA/mtk_mcl). It is thought that, since Pantoea ananatis has no gcl, imparting of only mtk and mcl was insufficient to allow further conversion of glyoxylate, and, therefore, the reaction t did not proceed further. From these results, it was shown that, as shown in FIG. 1, not only introduction of mtk and mcl but also linking to the downstream gcl pathway are necessary for conversion of $CO_2$ into acetyl-CoA.

Example 42

<Production of Glutamate by Pantoea Variants>

The amount of glutamate and the amounts of byproducts in the culture liquid in Example 41 were measured. The amount of glutamate in the culture sample was measured using a HPLC (2695, Waters) equipped with an NN-814 column (Showa Denko K.K.) and a UV/Vis detector (2489, Waters). The amounts of glucose and other products in the filtrate were measured using a HPLC (2695, Waters) equipped with an ULTRON PS-80H column (Shinwa Chemical Industries Ltd.) and an RI detector (2414, Waters). The results are shown in Tables 14 and 15.

TABLE 14

| Variant Name | Yield Relative to Sugar Consumption (24 h) | Confirmation of $^{13}C$ Incorporation |
|---|---|---|
| PA/vec | 9% | — |
| PA/mtk_mcl | 10% | — |
| PA/mtk_mcl/gcl | 11% | + |
| PAΔaceB/mtk_mcl/gcl | 16% | + |
| PAΔfumAC/mtk_mcl/gcl | 16% | + |

The mtk+mcl+gcl-induced variant (PA/mtk_mcl/gcl) showed an improved yield relative to sugar consumption, as compared with the control strain (PA/vec) and the mtk+mcl-induced variant (PA/mtk_mcl). In the case of disruption of the aceB gene or the fumAC gene (PAΔaceB/mtk_mcl/gcl, PAΔfumAC/mtk_mcl/gcl), the yield relative to sugar consumption was further increased.

Regarding the amounts of byproducts, when compared to the control strain (PA/vec), it was found that, unexpectedly, the amounts of succinate and 2,3-butanediol (2,3-BDO) were reduced and the total amount of byproducts were reduced in the mtk+mcl+gcl-introduced variant (PA/mtk_mcl/gcl). Further, when compared to the aceB gene-non-disrupted variant (PA/mtk_mcl/gcl), it was revealed that, unexpectedly, the amounts of succinate and acetate were reduced, and also the total amount of byproducts was remarkably reduced in the aceB gene-disrupted variant (PAΔaceB/mtk_mcl/gcl). In the fumAC gene-disrupted variant (PAΔfumAC/mtk_mcl/gcl), the amount of succinate was remarkably decreased compared to the fumAC gene-non-disrupted variant (PA/mtk_mcl/gcl), but the amount of acetate was increased and the total amount of byproducts was reduced. These variants are industrially preferable, since a smaller amount of byproducts allow a significant reduction in the purification load when glutamate is collected from a culture liquid.

The above effect of decreasing byproducts was similarly observed in the PA variant having no RSFCPG.

Example 43

<Preparation of Plasmid pCASET>

Amplification by a PCR method was carried out using pHSG298 (Takara) as a template and using CGCCTCGAGTGACTCATACCAGGCCTG (SEQ ID NO: 148) and CGCCTCGAGGCAACACCTTCTTCACGAG (SEQ ID NO: 149) as primers, and the DNA fragment obtained was digested with restriction enzyme XhoI and allowed to ligate using a ligase. Thereafter, Escherichia coli DH5α competent cells (Toyobo Co., Ltd., DNA-903) were transformed with the ligation product, and transformants that grew on an LB agar plate containing 25 µg/mL kanamycin were obtained. Plasmids were recovered from the bacterial cells obtained, and a plasmid in which a recognition site of XhoI is inserted in pHSG298 was named pHSG298-XhoI.

In order to obtain the tac promoter, amplification by a PCR method was carried out using pKK223-3 (Pharmacia) as a template and using ATCATCCAGCTGTCAGGCAGCCATCGGAAG (SEQ ID NO: 150) and ATCCCCGGGAATTCTGTT (SEQ ID NO: 151) as primers, and the DNA fragment obtained was digested with restriction enzymes PvuII and SmaI, as a result of which a DNA fragment of about 0.2 kbp encoding the tac promoter was obtained. The obtained DNA fragment was mixed with a DNA fragment of

TABLE 15

| | Byproducts (g/L/24 h) | | | | | | |
|---|---|---|---|---|---|---|---|
| Variant Name | Ethanol | Pyruvate | Succinate | Lactate | Acetate | 2,3-BDO | Total Amount of Byproducts |
| PA/vec | 0.0 | 0.0 | 4.3 | 0.8 | 0.0 | 0.7 | 5.8 |
| PA/mtk_mcl | 0.0 | 0.0 | 3.0 | 0.5 | 1.7 | 0.1 | 5.2 |
| PA/mtk_mcl/gcl | 0.0 | 0.0 | 3.2 | 0.5 | 1.2 | 0.1 | 5.0 |
| PAΔaceB/mtk_mcl/gcl | 0.0 | 0.0 | 0.3 | 0.4 | 0.0 | 0.0 | 0.7 |
| PAΔfumAC/mtk_mcl/gcl | 0.1 | 0.0 | 0.0 | 0.7 | 3.7 | 0.0 | 4.6 | about 2.4 kbp prepared by digesting the plasmid pHSG298-XhoI with restriction enzyme PvuII and subjecting the resulting product to alkaline phosphatase treatment, and the mixed fragments were ligated using a ligase. Thereafter, the *Escherichia coli* DH5α competent cells (Toyobo Co., Ltd., DNA-903) were transformed with the ligation product, and transformants that grew on an LB agar plate containing 25 µg/mL kanamycin were obtained. A plasmid was recovered from the bacterial cells obtained, thereby obtaining a plasmid pHSGT1 in which the lac promoter of pHSG298-XhoI is replaced by the tac promoter and the tac promoter is inserted in the same direction as the original lac promoter.

In order to ligate the multi-cloning site of pHSG298 to the downstream of the tac promoter of pHSGT1, pHSG298 was digested with restriction enzymes EcoRI and ClaI, thereby obtaining a DNA fragment of about 1.0 kbp containing the multi-cloning site of pHSG298. The DNA fragment obtained was mixed with a DNA fragment of about 1.7 kbp prepared by digesting the plasmid pHSGT1 with restriction enzymes EcoRI and ClaI and subjecting the resulting product to alkaline phosphatase treatment, and the mixed fragments were ligated using a ligase. Thereafter, *Escherichia coli* DH5α competent cells (Toyobo Co., Ltd., DNA-903) were transformed with the ligation product, and transformants that grew on an LB agar plate containing 25 µg/mL kanamycin were obtained. A plasmid was recovered the bacterial cells obtained, thereby obtaining a plasmid pHSGT2 in which the multi-cloning site of pHSG298 is ligated to the downstream of the tac promoter.

The following DNA fragment (SEQ ID NO:152) containing the replication origin, repA, and repB of pCASE1 (Appl Microbiol Biotechnol (2009) 81:1107-1115) isolated from *Corynebacterium casei* JCM 12072 was prepared by DNA synthesis. The sequence thereof is shown below.

```
CGCCTCGAGCACTGGAAGGGTTCTTCAGGGGAACCCCCGGAAACCGGGG
AAACATCTGACTTGGTTAAATGTCGTATTATGAACACGCCGAGGAATGA
AAACCGACCGTGCACGCTCGTGTGAGAAAGTCAGCTACATGAGACCAAC
TACCCGCCCTGAGGGACGCTTTGAGCAGCTGTGGCTGCCGCTGTGGCCA
TTGGCAAGCGATGACCTCCGTGAGGGCATTTACCGCACCTCACGGAAGA
ACGCGCTGGATAAGCGCTACGTCGAAGCCAATCCCGACGCGCTCTCTAA
CCTCCTGGTCGTTGACATCGACCAGGAGGACGCGCTTTTGCGCTCTTTG
TGGGACAGGGAGGACTGGAGACCTAACGCGGTGGTTGAAAACCCCTTAA
ACGGGCACGCACACGCTGTCTGGGCGCTCGCGGAGCCATTTACCCGCAC
CGAATACGCCAAACGCAAGCCTTTGGCCTATGCCGCGGCTGTCACCGAA
GGCCTACGGCGCTCTGTCGATGGCGATAGCGGATACTCCGGGCTGATCA
CCAAAAACCCCGAGCACACTGCATGGGATAGTCACTGGATCACCGATAA
GCTGTATACGCTCGATGAGCTGCGCTTTTGGCTCGAAGAAACCGGCTTT
ATGCCGCCTGCGTCCTGGAGGAAAACGCGGCGGTTCTCGCCAGTTGGTC
TAGGTCGTAATTGCGCACTCTTTGAAAGCGCACGTACGTGGGCATATCG
GGAGGTCAGAAAGCATTTTGGAGACGCTGACGGCCTAGGCCGCGCAATC
CAAACCACCGCGCAAGCACTTAACCAAGAGCTGTTTGATGAACCACTAC
CTGTGGCCGAAGTTGACTGTATTGCCAGGTCAATCCATAAATGGATCAT
CACCAAGTCACGCATGTGGACAGACGGCGCCGCCGTCTACGACGCCACA
TTCACCGCAATGCAATCCGCACGCGGGAAGAAAGGCTGGCAACGAAGCG
CTGAGGTGCGTCGTGAGGCTGGACATACTCTTTGGAGGAACATTGGCTA
AGGTTTATGCACGTTATCCACGCAACGGAAAAACAGCCCGCGAGCTGGC
AGAACGTGCCGGTATGTCGGTGAGAACAGCTCAACGATGGACTTCCGAA
CCGCGTGAAGTGTTCATTAAACGTGCCAACGAGAAGCGTGCTCGCGTCC
AGGAGCTGCGCGCCAAAGGTCTGTCCATGCGCGCTATCGCGGCAGAGAT
TGGTTGCTCGGTGGGCACGGTTCACCGCTACGTCAAAGAAGTTGAAGAG
AAGAAAACCGCGTAAATCCAGCGGTTTAGTCACCCTCGGCGTGTTCAAA
GTCCATCGTAACCAAGTCAGCTCGAGGCG
```

The DNA fragment prepared was digested with restriction enzyme XhoI. The DNA fragment obtained was mixed with a DNA fragment prepared by digesting the plasmid pHSGT2 with restriction enzyme XhoI and subjecting the resulting product to alkaline phosphatase treatment, and the mixed fragments were ligated using a ligase. Thereafter, *Escherichia coli* DH5α competent cells (Toyobo Co., Ltd., DNA-903) were transformed with the ligation product, and transformants that grew on an LB agar plate containing 25 µg/mL kanamycin were obtained. Plasmids were recovered from the bacterial cells obtained, and a plasmid in which the DNA fragment containing the replication origin, repA, and repB of pCASE1 is inserted at the XhoI recognition site of pHSGT2 was named pCASET. In the pCASET recovered, the repA derived from pCASE1 was inserted in the opposite direction with respect to the tac promoter.

Example 44

<Construction of Plasmid pCASEL>

The DNA fragment synthesized in Example 43 (SEQ ID NO: 152) containing the replication origin, repA, and repB of pCASE1 was digested with restriction enzyme XhoI. The DNA fragment obtained was mixed with a DNA fragment prepared by digesting the plasmid pHSG298-XhoI prepared in Example 43 with restriction enzyme XhoI and subjecting the resulting product to alkaline phosphatase treatment, and the mixed fragments were ligated using a ligase. Thereafter, *Escherichia coli* DH5α competent cells were transformed with the ligation product, and transformants that grew on an LB agar plate containing 25 µg/mL kanamycin were obtained. Plasmids were recovered from the bacterial cells obtained, and a plasmid in which the DNA fragment containing the replication origin, repA, and repB of pCASE1 is inserted at the XhoI recognition site of pHSG298-XhoI was named pCASEL. In the pCASEL recovered, the repA derived from pCASE1 was inserted in the opposite direction with respect to the lac promoter derived from pHSG298.

Example 45

<Construction of Expression Plasmid for Mtk and Mcl Derived from *Methylococcus capsulatus*>

PCR was carried out using pMWGKC_mcl(Mc)_mtk (Mc) as a template and using a primer pair of GGAATTCACAAAAAGGATAAAACAATGGCTGTCAAGAACCGTCTAC (SEQ ID NO: 153) and CGAATTCTCAGAATCTGATTCCGTGTTCCTG (SEQ ID NO: 154), as a result of which a DNA fragment containing mcl-mtk of *Methylococcus* was obtained. Each of the primers of SEQ ID NOs: 153 and 154 has an EcoRI recognition site in the 5'-end side. Each of the DNA fragment obtained and plasmid pCASET were digested with EcoRI and dephosphorylated, and the resulting fragments were allowed to be ligated. Similarly, the DNA fragment obtained and plasmid pCASEL were digested. By DNA sequencing, it was confirmed that the mcl-mtk fragment was inserted in the direction appropriate for expression with the promoter of the plasmid. The plasmid obtained was named pCASET_mcl(Mc)_mtk(Mc) or pCASEL_mcl(Mc)_mtk(Mc).

Example 46

<Construction of Expression Plasmids for mtk Derived from *Granulibacter bethesdensis*, *Nitrosomonas europaea*, and *Hyphomicrobium methylovorum*> dam⁻/dcm⁻ Competent *Escherichia coli* cells (New England Biolabs) were transformed with each of pMWGKC_mcl(Hme)_mtk(Gb), pMWGKC_mcl(Hme)_mtk(Hme)_mcl, and pMWGKC_mcl(Ne)_mtk(Ne), and grown on an LB medium containing 30 µg/mL chloramphenicol. A plasmid was recovered therefrom digested with restriction enzymes EcoRI and XbaI, as a result of which a DNA fragment of about 3 kb containing mtk and mcl was obtained. The DNA fragment containing mtk and mcl was ligated to a plasmid pCASEL that had been digested with restriction enzymes EcoRI and XbaI, thereby preparing vectors pCASEL_mcl(Hme)_mtk(Gb), pCASEL_mcl(Hme)_mtk(Hme), and pCASEL_mcl(Ne)_mtk(Ne) for expressing mtk and mcl in *Corynebacterium*. Each of these vectors has mtk of *Granulibacter bethesdensis*, *Nitrosomonas europaea*, or *Hyphomicrobium methylovorum*.

The plasmids for *Corynebacterium* prepared are summarized in Table 16.

TABLE 16

| Variant Number | Plasmid | mtk Origin | mcl Origin |
| --- | --- | --- | --- |
| MT-9 | pCASEL_mcl(Hme)_mtk(Gb) | Granulibacter bethesdensis | Hyphomicrobium methylovorum |
| MT-10 | pCASEL_mcl(Hme)_mtk(Hme) | Hyphomicrobium methylovorum | Hyphomicrobium methylovorum |
| MT-11 | pCASEL_mcl(Ne)_mtk(Ne) | Nitrosomonas europaea | Nitrosomonas europaea |
| MT-12 | pCASEL_mcl(Mc)_mtk(Mc) | Methylococcus capsulatus | Methylococcus capsulatus |
| MT-13 | pCASET_mcl(Mc)_mtk(Mc) | Methylococcus capsulatus | Methylococcus capsulatus |

Example 47

<Measurement of mtk Activity in *Corynebacterium*>

*Corynebacterium glutamicum* ATCC 13012 was transformed with each of the plasmids prepared in Example 45 and Example 46 by electroporation. The resultant was applied to an LB agar plate containing 15 µg/mg kanamycin, and cultured at 30° C. for 1 to 4 days. The colonies obtained was cultured at 30° C. for 1 to 4 days in an LB liquid medium containing 15 µg/mg kanamycin, and bacterial cells were collected by centrifugal separation. The bacterial cells were suspended in MOPS-K buffer (pH 7.7), and suspension obtained was crushed with 0.1 mm glass beads using a Beads Shocker (MB5000, Yasui Kikai Corporation). Thereafter, the supernatant obtained by centrifugal separation (13,000 rpm for 2 minutes) was used as a mutant crude enzyme extract. The activity in the bacterial cells was measured using the extract in the same manner as in Example 16. The results are shown in Table 17.

TABLE 17

| Variant Number | Plasmid | Activity (nmol/min/mg) |
| --- | --- | --- |
| MT-9 | pCASEL_mcl(Hme)_mtk(Gb) | 5.5 |
| MT-10 | pCASEL_mcl(Hme)_mtk(Hme) | 8.3 |
| MT-11 | pCASEL_mcl(Ne)_mtk(Ne) | 11.0 |
| MT-12 | pCASEL_mcl(Mc)_mtk(Mc) | 51.3 |
| MT-13 | pCASET_mcl(Mc)_mtk(Mc) | 99.1 |

In a case in which the pCASEL plasmid was used as the expression vector, the plasmid expressing mtk derived from *Methylococcus capsulatus* provided the highest value of activity. Further, when compared to Table 9, almost the same correlation was observed between mtk having high activity and mtk having low activity. The evaluation of the activities of *Methylococcus capsulatus*-derived mtk introduced into pCASEL and that introduced into pCASET showed a higher activity in the variant having mtk introduced into pCASET.

Example 48

<Construction of Expression Plasmid for mtk, mcl, gcl, and glxR in *Corynebacterium*>

*Rhodococcus jostii* NBRC16295 was purchased from NBRC (Biological Resource Center, Biotechnology Field, National Institute of Technology and Evaluation). NBRC16295 was cultured in a medium (medium number: 802, NBRC), and genomic DNA was obtained therefrom using DNeasy Blood &Tissue Kit (QIAGEN). PCR was carried out using this genomic DNA as a template and using CGAGCTCAAGCTTACAAAAAGGATAAAACAAT-GAGCACCATTGCATTCATCGG (SEQ ID NO: 155) and CGGGATCCCTAGTCCAGCAGCATGAGAG (SEQ ID NO: 156) as primers, as a result of which a glxR-gcl fragment of *Rhodococcus* (SEQ ID NO: 157) was obtained. The fragment obtained was digested with SacI and BamHI, and the resultant was ligated to a fragment obtained by digesting pCASET_mcl(Mc)_mtk(Mc) with SacI and BamHI. The plasmid obtained was named pCASET_mcl(Mc)_mtk(Mc)_glxR(Rj)_gcl(Rj).

Example 49

<Construction of *Corynebacterium glutamicum* Variant for Evaluation of Glutamate Production and Incorporation of ¹³C>

*Corynebacterium glutamicum* DSM1412 (hereinafter sometimes referred to as "CG strain") was transformed with each of the plasmids constructed in Examples 43, 45, and 48 by electroporation, and applied to an LB agar plate containing 15 μg/mL kanamycin. The colony that grew on the plate was used as the variant for evaluation. The obtained variants are summarized in Table 18.

TABLE 18

| Variant Name | Plasmid/Variant | Feature |
| --- | --- | --- |
| CG/vec | pCASET/C. glutamicam | No mtk, mcl, gcl, and glxR |
| CG/mtk_mcl | pCASET_mcl(Mc)_mtk(Mc)/C. glutamicam | Expression of mtk and mcl, No gcl and glxR |
| CG/mtk_mcl/gcl-glxR | pCASET_mcl(Mc)_mtk(Mc)_glxR(Rj)_gcl(Rj)/C. glutamicam | Expression of mtk, mcl, gcl, and glxR |

Example 50

<Confirmation of Introduction of $^{13}C$-labeled $CO_2$ into Glutamate in Corynebacterium Variants>

Each of the microorganism variants to be analyzed was cultured in 2 mL of LB liquid medium containing 15 μg/mL kanamycin at 30° C. and 280 rpm until sufficient growth was achieved. In a 100-mL Erlenmeyer flask equipped with stirrer blades, 10 mL of minimal medium [30 g/L $(NH_4)_2SO_4$, 3 g/L $Na_2HPO_4$, 6 g/L $KH_2PO_4$, 2 g/L NaCl, 84 mg/L $CaCl_2$, 3.9 mg/L $FeCl_3$, 0.9 mg/L $ZnSO_4.7H_2O$, 0.3 mg/L $CuCl_2.H_2O$, 5.56 mg/L $MnSO_4.5H_2O$, 0.1 mg/L $(NH_4)_6Mo_7O_{24}.4H_2O$, 0.3 mg/L $Na_2B_4O_7.10H_2O$, 0.4 g/L $MgSO_4.7H_2O$, 40 mg/L $FeSO_4.7H_2O$, 500 μg/L Vitamine B1.HCl, 0.1 g/L EDTA, 10 μg/L Biotin] for Corynebacterium containing 20 g/L glucose and 15 μg/mL kanamycin was prepared. 1 mL of culture in the LB liquid medium above was added thereto, and the mixture was cultured for 1 to 4 days until sufficient growth was achieved, whereby a preculture was obtained. From the preculture, bacterial cells were collected by centrifugal separation (5,000 rpm for 5 minutes).

2 mL of the minimal medium for Corynebacterium (the final concentration of Biotin was changed to 2 μg/L) containing 100 mM sodium hydrogen carbonate ($^{13}C$-labeled), 20 g/L glucose, 1.5% (w/v) Tween 60 (manufactured by Sigma-Aldrich Co.), and 15 μg/mL kanamycin was prepared, and the bacterial cells from preculture were added thereto such that the OD was adjusted to within the range of 1 to 5. After tightly sealing the culture vessel, the bacterial cells were cultured at 30° C. and 150 rpm for 1 to 2 days. The culture liquid was periodically sampled, and the bacterial cells were removed by centrifugal separation (Millipore Corporation, 12,000 rpm for 3 minutes). The supernatant obtained was filtered through a hydrophilic PTFE membrane filter (Millipore Corporation, MSGVN2B50), thereby obtaining a culture sample. The $^{13}C$ content of the culture sample was analyzed in the same manner as in Example 41. That is, respective areas of the peaks at molecular weights of 432, 433, and 434 in GC-MS analysis were defined as [M], [M+1], and [M+2], respectively, and the value of [M+1]/[M] was plotted on the x-axis and the value of [M+2]/[M] was plotted on the y-axis. The reference line was obtained by a calculation according to the method described in Example 41.

Figure 5:
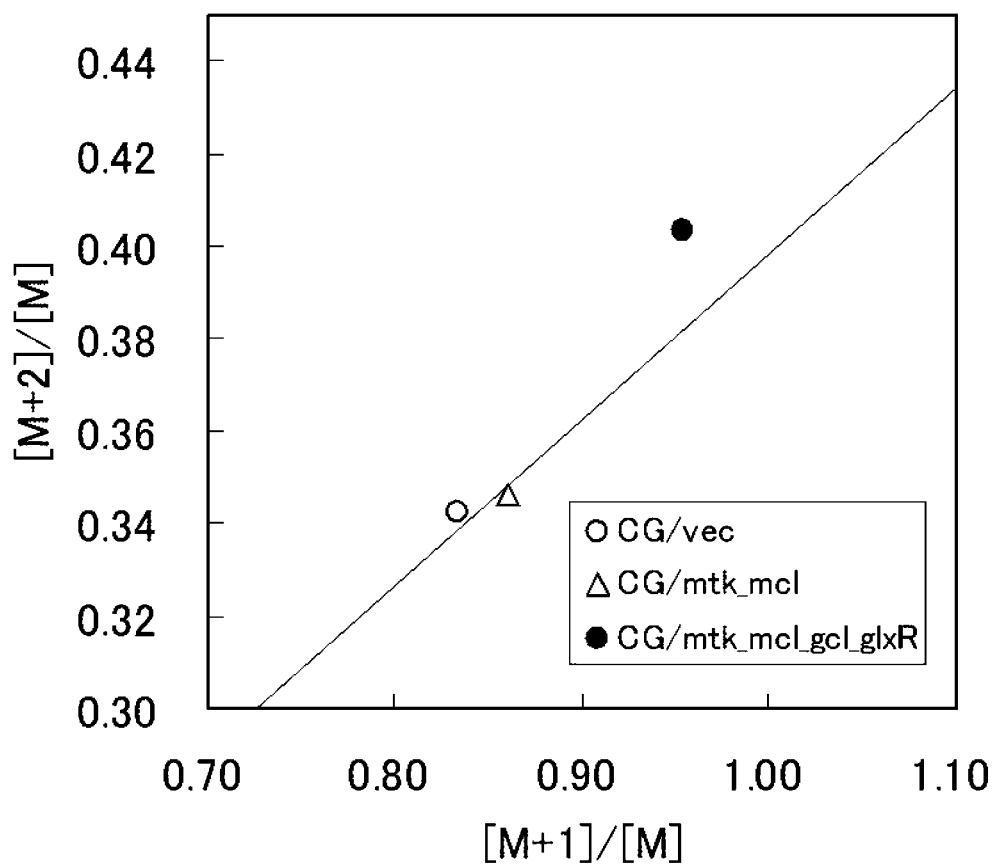
FIG. 5 is a graph showing the $^{13}C$-incorporation pattern of glutamate produced by various *Corynebacterium* bacteria according to Example 50.

Based on FIG. 5, the mtk+mcl+gcl+glxR-introduced variant (CG/mtk_mcl_gcl_glxR) gave a value plotted above the reference line, and it is thought that fixed $CO_2$ was incorporated into glutamate via acetyl-CoA. On the other hand, the control strain (CG/vec) gave a value plotted almost on the reference line, and incorporation of $^{13}C$ via acetyl-CoA was not observed. Similarly, the mtk+mcl-introduced variant (CG/mtk_mcl) gave a value plotted almost on the reference line, and incorporation of $^{13}C$ via acetyl-CoA was not observed. It is thought that, since Corynebacterium glutamicum have no gcl and glxR, imparting of only mtk and mcl was insufficient to allow the reaction to proceed, as in the case of Pantoea ananatis.

Example 51

<Test for Production of Glutamate in Corynebacterium Variants>

The amount of glutamate and the amounts of byproducts in the culture liquid in Example 50 were measured. In the same manner as in Example 42, glutamate, glucose, and other organic compounds in the culture liquid were analyzed. The results are shown in Tables 19 and 20.

TABLE 19

| Variant Name | Yield Relative to Sugar Consumption (24 h) | Result of $^{13}C$ Analysis |
| --- | --- | --- |
| CG/vec | 2% | − |
| CG/mtk_mcl | 3% | − |
| CG/mtk_mcl_gcl_glxR | 6% | + |

TABLE 20

| | Byproducts (g/L/24 h) | | | | | |
| --- | --- | --- | --- | --- | --- | --- |
| Variant Name | Ethanol | Pyruvate | Succinate | Lactate | Acetate | Total Amount of Byproducts |
| CG/vec | 0.0 | 0.0 | 0.2 | 1.6 | 0.3 | 2.1 |
| CG/mtk_mcl | 0.0 | 0.0 | 0.3 | 1.6 | 0.3 | 2.2 |
| CG/mtk_mcl_gcl_glxR | 0.0 | 0.0 | 0.1 | 0.6 | 0.2 | 0.9 |

The mtk+mcl+gcl+glxR-introduced variant (CG/mtk_mcl_gcl_glxR) showed an improved yield relative to sugar consumption, as compared with the control strain (CG/vec) and the variant (CG/mtk_mcl) in which only mtk+mcl was introduced.

Regarding the amounts of byproducts, as compared with the control strain (CG/vec), it was found that, unexpectedly, the amount of lactate was mainly reduced and the total amount of byproducts were reduced in the mtk+mcl+gcl+glxR-introduced variant (CG/mtk_mcl_gcl_glxR). In the variant (CG/mtk_mcl) in which only mtk+mcl was introduced, the amounts of byproducts were almost the same as those in the control strain.

Example 52

<Enhancement of Activity by Introduction of Mutations into Malate Thiokinase Gene Derived from *Methylobacterium extorquens*>

PCR was carried out using pMWGKC_mtk(Mex)_mcl as a template and each of the primer pairs shown in Table 21. The template was digested with restriction enzyme DpnI. Thereafter, *Escherichia coli* DH5α competent cells were transformed with the obtained product, and transformants that grew on an LB agar plate containing 10 μg/mL chloramphenicol were obtained. The colonies obtained were cultured at 30° C. overnight in an LB liquid medium containing 10 μg/mL chloramphenicol. A plasmid was recovered from a part of the culture liquid, and the DNA sequence thereof was checked. A plasmid in which the intended mutation was properly introduced was used as the mutant sample. This sample was pre-cultured in an LB liquid medium containing 10 μg/mL chloramphenicol, and then inoculated into 3 mL of LB liquid medium containing 10 μg/mL chloramphenicol and cultured at 30° C. and 280 rpm overnight. Two milliliters of the culture was separated by centrifugation at 10,000 rpm for 5 minutes to remove the supernatant, and 2 mL of 10 mM phosphate buffer (pH 7.0) was added thereto, followed by washing the cells. The washing operation was repeated once, and the cells were suspended in 500 μL of 10 mM phosphate buffer (pH 7.0). The suspension obtained was crushed with 0.1 mm glass beads using a Beads Shocker (MB5000, Yasui Kikai Corporation), and the supernatant obtained by centrifugal separation (13,000 rpm for 2 minutes) was used as a mutant crude enzyme extract.

The activity of each mutant crude enzyme extract was evaluated in accordance with the method described in Example 16. The results are shown in Table 21. As a result, the Q244E mutation in mtkB and the L144I mutation in mtkB improved the activity value compared to the non-mutated mtkB. In addition, the activity was improved by introducing another amino acid into the Q244 position of mtkB, when the introduced amino acid was A, L, I, M, N, Y, K, or R. Further, the activity was improved by introducing a mutation into the L144 position of mtkB, when the introduced amino acid was N, D, K, R, H, Q, or P.

TABLE 21

| Mutation Type | Relative Activity | Position |
| --- | --- | --- |
| (Wild Type) | (1) | — |
| mtkB_Q244E | 1.9 | 158, 159 |
| mtkB_Q244A | 1.2 | 160, 161 |
| mtkB_Q244L | 1.1 | 162, 163 |
| mtkB_Q244I | 1.2 | 164, 165 |
| mtkB_Q244M | 1.1 | 166, 167 |
| mtkB_Q244N | 1.2 | 168, 169 |
| mtkB_Q244Y | 1.1 | 170, 171 |
| mtkB_Q244K | 1.3 | 172, 173 |
| mtkB_Q244R | 1.3 | 174, 175 |
| mtkB_L144I | 1.1 | 176, 177 |
| mtkB_L144N | 2.1 | 178, 179 |
| mtkB_L144D | 1.8 | 180, 181 |
| mtkB_L144K | 1.5 | 182, 183 |
| mtkB_L144R | 1.9 | 184, 185 |
| mtkB_L144H | 1.4 | 186, 187 |
| mtkB_L144Q | 1.4 | 188, 189 |
| mtkB_L144P | 2.4 | 190, 191 |

According to the invention, $CO_2$ can be converted into acetyl-CoA. Further, according to the invention, substances derived from acetyl-CoA such as isopropyl alcohol, acetone, and glutamic acid can be efficiently produced.

The disclosure of Japanese Patent Application No. 2011-167808 filed on Jul. 29, 2011 is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. An acetyl-CoA producing microorganism comprising:
a microorganism belonging to Enterobacteriaceae or a microorganism belonging to coryneform bacteria; and
an acetyl-CoA production cycle obtained by imparting enzymatic activity of malate thiokinase, and optionally imparting at least one type of enzymatic activity selected from the group consisting essentially of malyl-CoA lyase, glyoxylate carboligase, 2-hydroxy-3-oxo-propionate reductase, and hydroxypyruvate reductase, to a microorganism that does not have any of:
(a) a carbon dioxide fixation cycle having an enzymatic reaction from malonyl-CoA to malonate semialdehyde or 3-hydroxypropionate;
(b) a carbon dioxide fixation cycle having an enzymatic reaction from acetyl-CoA and $CO_2$ to pyruvate;
(c) a carbon dioxide fixation cycle having an enzymatic reaction from crotonyl-CoA and $CO_2$ to ethylmalonyl-CoA or glutaconyl-CoA;
(d) a carbon dioxide fixation cycle having an enzymatic reaction from $CO_2$ to formate; or
(e) at least one selected from the group consisting of malate thiokinase and malyl-CoA lyase,
wherein none of (a), (b), (c), or (d) is imparted to the microorganism, or the microorganism exhibits none of the functions of (a), (b), (c), and (d) even though at least one of (a), (b), (c), or (d) is imparted.

2. The acetyl-CoA producing microorganism according to claim 1, comprising an acetyl-CoA production cycle wherein phosphoenolpyruvate or pyruvate is converted to oxaloacetate, and then to 2-hydroxy-3-oxopropionate due to actions of malate thiokinase, malyl-CoA lyase, glyoxylate carboligase, and then to phosphoenol pyruvate again via 2-phosphoglycerate.

3. The acetyl-CoA producing microorganism according to claim 1, comprising an acetyl-CoA production cycle comprising:

(f) at least one selected from the group consisting of:
pyruvate kinase and pyruvate carboxylase;
phosphoenolpyruvate carboxylase; and
phosphoenolpyruvate carboxykinase;
(g) malate dehydrogenase;
(h) malate thiokinase;
(i) malyl-CoA lyase;
(j) glyoxylate carboligase;
(k) at least one selected from the group consisting of:
2-hydroxy-3-oxopropionate reductase; and
hydroxypyruvate isomerase and hydroxypyruvate reductase;
(l) at least one selected from the group consisting of:
glycerate 2-kinase; and
phosphoglycerate mutase and glycerate 3-kinase; and
(m) enolase.

4. The acetyl-CoA producing microorganism according to claim 1, wherein the microorganism is *Escherichia* bacteria or *Pantoea* bacteria belonging to Enterobacteriaceae, or the microorganism is *Corynebacterium* bacteria belonging to coryneform bacteria.

5. The acetyl-CoA producing microorganism according to claim 1, wherein the microorganism is an *Escherichia* bacterium in which an activity of lactate dehydrogenase possessed by the *Escherichia* bacterium is inactivated or reduced.

6. The acetyl-CoA producing microorganism according to claim 1, wherein the microorganism is an *Escherichia* bacterium in which an activity of at least one enzyme selected from the group consisting of isocitrate lyase and malate synthase possessed by the *Escherichia* bacterium is inactivated or reduced.

7. The acetyl-CoA producing microorganism according to claim 1, wherein the microorganism is an *Escherichia* bacterium in which a thiolase activity, a CoA transferase activity, and an acetoacetate decarboxylase activity are imparted or enhanced.

8. The acetyl-CoA producing microorganism according to claim 1, wherein the microorganism is an *Escherichia* bacterium in which a thiolase activity, a CoA transferase activity, an acetoacetate decarboxylase activity, and an isopropyl alcohol dehydrogenase activity are imparted or enhanced.

9. The acetyl-CoA producing microorganism according to claim 1, wherein the microorganism is a *Pantoea* bacterium in which activities of fumarate hydratase A and fumarate hydratase C possessed by the *Pantoea* bacterium are inactivated or reduced.

10. The acetyl-CoA producing microorganism according to claim 1, wherein the microorganism is a *Pantoea* bacterium in which an activity of malate synthase possessed by the *Pantoea* bacterium is inactivated or reduced.

11. The acetyl-CoA producing microorganism according to claim 1, wherein the malate thiokinase used is a malate thiokinase obtained by modifying malate thiokinase large subunit (mtkB) derived from *Methylobacterium extorquens* so as to alter an amino acid corresponding to the 144th amino acid to isoleucine, asparagine, aspartic acid, lysine, arginine, histidine, glutamine, or proline, and/or so as to alter the 244th amino acid to glutamic acid, alanine, leucine, isoleucine, methionine, asparagine, tyrosine, lysine, or arginine, in an amino acid sequence of SEQ ID NO: 71.

12. A method of producing acetyl-CoA, comprising producing acetyl-CoA from a carbon source material using the acetyl-CoA producing microorganism according to claim 1.

13. A method of producing acetone, comprising producing acetone from a carbon source material using the acetyl-CoA producing microorganism according to claim 8.

14. A method of producing isopropyl alcohol, comprising producing isopropyl alcohol from a carbon source material using the acetyl-CoA producing microorganism according to claim 8.

15. A method of producing glutamate, comprising producing glutamate from a carbon source material using the acetyl-CoA producing microorganism according to claim 4.

16. A method of producing acetyl-CoA, comprising producing acetyl-CoA from a carbon source material using the acetyl-CoA producing microorganism according to claim 11.

17. A method of producing acetone, comprising producing acetone from a carbon source material using the acetyl-CoA producing microorganism according to claim 11.

18. A method of producing isopropyl alcohol, comprising producing isopropyl alcohol from a carbon source material using the acetyl-CoA producing microorganism according to claim 11.

19. A method of producing glutamate, comprising producing glutamate from a carbon source material using the acetyl-CoA producing microorganism according to claim 9.

20. A method of producing glutamate, comprising producing glutamate from a carbon source material using the acetyl-CoA producing microorganism according to claim 10.

21. A method of producing glutamate, comprising producing glutamate from a carbon source material using the acetyl-CoA producing microorganism according to claim 11.

22. A method of producing acetone, comprising producing acetone from a carbon source material using the acetyl-CoA producing microorganism according to claim 7.

23. The acetyl-CoA producing microorganism of claim 1, wherein the acetyl-CoA production cycle is obtained by imparting at least one type of enzymatic activity selected from the group consisting of malyl-CoA lyase, glyoxylate carboligase, 2-hydroxy-3-oxopropionate reductase, and hydroxypyruvate reductase.

* * * * *

SEQUENCE LISTING

<160> NUMBER OF SEQ ID NOS: 191

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgctcaattg caatgattga cacgattccg                                      30

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acagaattcg ctatttgtta gtgaataaaa gg                                   32

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgaattcgct ggtggaacat atgaaaacaa aattgatgac attacaagac         50

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcggtacctt atttgctctc ctgtgaaacg                                30

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctctagatg ctgaaatcca ctagtcttgt c                              31

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tactgcagcg ttccagcacc ttatcaacc                                 29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtctagagc aatgattgac acgattccg                                 29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caggaattcg ctatatctgg ctctgcacg                                 29

```
<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagtctagag caatactctt ctgattttga g                              31

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagtctagat catcgtcgat atgtaggcc                                 29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gacctgcaga tcatccgtca gctgtacgc                                 29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggaattcggg tcaattttca ccctctatc                                 29

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgggccgtc ctgaaggtac aaaagagata gattctc                        37

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcttttgta ccttcaggac ggcccacaaa tttgaag                        37

<210> SEQ ID NO 15
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggaattccca gccccgcaag gccgatggc                                              29

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgccatatga atggcgcggc ggggccggtg g                                           31

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tggagctctg tttactcctg tcaggggg                                               28

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tggagctctc tgatttaatc aacaataaaa ttg                                         33

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgggatccac caccataacc aaacgacgg                                              29

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaattcgac catcgcttac ggtcaattg                                              29

<210> SEQ ID NO 21
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gagcggcaag aaagactttc tccagtgatg ttg                                33

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggagaaagtc tttcttgccg ctcccctgca ac                                 32

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggaattcttt agcaaatggc tttcttc                                       27

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggaattcatt cagctgttgc gcatcgattc                                    30

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cggttgttgt tgccgtgcag ctcctcgtca tggatc                             36

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggagctgcac ggcaacaaca accgttgctg actg                               34

<210> SEQ ID NO 27
<211> LENGTH: 29
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 27
ggaattccag gcaggtatca ataaataac        29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ggaattccag gagaaagggc tggcacggg        29

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
cttttttgac gctatgttta tctcctcgtt ttcgc        35

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gagataaaca tagcgtcaaa aaagccccgg c        31

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ggaattccgt ccatcattgc taccagcc        28

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cgccatatga tcgccagcgc gcgggatttt tc        32

<210> SEQ ID NO 33
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 33
cgagctctgt tctctcactt actgcctgg                                            29

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
atgagctctc tgcaacatac aggtgcag                                             28

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgggatccac tacgcgcacg atggtcaag                                            29

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgagctacat atgcaatgat tgacacgatt ccg                                       33

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgcgcgcatg ctatttgtta gtgaataaaa gg                                        32

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aatatgcatg ctggtggaac atatgaaagg ttttgcaatg ctagg                          45

<210> SEQ ID NO 39
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 39
acgcgtcgac ttataatata actactgctt taattaagtc                                40

<210> SEQ ID NO 40
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
acgcgtcgac gctggtggaa catatgttaa aggatgaagt aattaaacaa attagc            56

<210> SEQ ID NO 41
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gctctagagg taccttactt aagataatca tatataactt cagc                          44

<210> SEQ ID NO 42
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gctctagacg gagaaagtct tatggcggta acgcaaacag cccagg                        46

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgggatcccg gagaaagtct tatgaagcaa acagtttata tcgcc                         45

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccgctcgagc atatgctgtc gcaatgattg acacg                                    35

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 45
gctattccat atgcagggtt attgtctcat gagc					34

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tcggcacgta agaggttcc					19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgggtcgaat ttgctttcg					19

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctagatctga cagtaagacg ggtaagcc					28

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctagatctca gggttattgt ctcatgagc					29

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccgctcgagc atatgctgtc gcaatgattg acacg					35

<210> SEQ ID NO 51
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gctattccat atgcagggtt attgtctcat gagc							34

<210> SEQ ID NO 52
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaaaggcgga attcacaaaa aggataaaac aatggacgtt cacgagtacc aagcc							55

<210> SEQ ID NO 53
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
catgcctgca ggtcgactct agaggcgagg ttcttttttcc ggactc							46

<210> SEQ ID NO 54
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggatcctcta gactggtgga atatatgagc ttcaccctga tccagcag							48

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggcatgcaag cttttacttt ccgcccatcg cgtc							34

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
atgaccgtca cgcctcacct							20

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gaagcggccg gcatccgaga agccggtctg gat                33

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggaattcaca aaaggataa aacaatgagc tacacgcttt acccg      45

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gctctagatt acgcgacttt cttacgctgg ttg                 33

<210> SEQ ID NO 60
<211> LENGTH: 963
<212> TYPE: DNA
<213> ORGANISM: Hyphomicrobium methylovorum

<400> SEQUENCE: 60

| | |
|---|---|
| atgagctaca cgctttaccc gacccgcaag cagcgcctgc agcgctcgta cctcgcagtg | 60 |
| ccgggctcca acccgagcat gatcgatcgc gcactcaaga gcgcagccga ctatgtgttt | 120 |
| ctcgattgcg aagacgccgt cgcgccgccc gagaaagaac aggctcgcaa gaacatcatt | 180 |
| caggcgctga acgatctcga ctggaagggc gcaggcaaga gcgtctcggt tcgcatcaac | 240 |
| ggcctcgaca cgcactacat gtaccgcgac gttgtcgaca tcgtggagca ggctggctcc | 300 |
| aagctcgaca cgatcctcat tcccaaggtc ggcgttccgg ctgacgtcta cacggtcgaa | 360 |
| tgcatcgtga gccagatcga agtcgcgaag ggtcttccgc accagatcgg caccgaagcg | 420 |
| ctcatcgaaa cgccgctcgg catggcaaac gtcgaagcca tcgcgtcggc aagcagccgc | 480 |
| ctcgagtcca tgcacttcgg cgttgctgac tactccgcct tcaacaaggc acgcaccgtc | 540 |
| gtcatcggcg gcttgaaccc tgattacccg ggtgaccagt ggcacttccc gctgtcgcgt | 600 |
| atgaccgttg cctgccgcgc attcggcctt cgtccgatcg acggcccgtt cggtggcatc | 660 |
| gacgatccgg aaggctacaa ggccgccgct cgccgtggcg ctgctctcgg catggaaggc | 720 |
| aagtgggcca tccatccgtc gcagatcgaa ctcgccaacg aaatctattc gccgacggcg | 780 |
| aaggaagtcg aacgcgctga acgcatcctc gttgcactga aggaagctga agctcaaggt | 840 |
| aagggcgcag cgtcgcttga cggcaagatg atcgacgccg catctgaaaa gatggcgcgc | 900 |
| aacctgctct cgactgccga gcagatcaag aaggccgagg ccgctcacgc agctcagaag | 960 |
| aaa | 963 |

<210> SEQ ID NO 61
<211> LENGTH: 1161
<212> TYPE: DNA
<213> ORGANISM: Hyphomicrobium methylovorum

<400> SEQUENCE: 61

```
atggacgttc acgagtatca ggccaaagag cttctcgcga agttcggcgt gccgatcgcg      60
cgcggcgggc ttgcttacag cccggagcag gcaacatatc gtgcaagcga gcttggcggc     120
accgtcgtcg tcaaggcgca gattcactct ggcgcgcgcg gcaaagctgg cggcgtcaaa     180
gtctgcaaga acgagaaaga gatcgaagac gcggctgagt tcatgctcgg ccgcaagctg     240
gtcacgcatc agaccggccc ggcgggcaag ctcgtctcgc gtctttacat cgaagaagcg     300
accaacatcg atcgcgagat ctatctcggc ttcgtgatgg atcgcgcctc cgagcgtatc     360
gtcgtcgttg catccgccgc tggcggcatg gacatcgagg aaatctctgc gagccagccc     420
gacacgatca tccgcgtgag cgttgatccg gccgtcggca tgcagcagtt ccaggcgcgt     480
gaactcgcgt tcggtctcgg cgtcgatccg gagatcgtca acaagctcgt tccggcgatc     540
atgggatgct accgcgcatt ccgcgatctc gacgcgacca tggttgaggt caacccgctc     600
gtcatcacca aggaaaagca ggttctcgcg ctcgacgcta agatgtcgtt cgatgacaac     660
gcgctgttcc gccgtccgca catcgcagag ctgcgggaca agagccagga agacccgcgc     720
gaaacctacg cgtcggatcg tggcctctcc tacgttggtc tcgatggcga catcggctgc     780
atcgtcaacg gcgcaggtct cgccatggcg acgctcgaca tgatcaagct cgcaggcggt     840
gagccggcga acttcctcga cattggcggc ggagcgtctc cggaacgcgt caccaagtcg     900
ttcaaggctg ttcttcgcga caagaacgtc aaggcgatcc tcgtgaacgt cttcgccggt     960
atcaaccgtt gcgactgggt tgccaagggc gtggtcgatg ccgtgaagga actcgagatc    1020
aagatgccga tcgtcgttcg cctcgcaggc acgaacgtcg aagaaggccg caagatcatc    1080
gacaacagcg gcttgaccgt catcagtgca gatactctcg ctgacgcggc caagcaggcc    1140
gtcgacgctg cgaaaaaagc g                                              1161
```

<210> SEQ ID NO 62
<211> LENGTH: 897
<212> TYPE: DNA
<213> ORGANISM: Hyphomicrobium methylovorum

<400> SEQUENCE: 62

```
atggctatct tcatcaatga aaagacgccg atcctgatcc agggcttcac cggacgtatc      60
ggcacctttc acgctcaaga aatgatcgac tacggctcca atgttgtcgg cggtgttacg     120
cccggcaaag gcggtacctc gcacctcggc cgtccggtgt tcaacaccgt gaagggcgcg     180
gccgatgaaa ccggcgccga agcctcgatc gtattcgtgc cgccgccgtt cgcggcggac     240
gcgatcatgg aagcagcaga cgctggcatc aaatactgcg tctgcatcac ggacggcatt     300
cctgctcagg atatgatccg cgtgaagcgc tacatgcgcc gctacaagaa agagagccgc     360
atggttctca ccggcccgaa ctgcgccggc acgatctcgc ccgtaaggc gatgctcggc      420
attatgccgg gacacatctt ccttccgggt cgcgtcggca tcgtcggacg ctcgggcacg     480
ctgggctatg aagccgcagc gcagctcaag gcgctgggca tcggcgtttc gacctcggtc     540
ggtatcggcg gcgatccgat caacggttcg tcgcatcgtg acattctcga agcgttcgag     600
agcgatcccg agaccgatgc ggtgctcatg atcggtgaaa tcggcggacc gcaggaagcg     660
gaagccggtc tcttcgcgaa agagcacatg aagaagccgg tcatcgccta catcgcaggc     720
ctttcggcac cgaagggtcg ccgcatgggc cacgcaggcg ctatcgtttc ggcattcggt     780
gaatcggccg ctgagaaggt cgagatcctg aaaggctgca acgtgacgat cgccgcgacg     840
ccgtcggaga tgggttcgac ggtcgcgcag gttctcaacc agcgtaagaa agtcgcg        897
```

<210> SEQ ID NO 63
<211> LENGTH: 2105
<212> TYPE: DNA
<213> ORGANISM: Rhizobium sp. NGR234

<400> SEQUENCE: 63

```
catatggaca ttcacgaata tcaagcgaaa gaactgctga gccgttatca aattcacatc      60
ccgcgtggtg gtctggccta ctccccggaa caagctgcct atcgtgcacg cgaaatcggc     120
ggtgatcgct gggtggttaa agctcagatt catagcggtg cacgtggcaa agctggcggt     180
atcaaactgt gctctaccga tcacgaaatt gttgaagcgg ccgacagtat gctgggccgc     240
accatcgtga cgcatcagac cggtccgcaa ggcaaactgg tttctcgcct gtatgtcgaa     300
gaagcgatgg atattgcccg tgaaatttac atcggttttg ttctggaccg taaaagtgaa     360
cgcattatga tcgtcgcgag ctctagtggc ggtatggaaa ttgaagaaat cgcagaagct     420
gaaccggata gcattatccg cgccacggtg gatccgggtg ttggcatgca ggactttcaa     480
gcacgtgaaa ttgctttcgg tctgggcatc gataacgcgc tgattggccg cgccacccaa     540
acgctgctgg gttgttatcg tgcattcgtt gattacgacg cttctatgct ggaaattaac     600
ccgctggtcg tgacccgtcg cggtgatctg gtggcgctgg acgccaaaat gtcgtttgat     660
gaaaatgcac tgttccgtcg cccgcacatc gctgaaatgc gcgataaaag ccaggaagac     720
caacgcgaaa cgtatgcatc cgatcgtggt ctgtcatacg ttggtctgga cggcaacatt     780
ggttgcatta tcaatggtgc cggcctggcg atggccacca tggatatgat taaaatcgca     840
ggcggtgaac cggctaattt tctggatatc ggcggtggcg catcgccgga ccgtgtcgca     900
aaaagcttcc gcgccgtgct gacggatcgt caggtggaaa ccattctggt taacatcttt     960
gcgggcatta tcgttgtga ctgggtcgcg gaaggcgtga tcaaagcact gcgtgaagtg    1020
ggtgttccgg tcccgctggt tgtccgtctg tccggtacga acatggaaga aggtcgtcgc    1080
attctggcga aatcaggtga aaatattatc gtggccgaaa ccctggcaga agctgctgat    1140
aaagcagtgg ctgcgtggcg ttcgttcacc gctaataaag ctgcgtaagg tcgcctccca    1200
tgtccattct gctggataaa aatacccgtg tgatcgtgca aggctttacc ggcaaaatcg    1260
gctcattcca tgctgaagat atgaaacgct acggcaccaa cgtggttggc ggtgttacgc    1320
cgggcaaagg cggtcaggca catctgggta tgccggtgtt taataccgtt aaaggcgcgg    1380
tccaagaaac gggtgcggat gccagtatta tctttgtccc gccgccgttc gcggccgatt    1440
ccattatgga agcagctgac gcgggcatcc gtctgtgcgt gtgtattacc gatggtatcc    1500
cgagtcagga catgattcgt gttaaacgct atatgcgtcg ctaccgtttc gaagaccgca    1560
tgaccctgat tggtccgaac tgcgcaggca tgatcacgcc gggtgaagct atgatgggta    1620
ttatgccggg ctctatctat ctgccgggcc gtattggtat cgttggtcgt agcggtaccc    1680
tgggttacga agcagcctct caaatgaaag cgctgggcgt cggtgtgagt acgtccattg    1740
gcatcggcgg tgatccggtc aatggtagct cttttaaaga catgctggaa ctgttcgaaa    1800
aagatccggg caccgacgcc gtgctgatga ttggtgaaat cggcggtccg caggaagcgg    1860
aagcagctct gtgggcccgc gatcacatga aaaaaccgct gatcgcgtat atcgcaggtc    1920
tgtcagcacc gaaaggtcgt cgcatgggtc acgcaggcgc tattatctca gcatttggcg    1980
aatcggctca agaaaaagtg gaaattctga atcggcagg tgttacgatc gtcccgaccc    2040
cgtcctcttt tggtgaaacc gttgcggatg tgctgtcggc tatgagtaaa gcggcttaat    2100
ctaga                                                              2105
```

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
ggaattccat atggcaaaag cgtcacgcct                                           30

<210> SEQ ID NO 65
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
gctctagact atatcacccg ctttgaacg                                            29

<210> SEQ ID NO 66
<211> LENGTH: 975
<212> TYPE: DNA
<213> ORGANISM: Methylobacterium extorquens

<400> SEQUENCE: 66
atgagcttca ccctgatcca gcaggccacc ccgcgcctgc accgctcgga actcgcggtt          60
cccggctcca acccgacctt catggagaag tcggctgcct cgaaggccga cgtgatcttc         120
ctcgacctcg aggacgcggt cgcgcccgac gacaaggagc aggcccgcaa gaacatcatc         180
caggctctta acgacctgga ttggggcaac aagaccatga tgatccgcat caacggtctc         240
gacacccact acatgtaccg cgacgtggtg gacatcgtgg aggcctgccc gcgcctcgac         300
atgatcctga tccccaaggt cggcgtgccg gccgacgtct acgccatcga cgtgctgacg         360
acgcagatcg agcaggccaa gaagcgcgag aagaagatcg gcttcgaggt gctgatcgag         420
accgcgctcg gcatggccaa tgtcgaggcg atcgcgacct cgtccaagcg cctcgaggcg         480
atgtccttcg gtgtcgccga ctacgccgcc tccactcgcg cccgctccac cgtgatcggc         540
ggcgtcaacg ccgattacag cgtgctcacc gacaaggacg aggcgggcaa ccgccagacc         600
cactggcagg atccgtggct gttcgcccag aaccgcatgc tggtcgcctg ccgcgcctac         660
ggcctgcgcc cgatcgacgg tcccttcggc gacttctccg atccgacgg ctacacctcg          720
gccgctcgcc gctgcgccgc gctcggcttc gagggcaagt gggcgatcca ccctcgcag          780
atcgatctgg ccaacgaggt gttcacccc tccgaggccg aggtcaccaa ggcccgccgc          840
atcctggaag ccatggaaga ggccgccaag gccggccgcg gcgccgtctc gctcgacggc         900
cgcctcatcg acatcgcctc gatccgcatg gccgaggcgc tgatccagaa ggccgacgcg         960
atgggcggga agtaa                                                          975

<210> SEQ ID NO 67
<211> LENGTH: 891
<212> TYPE: DNA
<213> ORGANISM: Methylobacterium extorquens

<400> SEQUENCE: 67
atgagcattc tcatcgacga gaagacccccg atcctggtcc agggcatcac gggcgacaag          60

```
ggcaccttcc acgccaagga gatgatcgcc tacggctcga acgtcgtcgg cggcgtcacc    120
ccgggcaagg gcggcaagac ccattgcggc gtgccggtgt tcaacaccgt caaggaggcc    180
gtggaggcga ccggcgccac cacctcgatc accttcgtgg cgccccccct cgcggcggac    240
gcgatcatgg aggcggccga cgccggcctc aagctcgtct gctcgatcac cgacggcatc    300
cccgctcagg acatgatgcg ggtgaaacgc tacctccggc gctatccgaa ggagaagcgc    360
acgatggtgg tgggcccgaa ctgcgcgggc atcatctcgc cggcaagtc gatgctcggc     420 atcatgcccg ccacatctta cctcccgggc aaggtcggcg tcatctcccg ttccggcacg    480
ctgggctacg aggccgccgc gcagatgaag gagctcggca tcggcatctc gacctccgtc    540
ggcatcggcg gcgatccgat caacggctcc tccttcctcg accacctcgc tctgttcgag    600
caggatcccg agacggaagc cgtgctgatg atcggcgaga tcggcgggcc gcaggaggcc    660
gaggcctcgg cctggatcaa ggagaacttt tccaagcccg tgatcggctt cgtggcgggc    720
ctcaccgccc ccaagggccg ccgcatgggg catgccggcg cgatcatctc ggcgaccggc    780
gacagcgccg cggagaaggc cgagatcatg cgctcctatg gcctgaccgt ggcgcccgat    840
ccgggctcct tcggcagcac cgtggccgac gtgctcgccc gcgcggcgtg a             891

<210> SEQ ID NO 68
<211> LENGTH: 1173
<212> TYPE: DNA
<213> ORGANISM: Methylobacterium extorquens

<400> SEQUENCE: 68
atggacgttc acgagtacca agccaaggag ctgctcgcga gcttcggggt cgccgtcccg     60
aagggcgccg tggctttcag cccggatcaa gcggtctatg cggcgaccga gctcggcggc    120
tcgttctggg cggtgaaggc tcagatccat gccggcgcgc gcggcaaggc gggcgggatc    180
aagctttgcc gcacctacaa tgaagtgcgc gacgccgccc gcgacctgct gggaaaaacgc   240 ctcgtgacgc tccagaccgg ccccgagggc aagccggtgc agcgcgtcta cgtcgagacc    300
gccgacccgt tcgagcgtga actctatctc ggctacgtgc tcgatcggaa ggccgagcgc    360
gtccgtgtca tcgcctccca gcgcggcggc atggatatcg aggagatcgc cgccaaggag    420
cccgaggcgc tgatccaggt cgtggtcgag ccggcggtgg gcctgcagca gttccaggcc    480
cgcgagatcg cgttccagct cggcctcaac atcaagcagg tctcggccgc ggtgaagacc    540
atcatgaacg cctaccgggc gttccgcgac tgcgacggca ccatgctgga gatcaacccg    600
ctcgtcgtca ccaaggacga ccgggttctg gcactgacg ccaagatgtc cttcgacgac     660
aacgccctgt tccgccgccg caacatcgcg gacatgcacg atccatcgca gggcgatccc    720
cgcgaggccc aggctgccga gcacaatctc agctatatcg gcctcgaggg cgaaattggc    780
tgcatcgtca acggcgcggg tctggccatg gcgaccatgg acatgatcaa gcacgcgggc    840
ggcgagccgg caaacttcct ggatgtgggc ggcggtgcca gcccgaccg cgtcgccacg     900 gccttccgcc tcgttctgtc ggaccgcaac gtgaaggcga tcctcgtcaa catcttcgcc    960
ggcatcaacc gctgcgactg gtcgcggag ggcgtggtca aggccgcgcg cgaggtgaag     1020
atcgacgtgc cgctcatcgt gcggctcgcc ggcacgaacg tcgatgaagg caagaagatc    1080
ctcgccgaga gcgggctcga cctcatcacc gccgacaccc ttacggaagc cgcgcgcaag    1140
gctgtcgaag cctgccacgg cgccaagcac tga                                 1173

<210> SEQ ID NO 69
<211> LENGTH: 324
```

<212> TYPE: PRT
<213> ORGANISM: Methylobacterium extorquens

<400> SEQUENCE: 69

Met Ser Phe Thr Leu Ile Gln Gln Ala Thr Pro Arg Leu His Arg Ser
1               5                   10                  15

Glu Leu Ala Val Pro Gly Ser Asn Pro Thr Phe Met Glu Lys Ser Ala
            20                  25                  30

Ala Ser Lys Ala Asp Val Ile Phe Leu Asp Leu Glu Asp Ala Val Ala
        35                  40                  45

Pro Asp Asp Lys Glu Gln Ala Arg Lys Asn Ile Ile Gln Ala Leu Asn
50                  55                  60

Asp Leu Asp Trp Gly Asn Lys Thr Met Met Ile Arg Ile Asn Gly Leu
65                  70                  75                  80

Asp Thr His Tyr Met Tyr Arg Asp Val Val Asp Ile Val Glu Ala Cys
                85                  90                  95

Pro Arg Leu Asp Met Ile Leu Ile Pro Lys Val Gly Val Pro Ala Asp
            100                 105                 110

Val Tyr Ala Ile Asp Val Leu Thr Thr Gln Ile Glu Gln Ala Lys Lys
        115                 120                 125

Arg Glu Lys Lys Ile Gly Phe Glu Val Leu Ile Glu Thr Ala Leu Gly
    130                 135                 140

Met Ala Asn Val Glu Ala Ile Ala Thr Ser Ser Lys Arg Leu Glu Ala
145                 150                 155                 160

Met Ser Phe Gly Val Ala Asp Tyr Ala Ala Ser Thr Arg Ala Arg Ser
                165                 170                 175

Thr Val Ile Gly Gly Val Asn Ala Asp Tyr Ser Val Leu Thr Asp Lys
            180                 185                 190

Asp Glu Ala Gly Asn Arg Gln Thr His Trp Gln Asp Pro Trp Leu Phe
        195                 200                 205

Ala Gln Asn Arg Met Leu Val Ala Cys Arg Ala Tyr Gly Leu Arg Pro
    210                 215                 220

Ile Asp Gly Pro Phe Gly Asp Phe Ser Asp Pro Asp Gly Tyr Thr Ser
225                 230                 235                 240

Ala Ala Arg Arg Cys Ala Ala Leu Gly Phe Glu Gly Lys Trp Ala Ile
                245                 250                 255

His Pro Ser Gln Ile Asp Leu Ala Asn Glu Val Phe Thr Pro Ser Glu
            260                 265                 270

Ala Glu Val Thr Lys Ala Arg Arg Ile Leu Glu Ala Met Glu Glu Ala
        275                 280                 285

Ala Lys Ala Gly Arg Gly Ala Val Ser Leu Asp Gly Arg Leu Ile Asp
    290                 295                 300

Ile Ala Ser Ile Arg Met Ala Glu Ala Leu Ile Gln Lys Ala Asp Ala
305                 310                 315                 320

Met Gly Gly Lys

<210> SEQ ID NO 70
<211> LENGTH: 296
<212> TYPE: PRT
<213> ORGANISM: Methylobacterium extorquens

<400> SEQUENCE: 70

Met Ser Ile Leu Ile Asp Glu Lys Thr Pro Ile Leu Val Gln Gly Ile
1               5                   10                  15

Thr Gly Asp Lys Gly Thr Phe His Ala Lys Glu Met Ile Ala Tyr Gly

```
            20                  25                  30
Ser Asn Val Val Gly Val Thr Pro Gly Lys Gly Lys Thr His
        35                  40                  45
Cys Gly Val Pro Val Phe Asn Thr Val Lys Glu Ala Val Ala Thr
    50                  55                  60
Gly Ala Thr Thr Ser Ile Thr Phe Val Ala Pro Phe Ala Ala Asp
65                  70                  75                  80
Ala Ile Met Glu Ala Ala Asp Ala Gly Leu Lys Leu Val Cys Ser Ile
                85                  90                  95
Thr Asp Gly Ile Pro Ala Gln Asp Met Met Arg Val Lys Arg Tyr Leu
            100                 105                 110
Arg Arg Tyr Pro Lys Glu Lys Arg Thr Met Val Val Gly Pro Asn Cys
            115                 120                 125
Ala Gly Ile Ile Ser Pro Gly Lys Ser Met Leu Gly Ile Met Pro Gly
            130                 135                 140
His Ile Tyr Leu Pro Gly Lys Val Gly Val Ile Ser Arg Ser Gly Thr
145                 150                 155                 160
Leu Gly Tyr Glu Ala Ala Ala Gln Met Lys Glu Leu Gly Ile Gly Ile
                165                 170                 175
Ser Thr Ser Val Gly Ile Gly Gly Asp Pro Ile Asn Gly Ser Ser Phe
            180                 185                 190
Leu Asp His Leu Ala Leu Phe Glu Gln Asp Pro Glu Thr Glu Ala Val
            195                 200                 205
Leu Met Ile Gly Glu Ile Gly Gly Pro Gln Glu Ala Glu Ala Ser Ala
210                 215                 220
Trp Ile Lys Glu Asn Phe Ser Lys Pro Val Ile Gly Phe Val Ala Gly
225                 230                 235                 240
Leu Thr Ala Pro Lys Gly Arg Arg Met Gly His Ala Gly Ala Ile Ile
            245                 250                 255
Ser Ala Thr Gly Asp Ser Ala Ala Glu Lys Ala Glu Ile Met Arg Ser
            260                 265                 270
Tyr Gly Leu Thr Val Ala Pro Asp Pro Gly Ser Phe Gly Ser Thr Val
        275                 280                 285
Ala Asp Val Leu Ala Arg Ala Ala
        290                 295

<210> SEQ ID NO 71
<211> LENGTH: 390
<212> TYPE: PRT
<213> ORGANISM: Methylobacterium extorquens

<400> SEQUENCE: 71

Met Asp Val His Glu Tyr Gln Ala Lys Glu Leu Leu Ala Ser Phe Gly
1               5                   10                  15
Val Ala Val Pro Lys Gly Ala Val Ala Phe Ser Pro Asp Gln Ala Val
            20                  25                  30
Tyr Ala Ala Thr Glu Leu Gly Gly Ser Phe Trp Ala Val Lys Ala Gln
        35                  40                  45
Ile His Ala Gly Ala Arg Gly Lys Ala Gly Ile Lys Leu Cys Arg
    50                  55                  60
Thr Tyr Asn Glu Val Arg Asp Ala Ala Arg Asp Leu Leu Gly Lys Arg
65                  70                  75                  80
Leu Val Thr Leu Gln Thr Gly Pro Glu Gly Lys Pro Val Gln Arg Val
            85                  90                  95
```

```
Tyr Val Glu Thr Ala Asp Pro Phe Glu Arg Glu Leu Tyr Leu Gly Tyr
                100                 105                 110

Val Leu Asp Arg Lys Ala Glu Arg Val Arg Val Ile Ala Ser Gln Arg
            115                 120                 125

Gly Gly Met Asp Ile Glu Glu Ile Ala Ala Lys Glu Pro Glu Ala Leu
        130                 135                 140

Ile Gln Val Val Glu Pro Ala Val Gly Leu Gln Gln Phe Gln Ala
145                 150                 155                 160

Arg Glu Ile Ala Phe Gln Leu Gly Leu Asn Ile Lys Gln Val Ser Ala
                165                 170                 175

Ala Val Lys Thr Ile Met Asn Ala Tyr Arg Ala Phe Arg Asp Cys Asp
            180                 185                 190

Gly Thr Met Leu Glu Ile Asn Pro Leu Val Val Thr Lys Asp Asp Arg
        195                 200                 205

Val Leu Ala Leu Asp Ala Lys Met Ser Phe Asp Asp Asn Ala Leu Phe
    210                 215                 220

Arg Arg Arg Asn Ile Ala Asp Met His Asp Pro Ser Gln Gly Asp Pro
225                 230                 235                 240

Arg Glu Ala Gln Ala Ala Glu His Asn Leu Ser Tyr Ile Gly Leu Glu
                245                 250                 255

Gly Glu Ile Gly Cys Ile Val Asn Gly Ala Gly Leu Ala Met Ala Thr
            260                 265                 270

Met Asp Met Ile Lys His Ala Gly Gly Glu Pro Ala Asn Phe Leu Asp
        275                 280                 285

Val Gly Gly Gly Ala Ser Pro Asp Arg Val Ala Thr Ala Phe Arg Leu
    290                 295                 300

Val Leu Ser Asp Arg Asn Val Lys Ala Ile Leu Val Asn Ile Phe Ala
305                 310                 315                 320

Gly Ile Asn Arg Cys Asp Trp Val Ala Glu Gly Val Val Lys Ala Ala
                325                 330                 335

Arg Glu Val Lys Ile Asp Val Pro Leu Ile Val Arg Leu Ala Gly Thr
            340                 345                 350

Asn Val Asp Glu Gly Lys Lys Ile Leu Ala Glu Ser Gly Leu Asp Leu
        355                 360                 365

Ile Thr Ala Asp Thr Leu Thr Glu Ala Ala Arg Lys Ala Val Glu Ala
    370                 375                 380

Cys His Gly Ala Lys His
385                 390

<210> SEQ ID NO 72
<211> LENGTH: 321
<212> TYPE: PRT
<213> ORGANISM: Hyphomicrobium methylovorum

<400> SEQUENCE: 72

Met Ser Tyr Thr Leu Tyr Pro Thr Arg Lys Gln Arg Leu Gln Arg Ser
1               5                   10                  15

Tyr Leu Ala Val Pro Gly Ser Asn Pro Ser Met Ile Asp Arg Ala Leu
            20                  25                  30

Lys Ser Ala Ala Asp Tyr Val Phe Leu Asp Cys Glu Asp Ala Val Ala
        35                  40                  45

Pro Pro Glu Lys Glu Gln Ala Arg Lys Asn Ile Ile Gln Ala Leu Asn
    50                  55                  60

Asp Leu Asp Trp Lys Gly Ala Gly Lys Ser Val Ser Val Arg Ile Asn
65                  70                  75                  80
```

```
Gly Leu Asp Thr His Tyr Met Tyr Arg Asp Val Val Asp Ile Val Glu
                85                  90                  95

Gln Ala Gly Ser Lys Leu Asp Thr Ile Leu Ile Pro Lys Val Gly Val
            100                 105                 110

Pro Ala Asp Val Tyr Thr Val Glu Cys Ile Val Ser Gln Ile Glu Val
        115                 120                 125

Ala Lys Gly Leu Pro His Gln Ile Gly Thr Glu Ala Leu Ile Glu Thr
    130                 135                 140

Pro Leu Gly Met Ala Asn Val Glu Ala Ile Ala Ser Ala Ser Ser Arg
145                 150                 155                 160

Leu Glu Ser Met His Phe Gly Val Ala Asp Tyr Ser Ala Phe Asn Lys
                165                 170                 175

Ala Arg Thr Val Val Ile Gly Gly Leu Asn Pro Asp Tyr Pro Gly Asp
            180                 185                 190

Gln Trp His Phe Pro Leu Ser Arg Met Thr Val Ala Cys Arg Ala Phe
        195                 200                 205

Gly Leu Arg Pro Ile Asp Gly Pro Phe Gly Gly Ile Asp Asp Pro Glu
    210                 215                 220

Gly Tyr Lys Ala Ala Arg Arg Gly Ala Ala Leu Gly Met Glu Gly
225                 230                 235                 240

Lys Trp Ala Ile His Pro Ser Gln Ile Glu Leu Ala Asn Glu Ile Tyr
                245                 250                 255

Ser Pro Thr Ala Lys Glu Val Glu Arg Ala Glu Arg Ile Leu Val Ala
            260                 265                 270

Leu Lys Glu Ala Glu Ala Gln Gly Lys Gly Ala Ala Ser Leu Asp Gly
        275                 280                 285

Lys Met Ile Asp Ala Ala Ser Glu Lys Met Ala Arg Asn Leu Leu Ser
    290                 295                 300

Thr Ala Glu Gln Ile Lys Lys Ala Glu Ala His Ala Ala Gln Lys
305                 310                 315                 320

Lys

<210> SEQ ID NO 73
<211> LENGTH: 387
<212> TYPE: PRT
<213> ORGANISM: Hyphomicrobium methylovorum

<400> SEQUENCE: 73

Met Asp Val His Glu Tyr Gln Ala Lys Glu Leu Leu Ala Lys Phe Gly
1               5                   10                  15

Val Pro Ile Ala Arg Gly Gly Leu Ala Tyr Ser Pro Glu Gln Ala Thr
            20                  25                  30

Tyr Arg Ala Ser Glu Leu Gly Gly Thr Val Val Lys Ala Gln Ile
        35                  40                  45

His Ser Gly Ala Arg Gly Lys Ala Gly Gly Val Lys Val Cys Lys Asn
    50                  55                  60

Glu Lys Glu Ile Glu Asp Ala Ala Glu Phe Met Leu Gly Arg Lys Leu
65                  70                  75                  80

Val Thr His Gln Thr Gly Pro Ala Gly Lys Leu Val Ser Arg Leu Tyr
                85                  90                  95

Ile Glu Glu Ala Thr Asn Ile Asp Arg Glu Ile Tyr Leu Gly Phe Val
            100                 105                 110

Met Asp Arg Ala Ser Glu Arg Ile Val Val Ala Ser Ala Ala Gly
        115                 120                 125
```

Gly Met Asp Ile Glu Glu Ile Ser Ala Ser Gln Pro Asp Thr Ile Ile
        130                 135                 140

Arg Val Ser Val Asp Pro Ala Val Gly Met Gln Gln Phe Gln Ala Arg
145                 150                 155                 160

Glu Leu Ala Phe Gly Leu Gly Val Asp Pro Glu Ile Val Asn Lys Leu
                165                 170                 175

Val Pro Ala Ile Met Gly Cys Tyr Arg Ala Phe Arg Asp Leu Asp Ala
            180                 185                 190

Thr Met Val Glu Val Asn Pro Leu Val Ile Thr Lys Glu Lys Gln Val
        195                 200                 205

Leu Ala Leu Asp Ala Lys Met Ser Phe Asp Asp Asn Ala Leu Phe Arg
210                 215                 220

Arg Pro His Ile Ala Glu Leu Arg Asp Lys Ser Gln Glu Asp Pro Arg
225                 230                 235                 240

Glu Thr Tyr Ala Ser Asp Arg Gly Leu Ser Tyr Val Gly Leu Asp Gly
                245                 250                 255

Asp Ile Gly Cys Ile Val Asn Gly Ala Gly Leu Ala Met Ala Thr Leu
            260                 265                 270

Asp Met Ile Lys Leu Ala Gly Gly Glu Pro Ala Asn Phe Leu Asp Ile
        275                 280                 285

Gly Gly Gly Ala Ser Pro Glu Arg Val Thr Lys Ser Phe Lys Ala Val
290                 295                 300

Leu Arg Asp Lys Asn Val Lys Ala Ile Leu Val Asn Val Phe Ala Gly
305                 310                 315                 320

Ile Asn Arg Cys Asp Trp Val Ala Lys Gly Val Asp Ala Val Lys
                325                 330                 335

Glu Leu Glu Ile Lys Met Pro Ile Val Val Arg Leu Ala Gly Thr Asn
            340                 345                 350

Val Glu Glu Gly Arg Lys Ile Ile Asp Asn Ser Gly Leu Thr Val Ile
        355                 360                 365

Ser Ala Asp Thr Leu Ala Asp Ala Ala Lys Gln Ala Val Asp Ala Ala
370                 375                 380

Lys Lys Ala
385

<210> SEQ ID NO 74
<211> LENGTH: 299
<212> TYPE: PRT
<213> ORGANISM: Hyphomicrobium methylovorum

<400> SEQUENCE: 74

Met Ala Ile Phe Ile Asn Glu Lys Thr Pro Ile Leu Ile Gln Gly Phe
1               5                   10                  15

Thr Gly Arg Ile Gly Thr Phe His Ala Gln Glu Met Ile Asp Tyr Gly
            20                  25                  30

Ser Asn Val Val Gly Gly Val Thr Pro Gly Lys Gly Gly Thr Ser His
        35                  40                  45

Leu Gly Arg Pro Val Phe Asn Thr Val Lys Gly Ala Ala Asp Glu Thr
    50                  55                  60

Gly Ala Glu Ala Ser Ile Val Phe Val Pro Pro Phe Ala Ala Asp
65                  70                  75                  80

Ala Ile Met Glu Ala Ala Asp Ala Gly Ile Lys Tyr Cys Val Cys Ile
                85                  90                  95

Thr Asp Gly Ile Pro Ala Gln Asp Met Ile Arg Val Lys Arg Tyr Met

```
                100                 105                 110
Arg Arg Tyr Lys Lys Glu Ser Arg Met Val Leu Thr Gly Pro Asn Cys
        115                 120                 125

Ala Gly Thr Ile Ser Pro Gly Lys Ala Met Leu Gly Ile Met Pro Gly
130                 135                 140

His Ile Phe Leu Pro Gly Arg Val Gly Ile Val Gly Arg Ser Gly Thr
145                 150                 155                 160

Leu Gly Tyr Glu Ala Ala Ala Gln Leu Lys Ala Leu Gly Ile Gly Val
                165                 170                 175

Ser Thr Ser Val Gly Ile Gly Gly Asp Pro Ile Asn Gly Ser Ser His
                180                 185                 190

Arg Asp Ile Leu Glu Ala Phe Glu Ser Asp Pro Glu Thr Asp Ala Val
                195                 200                 205

Leu Met Ile Gly Glu Ile Gly Gly Pro Gln Ala Glu Ala Gly Leu
                210                 215                 220

Phe Ala Lys Glu His Met Lys Lys Pro Val Ile Ala Tyr Ile Ala Gly
225                 230                 235                 240

Leu Ser Ala Pro Lys Gly Arg Arg Met Gly His Ala Gly Ala Ile Val
                245                 250                 255

Ser Ala Phe Gly Glu Ser Ala Ala Glu Lys Val Glu Ile Leu Lys Gly
                260                 265                 270

Cys Asn Val Thr Ile Ala Ala Thr Pro Ser Glu Met Gly Ser Thr Val
                275                 280                 285

Ala Gln Val Leu Asn Gln Arg Lys Lys Val Ala
                290                 295

<210> SEQ ID NO 75
<211> LENGTH: 299
<212> TYPE: PRT
<213> ORGANISM: Rhizobium sp.

<400> SEQUENCE: 75

Met Ser Ile Leu Leu Asp Lys Asn Thr Arg Val Ile Val Gln Gly Phe
1               5                   10                  15

Thr Gly Lys Ile Gly Ser Phe His Ala Glu Asp Met Lys Arg Tyr Gly
                20                  25                  30

Thr Asn Val Val Gly Gly Val Thr Pro Gly Lys Gly Gly Gln Ala His
                35                  40                  45

Leu Gly Met Pro Val Phe Asn Thr Val Lys Gly Ala Val Gln Glu Thr
    50                  55                  60

Gly Ala Asp Ala Ser Ile Ile Phe Val Pro Pro Phe Ala Ala Asp
65                  70                  75                  80

Ser Ile Met Glu Ala Ala Asp Ala Gly Ile Arg Leu Cys Val Cys Ile
                85                  90                  95

Thr Asp Gly Ile Pro Ser Gln Asp Met Ile Arg Val Lys Arg Tyr Met
                100                 105                 110

Arg Arg Tyr Arg Phe Glu Asp Arg Met Thr Leu Ile Gly Pro Asn Cys
                115                 120                 125

Ala Gly Met Ile Thr Pro Gly Glu Ala Met Met Gly Ile Met Pro Gly
130                 135                 140

Ser Ile Tyr Leu Pro Gly Arg Ile Gly Ile Val Gly Arg Ser Gly Thr
145                 150                 155                 160

Leu Gly Tyr Glu Ala Ala Ser Gln Met Lys Ala Leu Gly Val Gly Val
                165                 170                 175
```

```
Ser Thr Ser Ile Gly Ile Gly Asp Pro Val Asn Gly Ser Ser Phe
            180                 185                 190

Lys Asp Met Leu Glu Leu Phe Glu Lys Asp Pro Gly Thr Asp Ala Val
        195                 200                 205

Leu Met Ile Gly Glu Ile Gly Gly Pro Gln Glu Ala Glu Ala Ala Leu
        210                 215                 220

Trp Ala Arg Asp His Met Lys Lys Pro Leu Ile Ala Tyr Ile Ala Gly
225                 230                 235                 240

Leu Ser Ala Pro Lys Gly Arg Arg Met Gly His Ala Gly Ala Ile Ile
                245                 250                 255

Ser Ala Phe Gly Glu Ser Ala Gln Glu Lys Val Glu Ile Leu Lys Ser
            260                 265                 270

Ala Gly Val Thr Ile Val Pro Thr Pro Ser Ser Phe Gly Glu Thr Val
        275                 280                 285

Ala Asp Val Leu Ser Ala Met Ser Lys Ala Ala
        290                 295
```

<210> SEQ ID NO 76
<211> LENGTH: 394
<212> TYPE: PRT
<213> ORGANISM: Rhizobium sp.

<400> SEQUENCE: 76

```
Met Asp Ile His Glu Tyr Gln Ala Lys Glu Leu Leu Ser Arg Tyr Gln
1               5                   10                  15

Ile His Ile Pro Arg Gly Gly Leu Ala Tyr Ser Pro Glu Gln Ala Ala
                20                  25                  30

Tyr Arg Ala Arg Glu Ile Gly Gly Asp Arg Trp Val Val Lys Ala Gln
            35                  40                  45

Ile His Ser Gly Ala Arg Gly Lys Ala Gly Gly Ile Lys Leu Cys Ser
        50                  55                  60

Thr Asp His Glu Ile Val Glu Ala Ala Asp Ser Met Leu Gly Arg Thr
65                  70                  75                  80

Ile Val Thr His Gln Thr Gly Pro Gln Gly Lys Leu Val Ser Arg Leu
                85                  90                  95

Tyr Val Glu Glu Ala Met Asp Ile Ala Arg Glu Ile Tyr Ile Gly Phe
            100                 105                 110

Val Leu Asp Arg Lys Ser Glu Arg Ile Met Ile Val Ala Ser Ser Ser
        115                 120                 125

Gly Gly Met Glu Ile Glu Glu Ile Ala Glu Ala Glu Pro Asp Ser Ile
    130                 135                 140

Ile Arg Ala Thr Val Asp Pro Gly Val Gly Met Gln Asp Phe Gln Ala
145                 150                 155                 160

Arg Glu Ile Ala Phe Gly Leu Gly Ile Asp Asn Ala Leu Ile Gly Arg
                165                 170                 175

Ala Thr Gln Thr Leu Leu Gly Cys Tyr Arg Ala Phe Val Asp Tyr Asp
            180                 185                 190

Ala Ser Met Leu Glu Ile Asn Pro Leu Val Val Thr Arg Arg Gly Asp
        195                 200                 205

Leu Val Ala Leu Asp Ala Lys Met Ser Phe Asp Glu Asn Ala Leu Phe
    210                 215                 220

Arg Arg Pro His Ile Ala Glu Met Arg Asp Lys Ser Gln Glu Asp Gln
225                 230                 235                 240

Arg Glu Thr Tyr Ala Ser Asp Arg Gly Leu Ser Tyr Val Gly Leu Asp
                245                 250                 255
```

```
Gly Asn Ile Gly Cys Ile Ile Asn Gly Ala Gly Leu Ala Met Ala Thr
            260                 265                 270

Met Asp Met Ile Lys Ile Ala Gly Gly Glu Pro Ala Asn Phe Leu Asp
        275                 280                 285

Ile Gly Gly Ala Ser Pro Asp Arg Val Ala Lys Ser Phe Arg Ala
290                 295                 300

Val Leu Thr Asp Arg Gln Val Glu Thr Ile Leu Val Asn Ile Phe Ala
305                 310                 315                 320

Gly Ile Asn Arg Cys Asp Trp Val Ala Glu Gly Val Ile Lys Ala Leu
                325                 330                 335

Arg Glu Val Gly Val Pro Val Pro Leu Val Val Arg Leu Ser Gly Thr
            340                 345                 350

Asn Met Glu Glu Gly Arg Arg Ile Leu Ala Glu Ser Gly Glu Asn Ile
        355                 360                 365

Ile Val Ala Glu Thr Leu Ala Glu Ala Ala Asp Lys Ala Val Ala Ala
    370                 375                 380

Trp Arg Ser Phe Thr Ala Asn Lys Ala Ala
385                 390
```

```
<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccctgaggag ggtccaagag atggacgtcc atgagtacca                              40

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gctctagatc aggctgcctg acgccca                                            27

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggaattcaca aaaggataa aa                                                  22

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tggtactcat ggacgtccat ctcttggacc ctcctcaggg                              40
```

<210> SEQ ID NO 81
<211> LENGTH: 897
<212> TYPE: DNA
<213> ORGANISM: Granulibacter bethesdensis

<400> SEQUENCE: 81

```
atgagcattc tgatcaataa gcagaccaag atcatcattc agggcttcac cggcgacaag      60
ggcacgttcc acgtcgcga gatgatcgat tacggcacca atgtcgtcgg tggcgtgacg     120
cccggtaaag gcggccagac ccatctgggt cgtcccgtgt tcaacacggt cgaggacgcg     180
gtgcgtgaaa ccggtgccca ggcgtcgatc acctttgtgg cacctgcctt ttgcgccgat     240
gcgatcatgg aaggcgccga tgcggggctg gagctgatct gcaccatcac ggacggtatt     300
ccggcgcagg atatgatgcg cgtgaagcgt tatctgcgcc gctaccagaa ggatcgtcgc     360
acgcgtctgg tggggccgaa ctgcgcgggc atcatcagcc cgggccaggc catgctgggc     420
atcatgccgg ccatatccta caaggaaggc catgtcggca ttgtttcccg ctcaggcacg     480
ctcggctatg aagccgccgc gcagctgaag gagctgggca tcggtgtgtc caccagtgtg     540
ggtatcggtg tgaccccgat caatggttct tccttccttg atcaccttca gctgttcgaa     600
gccgaccccg agactcatgc cgtgctgatg atcggcgaga tcggtggccc gcaggaagcc     660
gaagcggcga gtggatcag cgagaacatg tcgaagccgg tggttggcta cgttgccggc     720
ctgaccgctc cgaaggggcg tcgtatgggc catgccggtg cgatcatctc tggcgaaggc     780
gacagcgccg ccgaaaagag cgagatcatg cgctcctacg gtctgacggt tgctcccagc     840
ccgggtgaac tcggctcgac cgttgccgcg gtgctggctg ggcgtcaggc agcctga      897
```

<210> SEQ ID NO 82
<211> LENGTH: 1170
<212> TYPE: DNA
<213> ORGANISM: Granulibacter bethesdensis

<400> SEQUENCE: 82

```
atggacgtcc atgagtacca ggcaaaagaa ttgcttgcga gcgccggtgt ggccgtgccc      60
cgcggtgcaa tcgctttcag cgctgatcag gccgtgtatg ccgcgaccga actgggtggc     120
tggcactggg cggtgaaagc ccagattcat gccggtgcgc gcggcaaggc cggcggcatc     180
aagctgtgca agacgtatca tgaagtgcgc gaggctgctg ccggtatgct cggcaagcgt     240
ctggtcacgc atcagaccgg tccggaaggc aagcctgtcc agcgcgtgta tgtcgaggtc     300
gccgatccct tcgagaaaga attctatctg ggctttgtgc tggatcgtaa gctggagcgc     360
gtgcgtgtga tcgcctccgc cgagggcggc atggagatcg aggaaatcgc ttccaagcat     420
ccggaaaagc tgatccaggt gatcgtggag ccggcggttg gtcttcagca gttccaggcc     480
cgccagatcg ccttcaagct gggcctgtcc agccgtcagg tacagcgtgc ggtgaccagc     540
atcatgggcg cttatcgcgc attccgcgat cacgacgcga ccatgctgga atcaatcct     600
ctggttctga ccaaggatga ccgtattctg gcgctcgatg cgaagatgag cttcgacgac     660
aacgccttgt tccgtcgcaa caacgtcgcc aacatgcatg ccccctctca ggacgatccg     720
cgtgaggcgc aggctgccga gcacaacctc aactatgtgg tctggaagg cgatatcggc     780
tgcgtggtga atggcgccgg cctggcgatg cgaccatgg acgtcatcaa atatgcgggt     840
ggtgagcctg ccaacttcct cgatgtcggc ggcggggcaa gccccgagcg taccgcgacg     900
gcgttccgtc tggtgctgtc cgacaagaac gtgaaggttg ttctggtcaa catcttcgcc     960
```

```
ggcatcaacc gctgcgactg gatcgcggaa ggcgtggtgc acgcggtgaa agaagtcgat    1020
ctgaagcttc cgctggtggt gcgtctggca ggcaccaatg tggaggaagg ccgccgtatt    1080
ctgaaagaaa gcggcatttc cgtcatcatg gccgaaagcc tgaccgaagc ggccgaaaag    1140
gccgtcgagg ccgcgaaggc cgcggcgtaa                                     1170

<210> SEQ ID NO 83
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
accagggaat tcacaaaaag gataaaacaa tgagctatac cctctaccca accgtaagc      59

<210> SEQ ID NO 84
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gcccactcta gatcaggcaa ctttttttctg cttgccgaga acc                      43

<210> SEQ ID NO 85
<211> LENGTH: 963
<212> TYPE: DNA
<213> ORGANISM: Hyphomicrobium denitrificans

<400> SEQUENCE: 85
atgagctata ccctctaccc gaaccgtaag cagcgtctgc agcgttctta tctcgccgtg     60
ccgggctcca acccgacgat gatcgaccgc gccctcaaga gcgccgccga ctacgtttc    120 cttgattgcg aagacgccgt cgcgccgccc gagaaagagc aggctcgcaa gaacatcatc    180
caggctctga cgatctcga ctggaagggc gcgggcaaga gcgtctcggt ccgcatcaac    240
ggcctcgaca cgcattattg ctaccgcgac gtcgtcgaca tcgtcgagca ggctggtgcc    300
aagctcgata cgatcctcat tccgaaggtc ggcgttccgg ccgacgtcta cgccatcgaa    360
agcttcgtca gccagatcga agtcgcgaag ggtctcccgc accagatcgg catggaagcc    420
ctcatcgaaa cgccgctcgg catggccaac gtcgaagcca tcgcgtctgc aacagccgc    480 cttgagtcga tgcacttcgg cgttgccgac tactccgcat tcaacaaggc ccgcaccgtc    540
gtcatcggcg gcttgaaccc cgactatccg ggtgaccagt ggcacttccc gctgtcgcgc    600
atgacggtcg cctgccgcgc attcggtctc cgtccgatcg acggcccgtt cggcggcatc    660
gacgatccgg aaggctacaa ggccgctgcg cgccgtggtg ccgctctcgg catggaaggc    720
aagtgggcga tccaccccctc gcagatcgaa ctcgccaacg aaatctactc tccgacggcg    780
aaggaaatcg aacgcgccga gcgcatcctg gtcgcactca aggaagccga agcgcagggc    840
aagggcgcag catcgctcga cggcaagatg atcgacgcgg catctgaaaa gatggcgaag    900
aacctgctgg tcacggcagc ggcgatcaag gcaggcgaag aagctcgcgc aaagagcaaa    960
taa                                                                  963

<210> SEQ ID NO 86
<211> LENGTH: 900
```

```
<212> TYPE: DNA
<213> ORGANISM: Hyphomicrobium denitrificans

<400> SEQUENCE: 86
atggcaatct ttatcaatga aaagacgccg atcctgatcc agggctttac cggtcgcatc    60
ggcacgttcc acgcccagga aatgatcgac tacggctcca acgtcgttgg cggcgtgacg   120
cccggtaaag gcggcacctc gcatctcggc cgtccggtgt caacaccgt caagggcgcc    180
gtcgacgaga cgggcgctga agcctccatc gtgttcgtgc cgccgccgtt cgcggctgac   240
gcgatcatgg aagcggccga cgctgggatc aaatactgcg tctgcatcac ggacggcatt   300
cctgctcagg atatgatccg cgtgaagcgc tacatgcgcc gctacaagaa agaagcgcgc   360
atgatcctga ccggcccgaa ctgcgccggc acgatctcgc caggcaaggc gatgctcggc   420
atcatgccgg acacatctca ccttccgggc gcgtcggca tcgtcggccg ctccggtacg    480
ctcggctacg aagccgccgc gcagctcaag gcccttggca tcggcgtctc gacgtcggtt   540
ggtatcggcg cgacccgat caacggctcg tcgcatcgtg acgtcctcga gcacttcgag    600
aacgatcccg agaccgacgc gatcctgatg atcggcgaaa tcggtggtcc gcaggaagcc   660
gaagccggcc tcttcgccaa agagcacatg aagaagcctg tcatcgccta catcgccggt   720
ctgtcggccc cgaagggccg ccgcatgggc cacgctggcg ccatcgtttc ggcattcggc   780
gagtcggctg ctgagaaggt cgagatcctg aagggctgcg gcgtcgctat cgcgccgacg   840
ccgtcggaaa tgggctcgac cgtcgcgcag gttctcggca gcagaaaaa agttgcctga   900

<210> SEQ ID NO 87
<211> LENGTH: 1164
<212> TYPE: DNA
<213> ORGANISM: Hyphomicrobium denitrificans

<400> SEQUENCE: 87
atggacattc atgaatacca ggccaaagag cttcttgcga agttcggcgt gccgatcgcc    60
cgcggcggac ttgcctacag ccctgaacag gccacctatc gcgccagcga gcttggcggc   120
acggtcgtcg tcaaggcgca gattcactcc ggcgcgcgcg gtaaagccgg cggcgtcaag   180
gtctgcaaga cggaaaagga aatcgaggat gcagccgagt tcatgctcgg ccgcaagctc   240
gtcacgcacc aaacgggatc ggccggcaag ctggtctcgc gcctctacat cgaagaagcg   300
acgaacatcg atcgcgaaat ctatctcggt ttcgtgatgg accgcgcttc ggagcgcatc   360
gtcgtcgtgg cctcggccgc gggcggcatg gacatcgagg aaatctcggc gtcgcagccc   420
gacacgatca tccgcgtcgc cgtcgacccg cggtcggca tgcagcagtt ccaggcacgt   480
gagctggcat tcggacttgg cgtcgatcct gagatcgtca acaagctcgt gcccgcgatc   540
atgggctgct atcgcgcctt ccgcgatctc gatgcgatga tggttgaaat caacccgctc   600
gtcatcacca aggaaaagca ggtcgttgcg ctcgacgcca agatgtcgtt cgacgacaac   660
gcgctgttcc gccgtccgca catcgccgag ctgcgcgaca agagccagga agatccccgc   720
gaaacctacg cgtcggatcg tggtctctcg tacgtcggtc tcgatggcga catcggctgc   780
atcgtcaacg gtgccggtct cgcgatggcg acgctcgaca tgatcaagct tgcgggcggc   840
gagcctgcga acttcctcga catcggcggc ggcgcctctc ccgagcgcgt caccaagtcg   900
ttcaaggcgg ttctgcgcga caagaacgtc aaggccatcc tggtcaacgt cttcgccggc   960
atcaaccgtt gcgactgggt tgccaagggt gtcgtcgacg ccgtcaagga actcgatatc  1020
aagctgccga tcgtcgttcg cctcgcaggc accaacgtcg aagaaggccg caagatcatc  1080
```

```
gacaacagcg gcctgacggt catcagcgcg gaaactctcg ccgatgctgc caagcaggcg    1140
gtcgaagcgg ccaaaaaagc ctaa                                           1164
```

<210> SEQ ID NO 88
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

```
gcgggggaat tcacaaaaag gataaaacaa tgagtcatac cctgtatgaa ccaaaacacc    60
```

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89

```
caggcgtcta gattagagtc cggccagaac ttttgcgacg                          40
```

<210> SEQ ID NO 90
<211> LENGTH: 951
<212> TYPE: DNA
<213> ORGANISM: Nitrosomonas europaea

<400> SEQUENCE: 90

```
atgagtcata ccctgtatga aaccaaaaca ccgcgtgtac agcgctgcga actggctgtt    60
ccgggttccc gtcccgaaat gtttgaaaaa gcgctgaaaa gcggagtgga cttcatattt   120
ctggatctgg aggatgcagt cgcaccagat gacaagatcc aggcaagaaa aaatatcatt   180
caggcaatca atgatctgga ctggaaaagt cacggtgtca cgctttctgt acgcatcaat   240
ggtctcgata cccaatatat ggtgcgtgat gtggtcgatc tggtagagca ggccgggcac   300
aagatcgata cgttgctgat tcccaaagta ggtgtttatg ctgatgttta catggtcgaa   360
gccatgctca gccagcttga aatgcagcag gggctgaaaa accgaattgg tgtggaagca   420
ctgatcgaaa cggcactggg gatggccaat gttgaagata tcgcccgcag aggaacggcc   480
gggcgtctgg aagcattgca tttcggtgta gctgactacg ctgccagcaa tcgtgcacgt   540
accaccaata tcggcgggct caatccggat tatccagggg atcagtggca cgcagccatc   600
agcagaatga ccgttgcctg ccgcgcattc ggcctgcgac caatcgatgg cccatttggt   660
gacattcagg atcccgaagg ttacaaacag gcagccagac gtgctgcagc actgggttgt   720
gaaggtaaat gggcaattca tccgacacag atcgcgctgg ccaatgaagt ctttacgccg   780
cccacagcag aagtcgacaa agccaaacgc attctgacag cattgaagga agctgcagct   840
caaggtaaag gtgcagcctc acttgatggc cgcctgatcg atgccgcttc ggaaagaatg   900
gcaaataaca tcgtcaaaat ggcggaagca attgctgcca aaagcaaata a            951
```

<210> SEQ ID NO 91
<211> LENGTH: 888
<212> TYPE: DNA
<213> ORGANISM: Nitrosomonas europaea

<400> SEQUENCE: 91

```
gtggcaattc tcatcaatga gcagacgcgg atcatcgtac agggctttac cggccggatc    60
```

```
ggcaccttcc atgctcagga aatgatcgat tacggatcta atgtagtggg aggcgtaacg      120
cccggcaaag gcgggcagaa acacctgggg ctgccagtat tcaataccgt ccgggaagca      180
gtcgagcagg caggtgcgga agccagcatt gtattcgtcc cgccggcatt tgcggctgat      240
tcgattatgg aagcagccga tgccggtatc aaatattgcg tatccatcac cgatggcatt      300
ccaacccagg acatgatgac cgtcaaaaac ttcttacgcc tcttccctga ggaggacaga      360
atgatgctga ccgccccaa ctgttcaggc actatcagcc ccggacgggc gatgttgggc       420
atcatgccgg ggcatattta cagccgtggg gtcgttggtg tcgtcggccg ttccggtaca      480
ctgggttatg aagctgccga ccagatgcga cggctgaata tcgggatttc gacttcggta      540
ggtattggcg gagacccgat catcggcagt tcgcaccgga atgtgctgca aaagctggaa      600
gaagatccgg aaaccaaagt cacgctgatg attggtgaaa ttggtggccc aatgaagta     660 gaagccggac tgttcgcaaa ggaaaacatg agcaaaccgc tggttgccta cattgccggc      720
ctgactgcac ctcccggaag acggatgggg cacgccggag caatcatctc ttcagccggt      780
gaaagcgcag cagaaaaagt ggaaagactg aaagaactgg gcgtcaccat ctgcccgact      840
ccgtctctga tgggtgaaac cgtcgcaaaa gttctggccg gactctaa                  888

<210> SEQ ID NO 92
<211> LENGTH: 1173
<212> TYPE: DNA
<213> ORGANISM: Nitrosomonas europaea

<400> SEQUENCE: 92
ttggatatcc atgaatatca ggccaaggaa atcctggctg aatacggtat caagctggct       60
gaaggcggat tggcgcacac tgtggaagaa gcggtacaac gcagccggga aatcgatggc      120
aatgtgtggg tcgtcaaggc acaaatccat tccggcgccc gtggtaaagc aggcggtgtc      180
aaagtatgcc ggacacatga agaaatcgaa gtcgcagctg aatcactgct ggggaaaaaa      240
ctggtcacac accaaaccgg cccggcgggt aaactctgct ccagactgta tatcgaagcc      300
ggtaccgaaa ttgcccggga agtgtatctc gctttcatga tcgatcgcag tcatgaacgt      360
atcgtcatgg tgggttccgc acaggggga atggatatcg agaccctggc agccacgaat      420
cctgatgcca tcaaaaaaat tcacatcgag cctgctgtcg gcctgcagga tttccaggca      480
agaaccatgg cttttgcact gggtctggaa gatgttctgc tcaatcacgc cgtcaagacg      540
atcagaggtt gctaccgcgc catgcgcgat ctggatgcga acatactcga aatcaacccg      600
ctggttgtca cgcgcaacaa cgagctgatc gcactggatg cgaagatgag ctttgatgaa      660
aatgcactgt tccggcgcca ccggatttcc gaattgcgtg acaactcaca aatcgattcg      720
cgcgaaattg ctgcagcgga agcaggcttg agctacgtcg ggctggatgg agacatcggc      780
tgcatgatca atggcgccgg gctggcaatg gccaccatgg acatgatcaa actggccggc      840
ggcgaaccgg ccaattttct ggatgtcggc ggcggcgcat ctgccgagcg aactgaaaaa      900
gcattccggc tggtactggc ggataacaac gtaaaagcca tgctggtcaa tatctttgcc      960
ggtattaacc gctgtgactg gattgccgaa ggtgtggttc aggctgtacg gaatatcgga     1020
atgacggtcc ctctggtcgt gcgcctgtct ggcaccaacg tggaagaagg ccgccgtatc     1080
atcgctgaca gcgggttgcc gatcattact gcagaaaccc tggccgatgc agcagagaaa     1140
gtagtgcacg ctcgcaacca ggctgcagtt tga                                   1173

<210> SEQ ID NO 93
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggaattccat atggctgtta aaaatcgtct ac                                    32

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gctctagatc agaatctgat tccgtgttc                                        29

<210> SEQ ID NO 95
<211> LENGTH: 963
<212> TYPE: DNA
<213> ORGANISM: Methylococcus capsulatus

<400> SEQUENCE: 95
atggctgtca agaaccgtct acaccgcagc gaactcgcgg tgccgggcag caatccacgc      60
atgctcgaga agcgccgga agccggcgcc gacatcgtct ttctggacct ggaagatgcg     120
gttgcgccgg atgacaagga gcaagcgcgc cggaacatcg tcttcgcgct caacacctac     180
gactggtcca gatgcgcggt ctccgtccgc atcaacggcc tcgacaccca ttacgcctac     240 cgggaccctcg ttgagatcgt cgagtcctgc ggcgacaagc tcgacaccat tctggtgccg    300
aaagtcggca gcgcctcgga cgttctgttc gtcgcgactt actttcccca gatcgaggcc    360
tacaaaggtt tcaaaccgat caatatccac gtgctgatcg aaacggccat gggcatggcc    420
aacgtggagg agatcgcccg cacctgtcct gaacgcatgg aggccatggt gttcggcgtg    480
gccgactacg ctgcgtcggt gcgcgcccgc acgaccaaca tcggcggcgc caacccggat    540
tacggcatgc tgaccgaccc tgacgaaagc ggtacccgcg cctatcactg ggccgaccag    600
tggcatttcg gcatttcccg catggtcgcg gcctgccgcg cctatgggct cgcccccatc    660
gacggcccct tcggcgattt cagcgatccg gaaggattcc gcgccgcagc ccgccgtgcc    720
gcggcactgg gctgcgaagg gaagtgggcg atccatccct cccagattcc actgtgcaac    780
gaaatcttca cacccacgga aaaagaggtc acgcgggcct accgcatcct ggaagccatg    840
gagcaggcgg caaaggaggg caaaggcgcg gtgtctctgg atgggcggct gatcgatgcc    900
gcctcgatcc ggatggcgga gaacgtggtc cgccagatga agcagatcga gtcgcgtcgg    960
tag                                                                  963

<210> SEQ ID NO 96
<211> LENGTH: 903
<212> TYPE: DNA
<213> ORGANISM: Methylococcus capsulatus

<400> SEQUENCE: 96
atgagcgtat tcgttaacaa gcactccaag gtcatcttcc agggcttcac cggcgagcac      60
gccaccttcc acgccaagga cgccatgcgg atgggcaccc gggtggtcgg cggtgtcacc     120
cctggcaaag gcggcacccg ccatcccgat ccgaactcg ctcatctgcc ggtgttcgac     180
```

```
accgtggctg aagccgtggc cgccaccggc gccgacgtct ccgccgtgtt cgtgccgccg      240
cccttcaatg cggacgcgtt gatggaagcc atagacgccg gcatccgggt cgccgtgacc      300
atcgccgacg gcatcccggt acacgacatg atccgactgc agcgctaccg ggtgggtaag      360
gattccatcg tgatcggacc gaacaccccc ggcatcatca cgccgggcga gtgcaaggtg      420
ggcatcatgc cttcgcacat ttacaagaag ggcaacgtcg gcatcgtgtc gcgctccggc      480
accctcaatt acgaggcgac ggaacagatg gccgcgcttg gctgggcat caccacctcg       540 gtcggtatcg gcggtgaccc catcaacgga accgatttcg tcactgtcct gcgcgccttc      600
gaagccgacc cggaaaccga gatcgtggtg atgatcggcg aaatcggcgg cccccaggaa      660
gtcgccgccg cccgctgggc caaggaaaac atgacaaagc cggtcatcgg cttcgtcgca      720
ggccttgccg caccgaccgg ccgacgcatg ggccatgccg cgccatcat ctccagcgag        780 gccgacaccg ccggagccaa gatggacgcc atggaagcct ggggctgta tgtcgcccgc       840 aacccggcac agatcggcca gaccgtgcta cgcgccgcgc aggaacacgg aatcagattc      900
tga                                                                    903

<210> SEQ ID NO 97
<211> LENGTH: 1170
<212> TYPE: DNA
<213> ORGANISM: Methylococcus capsulatus

<400> SEQUENCE: 97
gtgaatatcc atgagtacca ggccaaggag ctgctcaaga cctatggcgt gcccgtgccc       60
gacggcgccg ttgcctattc cgacgcgcag gccgccagcg tcgccgagga gatcggcggc      120
agccgctggg tggtcaaggc gcagatccat gccggcggtc gcggcaaggc cgggggcgta      180
aaggtcgccc actccatcga ggaagtccgc caatacgccg acgccatgct cggcagccac      240
ctcgtcaccc atcagaccgg cccgggaggc tcgctggttc agcgtctgtg ggtggaacag      300
gccagccata tcaaaaagga atactacctg ggcttcgtga tcgatcgcgg caatcaacgc      360
atcaccctga tcgcctccag cgagggcggc atggaaatcg aggaagtcgc aaaggaaacc      420
ccggagaaaa tcgtcaagga agtcgtcgat ccggccatag gcctgctgga cttccagtgc      480
cgcaaggtcg ccacggcgat cggcctgaaa ggcaaactga tgccccaggc cgtcaggctg      540
atgaaggcca tctaccgctg catgcgcgac aaagatgccc tgcaggccga aatcaatcct      600
ctggccatcg tgggcgaaag cgacgaatcg ctcatggtcc tggatgccaa gttcaacttc      660
gacgacaacg ccctgtaccg gcagcgcacc atcaccgaga tgcgcgacct ggccgaggaa      720 gaccccgaaag aggtcgaagc ctccggccac ggtctcaatt acatcgccct cgacggcaac      780
atcggctgca tcgtcaatgg cgccggcctc gccatggctt cgctcgacgc catcaccctg      840
catggcggcc gtccggccaa cttcctcgac gtgggcggcg gcgcctcccc cgagaaggtc      900
accaatgcct gccgcatcgt actggaagat cccaacgtcc gctgcatcct ggtcaacatc      960
tttgccggca tcaaccgctg tgactggatc gccaagggcc tgatccaggc ctgcgacagc     1020
ctgcagatca aggtgccgct gatcgtgcgc ctggccggga cgaacgtcga cgagggccgc     1080
aagatcctgg ccgaatccgg cctctccttc atcaccgcgg aaaatctgga cgacgcggcc     1140
gccaaggccg tcgccatcgt caagggataa                                     1170

<210> SEQ ID NO 98
<211> LENGTH: 2072
<212> TYPE: DNA
```

<213> ORGANISM: Unknown
<220> FEATURE:
<223> OTHER INFORMATION: Description of Unknown: Uncultured gamma proteobacterium

<400> SEQUENCE: 98

```
atgaacattc acgaatatca ggccaaggag ctgcttcgtt cttacggtgt ccccgttcca      60
gccgggaacg tcgcctattc cgatcgccaa gcgcaggcag tggccgaaca gatcggcggg     120
gacggatggg tagtaaaagc gcaaatccat accggcgggc gaggcaaggc cggcggcgtt     180
aaactcgccc aatccttgga ggaagtccgc aagatagccg acgaaatgat cggcaaaact     240
ttggtgactc ctcaaaccgg gcccaaaggc aaagtggtcc ggcgcgtatt ggtggaagaa     300
gcggttagtc cgcaacggga attgtacctt gggttggtca tcgaccggcg cagccaacgc     360
atcaccatcg tggcttccgc ggaaggaggg gtagagatcg aggaagtggc ggccaggagt     420
ccggagaaaa tcgtgcggga ggcgatcgac ccggccatcg gtctgcgcga ttttcaatgc     480
cgtaaggtcg ccgccgccat ggcctgcgc gacaaacatc taatggcgca ggcggtgcgc     540
ctcatgcagc gcatctatcg cctgtttcgt gacaaggatg ccctccaggt ggagatcaat     600
cctctaggca tcgtcggcag cgagccaaag ctggtttgtt tggacgccaa attcaatttc     660
gaccccaacg cccttttccg acatccggaa atcaacgagc tgcgcgattt ggaagaggaa     720
gacccgcggg aggtggaagc cttaggtcac gggctcaact acatcgcttt agacggcgat     780
atcggctgca tcgtcaacgg cgccggcctg gccatggcga ccatggacgc catcgtgttt     840
catggtggtt ggccggcgaa tttcctggat atcggggggtg gggcctcgcc ggagaaagtg     900
caaaacgctt gtcggatcgt gattcaggac cagaacgtca agactttgtt ggtcaatatc     960
tttgccggca tcaaccgctg cgattggatc gctaccggtc tagtccaggc ttacaccagc    1020
ttgcgcatcg acaagccctg cgtcgtgcgc cttgcaggaa cgaatgtaga ggaggggcta    1080
aggattttga ccgactcggg tcttgctttc gtaaaagcga gcaatctgga cgatgcggca    1140
gctaaagccg tcgccatcgc tcatgggagg aacgtatgag tatttttgtc aaccgccatt    1200
cgcgggtgat catccaggga ttcaccggcc aacacgctac gtttcacgcc agcgaggcga    1260
ttcggtacgg cactcaagtg gtcggcggcg tcaccccggg caagggagga agtaagcacc    1320
ttggattgcc ggtgttcgat acagtttctg aagcggtttc agagacgggc gccgatgtct    1380
ctgggatttt tgtgccccca gcgtttgctg ccgacgccat catggaagcg atcgaagccg    1440
ggatccgggt aatcgtggtg attgccgatg gcatcccggt gcaagacatg attcgagtgc    1500
agcgctaccg gctcggacgc gactgtctgg tgcttgggcc aaacacgcct ggaatcatca    1560
ctcctggaga gtgcaaggtg gggatcatgc ctgctggaat ttaccgtcca ggaagaattg    1620
gggtagtgtc gcggtccgga acgctgaatt acgaggccgt cgaacaattg gcaaactgg     1680
gtttgggtca atccaccgcg gttggcatcg gtggggatcc ggtcaacggc accgactttg    1740
tgactgtgct caaagccttc gaacaagatc cggacaccga tgcgatcgtc atgatcggcg    1800
aaatcggcgg gccgcaagaa gtcgccgctg cccgctgggc caaagaaaat atgcaaaagc    1860
cgctcatcgg ttttgtggcg ggggcctcgg ctccaccggg gcggcgcatg gggcatgctg    1920
gggcgatcat cgaaggtgag gaagacaccg ccaaagccaa gatggacgcg atggaggagc    1980
ttggggtata cgtggtcaga aatcccgccc ggatcggcga aacggtttta agggcgctca    2040
aggagcgcct gggatctgca gtttctggct aa                                  2072
```

<210> SEQ ID NO 99

```
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gttgaacgag gagatcgtcc atgaacattc acgaatatca                              40

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gctctagatt agccagaaac tgcagatcc                                          29

<210> SEQ ID NO 101
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
tgatattcgt gaatgttcat ggacgatctc ctcgttcaac                              40

<210> SEQ ID NO 102
<211> LENGTH: 897
<212> TYPE: DNA
<213> ORGANISM: Unknown
<220> FEATURE:
<223> OTHER INFORMATION: Description of Unknown:
      Uncultured gamma proteobacterium

<400> SEQUENCE: 102
atgagtattt ttgtcaaccg ccattcgcgg gtgatcatcc agggattcac cggccaacac        60
gctacgtttc acgccagcga ggcgattcgg tacggcactc aagtggtcgg cggcgtcacc       120
ccgggcaagg gaggaagtaa gcaccttgga ttgccggtgt tcgatacagt ttctgaagcg       180
gtttcagaga cgggcgccga tgtctctggg atttttgtgc cccagcgtt tgctgccgac        240 gccatcatgg aagcgatcga agccgggatc cgggtaatcg tggtgattgc cgatggcatc       300
ccggtgcaag acatgattcg agtgcagcgc taccggctcg gacgcgactg tctggtgctt       360
gggccaaaca cgcctggaat catcactcct ggagagtgca aggtggggat catgcctgct       420
ggaatttacc gtccaggaag aattggggta gtgtcgcggt ccggaacgct gaattacgag       480
gccgtcgaac aattgggcaa actgggtttg ggtcaatcca ccgcggttgg catcggtggg       540
gatccggtca acggcaccga ctttgtgact gtgctcaaag ccttcgaaca agatccggac       600
accgatgcga tcgtcatgat cggcgaaatc ggcgggccgc aagaagtcgc cgctgcccgc       660
tgggccaaag aaaatatgca aaagccgctc atcggttttg tggcggggc ctcggctcca        720 ccggggcggc gcatggggca tgctggggcg atcatcgaag gtgaggaaga caccgccaaa       780
gccaagatgg acgcgatgga ggagcttggg gtatacgtgg tcagaaatcc cgcccggatc       840
ggcgaaacgg tttaagggc gctcaaggag cgcctgggat ctgcagtttc tggctaa           897
```

```
<210> SEQ ID NO 103
<211> LENGTH: 1179
<212> TYPE: DNA
<213> ORGANISM: Unknown
<220> FEATURE:
<223> OTHER INFORMATION: Description of Unknown:
      Uncultured gamma proteobacterium

<400> SEQUENCE: 103
atgaacattc acgaatatca ggccaaggag ctgcttcgtt cttacggtgt ccccgttcca      60
gccgggaacg tcgcctattc cgatcgccaa gcgcaggcag tggccgaaca gatcggcggg     120
gacggatggg tagtaaaagc gcaaatccat accggcgggc gaggcaaggc cggcggcgtt     180
aaactcgccc aatccttgga ggaagtccgc aagatagccg acgaaatgat cggcaaaact     240
ttggtgactc ctcaaaccgg gcccaaaggc aaagtggtcc ggcgcgtatt ggtgaagaa      300 gcggttagtc cgcaacggga attgtaccct gggttggtca tcgaccggcg cagccaacgc     360
atcaccatcg tggcttccgc ggaaggaggg gtagagatcg aggaagtggc ggccaggagt     420
ccggagaaaa tcgtgcggga ggcgatcgac ccggccatcg gtctgcgcga ttttcaatgc     480
cgtaaggtcg ccgccgccat tggcctgcgc gacaaacatc taatggcgca ggcggtgcgc     540
ctcatgcagc gcatctatcg cctgtttcgt gacaaggatg ccctccaggt ggagatcaat     600
cctctaggca tcgtcggcag cgagccaaag ctggtttgtt tggacgccaa attcaatttc     660
gaccccaacg ccctttttccg acatccggaa atcaacgagc tgcgcgattt ggaagaggaa     720
gacccgcggg aggtggaagc cttaggtcac gggctcaact acatcgcttt agacggcgat     780
atcggctgca tcgtcaacgg cgccggcctg gccatggcga ccatggacgc catcgtgttt     840
catggtggtt ggccggcgaa tttcctggat atcgggggtg gggcctcgcc ggagaaagtg     900
caaaacgctt gtcggatcgt gattcaggac cagaacgtca agactttgtt ggtcaatatc     960
tttgccggca tcaaccgctg cgattggatc gctaccggtc tagtccaggc ttacaccagc    1020
ttgcgcatcg acaagccctg cgtcgtgcgc cttgcaggaa cgaatgtaga ggaggggcta    1080
aggattttga ccgactcggg tcttgctttc gtaaaagcga gcaatctgga cgatgcggca    1140
gctaaagccg tcgccatcgc tcatgggagg aacgtatga                           1179

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gttatgtggt ggtcgtgcag ctcctcgtca tgg                                   33

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gagctgcacg accaccacat aactatggag                                       30

<210> SEQ ID NO 106
<211> LENGTH: 28
```

-continued

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
ggaattccag ttgaacgacg gcgagcag                                        28

<210> SEQ ID NO 107
<211> LENGTH: 298
<212> TYPE: PRT
<213> ORGANISM: Granulibacter bethesdensis

<400> SEQUENCE: 107

Met Ser Ile Leu Ile Asn Lys Gln Thr Lys Ile Ile Gln Gly Phe
1               5                  10                  15

Thr Gly Asp Lys Gly Thr Phe His Gly Arg Glu Met Ile Asp Tyr Gly
            20                  25                  30

Thr Asn Val Val Gly Gly Val Thr Pro Lys Gly Gly Gln Thr His
        35                  40                  45

Leu Gly Arg Pro Val Phe Asn Thr Val Glu Asp Ala Val Arg Glu Thr
    50                  55                  60

Gly Ala Gln Ala Ser Ile Thr Phe Val Ala Pro Ala Phe Cys Ala Asp
65                  70                  75                  80

Ala Ile Met Glu Gly Ala Asp Ala Gly Leu Glu Leu Ile Cys Thr Ile
                85                  90                  95

Thr Asp Gly Ile Pro Ala Gln Asp Met Met Arg Val Lys Arg Tyr Leu
            100                 105                 110

Arg Arg Tyr Gln Lys Asp Arg Arg Thr Arg Leu Val Gly Pro Asn Cys
        115                 120                 125

Ala Gly Ile Ile Ser Pro Gly Gln Ala Met Leu Gly Ile Met Pro Gly
    130                 135                 140

His Ile Tyr Lys Glu Gly His Val Gly Ile Val Ser Arg Ser Gly Thr
145                 150                 155                 160

Leu Gly Tyr Glu Ala Ala Ala Gln Leu Lys Glu Leu Gly Ile Gly Val
                165                 170                 175

Ser Thr Ser Val Gly Ile Gly Gly Asp Pro Ile Asn Gly Ser Ser Phe
            180                 185                 190

Leu Asp His Leu Gln Leu Phe Glu Ala Asp Pro Glu Thr His Ala Val
        195                 200                 205

Leu Met Ile Gly Glu Ile Gly Gly Pro Gln Glu Ala Glu Ala Ala Lys
    210                 215                 220

Trp Ile Ser Glu Asn Met Ser Lys Pro Val Val Gly Tyr Val Ala Gly
225                 230                 235                 240

Leu Thr Ala Pro Lys Gly Arg Arg Met Gly His Ala Gly Ala Ile Ile
                245                 250                 255

Ser Gly Glu Gly Asp Ser Ala Ala Glu Lys Ser Glu Ile Met Arg Ser
            260                 265                 270

Tyr Gly Leu Thr Val Ala Pro Ser Pro Gly Glu Leu Gly Ser Thr Val
        275                 280                 285

Ala Ala Val Leu Ala Gly Arg Gln Ala Ala
    290                 295

<210> SEQ ID NO 108
<211> LENGTH: 389
<212> TYPE: PRT

<213> ORGANISM: Granulibacter bethesdensis

<400> SEQUENCE: 108

```
Met Asp Val His Glu Tyr Gln Ala Lys Glu Leu Leu Ala Ser Ala Gly
1               5                   10                  15

Val Ala Val Pro Arg Gly Ala Ile Ala Phe Ser Ala Asp Gln Ala Val
            20                  25                  30

Tyr Ala Ala Thr Glu Leu Gly Gly Trp His Trp Ala Val Lys Ala Gln
        35                  40                  45

Ile His Ala Gly Ala Arg Gly Lys Ala Gly Gly Ile Lys Leu Cys Lys
    50                  55                  60

Thr Tyr His Glu Val Arg Glu Ala Ala Gly Met Leu Gly Lys Arg
65                  70                  75                  80

Leu Val Thr His Gln Thr Gly Pro Glu Gly Lys Pro Val Gln Arg Val
                85                  90                  95

Tyr Val Glu Val Ala Asp Pro Phe Glu Lys Glu Phe Tyr Leu Gly Phe
            100                 105                 110

Val Leu Asp Arg Lys Leu Glu Arg Val Arg Val Ile Ala Ser Ala Glu
        115                 120                 125

Gly Gly Met Glu Ile Glu Ile Ala Ser Lys His Pro Glu Lys Leu
    130                 135                 140

Ile Gln Val Ile Val Glu Pro Ala Val Gly Leu Gln Gln Phe Gln Ala
145                 150                 155                 160

Arg Gln Ile Ala Phe Lys Leu Gly Leu Ser Ser Arg Gln Val Gln Arg
                165                 170                 175

Ala Val Thr Ser Ile Met Gly Ala Tyr Arg Ala Phe Arg Asp His Asp
            180                 185                 190

Ala Thr Met Leu Glu Ile Asn Pro Leu Val Leu Thr Lys Asp Asp Arg
        195                 200                 205

Ile Leu Ala Leu Asp Ala Lys Met Ser Phe Asp Asp Asn Ala Leu Phe
    210                 215                 220

Arg Arg Asn Asn Val Ala Asn Met His Asp Pro Ser Gln Asp Asp Pro
225                 230                 235                 240

Arg Glu Ala Gln Ala Ala Glu His Asn Leu Asn Tyr Val Gly Leu Glu
                245                 250                 255

Gly Asp Ile Gly Cys Val Val Asn Gly Ala Gly Leu Ala Met Ala Thr
            260                 265                 270

Met Asp Val Ile Lys Tyr Ala Gly Gly Glu Pro Ala Asn Phe Leu Asp
        275                 280                 285

Val Gly Gly Gly Ala Ser Pro Glu Arg Thr Ala Thr Ala Phe Arg Leu
    290                 295                 300

Val Leu Ser Asp Lys Asn Val Lys Val Val Leu Val Asn Ile Phe Ala
305                 310                 315                 320

Gly Ile Asn Arg Cys Asp Trp Ile Ala Glu Gly Val Val His Ala Val
                325                 330                 335

Lys Glu Val Asp Leu Lys Leu Pro Leu Val Val Arg Leu Ala Gly Thr
            340                 345                 350

Asn Val Glu Glu Gly Arg Arg Ile Leu Lys Glu Ser Gly Ile Ser Val
        355                 360                 365

Ile Met Ala Glu Ser Leu Thr Glu Ala Ala Glu Lys Ala Val Glu Ala
    370                 375                 380

Ala Lys Ala Ala Ala
385
```

<210> SEQ ID NO 109
<211> LENGTH: 320
<212> TYPE: PRT
<213> ORGANISM: Hyphomicrobium denitrificans

<400> SEQUENCE: 109

Met Ser Tyr Thr Leu Tyr Pro Asn Arg Lys Gln Arg Leu Gln Arg Ser
1               5                   10                  15

Tyr Leu Ala Val Pro Gly Ser Asn Pro Thr Met Ile Asp Arg Ala Leu
            20                  25                  30

Lys Ser Ala Ala Asp Tyr Val Phe Leu Asp Cys Glu Asp Ala Val Ala
        35                  40                  45

Pro Pro Glu Lys Glu Gln Ala Arg Lys Asn Ile Ile Gln Ala Leu Asn
    50                  55                  60

Asp Leu Asp Trp Lys Gly Ala Gly Lys Ser Val Ser Val Arg Ile Asn
65                  70                  75                  80

Gly Leu Asp Thr His Tyr Cys Tyr Arg Asp Val Val Asp Ile Val Glu
                85                  90                  95

Gln Ala Gly Ala Lys Leu Asp Thr Ile Leu Ile Pro Lys Val Gly Val
            100                 105                 110

Pro Ala Asp Val Tyr Ala Ile Glu Ser Phe Val Ser Gln Ile Glu Val
        115                 120                 125

Ala Lys Gly Leu Pro His Gln Ile Gly Met Glu Ala Leu Ile Glu Thr
    130                 135                 140

Pro Leu Gly Met Ala Asn Val Glu Ala Ile Ala Ser Ala Asn Ser Arg
145                 150                 155                 160

Leu Glu Ser Met His Phe Gly Val Ala Asp Tyr Ser Ala Phe Asn Lys
                165                 170                 175

Ala Arg Thr Val Val Ile Gly Gly Leu Asn Pro Asp Tyr Pro Gly Asp
            180                 185                 190

Gln Trp His Phe Pro Leu Ser Arg Met Thr Val Ala Cys Arg Ala Phe
        195                 200                 205

Gly Leu Arg Pro Ile Asp Gly Pro Phe Gly Gly Ile Asp Asp Pro Glu
    210                 215                 220

Gly Tyr Lys Ala Ala Arg Arg Gly Ala Ala Leu Gly Met Glu Gly
225                 230                 235                 240

Lys Trp Ala Ile His Pro Ser Gln Ile Glu Leu Ala Asn Glu Ile Tyr
                245                 250                 255

Ser Pro Thr Ala Lys Glu Ile Glu Arg Ala Glu Arg Ile Leu Val Ala
            260                 265                 270

Leu Lys Glu Ala Glu Ala Gln Gly Lys Gly Ala Ala Ser Leu Asp Gly
        275                 280                 285

Lys Met Ile Asp Ala Ala Ser Glu Lys Met Ala Lys Asn Leu Leu Val
    290                 295                 300

Thr Ala Ala Ala Ile Lys Ala Gly Glu Glu Ala Arg Ala Lys Ser Lys
305                 310                 315                 320

<210> SEQ ID NO 110
<211> LENGTH: 299
<212> TYPE: PRT
<213> ORGANISM: Hyphomicrobium denitrificans

<400> SEQUENCE: 110

Met Ala Ile Phe Ile Asn Glu Lys Thr Pro Ile Leu Ile Gln Gly Phe
1               5                   10                  15

```
Thr Gly Arg Ile Gly Thr Phe His Ala Gln Glu Met Ile Asp Tyr Gly
             20                  25                  30

Ser Asn Val Val Gly Val Thr Pro Lys Gly Gly Thr Ser His
         35                  40                  45

Leu Gly Arg Pro Val Phe Asn Thr Val Lys Gly Ala Val Asp Glu Thr
     50                  55                  60

Gly Ala Glu Ala Ser Ile Val Phe Val Pro Pro Pro Phe Ala Ala Asp
65                  70                  75                  80

Ala Ile Met Glu Ala Ala Asp Ala Gly Ile Lys Tyr Cys Val Cys Ile
                 85                  90                  95

Thr Asp Gly Ile Pro Ala Gln Asp Met Ile Arg Val Lys Arg Tyr Met
             100                 105                 110

Arg Arg Tyr Lys Lys Glu Ala Arg Met Ile Leu Thr Gly Pro Asn Cys
         115                 120                 125

Ala Gly Thr Ile Ser Pro Gly Lys Ala Met Leu Gly Ile Met Pro Gly
     130                 135                 140

His Ile Tyr Leu Pro Gly Arg Val Gly Ile Val Gly Arg Ser Gly Thr
145                 150                 155                 160

Leu Gly Tyr Glu Ala Ala Ala Gln Leu Lys Ala Leu Gly Ile Gly Val
                 165                 170                 175

Ser Thr Ser Val Gly Ile Gly Gly Asp Pro Ile Asn Gly Ser Ser His
             180                 185                 190

Arg Asp Val Leu Glu His Phe Glu Asn Asp Pro Glu Thr Asp Ala Ile
         195                 200                 205

Leu Met Ile Gly Glu Ile Gly Gly Pro Gln Glu Ala Glu Ala Gly Leu
     210                 215                 220

Phe Ala Lys Glu His Met Lys Lys Pro Val Ile Ala Tyr Ile Ala Gly
225                 230                 235                 240

Leu Ser Ala Pro Lys Gly Arg Arg Met Gly His Ala Gly Ala Ile Val
                 245                 250                 255

Ser Ala Phe Gly Glu Ser Ala Ala Glu Lys Val Glu Ile Leu Lys Gly
             260                 265                 270

Cys Gly Val Ala Ile Ala Pro Thr Pro Ser Glu Met Gly Ser Thr Val
         275                 280                 285

Ala Gln Val Leu Gly Lys Gln Lys Lys Val Ala
     290                 295

<210> SEQ ID NO 111
<211> LENGTH: 387
<212> TYPE: PRT
<213> ORGANISM: Hyphomicrobium denitrificans

<400> SEQUENCE: 111

Met Asp Ile His Glu Tyr Gln Ala Lys Glu Leu Leu Ala Lys Phe Gly
1               5                   10                  15

Val Pro Ile Ala Arg Gly Gly Leu Ala Tyr Ser Pro Glu Gln Ala Thr
             20                  25                  30

Tyr Arg Ala Ser Glu Leu Gly Gly Thr Val Val Lys Ala Gln Ile
         35                  40                  45

His Ser Gly Ala Arg Gly Lys Ala Gly Gly Val Lys Val Cys Lys Thr
     50                  55                  60

Glu Lys Glu Ile Glu Asp Ala Ala Glu Phe Met Leu Gly Arg Lys Leu
65                  70                  75                  80

Val Thr His Gln Thr Gly Ser Ala Gly Lys Leu Val Ser Arg Leu Tyr
                 85                  90                  95
```

```
Ile Glu Glu Ala Thr Asn Ile Asp Arg Glu Ile Tyr Leu Gly Phe Val
            100                 105                 110

Met Asp Arg Ala Ser Glu Arg Ile Val Val Ala Ser Ala Ala Gly
        115                 120                 125

Gly Met Asp Ile Glu Ile Ser Ala Ser Gln Pro Asp Thr Ile Ile
130                 135                 140

Arg Val Ala Val Asp Pro Ala Val Gly Met Gln Gln Phe Gln Ala Arg
145                 150                 155                 160

Glu Leu Ala Phe Gly Leu Gly Val Asp Pro Glu Ile Val Asn Lys Leu
                165                 170                 175

Val Pro Ala Ile Met Gly Cys Tyr Arg Ala Phe Arg Asp Leu Asp Ala
                180                 185                 190

Met Met Val Glu Ile Asn Pro Leu Val Ile Thr Lys Glu Lys Gln Val
        195                 200                 205

Val Ala Leu Asp Ala Lys Met Ser Phe Asp Asn Ala Leu Phe Arg
210                 215                 220

Arg Pro His Ile Ala Glu Leu Arg Asp Lys Ser Gln Glu Asp Pro Arg
225                 230                 235                 240

Glu Thr Tyr Ala Ser Asp Arg Gly Leu Ser Tyr Val Gly Leu Asp Gly
                245                 250                 255

Asp Ile Gly Cys Ile Val Asn Gly Ala Gly Leu Ala Met Ala Thr Leu
                260                 265                 270

Asp Met Ile Lys Leu Ala Gly Gly Glu Pro Ala Asn Phe Leu Asp Ile
        275                 280                 285

Gly Gly Gly Ala Ser Pro Glu Arg Val Thr Lys Ser Phe Lys Ala Val
290                 295                 300

Leu Arg Asp Lys Asn Val Lys Ala Ile Leu Val Asn Val Phe Ala Gly
305                 310                 315                 320

Ile Asn Arg Cys Asp Trp Val Ala Lys Gly Val Val Asp Ala Val Lys
                325                 330                 335

Glu Leu Asp Ile Lys Leu Pro Ile Val Val Arg Leu Ala Gly Thr Asn
                340                 345                 350

Val Glu Glu Gly Arg Lys Ile Ile Asp Asn Ser Gly Leu Thr Val Ile
        355                 360                 365

Ser Ala Glu Thr Leu Ala Asp Ala Ala Lys Gln Ala Val Glu Ala Ala
370                 375                 380

Lys Lys Ala
385

<210> SEQ ID NO 112
<211> LENGTH: 316
<212> TYPE: PRT
<213> ORGANISM: Nitrosomonas europaea

<400> SEQUENCE: 112

Met Ser His Thr Leu Tyr Glu Thr Lys Thr Pro Arg Val Gln Arg Cys
1               5                   10                  15

Glu Leu Ala Val Pro Gly Ser Arg Pro Glu Met Phe Glu Lys Ala Leu
            20                  25                  30

Lys Ser Gly Val Asp Phe Ile Phe Leu Asp Leu Glu Asp Ala Val Ala
        35                  40                  45

Pro Asp Asp Lys Ile Gln Ala Arg Lys Asn Ile Ile Gln Ala Ile Asn
    50                  55                  60

Asp Leu Asp Trp Lys Ser His Gly Val Thr Leu Ser Val Arg Ile Asn
```

```
                65                  70                  75                  80
Gly Leu Asp Thr Gln Tyr Met Val Arg Asp Val Val Asp Leu Val Glu
                85                  90                  95

Gln Ala Gly His Lys Ile Asp Thr Leu Leu Ile Pro Lys Val Gly Val
                100                 105                 110

Tyr Ala Asp Val Tyr Met Val Glu Ala Met Leu Ser Gln Leu Glu Met
                115                 120                 125

Gln Gln Gly Leu Lys Asn Arg Ile Gly Val Glu Ala Leu Ile Glu Thr
            130                 135                 140

Ala Leu Gly Met Ala Asn Val Glu Asp Ile Ala Arg Arg Gly Thr Ala
145                 150                 155                 160

Gly Arg Leu Glu Ala Leu His Phe Gly Val Ala Asp Tyr Ala Ala Ser
                165                 170                 175

Asn Arg Ala Arg Thr Thr Asn Ile Gly Gly Leu Asn Pro Asp Tyr Pro
                180                 185                 190

Gly Asp Gln Trp His Ala Ala Ile Ser Arg Met Thr Val Ala Cys Arg
            195                 200                 205

Ala Phe Gly Leu Arg Pro Ile Asp Gly Pro Phe Gly Asp Ile Gln Asp
210                 215                 220

Pro Glu Gly Tyr Lys Gln Ala Ala Arg Arg Ala Ala Leu Gly Cys
225                 230                 235                 240

Glu Gly Lys Trp Ala Ile His Pro Thr Gln Ile Ala Leu Ala Asn Glu
                245                 250                 255

Val Phe Thr Pro Pro Thr Ala Glu Val Asp Lys Ala Lys Arg Ile Leu
                260                 265                 270

Thr Ala Leu Lys Glu Ala Ala Gln Gly Lys Gly Ala Ala Ser Leu
            275                 280                 285

Asp Gly Arg Leu Ile Asp Ala Ala Ser Glu Arg Met Ala Asn Asn Ile
            290                 295                 300

Val Lys Met Ala Glu Ala Ile Ala Ala Lys Ser Lys
305                 310                 315

<210> SEQ ID NO 113
<211> LENGTH: 295
<212> TYPE: PRT
<213> ORGANISM: Nitrosomonas europaea

<400> SEQUENCE: 113

Met Ala Ile Leu Ile Asn Glu Gln Thr Arg Ile Ile Val Gln Gly Phe
1               5                   10                  15

Thr Gly Arg Ile Gly Thr Phe His Ala Gln Glu Met Ile Asp Tyr Gly
                20                  25                  30

Ser Asn Val Val Gly Gly Val Thr Pro Gly Lys Gly Gly Gln Lys His
            35                  40                  45

Leu Gly Leu Pro Val Phe Asn Thr Val Arg Glu Ala Val Glu Gln Ala
50                  55                  60

Gly Ala Glu Ala Ser Ile Val Phe Val Pro Ala Phe Ala Ala Asp
65                  70                  75                  80

Ser Ile Met Glu Ala Ala Asp Ala Gly Ile Lys Tyr Cys Val Ser Ile
                85                  90                  95

Thr Asp Gly Ile Pro Thr Gln Asp Met Met Thr Val Lys Asn Phe Leu
            100                 105                 110

Arg Leu Phe Pro Glu Glu Asp Arg Met Met Leu Thr Gly Pro Asn Cys
            115                 120                 125
```

```
Ser Gly Thr Ile Ser Pro Gly Arg Ala Met Leu Gly Ile Met Pro Gly
    130                 135                 140

His Ile Tyr Ser Arg Gly Val Gly Val Val Gly Arg Ser Gly Thr
145                 150                 155                 160

Leu Gly Tyr Glu Ala Ala Asp Gln Met Arg Arg Leu Asn Ile Gly Ile
                165                 170                 175

Ser Thr Ser Val Gly Ile Gly Gly Asp Pro Ile Ile Gly Ser Ser His
            180                 185                 190

Arg Asn Val Leu Gln Lys Leu Glu Glu Asp Pro Glu Thr Lys Val Thr
                195                 200                 205

Leu Met Ile Gly Glu Ile Gly Gly Pro Met Glu Val Glu Ala Gly Leu
210                 215                 220

Phe Ala Lys Glu Asn Met Ser Lys Pro Leu Val Ala Tyr Ile Ala Gly
225                 230                 235                 240

Leu Thr Ala Pro Pro Gly Arg Arg Met Gly His Ala Gly Ala Ile Ile
                245                 250                 255

Ser Ser Ala Gly Glu Ser Ala Ala Glu Lys Val Glu Arg Leu Lys Glu
            260                 265                 270

Leu Gly Val Thr Ile Cys Pro Thr Pro Ser Leu Met Gly Glu Thr Val
                275                 280                 285

Ala Lys Val Leu Ala Gly Leu
290                 295

<210> SEQ ID NO 114
<211> LENGTH: 390
<212> TYPE: PRT
<213> ORGANISM: Nitrosomonas europaea

<400> SEQUENCE: 114

Met Asp Ile His Glu Tyr Gln Ala Lys Glu Ile Leu Ala Glu Tyr Gly
1               5                   10                  15

Ile Lys Leu Ala Glu Gly Gly Leu Ala His Thr Val Glu Glu Ala Val
                20                  25                  30

Gln Arg Ser Arg Glu Ile Asp Gly Asn Val Trp Val Val Lys Ala Gln
            35                  40                  45

Ile His Ser Gly Ala Arg Gly Lys Ala Gly Gly Val Lys Val Cys Arg
    50                  55                  60

Thr His Glu Glu Ile Glu Val Ala Ala Glu Ser Leu Leu Gly Lys Lys
65                  70                  75                  80

Leu Val Thr His Gln Thr Gly Pro Ala Gly Lys Leu Cys Ser Arg Leu
                85                  90                  95

Tyr Ile Glu Ala Gly Thr Glu Ile Ala Arg Glu Val Tyr Leu Ala Phe
                100                 105                 110

Met Ile Asp Arg Ser His Glu Arg Ile Val Met Val Gly Ser Ala Gln
            115                 120                 125

Gly Gly Met Asp Ile Glu Thr Leu Ala Ala Thr Asn Pro Asp Ala Ile
    130                 135                 140

Lys Lys Ile His Ile Glu Pro Ala Val Gly Leu Gln Asp Phe Gln Ala
145                 150                 155                 160

Arg Thr Met Ala Phe Ala Leu Gly Leu Glu Asp Val Leu Leu Asn His
                165                 170                 175

Ala Val Lys Thr Ile Arg Gly Cys Tyr Arg Ala Met Arg Asp Leu Asp
            180                 185                 190

Ala Asn Ile Leu Glu Ile Asn Pro Leu Val Val Thr Arg Asn Asn Glu
                195                 200                 205
```

Leu Ile Ala Leu Asp Ala Lys Met Ser Phe Asp Glu Asn Ala Leu Phe
        210                 215                 220

Arg Arg His Arg Ile Ser Glu Leu Arg Asp Asn Ser Gln Ile Asp Ser
225                 230                 235                 240

Arg Glu Ile Ala Ala Glu Ala Gly Leu Ser Tyr Val Gly Leu Asp
            245                 250                 255

Gly Asp Ile Gly Cys Met Ile Asn Gly Ala Gly Leu Ala Met Ala Thr
            260                 265                 270

Met Asp Met Ile Lys Leu Ala Gly Gly Glu Pro Ala Asn Phe Leu Asp
        275                 280                 285

Val Gly Gly Gly Ala Ser Ala Glu Arg Thr Glu Lys Ala Phe Arg Leu
        290                 295                 300

Val Leu Ala Asp Asn Asn Val Lys Ala Met Leu Val Asn Ile Phe Ala
305                 310                 315                 320

Gly Ile Asn Arg Cys Asp Trp Ile Ala Glu Gly Val Val Gln Ala Val
            325                 330                 335

Arg Asn Ile Gly Met Thr Val Pro Leu Val Val Arg Leu Ser Gly Thr
            340                 345                 350

Asn Val Glu Glu Gly Arg Arg Ile Ile Ala Asp Ser Gly Leu Pro Ile
        355                 360                 365

Ile Thr Ala Glu Thr Leu Ala Asp Ala Ala Glu Lys Val Val His Ala
370                 375                 380

Arg Asn Gln Ala Ala Val
385                 390

<210> SEQ ID NO 115
<211> LENGTH: 320
<212> TYPE: PRT
<213> ORGANISM: Methylococcus capsulatus

<400> SEQUENCE: 115

Met Ala Val Lys Asn Arg Leu His Arg Ser Glu Leu Ala Val Pro Gly
1               5                   10                  15

Ser Asn Pro Arg Met Leu Glu Lys Ala Pro Glu Ala Gly Ala Asp Ile
            20                  25                  30

Val Phe Leu Asp Leu Glu Asp Ala Val Ala Pro Asp Lys Glu Gln
        35                  40                  45

Ala Arg Arg Asn Ile Val Phe Ala Leu Asn Thr Tyr Asp Trp Ser Arg
50                  55                  60

Cys Ala Val Ser Val Arg Ile Asn Gly Leu Asp Thr His Tyr Ala Tyr
65                  70                  75                  80

Arg Asp Leu Val Glu Ile Val Glu Ser Cys Gly Asp Lys Leu Asp Thr
            85                  90                  95

Ile Leu Val Pro Lys Val Gly Ser Ala Ser Asp Val Leu Phe Val Ala
            100                 105                 110

Thr Leu Leu Ser Gln Ile Glu Ala Tyr Lys Gly Phe Lys Pro Ile Asn
        115                 120                 125

Ile His Val Leu Ile Glu Thr Ala Met Gly Met Ala Asn Val Glu Glu
        130                 135                 140

Ile Ala Arg Thr Cys Pro Glu Arg Met Glu Ala Met Val Phe Gly Val
145                 150                 155                 160

Ala Asp Tyr Ala Ala Ser Val Arg Ala Arg Thr Thr Asn Ile Gly Gly
            165                 170                 175

Ala Asn Pro Asp Tyr Gly Met Leu Thr Asp Pro Asp Glu Ser Gly Thr

```
                    180                 185                 190
Arg Ala Tyr His Trp Ala Asp Gln Trp His Phe Gly Ile Ser Arg Met
                195                 200                 205

Val Ala Ala Cys Arg Ala Tyr Gly Leu Arg Pro Ile Asp Gly Pro Phe
            210                 215                 220

Gly Asp Phe Ser Asp Pro Glu Gly Phe Arg Ala Ala Arg Arg Ala
225                 230                 235                 240

Ala Ala Leu Gly Cys Glu Gly Lys Trp Ala Ile His Pro Ser Gln Ile
                245                 250                 255

Pro Leu Cys Asn Glu Ile Phe Thr Pro Thr Glu Lys Glu Val Thr Arg
            260                 265                 270

Ala Tyr Arg Ile Leu Glu Ala Met Glu Gln Ala Ala Lys Glu Gly Lys
                275                 280                 285

Gly Ala Val Ser Leu Asp Gly Arg Leu Ile Asp Ala Ala Ser Ile Arg
            290                 295                 300

Met Ala Glu Asn Val Val Arg Gln Met Lys Gln Ile Glu Ser Arg Arg
305                 310                 315                 320

<210> SEQ ID NO 116
<211> LENGTH: 300
<212> TYPE: PRT
<213> ORGANISM: Methylococcus capsulatus

<400> SEQUENCE: 116

Met Ser Val Phe Val Asn Lys His Ser Lys Val Ile Phe Gln Gly Phe
1               5                   10                  15

Thr Gly Glu His Ala Thr Phe His Ala Lys Asp Ala Met Arg Met Gly
                20                  25                  30

Thr Arg Val Val Gly Gly Val Thr Pro Gly Lys Gly Gly Thr Arg His
            35                  40                  45

Pro Asp Pro Glu Leu Ala His Leu Pro Val Phe Asp Thr Val Ala Glu
        50                  55                  60

Ala Val Ala Ala Thr Gly Ala Asp Val Ser Ala Val Phe Val Pro Pro
65                  70                  75                  80

Pro Phe Asn Ala Asp Ala Leu Met Glu Ala Ile Asp Ala Gly Ile Arg
                85                  90                  95

Val Ala Val Thr Ile Ala Asp Gly Ile Pro Val His Asp Met Ile Arg
            100                 105                 110

Leu Gln Arg Tyr Arg Val Gly Lys Asp Ser Ile Val Ile Gly Pro Asn
        115                 120                 125

Thr Pro Gly Ile Ile Thr Pro Gly Glu Cys Lys Val Gly Ile Met Pro
130                 135                 140

Ser His Ile Tyr Lys Lys Gly Asn Val Gly Ile Val Ser Arg Ser Gly
                145                 150                 155                 160

Thr Leu Asn Tyr Glu Ala Thr Glu Gln Met Ala Ala Leu Gly Leu Gly
            165                 170                 175

Ile Thr Thr Ser Val Gly Ile Gly Gly Asp Pro Ile Asn Gly Thr Asp
        180                 185                 190

Phe Val Thr Val Leu Arg Ala Phe Glu Ala Asp Pro Glu Thr Glu Ile
            195                 200                 205

Val Val Met Ile Gly Glu Ile Gly Gly Pro Gln Glu Val Ala Ala Ala
        210                 215                 220

Arg Trp Ala Lys Glu Asn Met Thr Lys Pro Val Ile Gly Phe Val Ala
225                 230                 235                 240
```

Gly Leu Ala Ala Pro Thr Gly Arg Arg Met Gly His Ala Gly Ala Ile
            245                 250                 255

Ile Ser Ser Glu Ala Asp Thr Ala Gly Ala Lys Met Asp Ala Met Glu
        260                 265                 270

Ala Leu Gly Leu Tyr Val Ala Arg Asn Pro Ala Gln Ile Gly Gln Thr
            275                 280                 285

Val Leu Arg Ala Ala Gln Glu His Gly Ile Arg Phe
    290                 295                 300

<210> SEQ ID NO 117
<211> LENGTH: 389
<212> TYPE: PRT
<213> ORGANISM: Methylococcus capsulatus

<400> SEQUENCE: 117

Met Asn Ile His Glu Tyr Gln Ala Lys Glu Leu Leu Lys Thr Tyr Gly
1               5                   10                  15

Val Pro Val Pro Asp Gly Ala Val Ala Tyr Ser Asp Ala Gln Ala Ala
            20                  25                  30

Ser Val Ala Glu Glu Ile Gly Gly Ser Arg Trp Val Lys Ala Gln
        35                  40                  45

Ile His Ala Gly Gly Arg Gly Lys Ala Gly Gly Val Lys Val Ala His
    50                  55                  60

Ser Ile Glu Glu Val Arg Gln Tyr Ala Asp Ala Met Leu Gly Ser His
65                  70                  75                  80

Leu Val Thr His Gln Thr Gly Pro Gly Gly Ser Leu Val Gln Arg Leu
                85                  90                  95

Trp Val Glu Gln Ala Ser His Ile Lys Lys Glu Tyr Tyr Leu Gly Phe
            100                 105                 110

Val Ile Asp Arg Gly Asn Gln Arg Ile Thr Leu Ile Ala Ser Ser Glu
        115                 120                 125

Gly Gly Met Glu Ile Glu Glu Val Ala Lys Glu Thr Pro Glu Lys Ile
    130                 135                 140

Val Lys Glu Val Val Asp Pro Ala Ile Gly Leu Leu Asp Phe Gln Cys
145                 150                 155                 160

Arg Lys Val Ala Thr Ala Ile Gly Leu Lys Gly Lys Leu Met Pro Gln
                165                 170                 175

Ala Val Arg Leu Met Lys Ala Ile Tyr Arg Cys Met Arg Asp Lys Asp
            180                 185                 190

Ala Leu Gln Ala Glu Ile Asn Pro Leu Ala Ile Val Gly Glu Ser Asp
        195                 200                 205

Glu Ser Leu Met Val Leu Asp Ala Lys Phe Asn Phe Asp Asp Asn Ala
    210                 215                 220

Leu Tyr Arg Gln Arg Thr Ile Thr Glu Met Arg Asp Leu Ala Glu Glu
225                 230                 235                 240

Asp Pro Lys Glu Val Glu Ala Ser Gly His Gly Leu Asn Tyr Ile Ala
                245                 250                 255

Leu Asp Gly Asn Ile Gly Cys Ile Val Asn Gly Ala Gly Leu Ala Met
            260                 265                 270

Ala Ser Leu Asp Ala Ile Thr Leu His Gly Gly Arg Pro Ala Asn Phe
        275                 280                 285

Leu Asp Val Gly Gly Gly Ala Ser Pro Glu Lys Val Thr Asn Ala Cys
    290                 295                 300

Arg Ile Val Leu Glu Asp Pro Asn Val Arg Cys Ile Leu Val Asn Ile
305                 310                 315                 320

```
Phe Ala Gly Ile Asn Arg Cys Asp Trp Ile Ala Lys Gly Leu Ile Gln
                325                 330                 335

Ala Cys Asp Ser Leu Gln Ile Lys Val Pro Leu Ile Val Arg Leu Ala
            340                 345                 350

Gly Thr Asn Val Asp Glu Gly Arg Lys Ile Leu Ala Glu Ser Gly Leu
            355                 360                 365

Ser Phe Ile Thr Ala Glu Asn Leu Asp Asp Ala Ala Lys Ala Val
    370                 375                 380

Ala Ile Val Lys Gly
385

<210> SEQ ID NO 118
<211> LENGTH: 298
<212> TYPE: PRT
<213> ORGANISM: Unknown
<220> FEATURE:
<223> OTHER INFORMATION: Description of Unknown:
      Uncultured gamma proteobacterium

<400> SEQUENCE: 118

Met Ser Ile Phe Val Asn Arg His Ser Arg Val Ile Ile Gln Gly Phe
1               5                   10                  15

Thr Gly Gln His Ala Thr Phe His Ala Ser Glu Ala Ile Arg Tyr Gly
                20                  25                  30

Thr Gln Val Val Gly Val Thr Pro Gly Lys Gly Ser Lys His
            35                  40                  45

Leu Gly Leu Pro Val Phe Asp Thr Val Ser Glu Ala Val Ser Glu Thr
    50                  55                  60

Gly Ala Asp Val Ser Gly Ile Phe Val Pro Ala Phe Ala Ala Asp
65                  70                  75                  80

Ala Ile Met Glu Ala Ile Glu Ala Gly Ile Arg Val Ile Val Val Ile
                85                  90                  95

Ala Asp Gly Ile Pro Val Gln Asp Met Ile Arg Val Gln Arg Tyr Arg
            100                 105                 110

Leu Gly Arg Asp Cys Leu Val Leu Gly Pro Asn Thr Pro Gly Ile Ile
            115                 120                 125

Thr Pro Gly Glu Cys Lys Val Gly Ile Met Pro Ala Gly Ile Tyr Arg
        130                 135                 140

Pro Gly Arg Ile Gly Val Val Ser Arg Ser Gly Thr Leu Asn Tyr Glu
145                 150                 155                 160

Ala Val Glu Gln Leu Gly Lys Leu Gly Leu Gly Gln Ser Thr Ala Val
                165                 170                 175

Gly Ile Gly Gly Asp Pro Val Asn Gly Thr Asp Phe Val Thr Val Leu
            180                 185                 190

Lys Ala Phe Glu Gln Asp Pro Asp Thr Asp Ala Ile Val Met Ile Gly
            195                 200                 205

Glu Ile Gly Gly Pro Gln Glu Val Ala Ala Ala Arg Trp Ala Lys Glu
        210                 215                 220

Asn Met Gln Lys Pro Leu Ile Gly Phe Val Ala Gly Ala Ser Ala Pro
225                 230                 235                 240

Pro Gly Arg Arg Met Gly His Ala Gly Ala Ile Ile Glu Gly Glu Glu
                245                 250                 255

Asp Thr Ala Lys Ala Lys Met Asp Ala Met Glu Glu Leu Gly Val Tyr
            260                 265                 270

Val Val Arg Asn Pro Ala Arg Ile Gly Glu Thr Val Leu Arg Ala Leu
```

```
            275                 280                 285
Lys Glu Arg Leu Gly Ser Ala Val Ser Gly
    290                 295

<210> SEQ ID NO 119
<211> LENGTH: 392
<212> TYPE: PRT
<213> ORGANISM: Unknown
<220> FEATURE:
<223> OTHER INFORMATION: Description of Unknown:
      Uncultured gamma proteobacterium

<400> SEQUENCE: 119

Met Asn Ile His Glu Tyr Gln Ala Lys Glu Leu Leu Arg Ser Tyr Gly
1               5                   10                  15

Val Pro Val Pro Ala Gly Asn Val Ala Tyr Ser Asp Arg Gln Ala Gln
            20                  25                  30

Ala Val Ala Glu Gln Ile Gly Gly Asp Gly Trp Val Val Lys Ala Gln
        35                  40                  45

Ile His Thr Gly Gly Arg Gly Lys Ala Gly Gly Val Lys Leu Ala Gln
    50                  55                  60

Ser Leu Glu Glu Val Arg Lys Ile Ala Asp Glu Met Ile Gly Lys Thr
65                  70                  75                  80

Leu Val Thr Pro Gln Thr Gly Pro Lys Gly Lys Val Val Arg Arg Val
                85                  90                  95

Leu Val Glu Glu Ala Val Ser Pro Gln Arg Glu Leu Tyr Leu Gly Leu
            100                 105                 110

Val Ile Asp Arg Arg Ser Gln Arg Ile Thr Ile Val Ala Ser Ala Glu
        115                 120                 125

Gly Gly Val Glu Ile Glu Glu Val Ala Ala Arg Ser Pro Glu Lys Ile
    130                 135                 140

Val Arg Glu Ala Ile Asp Pro Ala Ile Gly Leu Arg Asp Phe Gln Cys
145                 150                 155                 160

Arg Lys Val Ala Ala Ala Ile Gly Leu Arg Asp Lys His Leu Met Ala
                165                 170                 175

Gln Ala Val Arg Leu Met Gln Arg Ile Tyr Arg Leu Phe Arg Asp Lys
            180                 185                 190

Asp Ala Leu Gln Val Glu Ile Asn Pro Leu Gly Ile Val Gly Ser Glu
        195                 200                 205

Pro Lys Leu Val Cys Leu Asp Ala Lys Phe Asn Phe Asp Pro Asn Ala
    210                 215                 220

Leu Phe Arg His Pro Glu Ile Asn Glu Leu Arg Asp Leu Glu Glu Glu
225                 230                 235                 240

Asp Pro Arg Glu Val Glu Ala Leu Gly His Gly Leu Asn Tyr Ile Ala
                245                 250                 255

Leu Asp Gly Asp Ile Gly Cys Ile Val Asn Gly Ala Gly Leu Ala Met
            260                 265                 270

Ala Thr Met Asp Ala Ile Val Phe His Gly Gly Trp Pro Ala Asn Phe
        275                 280                 285

Leu Asp Ile Gly Gly Gly Ala Ser Pro Glu Lys Val Gln Asn Ala Cys
    290                 295                 300

Arg Ile Val Ile Gln Asp Gln Asn Val Lys Thr Leu Leu Val Asn Ile
305                 310                 315                 320

Phe Ala Gly Ile Asn Arg Cys Asp Trp Ile Ala Thr Gly Leu Val Gln
                325                 330                 335
```

```
Ala Tyr Thr Ser Leu Arg Ile Asp Lys Pro Cys Val Val Arg Leu Ala
            340                 345                 350

Gly Thr Asn Val Glu Glu Gly Leu Arg Ile Leu Thr Asp Ser Gly Leu
        355                 360                 365

Ala Phe Val Lys Ala Ser Asn Leu Asp Asp Ala Ala Ala Lys Ala Val
    370                 375                 380

Ala Ile Ala His Gly Arg Asn Val
385                 390
```

```
<210> SEQ ID NO 120
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ccgcggtacc gtataataaa gaataattat taatctgtag acaaattgtg aaagg      55

<210> SEQ ID NO 121
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
cttttgttta taagtgggta aaccgtgaat atcgtgttct tttcac                46

<210> SEQ ID NO 122
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
aagaactcta gaacaaaaag gataaaacaa tggcaaaaat gagagccgtt gacgcggcaa    60
tg                                                                  62

<210> SEQ ID NO 123
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gaccagctgc agtcaggcca gtttatggtt agccattaat tccagc                46

<210> SEQ ID NO 124
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
acacaactgc agacaaaaag gataaaacaa tgaagattgt cattgcgcca gactctttta    60
```

-continued aagagagct                                                            69

<210> SEQ ID NO 125
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gcccccaagc tttcagtttt taattccctg acctatttta atggcgcagg              50

<210> SEQ ID NO 126
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
aagaactcta gaacaaaaag gataaaacaa tggcaaaaat gagagccgtt gacgcggcaa   60
tg                                                                  62

<210> SEQ ID NO 127
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gcccccaagc tttcagtttt taattccctg acctatttta atggcgcagg              50

<210> SEQ ID NO 128
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gactctagag gatccccggg atgacagact cggttatcaa cagtgaatta cttttcag    58

<210> SEQ ID NO 129
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gacgggacgg cggctttgtt ggcttccgcg ttatgaaaaa agtagagagc              50

<210> SEQ ID NO 130
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ttgagacaca acgtggcttt cccagcaagg acagcgcgcg caatgaatg        49

<210> SEQ ID NO 131
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
atgaccatga ttacgaattc tcagggaagc aggcggtagc ctggcagagt cag        53

<210> SEQ ID NO 132
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tttttcataa cgcggaagcc aacaaagccg ccgtcccgtc aagtcagc        48

<210> SEQ ID NO 133
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
cgcgcgctgt ccttgctggg aaagccacgt tgtgtctcaa aatctctgat gttacattgc        60

<210> SEQ ID NO 134
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gccgccgaat tcccgaaaag tgccacctga cgtctaagaa acc        43

<210> SEQ ID NO 135
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
atgaccatga ttacgaattc tcagggaagc aggcggtagc ctggcagagt cag        53

<210> SEQ ID NO 136
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
agtctagaga tcctttttaa cccatcac                                          28

<210> SEQ ID NO 137
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
agtctagaag tcgataaaca gcaatatt                                          28

<210> SEQ ID NO 138
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gcaacgttgg ctctcatct                                                    19

<210> SEQ ID NO 139
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
cgggatccaa acacgcggcg gaaaaca                                           27

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
cgggatccgt taacgcaggc tgac                                              24

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
gctgctggcg tactggttc                                                    19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ctttacactt tatgcttcc                                                    19

<210> SEQ ID NO 143
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 143
ttgagctcga gaggtctgcc tcgtga                                           26

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 144
tcgccatgat gctgctgtg                                                   19

<210> SEQ ID NO 145
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 145
cgggatccga cttagcgtca tcggttg                                          27

<210> SEQ ID NO 146
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 146
cgggatccga tgaagattgc taacgacg                                         28

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 147
tgatgccgac aatattacgc                                                  20

<210> SEQ ID NO 148
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 148
cgcctcgagt gactcatacc aggcctg                                          27

<210> SEQ ID NO 149
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
cgcctcgagg caacaccttc ttcacgag                                      28

<210> SEQ ID NO 150
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
atcatccagc tgtcaggcag ccatcggaag                                    30

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
atccccggga attctgtt                                                 18

<210> SEQ ID NO 152
<211> LENGTH: 1352
<212> TYPE: DNA
<213> ORGANISM: Corynebacterium casei

<400> SEQUENCE: 152
cgcctcgagc actggaaggg ttcttcaggg gaaccccgg aaaccgggga aacatctgac    60
ttggttaaat gtcgtattat gaacacgccg aggaatgaaa accgaccgtg cacgctcgtg   120
tgagaaagtc agctacatga gaccaactac ccgccctgag ggacgctttg agcagctgtg   180
gctgccgctg tggccattgg caagcgatga cctccgtgag ggcatttacc gcacctcacg   240
gaagaacgcg ctggataagc gctacgtcga agccaatccc gacgcgctct ctaacctcct   300
ggtcgttgac atcgaccagg aggacgcgct tttgcgctct ttgtgggaca gggaggactg   360
gagacctaac gcggtggttg aaaacccctt aaacgggcac gcacacgctg tctgggcgct   420
cgcggagcca tttacccgca ccgaatacgc caaacgcaag cctttggcct atgccgcggc   480
tgtcaccgaa ggcctacggc gctctgtcga tggcgatagc ggatactccg ggctgatcac   540
caaaaacccc gagcacactg catgggatag tcactggatc accgataagc tgtatacgct   600
cgatgagctg cgcttttggc tcgaagaaac cggctttatg ccgcctgcgt cctggaggaa   660
aacgcggcgg ttctcgccag ttggtctagg tcgtaattgc gcactctttg aaagcgcacg   720
tacgtgggca tatcgggagg tcagaaagca ttttggagac gctgacggcc taggccgcgc   780
aatccaaacc accgcgcaag cacttaacca agagctgttt gatgaaccac tacctgtggc   840
cgaagttgac tgtattgcca ggtcaatcca taaatggatc atcaccaagt cacgcatgtg   900
gacagacggc gccgccgtct acgacgccac attcaccgca atgcaatccg cacgcgggaa   960

```
gaaaggctgg caacgaagcg ctgaggtgcg tcgtgaggct ggacatactc tttggaggaa    1020
cattggctaa ggtttatgca cgttatccac gcaacggaaa aacagcccgc gagctggcag    1080
aacgtgccgg tatgtcggtg agaacagctc aacgatggac ttccgaaccg cgtgaagtgt    1140
tcattaaacg tgccaacgag aagcgtgctc gcgtccagga gctgcgcgcc aaaggtctgt    1200
ccatgcgcgc tatcgcggca gagattggtt gctcggtggg cacggttcac cgctacgtca    1260
aagaagttga agagaagaaa accgcgtaaa tccagcggtt tagtcaccct cggcgtgttc    1320
aaagtccatc gtaaccaagt cagctcgagg cg                                   1352
```

<210> SEQ ID NO 153
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153

```
ggaattcaca aaaaggataa aacaatggct gtcaagaacc gtctac              46
```

<210> SEQ ID NO 154
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154

```
cgaattctca gaatctgatt ccgtgttcct g                              31
```

<210> SEQ ID NO 155
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155

```
cgagctcaag cttacaaaaa ggataaaaca atgagcacca ttgcattcat cgg      53
```

<210> SEQ ID NO 156
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156

```
cgggatccct agtccagcag catgagag                                  28
```

<210> SEQ ID NO 157
<211> LENGTH: 2727
<212> TYPE: DNA
<213> ORGANISM: Rhodococcus jostii

<400> SEQUENCE: 157

```
atgagcacca ttgcattcat cggactcgga atcatgggca gcccatggc cgttcatctc     60 gccaaggccg gccaccaggt ggtcggatac aaccgctcgc cgagcgcac cgcggcgctc    120 gtcgacgccg ggggcaccgc ggccgactcc atcgccaagg ccgttgccgg cgccgacgtc    180
```

```
gtggccgtga tggtccccga ctccccggac gtccaggccg tactcgccgg cgaggacgga    240
gtcttcgagc acgccccggc cggcgccctg atcatcgact tctccagcat ccggcccgac    300
gtcaccaccg ccctcgccgc gcaggcaacc gagcggggct ccggctgat cgacgccccg     360 gtatcgggtg gcgaggccgg tgcggtcaac gccgcactgt cgatcatggt cggcggcgcg    420
ccggaggatt tcgaggcggc caagccgatc ctcgacaccg tcggcaagac cgtggtgcac    480
gtgggcccga acggttccgg gcagacggtg aaggccgcga accagctgat cgtcgcgggc    540
aacatccaac tcctcgccga ggcgatcatc ttcctcgagg cctacggtgt cgacaccgcg    600
gctgcggtcg aggtgctcgg cggcgggctg gccggatcgg ccgtcctgaa ccagaaggca    660
cagaagatgc tggaccggtc cttcgaaccg ggattccgca tcgaactgca ccacaaggac    720
ctcggcatcg tgaccagcgc cgctcgcgag gccggtgtcg tgacacccct cggcgcggtc    780
gtcgcccagc tgatggcctc cgcccgtgcg aacggtgatg gtggcctgga ccattcgggc    840
ctgctgcgtg gagtggagcg gctgtccggc cgccccctcc agtgaccgt tccaactcgt     900 aatcctcgat ggagaagtga tatgcctcgt atgcgcgccg ctgacgcagc ggtcaagatt    960
ctggaactcg aaggtgccac tcaggccttc ggccttcccg gtgcggcgat caacccgttc    1020
tacgcagcaa tgcgtaacca cggaggaatc aagcacatcc tcgcccgcca cgtcgagggc    1080
gcctcccaca tggccagggg attcaccgc gccaaggccg gaaacatcgg agtctgcatc     1140
ggcacctccg ggcccgccgg aaccgacatg atcaccggtc tgtattcggc catggcggac    1200
tcgatcccga cctcgcgat caccggccaa gctcccgtgg cgcgcctgca caaggaagac    1260
ttccaggccg tcgacatcgc ctcgatcgca ggcccggtca cgaagatggc gatgacggtg    1320
ctcgagccgg cccaggttcc gggagcgttc gcgcaggcat ttcacttgat gcggtctggt    1380
cggccaggac cggtgctcat cgacctgccg atcgacgtgc agttggcgga gatcgacttc    1440
gacccggata cctaccagcc gctgcccgtg tacaagccgg ccgcgacccg cgcgcaggcg    1500
gagaaggcac tcgacatgct gggtgccgcc gaacgcccgc tgatcgttgc gggcggtggc    1560
atcatcaacg ccgacgccgc ggacctgctg gtggaactgg ccgaactgct ggacattccg    1620
gtcgtgccga cgctgatggg ctggggcacc atcccgacg accaccgtct cgccgccggg    1680
atggtcggac tgcagaccgc ccaccgatac ggcaacgcca cgatgctggc gtcggacttc    1740
gtcctcggca tcggcaaccg gtgggccaac cggcacacgg gcggtctcga cacctaccgg    1800
aagggccgca agttcgttca cgtcgacatc gaacccaccc agatcggtcg cgtgttcgcg    1860
cccgactacg ggatcgtgtc cgacgccaag gctgcgctcg aactgttcgt cgccgtcgcg    1920
aaggagcgca aggccgccgg aaccctggcg gaccgcagca cctgggtcga ggactgtgcc    1980
acccggaagc ggaccatgca gcgcaagacc cacttcgacg acgtcccggt caaaccgcag    2040
cgcgtgtacg aggagatgaa ccgcgtcttc gggcgcgaca cccggtacgt gagcacgatc    2100
gggctctcgc agatcgccgg cggccagttc ctgcacgtct acaaggcccg caactggatc    2160
aactgcgggc aggccgggcc gctcggctgg acgatccccg ccgctctcgg agtggttgcc    2220
gcggagccgg agacgcccgt cgtggcgctg tccggtgact acgacttcca gttcatgatc    2280
gaggaactgg ccgtgggcgc ccagttcaac ctgccgtaca tccacgtcgt ggtgaacaac    2340
tcctacctgg gactgatccg tcaggcacag cgcgcgttcg acatggactt ctgcgtgcaa    2400
ctgggcttcg acaacatcaa cacccaggag cggagcgagc acgagacgat gcccgcggtc    2460 ccgaagggt acggcgtcga tcacgtcaag gtcgccgagg gcctgggctg caaggccctg    2520
```

```
cgggtcaccg agccgggcga gatcgccggc gccctggaga aggcccgcga actcgccgga    2580
gaacacaagg tgccggtggt cgtcgaggtc ttcctcgagc gggtcaccaa catcgcgatg    2640
ggcaccgaac tcgacaacgt cgccgagttc gaggatctgg cggagagctg ggagcacgct    2700
cccacagccc tcatgctgct ggactag                                        2727
```

<210> SEQ ID NO 158
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 158

```
ccccgcgagg ccgaagctgc cgagcacaat c                                   31
```

<210> SEQ ID NO 159
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 159

```
gtgctcggca gcttcggcct cgcggggatc                                     30
```

<210> SEQ ID NO 160
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 160

```
ccccgcgagg ccgccgctgc cgagcacaat c                                   31
```

<210> SEQ ID NO 161
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 161

```
gtgctcggca gcggcggcct cgcggggatc                                     30
```

<210> SEQ ID NO 162
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 162

```
ccccgcgagg ccctggctgc cgagcacaat c                                   31
```

<210> SEQ ID NO 163
<211> LENGTH: 30
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 163
gtgctcggca gccagggcct cgcggggatc                                              30

<210> SEQ ID NO 164
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ccccgcgagg ccattgctgc cgagcacaat c                                            31

<210> SEQ ID NO 165
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gtgctcggca gcaatggcct cgcggggatc                                              30

<210> SEQ ID NO 166
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ccccgcgagg ccatggctgc cgagcacaat c                                            31

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gtgctcggca gccatggcct cgcggggatc                                              30

<210> SEQ ID NO 168
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
ccccgcgagg ccaatgctgc cgagcacaat c                                            31

<210> SEQ ID NO 169
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
                             primer

<400> SEQUENCE: 169
gtgctcggca gcattggcct cgcggggatc                                          30

<210> SEQ ID NO 170
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ccccgcgagg cctacgctgc cgagcacaat c                                        31

<210> SEQ ID NO 171
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gtgctcggca gcgtaggcct cgcggggatc                                          30

<210> SEQ ID NO 172
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
ccccgcgagg ccaaagctgc cgagcacaat c                                        31

<210> SEQ ID NO 173
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gtgctcggca gctttggcct cgcggggatc                                          30

<210> SEQ ID NO 174
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ccccgcgagg cccgcgctgc cgagcacaat c                                        31

<210> SEQ ID NO 175
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 175
gtgctcggca gcgcgggcct cgcggggatc                                              30

<210> SEQ ID NO 176
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gagcccgagg cgattattca ggtcgtggtc                                              30

<210> SEQ ID NO 177
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
cacgacctga ataatcgcct cgggctcctt g                                            31

<210> SEQ ID NO 178
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gagcccgagg cgaatattca ggtcgtggtc g                                            31

<210> SEQ ID NO 179
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cacgacctga atattcgcct cgggctcctt                                              30

<210> SEQ ID NO 180
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gagcccgagg cggatattca ggtcgtggtc g                                            31

<210> SEQ ID NO 181
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 181
cacgacctga atatccgcct cgggctcctt                                          30

<210> SEQ ID NO 182
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gagcccgagg cgaaaattca ggtcgtggtc g                                        31

<210> SEQ ID NO 183
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
cacgacctga attttcgcct cgggctcctt                                          30

<210> SEQ ID NO 184
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gagcccgagg cgcgcattca ggtcgtggtc g                                        31

<210> SEQ ID NO 185
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cacgacctga atgcgcgcct cgggctcctt                                          30

<210> SEQ ID NO 186
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gagcccgagg cgcacattca ggtcgtggtc g                                        31

<210> SEQ ID NO 187
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
```

```
<210> SEQ ID NO 188
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gagcccgagg cgcagattca ggtcgtggtc g                               31

<210> SEQ ID NO 189
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
cacgacctga atctgcgcct cgggctcctt                                 30

<210> SEQ ID NO 190
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gagcccgagg cgccgattca ggtcgtggtc g                               31

<210> SEQ ID NO 191
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
cacgacctga atcggcgcct cgggctcctt                                 30
```